United States Patent
Frederick et al.

(10) Patent No.: US 12,284,977 B2
(45) Date of Patent: Apr. 29, 2025

(54) METHODS AND COMPOSITIONS RELATED TO IMPROVED NITROGEN UTILIZATION EFFICIENCY IN TOBACCO

(71) Applicant: Altria Client Services LLC, Richmond, VA (US)

(72) Inventors: Jesse Frederick, Richmond, VA (US); Chengalrayan Kudithipudi, Midlothian, VA (US); Dongmei Xu, Glen Allen, VA (US)

(73) Assignee: Altria Client Services LLC, Richmond, VA (US)

( * ) Notice: Subject to any disclaimer, the term of this patent is extended or adjusted under 35 U.S.C. 154(b) by 0 days.

(21) Appl. No.: 18/163,499

(22) Filed: Feb. 2, 2023

(65) Prior Publication Data

US 2024/0099257 A1 Mar. 28, 2024

Related U.S. Application Data

(63) Continuation of application No. 17/116,816, filed on Dec. 9, 2020, now Pat. No. 11,602,118, which is a continuation of application No. 16/119,366, filed on Aug. 31, 2018, now Pat. No. 10,888,064.

(60) Provisional application No. 62/553,501, filed on Sep. 1, 2017.

(51) Int. Cl.
| | |
|---|---|
| *A01H 6/82* | (2018.01) |
| *A01H 5/10* | (2018.01) |
| *A01H 5/12* | (2018.01) |
| *C07K 14/415* | (2006.01) |
| *C12N 9/10* | (2006.01) |
| *C12N 9/88* | (2006.01) |
| *C12N 9/90* | (2006.01) |
| *C12N 15/82* | (2006.01) |

(52) U.S. Cl.
CPC .............. *A01H 6/823* (2018.05); *A01H 5/10* (2013.01); *A01H 5/12* (2013.01); *C07K 14/415* (2013.01); *C12N 9/1085* (2013.01); *C12N 9/88* (2013.01); *C12N 9/90* (2013.01); *C12N 15/8227* (2013.01); *C12N 15/8237* (2013.01); *C12N 15/8261* (2013.01); *C12Y 205/01054* (2013.01); *C12Y 402/01033* (2013.01); *C12Y 501/03015* (2013.01)

(58) Field of Classification Search
None
See application file for complete search history.

(56) References Cited

U.S. PATENT DOCUMENTS

| | | |
|---|---|---|
| 4,516,590 A | 5/1985 | Teng |
| 4,528,993 A | 7/1985 | Sensabaugh, Jr. et al. |
| 4,660,577 A | 4/1987 | Sensabaugh et al. |
| 4,683,195 A | 7/1987 | Mullis et al. |
| 4,683,202 A | 7/1987 | Mullis |
| 4,732,856 A | 3/1988 | Federoff |
| 4,761,373 A | 8/1988 | Anderson et al. |
| 4,762,785 A | 8/1988 | Comai |
| 4,769,061 A | 9/1988 | Comai |
| 4,800,159 A | 1/1989 | Mullis et al. |
| 4,810,648 A | 3/1989 | Stalker |
| 4,848,373 A | 7/1989 | Lenkey |
| 4,940,835 A | 7/1990 | Shah et al. |
| 4,945,050 A | 7/1990 | Sanford et al. |
| 4,965,188 A | 10/1990 | Mullis et al. |
| 4,975,374 A | 12/1990 | Goodman et al. |
| 4,987,907 A | 1/1991 | Townend |
| 5,004,863 A | 4/1991 | Umbeck |
| 5,013,658 A | 5/1991 | Dooner et al. |
| 5,013,659 A | 5/1991 | Bedbrook et al. |
| 5,104,310 A | 4/1992 | Saltin |
| 5,141,131 A | 8/1992 | Miller, Jr. et al. |
| 5,149,645 A | 8/1992 | Hoekema et al. |
| 5,159,135 A | 10/1992 | Umbeck |
| 5,162,602 A | 11/1992 | Somers et al. |
| 5,164,180 A | 11/1992 | Payne et al. |
| 5,177,010 A | 1/1993 | Goldman et al. |

(Continued)

FOREIGN PATENT DOCUMENTS

| | | |
|---|---|---|
| EP | 0242246 | 10/1987 |
| JP | A H09-503389 | 4/1997 |

(Continued)

OTHER PUBLICATIONS

Thalor, Sunil Kumar, et al. "Deregulation of sucrose-controlled translation of a bZIP-type transcription factor results in sucrose accumulation in leaves." PLoS One 7.3 (2012): e33111. (Year: 2012).*

(Continued)

*Primary Examiner* — Weihua Fan

(74) *Attorney, Agent, or Firm* — Arnold & Porter Kaye Scholer LLP

(57) ABSTRACT

The present disclosure provides metabolic signatures and genetic markers for tracking enhanced nitrogen utilization efficiency phenotypes in tobacco plants and for introgressing enhanced nitrogen utilization efficiency phenotypes into tobacco plants. The disclosure also provides tobacco plants comprising enhanced nitrogen utilization efficiency and methods to the creation of tobacco plants comprising enhanced nitrogen utilization efficiency. The disclosure also provides recombinant polynucleotides and polypeptides for enhancing nitrogen utilization efficiency in modified tobacco plants and tobacco plants comprising the provided recombinant polynucleotides and polypeptides.

10 Claims, 6 Drawing Sheets

Specification includes a Sequence Listing.

(56) References Cited

U.S. PATENT DOCUMENTS

| | | |
|---|---|---|
| 5,231,019 A | 7/1993 | Paszkowski et al. |
| 5,276,268 A | 1/1994 | Strauch et al. |
| 5,316,931 A | 5/1994 | Donson et al. |
| 5,372,149 A | 12/1994 | Roth |
| 5,463,174 A | 10/1995 | Moloney et al. |
| 5,464,763 A | 11/1995 | Schilperoort et al. |
| 5,469,976 A | 11/1995 | Burchell |
| 5,545,565 A | 8/1996 | De Greve et al. |
| 5,561,236 A | 10/1996 | Leemans et al. |
| 5,563,055 A | 10/1996 | Townsend et al. |
| 5,589,367 A | 12/1996 | Donson et al. |
| 5,659,026 A | 8/1997 | Baszczynski et al. |
| 5,767,366 A | 6/1998 | Sathasivan et al. |
| 5,789,156 A | 8/1998 | Bujard et al. |
| 5,814,618 A | 9/1998 | Bujard et al. |
| 5,866,785 A | 2/1999 | Donson et al. |
| 5,879,903 A | 3/1999 | Strauch et al. |
| 5,879,918 A | 3/1999 | Tomes et al. |
| 5,886,244 A | 3/1999 | Tomes et al. |
| 5,889,190 A | 3/1999 | Donson et al. |
| 5,889,191 A | 3/1999 | Turpen |
| 5,928,937 A | 7/1999 | Kakefuda et al. |
| 5,932,782 A | 8/1999 | Bidney |
| 5,981,840 A | 11/1999 | Zhao et al. |
| 6,072,050 A | 6/2000 | Bowen et al. |
| 6,084,155 A | 7/2000 | Volrath et al. |
| 6,166,302 A | 12/2000 | Merlo et al. |
| 6,451,732 B1 | 9/2002 | Beckett et al. |
| 6,451,735 B1 | 9/2002 | Ottaway et al. |
| 9,322,029 B2 | 4/2016 | Davenport et al. |
| 10,888,064 B2 | 1/2021 | Frederick et al. |
| 2001/0016956 A1 | 8/2001 | Ward et al. |
| 2003/0101487 A1 | 5/2003 | Kisaka et al. |
| 2003/0110530 A1 | 6/2003 | Shelp et al. |
| 2004/0118422 A1 | 6/2004 | Lundin et al. |
| 2005/0178398 A1 | 8/2005 | Breslin et al. |
| 2006/0191548 A1 | 8/2006 | Strickland et al. |
| 2012/0024301 A1 | 2/2012 | Carroll et al. |
| 2012/0031414 A1 | 2/2012 | Atchley et al. |
| 2012/0031416 A1 | 2/2012 | Atchley et al. |
| 2014/0223603 A1 | 8/2014 | Xu et al. |
| 2015/0173319 A1 | 6/2015 | Frederick et al. |

FOREIGN PATENT DOCUMENTS

| | | |
|---|---|---|
| JP | A 2012-501190 | 1/2012 |
| JP | A 2013-543377 | 12/2013 |
| WO | WO 95/09911 A1 | 4/1995 |
| WO | WO 2002/038736 | 5/2002 |
| WO | WO 2004/041006 A1 | 5/2004 |
| WO | WO 2007/092704 A2 | 8/2007 |
| WO | WO 2009/054735 | 4/2009 |
| WO | WO 2009/105612 | 8/2009 |
| WO | WO 2010/025465 A1 | 3/2010 |
| WO | WO 2011/025514 A1 | 3/2011 |
| WO | WO 2018/068000 | 4/2018 |

OTHER PUBLICATIONS

Edwards, Kieron D., et al. "A reference genome for Nicotiana tabacum enables map-based cloning of homeologous loci implicated in nitrogen utilization efficiency." BMC genomics 18 (2017): 1-14. (Year: 2017).*

Allen et al., "microRNA-Directed Phasing During *Trans*-Acting siRNA Biogenesis in Plants," *Cell*, 121:207-221 (2005).

Altschul et al., "Basic Local Alignment Search Tool," *J. Mol. Biol.*, 215:403-410 (1990).

Altschul et al., "Gapped Blast and PSI-Blast: a New Generation of Protein Database Search Programs," *Nucleic Acids Res.*, 25:3389-3402 (1997).

Bartel, "MicroRNAs: Genomics, Biogenesis, Mechanism, and Function," *Cell*, 116:281-297 (2004).

Bindler et al., "A High Density Genetic Map of Tobacco (*Nicotiana tabacum* L.) Obtained from Large Scale Microsatellite Marker Development," *Theor. Appl. Genet*, 123:219-230 (2011).

Bingguang et al., "SNP-based Genetic Linkage Map of Tobacco (*Nicotiana tabacum* L.) Using Next-Generation RAD Sequencing," *J. of Biol. Res- Thessaloniki*, 22:11 (2015).

Brauer et al., "Nitrogen Use Efficiency: re-construction of the Bioengineering Approach," *Botany*, 88(2):103-110 (2010).

Canevascini et al., "Tissue-Specific Expression and Promoter Analysis of the Tobacco Itp1 Gene," Plant Physiol., 112(2):513-524 (1996).

Chenna et al., "Multiple Sequence Alignment with the Clustal Series of Programs," *Nucleic Acids Research*, 31(13):3497-3500 (2003).

Christou et al., "Stable Transformation of Soybean Callus by DNA-Coated Gold Particles," *Plant Physiol.*, 87:671-674 (1988).

Christensen et al., "Sequence Analysis and Transcriptional Regulation by Heat Shock of Polyubiquitin Transcripts from Maize," *Plant Mol. Biol.*, 12:619-632 (1989).

Christensen et al., "Maize Polyubiquitin Genes: Structure, Thermal of Expression and Transcript Splicing, and Promoter Activity Following Transfer to Protoplasts by Electroporation," *Plant Mol. Biol.*, 18:675-689 (1992).

Crossway et al., "Micromanipulation Techniques in Plant Biotechnology," *Biotechniques*, 4:320-334 (1986).

Davis et al., "Tobacco, Production, Chemistry and Technology," eds., Blackwell Publishing, Oxford, Chapters 4B and 4C, pp. 70-103 (1999).

Dayhoff et al., "22 A Model of Evolutionary Change in Proteins," *Atlas of Protein Sequence and Structure*, 5(Suppl. 3):345-352 (1978).

D'Halluin et al., "Transgenic Maize Plants by Tissue Electroporation," *Plant Cell*, 4:1495-1505 (1992).

De Wet et al., "Exogenous Gene Transfer in Maize (*Zea mays*) Using DNA-treated Pollen," The Experimental Manipulation of Ovule Tissues, pp. 197-209 (1985).

Edwards, et al., "A reference genome for Nicotiana tabacum enables map-based cloning of homeologous loci implicated in nitrogen utilization efficiency," *BMC Genomics* 18.1:1-14 (2017).

Fedoroff et al., "Cloning of the bronze Locus in Maize by a Simple and Generalizable Procedure Using the Transposable Controlling Element *Activator (Ac),*" *Proc. Natl. Acad. Sci.*, 81:3825-3829 (1984).

Finer et al., "Transformation of Soybean via Particle Bombardment of Embryogenic Suspension Culture Tissue," *In Vitro Cell Dev. Biol.*, 27P:175-182 (1991).

Fischhoff et al., "Insect Tolerant Transgenic Tomato Plants," *Nature Biotechnology*, 5:807-813 (1987).

Gatz et al., "Regulation of a Modified CaMV 35S Promoter by the Tn 10-encoded Tet repressor in Transgenic Tobacco," Mol. Gen. Genet., 227:229-237 (1991).

GenBank Accession No. AF352732.1 "Nicotiana tabacum glutamate decarboxylase isozyme 1 mRNA, complete cds," 2 pages.

Goldman et al., "Female Sterile Tobacco Plants are Produced by Stigma-Specific Cell Ablation," *EMBO Journal*, 13:2976-2984 (1994).

Griffiths-Jones et al., "Rfam: an RNA Family Database," *Nucleic Acids Res.*, 31:439-441 (2003).

Guevara-Garcia et al., "Tissue-Specific and Wound-Inducible Pattern of Expression of the Mannopine Synthase Promoter is Determined by the Interaction Between Positive and Negative cis-regulatory Elements," *Plant J.*, 4(3):495-505 (1993).

Gut et al., "A Common Structural Basis for PH- and Calmodulin-mediated Regulation in Plant Glutamate Decarboxylase," *Journal of Molecular Biology*, 392(2):334-351 (2009).

Ha et al., "Cis-acting Regulatory Elements Controlling Temporal and Organ-Specific Activity of Nopaline Synthase Promoter," *Nucleic Acids Research*, 11;17(1):215-23 (1989).

Hansen et al., "Wound-inducible and Organ-Specific Expression of ORF13 from *Agrobacterium rhizogenes* 8196 T-DNA in Transgenic Tobacco Plants," *Molecular General Genetics*, 254(3):337-343 (1997).

Hildering et al., "The Use of Induced Mutations in Plant Breeding," Pergamon Press, pp. 317-320 (1965).

(56) References Cited

OTHER PUBLICATIONS

Hill et al., "Functional Analysis of Conserved Histidines in ADP-glucose Pyrophosphorylase from *Escherichia coli*," *Biochemical and Biophysical Research Communications*, 244(2):573-7 (1998).
Hoekema et al., "A Binary Plant Vector Strategy Based on Separation of *vir*- and T-region of the *Agrobacterium tumefaciens* Ti-plasmid," *Nature*, 303:179-180 (1983).
Horsch et al., "A Simple and General Method for Transferring Genes into Plants," *Science*, 227:1229-1231 (1985).
Hörtensteiner et al., "Chlorophyll Breakdown in Higher Plants," *Biochimica et Biophysica Acta*, 1807:977-988 (2011).
International Search Report and Written Opinion in International Application No. PCT/US2017/055635, dated Jan. 26, 2018, 16 pages.
International Search Report and Written Opinion in International Application PCT/US2018/049156 dated Jan. 28, 2019.
Kaeppler et al., "Silicon Carbide Fiber-mediated DNA Delivery into Plant Cells," *Plant Cell Reports*, 9:415-418 (1990).
Kaeppler et al., "Silicon Carbide Fiber-mediated Stable Transformation of Plant Cells," *Theor. Appl. Genet.*, 84:560-566 (1992).
Kawamata et al., "Temporal and Spatial Pattern of Expression of the Pea Phenylalanine Ammonia-Lyase Gene1 Promoter in Transgenic Tobacco," *Plant Cell Physiol.* 38(7):792-803 (1997).
Kim et al., "A 20 Nucleotide Upstream Element is Essential for the Nopaline Synthase (*nos*) Promoter Activity," *Plant Molecular Biology*, 24(1):105-17 (1994).
Kouranov et al., "Analysis of the Interactions of Preproteins with the Import Machinery over the Course of Protein Import into Chloroplasts," *Journal of Cell Biology*, 139(7):1677-1685 (1997).
Kouranov et al., "Tic20 and Tic22 are New Components of the Protein Import Apparatus at the Chloroplast Inner Envelope Membrane," *Journal of Cell Biology*, 143(4):991-1002 (1998).
Kumar et al., "Comparative Phylogenetic Analysis and Transcriptional Profiling of MADS-box Gene Family Identified DAM and FLC-like Genes in Apple (*Malus x domestica*)," *Scientific Reports*, 6:20695 (2016).
Ladha et al. "Efficiency of Fertilizer Nitrogen in Cereal Production Retrospects and Prospects," *Advances in Agronomy*, 87:85-156 (2005).
Lam, "8 Analysis of Tissue-Specific Elements in the CaMV 35S Promoter," *Results Probl. Cell Differ.*, 20:181-196 (1994).
Last et al., "pEmu: an Improved Promoter for Gene Expression in Cereal Cells," *Theor. Appl. Genet.*, 81:581-588 (1991).
Li et al., "A Fast Neutron Deletion Mutagenesis-based Reverse Genetics System for plants," *The Plant Journal*, 27(3):235-242 (2001).
Li et al., "Modularly Assembled Designer TAL Effector Nucleases for Targeted Gene Knockout and Gene Replacement in Eukaryotes," *Nucleic Acids Research* 39(14):6315-6325 (2011).
Lin-Hui et al., "Overexpression of *Arabidopsis* NLP7 Improves Plant Growth Under Both Nitrogen-limiting and -sufficient Conditions by Enhancing Nitrogen and Carbon Assimilation," *Scientific Reports*, 6:27795, 1-13 (2016).
Matsuoka et al., "Tissue-Specific Light-Regulated Expression Directed by the Promoter of a C4 Gene, Maize Pyruvate, Orthophosphate Dikinase, in a C3 Plant, Rice," Proc. Natl. Acad. Sci. USA, 90(20):9586-9590 (1993).
Matsuyama et al., "Characterization of Glutamate Decarboxylase Mediating y-Amino Butyric Acid Increase in the Early Germination Stage of Soybean," *Journal of Bioscience and Bioengineering*, 107(5):538-543 (2009).
Mayo et al., "Genetic Transformation of Tobacco NT1 Cells with *Agrobacterium tumefaciens*," *Nat. Protoc.*, 1:1105-11 (2006).
McCabe et al., "Stable Transformation of Soybean (Glycine Max) by Particle Acceleration," *Biotechnology*, 6:923-926 (1988).
McCallum et al., "Targeted Screening for Induced Mutations," *Nat. Biotechnol.*, 18:455-457 (2000).
McNellis et al., "Glucocorticoid-Inducible Expression of a Bacterial Avirulence Gene in Transgenic *Arabidopsis* Induces Hypersensitive Cell Death," *Plant J.* 14(2):247-257 (1998).

Nicotiana tomentosiformis kirola-like (LOC104105589), GenBank accession No. XM_009613937 (2016).
Odell et al., "Identification of DNA Sequences Required for Activity of the Cauliflower Mosaic Virus 35S Promoter," *Nature*, 313:810-812 (1985).
Orozco et al., "Localization of Light-Inducible and Tissue-Specific Regions of the Spinach Ribulose Bisphosphate Carboxylase/Oxygenase (subisco) Activase Promoter in Transgenic Tobacco Plants," *Plant Mol. Biol.*, 23(6):1129-1138 (1993).
Parizotto et al., "In vivo Investigation of the Transcription, Processing, Endonucleolytic Activity, and Functional Relevance of the Spatial Distribution of a Plant miRNA," *Genes Dev.*, 18:2237-2242 (2004).
Paszkowski et al., "Direct Gene Transfer to Plants," *EMBO J.*, 3(12):2717-2722 (1984).
Pochlman, "Breeding Field Crops," Van Nostrand Reinhold, New York (3.sup.rd ed.), (1987).
Porta et al., "Use of Viral Replicons for the Expression of Genes in Plants," Molecular Biotechnology, 5:209-221 (1996).
Reynolds et al., "Rational siRNA Design for RNA Interference," Nature Biotechnol., 22:326-330 (2004).
Riggs et al., "Stable Transformation of Tobacco by Electroporation: Evidence for Plasmid Concatenation," Proc. Natl. Acad. Sci. USA, 83:5602-5606 (1986).
Rinehart et al., "Tissue-Specific and Developmental Regulation of Cotton Gene FbL2A," Plant Physiol., 112(3):1331-1341 (1996).
Ruiter et al., "Spontaneous Mutation Frequency in Plants Obscures the Effect of Chimeraplasty," *Plant Molecular Biology*, 53(5):675-89 (2003).
Russell et al., "Tissue-Specific Expression in Transgenic Maize of Four Endosperm Promoters from Maize and Rice," Transgenic Res., 6(2):157-168 (1997).
Schena et al., "A Steroid-Inducible Gene Expression System for Plant Cells," Proc. Natl. Acad. Sci. USA, 88:10421-10425 (1991).
Search Report dated Mar. 28, 2022 in Chinese Appln. 2018800665073 along with English translation of related Office Action.
Shillito et al., "Direct Gene Transfer to Protoplasts of Dicotyledonous and Monocotyledonous Plants by a Number of Methods, Including Electroporation," *Meth. Enzymol.*, 153:313-336 (1987).
Sierro et al., "Reference genomes and transcriptomes of *Nicotiana sylvestris* and *Nicotiana tomentosiformis*," *Genome Biology* 14:R50:1-17 (2013).
Singh et al., "Cytological Characterization of Transgenic Soybean," *Theor. Appl. Genet.*, 96:319-324 (1998).
Tanaka et al., "Studies on Biological Effects of Ion Beams on Lethality, Molecular Nature of Mutation, Mutation Rate, and Spectrum of Mutation Phenotype for Mutation Breeding in Higher Plants," *J. Radiat. Res.*, 51:223-233 (2010).
Thompson et al., "Clustal W: Improving the Sensitivity of Progressive Multiple Sequence Alignment through Sequence Weighting, Position-Specific Gap Penalties and Weight Matrix Choice," *Nucl. Acids Res.*, 22:4673-4680 (1994).
Tomes et al., "16 Direct DNA Transfer into Intact Plant Cells via Microprojectile Bombardment," *Plant Cell, Tissue, and Organ Culture Fundamental Methods*, pp. 197-198 (1995).
Tso, "Chapter 1: Seed to Smoke," Tobacco: Production, Chemistry and Technology, Eds. Davis & Nelson, pp. 1-31 (1999).
Vaeck et al., "Transgenic Plants Protected from Insect Attack," *Nature*, 328:33-37 (1987).
Van Camp et al., "Tissue-Specific Activity of Two Manganese Superoxide Dismutase Promoters in Transgenic Tobacco," Plant Physiol., 112(2):525-535 (1996).
Verkerk, "Chimerism of the Tomato Plant After Seed Irradiation with Fast Neutrons," *Neth. J. Agric. Sci.*, 19:197-203 (1971).
Velten et al., "Isolation of a Dual Plant Promoter Fragment from the Ti Plasmid of *Agrobacterium tumefaciens*," *EMBO J.*, 3:2723-2730 (1984).
Weising et al., "Foreign Genes in Plants: Transfer, Structure, Expression, and Applications," *Annu. Rev. Genet.*, 22:421-477 (1988).
Wernsman et al., "Principles of cultivar development," Chapter Seventeen: Tobacco, MacMillan Publishing Company, New York, 2:669-698 (1987).

(56) References Cited

OTHER PUBLICATIONS

Wijnker et al., "Managing meiotic recombination in plant breeding," *Trends in Plant Science* 13:640-646 (2008).
Wright et al., "High-frequency Homologous Recombination in Plants Mediated by Zinc-Finger Nucleases," *The Plant Journal*, 44:693-705 (2005).
Yamamoto et al., "The Promoter of a Pine Photosynthetic Gene Allows Expression of a js-Glucuronidase Reporter Gene in Transgenic Rice Plants in a Light-Independent but Tissue-Specific Manner," Plant Cell Physiol., 35(5):773-778 (1994).
Yamamoto et al., "Light-Responsive Elements of the Tobacco PSI-D Gene are Located both Upstream and within the Transcribed Region," Plant J., 12(2):255-265 (1997).
Yevtushenko et al., "Calcium/calmodulin Activation of two Divergent Glutamate Decarboxylases from Tobacco," *Journal of Experimental Botany*, 54(389):2001-2002 (2003).
Yoo et al., "*Arabidopsis* Mesophyll Protoplasts: a Versatile Cell System for Transient Gene Expression Analysis," *Nature Protocols*, 2(7):1565-1572 (2007).
Yu et al., "Overexpression of *Arabidopsis* NLP7 Improves Plant Growth Under Both Nitrogen-limiting and Sufficient Conditions by Enhancing Nitrogen and Carbon Assimilation," *Scientific Reports*, 6(1):113 (2016).
Zhou et al., "The Plant Cyclin-dependent Kinase Inhibitor ICK1 has Distinct Functional Domains for In Vivo Kinase Inhibition, Protein Instability and Nuclear Localization," *The Plant Journal*, 35(4):476-89 (2003).

\* cited by examiner

METHODS AND COMPOSITIONS RELATED TO IMPROVED NITROGEN UTILIZATION EFFICIENCY IN TOBACCO

CROSS-REFERENCE TO RELATED APPLICATIONS

This application is a continuation application of U.S. patent application Ser. No. 17/116,816, filed Dec. 9, 2020, which is a continuation of Ser. No. 16/119,366, filed Aug. 31, 2018, now U.S. patent Ser. No. 10/888,064, issued Jan. 12, 2021, which claims the benefit of U.S. Provisional Application No. 62/553,501, filed Sep. 1, 2017, all of which are incorporated by reference in their entireties herein.

INCORPORATION OF SEQUENCE LISTING

A sequence listing contained in the file named "P34523US03_SL.TXT" which is 188,493 bytes (measured in MS-Windows®) and created on Feb. 2, 2023, is filed electronically herewith and incorporated by reference in its entirety.

FIELD

The present disclosure provides compositions and methods useful for making and identifying tobacco plants comprising improved nitrogen utilization efficiency via breeding, transgenic approaches, and cisgenic approaches.

BACKGROUND

Fertilizer is a major cost for tobacco growers, and increased fertilization has been tied to higher levels of alkaloids and tobacco-specific nitrosamines (TSNAs) in plant tissues. Different tobacco varieties require different levels of nitrogen fertilizer input to achieve the maximum yield for each variety. For example, Maryland tobacco varieties typically require approximately 25% less nitrogen input to achieve maximum yield as compared to Burley tobacco varieties.

Improving Nitrogen Utilization Efficiency (NUE) in tobacco would increase tobacco harvestable yield per unit of input nitrogen fertilizer. Nitrogen utilization efficiency improvement also allows decreases in on-farm input costs, decreased use and dependence on the non-renewable energy sources required for nitrogen fertilizer production, and reduces the environmental impact of nitrogen fertilizer manufacturing and agricultural use.

Methods and compositions for improving the nitrogen utilization efficiency of tobacco are provided herein.

SUMMARY

In one aspect, the present disclosure provides for, and includes, a method of determining the NUE of a tobacco line comprising obtaining at least one metabolite from a tobacco plant of a tobacco line, determining the amount of the obtained metabolites, and determining the NUE of the tobacco line based on the amount of the metabolites identified.

In one aspect, the present specification provides for, and includes, a method of determining the NUE of a tobacco line using a metabolite signature comprising isolating a metabolite signature from a tobacco plant of a tobacco line, determining the amount of each metabolite comprising a metabolite signature, and determining the NUE of a tobacco line by comparing the metabolite signature to a control metabolite signature from a control tobacco line comprising a known NUE.

In one aspect, the current specification provides for, and includes, a method of breeding a tobacco line comprising a metabolite signature associated with enhanced NUE comprising determining the metabolite signature of a first tobacco plant from a first tobacco line, where a first tobacco plant comprises enhanced NUE as compared to a control tobacco plant lacking the metabolite signature, crossing the first plant with a second plant of a second tobacco line, and obtaining at least one progeny seed from the crossing, where a progeny plant grown from at least one progeny seed comprises the metabolite signature, and where the progeny plant comprises enhanced NUE as compared to a control plant lacking the metabolite signature.

In one aspect, the present specification provides for, and includes, a method of selecting a tobacco plant comprising obtaining a population of tobacco plants, isolating at least one metabolite associated with enhanced NUE from at least one tobacco plant from the population of tobacco plants, and selecting at least one tobacco plant that comprises a higher amount of at least one metabolite as compared to a control tobacco plant. In a further aspect of this method, a selected tobacco plant comprises an enhanced NUE as compared to a control tobacco plant.

In one aspect, the present specification provides for, and includes, a method of selecting a tobacco plant comprising obtaining a population of tobacco plants, isolating at least one metabolite associated with enhanced NUE from at least one tobacco plant from the population of tobacco plants, and selecting at least one tobacco plant that comprises a lower amount of at least one metabolite as compared to a control tobacco plant.

In one aspect, the present specification provides for, and includes, a method of screening a tobacco plant for a first metabolite signature associated with enhanced NUE comprising isolating a first metabolite signature associated with enhanced NUE from a tobacco plant, determining the amount of at least one metabolite that comprises that first metabolite signature, comparing the first metabolite signature to a second metabolite signature of a control tobacco plant comprising a known NUE, and determining if the first metabolite signature is associated with enhanced NUE.

In one aspect, the present specification provides for, and includes, a modified tobacco seed, or tobacco plant grown therefrom, comprising a cisgenic polynucleotide comprising a heterologous promoter operably linked to a coding region, where the modified tobacco plant comprises enhanced nitrogen utilization efficiency as compared to an unmodified control tobacco plant lacking the cisgenic polynucleotide when grown under the same conditions.

In one aspect, the present specification provides for, and includes, a recombinant DNA construct comprising a heterologous promoter operably linked to a polynucleotide encoding a polypeptide at least 70% identical or similar to a polypeptide selected from the group consisting of SEQ ID NOs:1 to 8.

In one aspect, the present specification provides for, and includes, cured tobacco material, or a tobacco product comprising the cured tobacco material, where the cured tobacco material is made from a tobacco plant comprising a cisgenic polynucleotide comprising a heterologous promoter operably linked to a coding region, where the modified tobacco plant comprises enhanced nitrogen utilization efficiency as compared to an unmodified control tobacco plant lacking the cisgenic polynucleotide when grown under the same conditions.

In one aspect, the present specification provides for, and includes, a greenhouse, growth chamber, or field comprising the modified tobacco seed or plant disclosed herein.

In one aspect, the present specification provides for, and includes, a modified tobacco seed, or tobacco plant grown therefrom, comprising at least one mutation in an endogenous locus encoding a polypeptide selected from the group consisting of SEQ ID NOs:25 to 40, and where a modified tobacco seed or tobacco plant comprises enhanced nitrogen utilization efficiency as compared to an unmodified control tobacco plant lacking at least one mutation when grown under the same conditions.

In one aspect, the present specification provides for, and includes, a recombinant DNA construct comprising a heterologous promoter operably linked to a guide RNA comprising at least 18 contiguous nucleotides identical or complementary to a polynucleotide encoding a polypeptide selected from the group consisting of SEQ ID NOs:25 to 40.

In one aspect, the present specification provides for, and includes, cured tobacco material, or a tobacco product comprising the cured tobacco material, where the cured tobacco material is made from a tobacco plant comprising at least one mutation in an endogenous locus encoding a polypeptide selected from the group consisting of SEQ ID NOs:25 to 40, and where the modified tobacco seed or tobacco plant comprises enhanced NUE as compared to an unmodified control tobacco plant lacking the at least one mutation when grown under the same conditions.

In one aspect, the present specification provides for, and includes, a modified tobacco seed, or tobacco plant grown therefrom, comprising a cisgenic polynucleotide comprising a heterologous promoter operably linked to a polynucleotide encoding a small RNA (sRNA) at least 85% identical or complementary to a polynucleotide selected from the group consisting of SEQ ID NOs:41 to 56, and where the modified tobacco seed or tobacco plant comprises enhanced NUE as compared to an unmodified control tobacco plant lacking the cisgenic polynucleotide when grown under the same conditions.

In one aspect, the present specification provides for, and includes, a recombinant DNA construct comprising a heterologous promoter operably linked to a polynucleotide encoding a small RNA (sRNA) at least 85% identical or complementary to a polynucleotide selected from the group consisting of SEQ ID NOs:41 to 56.

In one aspect, the present specification provides for, and includes, cured tobacco material, or a tobacco product comprising the cured tobacco material, where the cured tobacco material is made from a tobacco plant comprising a cisgenic polynucleotide comprising a heterologous promoter operably linked to a polynucleotide encoding a sRNA at least 85% identical or complementary to a polynucleotide selected from the group consisting of SEQ ID NOs:41 to 56, and where the modified tobacco seed or tobacco plant comprises enhanced NUE as compared to an unmodified control tobacco plant lacking the cisgenic polynucleotide when grown under the same conditions.

In one aspect, the present specification provides for, and includes, a method of enhancing the NUE of a tobacco plant comprising introducing a cisgenic nucleic acid molecule into a tobacco cell, and regenerating a modified tobacco plant from that tobacco cell where the modified tobacco plant comprises enhanced NUE as compared to a tobacco plant lacking the cisgenic nucleic acid molecule.

In one aspect, the present specification provides for, and includes, a method of enhancing the NUE of a tobacco plant comprising introducing a modification to a nucleic acid molecule encoding a gene having a sequence selected from the group consisting of SEQ ID NOs:41 to 56 in a tobacco cell and regenerating a modified tobacco plant from the tobacco cell, where the modified tobacco plant comprises enhanced NUE as compared to a tobacco plant lacking the modification.

In one aspect, the present specification provides for, and includes, a method of enhancing the NUE of a tobacco plant comprising introducing a nucleic acid encoding a small RNA (sRNA) homologous to at least 18 contiguous nucleic acids of a nucleic acid molecule encoding a gene having a sequence selected from the group consisting of SEQ ID NOs:41 to 56 in a tobacco cell, and regenerating a modified tobacco plant from the tobacco cell, where the modified tobacco plant comprises enhanced NUE as compared to a tobacco plant lacking the sRNA.

In one aspect, the present specification provides for, and includes, a method comprising providing a first population of tobacco plants comprising enhanced NUE, genotyping a first population of tobacco plants for the presence of a molecular marker within 20 cM of an enhanced NUE locus; and selecting one or more tobacco plants genotyped and found to comprise the molecular marker.

In one aspect, the present specification provides for, and includes, a method comprising providing a first population of tobacco plants, genotyping the first population of tobacco plants for the presence of an enhanced NUE allele of a locus encoded by a sequence selected from the group consisting of SEQ ID NOs:9 to 16; and selecting one or more genotyped tobacco plants that comprise an enhanced NUE allele.

In one aspect, the present specification provides for, and includes, a method of introgressing an enhanced NUE trait into a tobacco variety comprising crossing a first tobacco variety comprising an enhanced nitrogen utilization efficiency trait with a second tobacco variety lacking the enhanced nitrogen utilization efficiency trait, obtaining progeny seed from the cross, genotyping at least one progeny seed for a molecular marker linked to an enhanced nitrogen utilization efficiency trait, where the molecular marker is within 20 cM of a locus having a sequence selected from the group consisting of SEQ ID NOs:9 to 16; and selecting a progeny seed comprising an enhanced nitrogen utilization efficiency trait.

In one aspect, the present specification provides for, and includes, a method of selecting a tobacco plant with an enhanced NUE trait comprising isolating nucleic acids from a collection of tobacco germplasm, assaying the isolated nucleic acids for one or more markers located within 20 cM of a locus selected from the group consisting of SEQ ID NOs:9 to 16, and selecting a tobacco plant comprising an enhanced NUE trait.

In one aspect, the present specification provides for, and includes, a method of selecting a tobacco plant with an enhanced NUE trait comprising isolating nucleic acids from a collection of tobacco germplasm, assaying the isolated nucleic acids for one or more markers located within 20 cM of a marker selected from the group consisting of SEQ ID NOs:57 to 64, and selecting a tobacco plant comprising an enhanced NUE trait.

BRIEF DESCRIPTION OF THE SEQUENCES

SEQ ID NOs: 1 to 8 are amino acid sequences of genes positively correlated with enhanced NUE in root tissue, leaf tissue, or both.

SEQ ID NOs: 9 to 16 are nucleotide sequences of genes positively correlated with enhanced NUE in root tissue, leaf tissue, or both.

SEQ ID NOs: 17 to 19 are nucleotide sequences of promoter regions for genes with leaf-preferred expression.

SEQ ID NOs: 20 to 24 are nucleotide sequences of promoter regions for genes with root-preferred expression.

SEQ ID NOs: 25 to 40 are amino acid sequences of genes negatively correlated with enhanced NUE in root tissue, leaf tissue, or both.

SEQ ID NOs: 41 to 56 are nucleotide sequences of genes negatively correlated with enhanced NUE in root tissue, leaf tissue, or both.

SEQ ID NOs:57 to 64 are nucleotide sequences of SNP markers comprising polymorphisms associated with enhanced NUE.

SEQ ID NO: 65 is the backbone sequence for expression vector p45-2-7.

DETAILED DESCRIPTION

Figure 1:
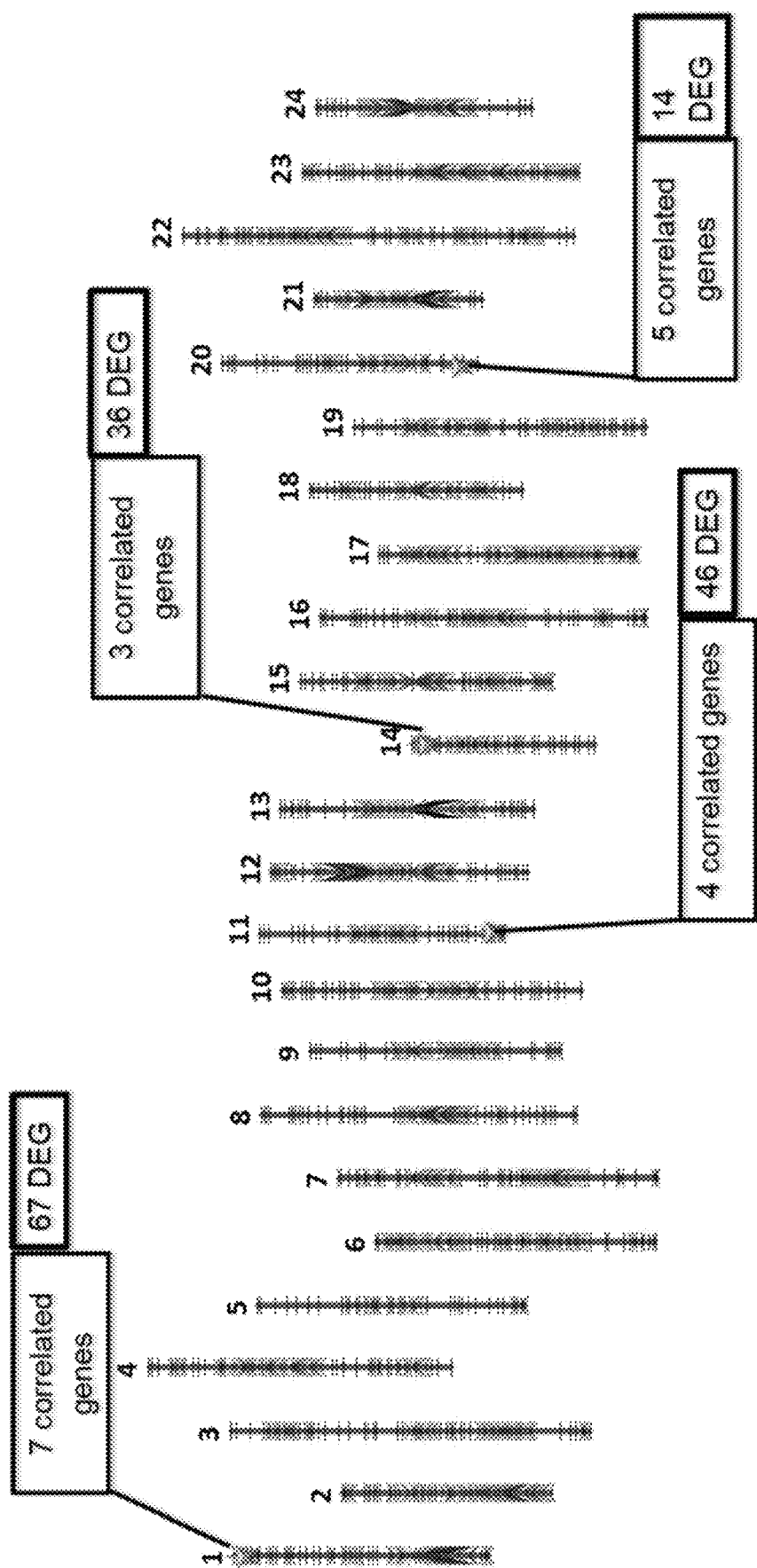
FIG. 1 depicts four gene clusters associated with NUE in the tobacco genome. Genes differentially expressed between low and normal nitrogen conditions in plants with an NUE metabolite fingerprint are indicated (correlated genes). The total number of differentially expressed genes (DEG), regardless of NUE metabolic fingerprinting, is also indicated.

Unless defined otherwise, technical and scientific terms used herein have the same meaning as commonly understood by one of ordinary skill in the art. One skilled in the art will recognize many methods can be used in the practice of the present disclosure. Indeed, the present disclosure is in no way limited to the methods and materials described. For purposes of the present disclosure, the following terms are defined below.

Unless defined otherwise, all technical and scientific terms used have the same meaning as commonly understood by one of ordinary skill in the art to which this disclosure belongs. Where a term is provided in the singular, the inventors also contemplate aspects of the disclosure described by the plural of that term. Where there are discrepancies in terms and definitions used in references that are incorporated by reference, the terms used in this application shall have the definitions given herein. Other technical terms used have their ordinary meaning in the art in which they are used, as exemplified by various art-specific dictionaries, for example, "The American Heritage® Science Dictionary" (Editors of the American Heritage Dictionaries, 2011, Houghton Mifflin Harcourt, Boston and New York), the "McGraw-Hill Dictionary of Scientific and Technical Terms" (6th edition, 2002, McGraw-Hill, New York), or the "Oxford Dictionary of Biology" (6th edition, 2008, Oxford University Press, Oxford and New York). The inventors do not intend to be limited to a mechanism or mode of action. Reference thereto is provided for illustrative purposes only.

The practice of this disclosure includes, unless otherwise indicated, conventional techniques of biochemistry, chemistry, molecular biology, microbiology, cell biology, genomics, biotechnology, metabolomics, plant breeding, and genetics, which are within the skill of the art. See, for example, Green and Sambrook, Molecular Cloning: A Laboratory Manual, 4th edition (2012); Current Protocols In Molecular Biology (F. M. Ausubel, et al. eds., (1987)); Plant Breeding Methodology (N. F. Jensen, Wiley-Interscience (1988)); the series Methods In Enzymology (Academic Press, Inc.): PCR 2: A Practical Approach (M. J. MacPherson, B. D. Hames and G. R. Taylor eds. (1995)); Harlow and Lane, eds. (1988) Antibodies, A Laboratory Manual; Animal Cell Culture (R. I. Freshney, ed. (1987)); Recombinant Protein Purification: Principles And Methods, 18-1142-75, GE Healthcare Life Sciences; C. N. Stewart, A. Touraev, V. Citovsky, T. Tzfira eds. (2011) Plant Transformation Technologies (Wiley-Blackwell); and R. H. Smith (2013) Plant Tissue Culture: Techniques and Experiments (Academic Press, Inc.).

Any references cited herein, including, e.g., all patents, published patent applications, and non-patent publications, are incorporated by reference in their entirety.

As used herein, the singular form "a," "an," and "the" include plural references unless the context clearly dictates otherwise. For example, the term "a compound" or "at least one compound" may include a plurality of compounds, including mixtures thereof.

As used herein, the term "sequence identity" or "identity" in the context of two polynucleotide or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." An alignment of two or more sequences may be performed using any suitable computer program. For example, a widely used and accepted computer program for performing sequence alignments is CLUSTALW v1.6 (Thompson, et al. (1994) Nucl. Acids Res., 22: 4673-4680).

As used herein, the term "complementary" in reference to a nucleic acid molecule refers to pairing of nucleotide bases such that adenine is complementary to thymine or uracil, and guanine is complementary to cytosine. Two complementary nucleic acid molecules are capable of hybridizing with each other. As an example, the two strands of double stranded DNA are complementary to each other.

A specific polynucleotide of at least three nucleotides in length may be referred to as an "oligonucleotide". Nucleic acid molecules provided herein include deoxyribonucleic acids (DNA) and ribonucleic acids (RNA) and functional analogues thereof, such as complementary DNA (cDNA). Nucleic acid molecules provided herein can be single stranded or double stranded. Nucleic acid molecules comprise the nucleotide bases adenine (A), guanine (G), thymine (T), cytosine (C). Uracil (U) replaces thymine in RNA molecules. The symbol "R" can be used to represent a purine (e.g., A or G) nucleotide base. The symbol "Y" can be used to represent a pyrimidine (e.g., a C or T) nucleotide base. The symbol "W" can be used to represent an A or a T nucleotide base. The symbol S can be used to represent a G or a C nucleotide base. The symbol "M" can be used to represent an A or a C nucleotide base. The symbol The symbol "K" can be used to represent a G or a T nucleotide base. The symbol "B" can be used to represent a G, C, or T nucleotide base. The symbol "H" can be used to represent an A, C, or T nucleotide base. The symbol "D" can be used to represent an A, G, or T nucleotide base. The symbol "V" can be used to represent an A, G, or C nucleotide base. The symbol "N" can be used to represent any nucleotide base (e.g., A, G, C, T, or U).

The use of the term "polynucleotide" is not intended to limit the present disclosure to polynucleotides comprising DNA. Those of ordinary skill in the art will recognize that polynucleotides and nucleic acid molecules can comprise ribonucleotides and combinations of ribonucleotides and deoxyribonucleotides. Such deoxyribonucleotides and ribonucleotides include both naturally occurring molecules and synthetic analogues. The polynucleotides of the present disclosure also encompass all forms of sequences including, but not limited to, single-stranded forms, double-stranded forms, hairpins, stem-and-loop structures, and the like.

As used herein, the term "polypeptide" refers to a chain of at least two covalently linked amino acids. Polypeptides can be encoded by polynucleotides provided herein.

Nucleic acid molecules, polypeptides, or proteins provided herein can be isolated or substantially purified. An "isolated" or "purified" nucleic acid molecule, polypeptide, protein, or biologically active portion thereof, is substantially or essentially free from components that normally accompany or interact with the polynucleotide or protein as found in its naturally occurring environment. For example, an isolated or purified polynucleotide or protein is substantially free of other cellular material, or culture medium when produced by recombinant techniques, or substantially free of chemical precursors or other chemicals when chemically synthesized. In one aspect, an isolated polynucleotide provided herein can contain less than 10000 nucleotides, less than 5000 nucleotides, less than 4000 nucleotides, less than 3000 nucleotides, less than 2000 nucleotides, less than 1000 nucleotides, less than 500 nucleotides, or less than 100 nucleotides of nucleic acid sequence that naturally flank the polynucleotide in genomic DNA of the cell from which the polynucleotide is derived. In one aspect, an isolated polynucleotide provided herein can contain 100 to 10000 nucleotides, 500 to 10000 nucleotides, 1000 to 10000 nucleotides, 2000 to 10000 nucleotides, 3000 to 10000 nucleotides, 4000 to 10000 nucleotides, 1 to 500 nucleotides, 1 to 1000 nucleotides, 1 to 2000 nucleotides, 1 to 3000 nucleotides, 1 to 4000 nucleotides, 1 to 5000 nucleotides, 1 to 10000 nucleotides, 100 to 500 nucleotides, 100 to 1000 nucleotides, 100 to 2000 nucleotides, 100 to 3000 nucleotides, or 100 to 4000 nucleotides of nucleic acid sequence that naturally flank the polynucleotide in genomic DNA of the cell from which the polynucleotide is derived. In another aspect, an isolated polypeptide provided herein is substantially free of cellular material in preparations having less than 30%, less than 20%, less than 10%, less than 5%, or less than 1% (by dry weight) of chemical precursors or non-protein-of-interest chemicals. Fragments of the disclosed polynucleotides and polypeptides encoded thereby are also encompassed by the present invention. Fragments of a polynucleotide may encode polypeptide fragments that retain the biological activity of the native polypeptide. Alternatively, fragments of a polynucleotide that are useful as hybridization probes or PCR primers using methods known in the art generally do not encode fragment polypeptides retaining biological activity. Fragments of a polynucleotide provided herein can range from at least 20 nucleotides, at least 50 nucleotides, at least 70 nucleotides, at least 100 nucleotides, at least 150 nucleotides, at least 200 nucleotides, at least 250 nucleotides, at least 300 nucleotides, and up to the full-length polynucleotide encoding the polypeptides of the invention, depending on the desired outcome.

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides. Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

In one aspect, this disclosure provides methods of detecting recombinant nucleic acids and polypeptides in plant cells. Without being limiting, nucleic acids also can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, NY).

Polypeptides can be detected using antibodies. Techniques for detecting polypeptides using antibodies include enzyme linked immunosorbent assays (ELISAs), Western blots, immunoprecipitations and immunofluorescence. An antibody provided herein can be a polyclonal antibody or a monoclonal antibody. An antibody having specific binding affinity for a polypeptide provided herein can be generated using methods well known in the art. An antibody provided herein can be attached to a solid support such as a microtiter plate using methods known in the art.

Detection (e.g., of an amplification product, of a hybridization complex, of a polypeptide) can be accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

As used herein, the phrase "associated with" or "linked to" refers to a recognizable and/or assayable relationship between two entities. For example, the phrase "associated with enhanced NUE" refers to a trait, locus, gene, allele, marker, phenotype, etc., or the expression thereof, the presence or absence of which can influence an extent, degree, and/or rate at which a plant or a part of interest thereof that has an enhanced NUE trait. As such, a marker is "associated with" a trait when it is linked to it and when the presence of the marker is an indicator of whether and/or to what extent the desired trait or trait form will occur in a plant/germplasm comprising the marker. Similarly, a marker is "associated with" an allele when it is linked to it and when the presence of the marker is an indicator of whether the allele is present in a plant/germplasm comprising the marker. For example, "a marker associated with enhanced NUE allele" refers to a marker whose presence or absence can be used to predict whether and to what extent a plant will display enhanced NUE phenotype.

As used herein, a "centimorgan" (cM) is a unit of measure of recombination frequency and genetic distance between two loci. One cM is equal to a 1% chance that a marker at one genetic locus will be separated from a marker at a second locus due to crossing over in a single generation.

As used herein, "closely linked" means that the marker or locus is within about 20 cM, 15 cM, 10 cM, 5 cM, 4 cM, 3 cM, 2 cM, 1 cM, 0.5 cM, or less than 0.5 cM of another marker or locus. For example, 20 cM means that recombination occurs between the marker and the locus with a frequency of equal to or less than about 20%.

As used herein, "plant" refers to a whole plant. A cell or tissue culture derived from a plant can comprise any plant components or plant organs (e.g., leaves, stems, roots, etc.), plant tissues, seeds, plant cells, and/or progeny of the same. A progeny plant can be from any filial generation, e.g., $F_1$, $F_2$, $F_3$, $F_4$, $F_5$, $F_6$, $F_7$, etc. A plant cell is a biological cell of a plant, taken from a plant or derived through culture from a cell taken from a plant.

As used herein, a tobacco plant can be from any plant from the *Nicotiana tabacum* genus including, but not limited to *Nicotiana tabacum tabacum*; *Nicotiana tabacum amplexicaulis* PI 271989; *Nicotiana tabacum benthamiana* PI 555478; *Nicotiana tabacum bigelovii* PI 555485; *Nicotiana tabacum debneyi*; *Nicotiana tabacum excelsior* PI 224063; *Nicotiana tabacum glutinosa* PI 555507; *Nicotiana tabacum goodspeedii* PI 241012; *Nicotiana tabacum gossei* PI 230953; *Nicotiana tabacum hesperis* PI 271991; *Nicotiana tabacum knightiana* PI 555527; *Nicotiana tabacum maritima* PI 555535; *Nicotiana tabacum megalosiphon* PI 555536; *Nicotiana tabacum nudicaulis* PI 555540; *Nicotiana tabacum paniculata* PI 555545; *Nicotiana tabacum plumbaginfolia* PI 555548; *Nicotiana tabacum repanda* PI 555552; *Nicotiana tabacum rustica*; *Nicotiana tabacum suaveolens* PI 230960; *Nicotiana tabacum sylvestris* PI 555569; *Nicotiana tabacum tomentosa* PI 266379; *Nicotiana tabacum tomentosiformis*; and *Nicotiana tabacum trigonophylla* PI 555572.

In one aspect, a plant component provided herein includes, but is not limited to, a leaf, a stem, a root, a seed, a flower, pollen, an anther, an ovule, a pedicel, a fruit, a meristem, a cotyledon, a hypocotyl, a pod, an embryo, endosperm, an explant, a callus, a tissue culture, a shoot, a cell, and a protoplast. In further aspects, this disclosure provides tobacco plant cells, tissues, and organs that are not reproductive material and do not mediate the natural reproduction of the plant. In another aspect, this disclosure also provides tobacco plant cells, tissues, and organs that are reproductive material and mediate the natural reproduction of the plant. In another aspect, this disclosure provides tobacco plant cells, tissues, and organs that cannot maintain themselves via photosynthesis. In another aspect, this disclosure provides somatic tobacco plant cells. Somatic cells, contrary to germline cells, do not mediate plant reproduction.

Provided cells, tissues and organs can be from seed, fruit, leaf, cotyledon, hypocotyl, meristem, embryos, endosperm, root, shoot, stem, pod, flower, inflorescence, stalk, pedicel, style, stigma, receptacle, petal, sepal, pollen, anther, filament, ovary, ovule, pericarp, phloem, and vascular tissue. In another aspect, this disclosure provides a tobacco plant chloroplast. In a further aspect, this disclosure provides an epidermal cell, a stomata cell, a leaf hair (trichome), a root hair, or a storage root. In another aspect, this disclosure provides a tobacco protoplast.

Skilled artisans understand that tobacco plants naturally reproduce via seeds, not via asexual reproduction or vegetative propagation. In one aspect, this disclosure provides tobacco endosperm. In another aspect, this disclosure provides a tobacco endosperm cell. In a further aspect, this disclosure provides a male or female sterile tobacco plant, which cannot reproduce without human intervention.

In one aspect, this disclosure provides methods and compositions related to modified tobacco plants, seeds, plant components, plant cells, and products made from modified tobacco plants, seeds, plant parts, and plant cells. In one aspect, a modified seed provided herein gives rise to a modified plant provided herein. In one aspect, a modified plant, seed, plant component, plant cell, or plant genome provided herein comprises a recombinant DNA construct provided herein. In another aspect, cured tobacco material or tobacco products provided herein comprise modified tobacco plants, plant components, plant cells, or plant genomes provided herein.

As used herein, "modified" refers to plants, seeds, plant components, plant cells, and plant genomes that have been subjected to mutagenesis, genome editing, genetic transformation, or a combination thereof.

As used herein, "cisgenesis" or "cisgenic" refers to genetic modification of a plant, plant cell, or plant genome in which all components (e.g., promoter, donor nucleic acid, selection gene) have only plant origins (e.g., no non-plant origin components are used). In one aspect, a modified plant, plant cell, or plant genome provided herein is cisgenic. Cisgenic plants, plant cells, and plant genomes provided herein can lead to ready-to-use tobacco lines. In another aspect, a modified tobacco plant provided herein comprises no non-tobacco genetic material or sequences.

As used herein, a "functional fragment" or "functional fragment thereof" refers to a nucleotide or amino acid sequence of any size that retains the function of the full length sequence to which it refers. In an aspect, a functional fragment can be at least 5, at least 10, at least 25, at least 50, at least 75, at least 100, at least 150, at least 200, at least 250, at least 300, at least 400, at least 500, at least 600, at least 700, at least 800, at least 900, at least 1000, at least 2000, at least 3000, at least 4000, at least 5000, or more than 5000 nucleotides in length. In an aspect, a functional fragment can be at least 5, at least 10, at least 25, at least 50, at least 75, at least 100, at least 150, at least 200, at least 250, at least 300, at least 400, at least 500, at least 600, at least 700, at least 800, at least 900, at least 1000, at least 2000, or more than 2000 amino acids in length. In an aspect, a functional fragment can be between 5 and 5000 nucleotides, between 10 and 4000 nucleotides, between 25 and 3000 nucleotides, between 50 and 2000 nucleotides, between 75 and 1000 nucleotides, between 100 and 900 nucleotides, between 150 and 800 nucleotides, between 200 and 700 nucleotides, between 250 and 600 nucleotides, or between 300 and 500 nucleotides in length. In an aspect, a functional fragment can be between 5 and 2000 amino acids, between 10 and 1000 amino acids, between 25 and 900 amino acids, between 50 and 800 amino acids, between 50 and 800 amino acids, between 75 and 700 amino acids, between 100 and 600 amino acids, between 150 and 500 amino acids, between 200 and 400 amino acids, or between 250 and 300 amino acids in length. In a further aspect, the polynucleotides described herein are envisioned in their entirety and as any functional fragments thereof. In a further aspect, the polypeptides described herein are envisioned in their entirety and as any functional fragments thereof. In a further aspect, the polynucleotides having the sequence of SEQ ID NOs: 9 to 24 and 41 to 56 are envisioned in their entirety and as any functional fragments thereof. In a further aspect, the polypeptides having the sequence of SEQ ID NOs: 1 to 8 and 25 to 40 are envisioned in their entirety and as any functional fragments thereof.

As used herein, the term "nitrogen utilization efficiency" (NUE) refers to the ability of a plant to absorb, assimilate and/or use nitrogen (e.g., from soil, water and/or nitrogen fertilizer). NUE genes affect yield and have utility for improving the use of nitrogen in crop plants. Enhanced nitrogen utilization efficiency can result from improved uptake and assimilation of nitrogen fertilizer and/or the subsequent remobilization and reutilization of accumulated nitrogen reserves, as well as increased tolerance of plants to stress situations such as low nitrogen environments. NUE genes can be used to alter the genetic composition of a plant, rendering it more productive with current fertilizer application standards or maintaining its productive rates with significantly reduced fertilizer or reduced nitrogen availability.

NUE has been defined in various ways, but yield per unit of nitrogen available in the soil integrates all key parameters for evaluating fitness of crop cultivars and it is a common measure of NUE. See, for example, Ladha et al. 2005. Advances in Agronomy, 87:85-156, which is incorporated herein in its entirety. This indicator is sometimes referred to as "agricultural NUE." As another measure of NUE, the ratio of the plant product (e.g., tobacco leaf tissue) to above-ground nitrogen in the plant can be determined (sometimes referred to as "physiological NUE"). Enhanced NUE is related to three key components: 1) yield is not significantly different when grown on 25% normal nitrogen content compared to a plant grown at 100% normal nitrogen content); 2) the rate of chlorophyll loss is reduced compared to plants without enhanced NUE; and 3) cured leaf quality is not significantly different when grown on 25% normal nitrogen content compared to a plant grown at 100% normal nitrogen content. In a preferred aspect, a plant with enhanced NUE is capable of generating similar yields and leaf quality when grown under 25% of the Burley fertilization rate as compared to a Burley plant grown under 100% of the normal Burley fertilization rate.

At least five approaches and indices of NUE are used in the art and are discussed below.

(1) Partial factor productivity (PFP) from applied nitrogen (N) is a measure of how much yield is produced for each unit of nitrogen applied:

$PFP_N$=kilograms of yield/kilograms of N applied $PFP_N = Y_{+N}/FN$

Where $Y_{+N}$ is the yield (kilograms/hectare; kg/ha) and FN is the amount of fertilizer applied (kg/ha).

(2) Agronomic efficiency (AE) of applied nitrogen (N) is a measure of how much additional yield is produced for each unit of nitrogen applied:

$AE_N$=kilograms of yield increase/kilograms of N applied $AE_N = (Y_{+N} - Y_{0N})/FN$ Where $Y_{+N}$ is the yield in a treatment with N application (kg/ha); $Y_{0N}$ is the yield in a control treatment without N application (kg/ha); and FN is the amount of N fertilizer applied (kg/ha).

(3) Recovery efficiency (RE) of applied nitrogen (N) is a measure of how much of the nitrogen that was applied was recovered and taken up by the crop.

$RE_N$=kilograms of N taken up/kilograms of N applied $RE_N = (UN_{+N} - UN_{0N})/FN$ Where $UN_{+N}$ is the total plant N uptake measured in aboveground biomass at physiological maturity (kg/ha) in plots that received applied N at the rate of FN (kg/ha); and $UN_{0N}$ is the total N uptake of a control plot without the addition of N.

(4) Physiological efficiency (PE) of applied nitrogen (N) is a measure of how much additional yield is produced for each additional unit of nitrogen uptake.

$PE_N$=kilograms of yield increase/kilograms of fertilizer N taken up $PE_N = (Y_{+N} - Y_{0N})/(UN_{+N} - UN_{0N})$ Where $Y_{+N}$ is the yield (kg/ha) in a treatment with N application; $Y_{0N}$ is the yield (kg/ha) in a control treatment without N application; $UN_{+N}$ is the total N uptake (kg/ha) in the treatment that receives fertilizer N application; and $UN_{0N}$ is the total N uptake (kg/ha) in the treatment without fertilizer N application.

(5) Internal efficiency (IE) of nitrogen (N) addresses how much yield is produced per unit N taken up from both fertilizer and indigenous (e.g., soil) nutrient sources:

IEN=kilograms of yield/kilograms of N taken up

IEN=Y/UN

Where Y is the yield (kg/ha); and UN is the total N uptake (kg/ha).

Nitrogen can be in any form, including organic and/or inorganic forms. Without being limiting, forms of nitrogen include nitrate (e.g, ammonium nitrate, calcium nitrate, potassium nitrate), nitrite, ammonia, aqua ammonia, anhydrous ammonia, ammonium sulfate, diammonium phosphate, a low-pressure nitrogen solution, a pressureless nitrogen solution, urea, and urea-ammonium nitrate (UAN). In an aspect, nitrogen is in a form that is immediately available to a plant (e.g., ammonia and/or nitrate) and/or can be readily converted to a form that is available to a plant (e.g., urea).

In an aspect, a modified tobacco plant comprising enhanced NUE provided herein comprises increased nitrogen uptake as compared to a control tobacco plant. In another aspect, a modified tobacco plant comprising enhanced NUE provided herein comprises increased nitrogen assimilation as compared to a control tobacco plant. In a further aspect, a modified tobacco plant comprising enhanced NUE provided herein comprises increased yield as compared to a control tobacco plant. In still another aspect, a modified tobacco plant comprising enhanced NUE provided herein comprises increased yield under low nitrogen conditions as compared to a control tobacco plant. In a preferred aspect, low nitrogen conditions as used in the field are approximately 25% nitrogen compared to levels typically used by those skilled in the art. In another aspect, low nitrogen conditions as used in the field can be between approximately 5% and 50% nitrogen compared to levels typically used by those skilled in the art. In a greenhouse setting, low nitrogen conditions are approximately 25 parts per million (ppm) and normal nitrogen conditions are approximately 100 ppm. In another aspect, low nitrogen conditions as used in a greenhouse can be between 5 ppm and 50 ppm.

In an aspect, a modified tobacco plant comprising enhanced NUE provided herein comprises a yield increase of at least 5%, at least 10%, at least 20%, at least 30%, at least 40%, at least 50%, at least 60%, at least 70%, at least 80%, at least 90%, at least 100%, at least 110%, at least 120%, at least 130%, at least 140%, at least 150%, at least 200%, at least 300%, at least 400%, or at least 500% as compared to a control tobacco plant grown under similar growth conditions. In an aspect, a modified tobacco plant comprising enhanced NUE provided herein comprises a yield increase of between 5% and 100%, between 10% and 100%, between 20% and 100%, between 30% and 100%, between 40% and 100%, between 50% and 100%, between 60% and 100%, between 70% and 100%, between 80% and 100%, between 90% and 100%, between 10% and 200%, between 10% and 300%, between 10% and 400%, between 10% and 500%, or between 5% and 500% as compared to a control tobacco plant grown under similar growth conditions.

In an aspect, a population of modified tobacco plants comprising enhanced NUE provided herein comprises a yield increase of at least 0.25 kg/ha, at least 0.5 kg/ha, at least 0.75 kg/ha, at least 1 kg/ha, at least 2 kg/ha, at least 3 kg/ha, at least 4 kg/ha, at least 5 kg/ha, at least 6 kg/ha, at least 7 kg/ha, at least 8 kg/ha, at least 9 kg/ha, at least 10 kg/ha, at least 15 kg/ha, at least 20 kg/ha, at least 25 kg/ha, at least 30 kg/ha, at least 35 kg/ha, at least 40 kg/ha, at least 45 kg/ha, at least 50 kg/ha, at least 75 kg/ha, at least 100 kg/ha, at least 200 kg/ha, at least 300 kg/ha, at least 400 kg/ha, or at least 500 kg/ha as compared to a population of control tobacco plants grown under similar growth conditions. In another aspect, a population of modified tobacco plant comprising enhanced NUE provided herein comprises a yield increase of between 0.25 kg/ha and 100 kg/ha, between 0.5 kg/ha and 100 kg/ha, between 0.75 kg/ha and 100 kg/ha, between 1 kg/ha and 100 kg/ha, between 2 kg/ha and 100 kg/ha, between 3 kg/ha and 100 kg/ha, between 4 kg/ha and 100 kg/ha, between 5 kg/ha and 100 kg/ha, between 6 kg/ha and 100 kg/ha, between 7 kg/ha and 100 kg/ha, between 8 kg/ha and 100 kg/ha, between 9 kg/ha and 100 kg/ha, between 10 kg/ha and 100 kg/ha, between 15 kg/ha and 100 kg/ha, between 20 kg/ha and 100 kg/ha, between 30 kg/ha and 100 kg/ha, between 40 kg/ha and 100 kg/ha, between 50 kg/ha and 100 kg/ha, between 75 kg/ha and 100 kg/ha, between 100 kg/ha and 500 kg/ha, between 100 kg/ha and 400 kg/ha, between 100 and 300 kg/ha, or between 100 kg/ha and 200 kg/ha as compared to a population of control tobacco plants when grown under similar growth conditions. As used herein, a "population" of tobacco plants can be of any size for example, 5, 10, 15, 20, 25, 30, 35, 40, 50, 100, 500, 1000, 5000, 10000, 25000, 50000, 100000, 500000, or more. A population can be from a single variety, cultivar, or line. A population can be created using any breeding techniques known in the art.

In an aspect, a modified tobacco plant comprising enhanced NUE provided herein comprises at least 1, at least 2, at least 3, at least 4, at least 5, at least 6, at least 7, at least 8, at least 9, at least 10, at least 11, at least 12, at least 13, at least 14, at least 15, at least 20, or at least 25 more leaves as compared to a control tobacco plant grown under similar growth conditions. In another aspect, a modified tobacco plant comprising enhanced NUE provided herein comprises between 1 and 25, between 2 and 25, between 3 and 25, between 4 and 25, between 5 and 25, between 6 and 25, between 7 and 25, between 8 and 25, between 9 and 25, between 10 and 25, between 11 and 25, between 12 and 25, between 13 and 25, between 14 and 25, between 15 and 25, or between 20 and 25 more leaves as compared to a control tobacco plant grown under similar growth conditions.

As used herein, "comparable conditions" "similar conditions" or "similar growth conditions" refers to similar environmental conditions, agronomic practices, and/or curing process for growing or curing tobacco and making meaningful comparisons between two or more plant genotypes so that neither environmental conditions nor agronomic practices (including curing process) would contribute to, or explain, any differences observed between the two or more plant genotypes. Environmental conditions include, for example, light, temperature, water, humidity, and nutrition (e.g., nitrogen and phosphorus). Agronomic practices include, for example, seeding, clipping, undercutting, transplanting, topping, suckering, and curing. See Chapters 4B and 4C of Tobacco, Production, Chemistry and Technology, Davis & Nielsen, eds., Blackwell Publishing, Oxford (1999), pp. 70-103.

In one aspect, a modified plant, seed, plant part, or plant cell provided herein comprises one or more non-naturally occurring mutations. In one aspect, a mutation provided herein improves nitrogen utilization efficiency in a plant. Types of mutations provided herein include, for example, substitutions (point mutations), deletions, insertions, duplications, and inversions. Such mutations are desirably present in the coding region of a gene; however, mutations in a promoter or other regulatory region, an intron, an intron-exon boundary, or an untranslated region of a gene may also be desirable.

In one aspect, methods provided herein are capable of producing a tobacco plant with enhanced nitrogen utilization efficiency as compared to a control tobacco plant. Mutagenesis methods include, without limitation, chemical mutagenesis, for example, treatment of seeds with ethyl methylsulfate (EMS) (Hildering and Verkerk, In, The use of induced mutations in plant breeding. Pergamon Press, pp. 317-320, 1965); or UV-irradiation, X-rays, electron beams, ion beams (e.g., carbon ion beam, helium ion beam, neon ion beam), and fast neutron irradiation (see, for example, Verkerk, *Neth. J. Agric. Sci.* 19:197-203, 1971; Poehlman, Breeding Field Crops, Van Nostrand Reinhold, New York (3.sup.rd ed.), 1987; and Tanaka, *J. Radiat. Res.* 51:223-233, 2010); transposon tagging (Fedoroff et al., 1984; U.S. Pat. Nos. 4,732,856 and 5,013,658); and T-DNA insertion methodologies (Hoekema et al., 1983; U.S. Pat. No. 5,149,645). EMS-induced mutagenesis consists of chemically inducing random point mutations over the length of a genome. Fast neutron mutagenesis consists of exposing seeds to neutron bombardment which causes large deletions through double stranded DNA breakage. Transposon tagging comprises inserting a transposon within an endogenous gene to reduce or eliminate expression of the gene.

In addition, a fast and automatable method for screening for chemically induced mutations, TILLING (Targeting Induced Local Lesions In Genomes), using denaturing high performance liquid chromatography (HPLC) or selective endonuclease digestion of selected PCR products is also applicable to the present disclosure. See, McCallum et al. (2000) Nat. Biotechnol. 18:455-457. Mutations that impact gene expression or that interfere with the function of genes provided herein can be determined using methods that are well known in the art. Insertional mutations in gene exons usually result in null-mutants. Mutations in conserved residues can be particularly effective in inhibiting the function of a protein.

The screening and selection of mutagenized tobacco plants can be through any methodologies known to those having ordinary skill in the art. Examples of screening and selection methodologies include, but are not limited to, Southern blots, PCR amplification for detection of a polynucleotide, Northern blots, RNase protection, primer-extension, RT-PCR amplification for detecting RNA transcripts, Sanger sequencing, Next Generation sequencing technologies (e.g., Illumina, PacBio, Ion Torrent, 454), enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known in the art.

In one aspect, a plant genome provided herein is mutated (edited) by a nuclease selected from the group consisting of a meganuclease, a zinc-finger nuclease (ZFN), a transcription activator-like effector nuclease (TALEN), a CRISPR/Cas9 nuclease, a CRISPR/Cpf1, or a CRISPR/Cmx1 nuclease. In another aspect, a plant genome provided herein is mutated by a CRISPR/CasX or a CRISPR/CasY nuclease. As used herein, "editing" or "genome editing" refers to targeted mutagenesis of at least 1, at least 2, at least 3, at least 4, at least 5, at least 6, at least 7, at least 8, at least 9, or at least 10 nucleotides of an endogenous plant genome nucleic acid sequence, or removal or replacement of an endogenous plant genome nucleic acid sequence.

Also provided herein are the transformation of tobacco plants with recombinant constructs or expression cassettes described herein using any suitable transformation methods known in the art. Methods for introducing polynucleotide sequences into tobacco plants are known in the art and include, but are not limited to, stable transformation methods, transient transformation methods, and virus-mediated methods. "Stable transformation" refers to transformation where the nucleotide construct of interest introduced into a plant integrates into a genome of a plant cell and is capable of being inherited by the progeny thereof. "Transient transformation" is intended to mean that a sequence is introduced into a plant or plant cell and is only temporally expressed or is only transiently present in the plant or plant cell.

In one aspect, methods and compositions provided herein comprise the introduction of one or more polynucleotides into one or more plant cells. In one aspect, a plant genome provided herein is modified to include an introduced polynucleotide or recombinant DNA construct. As used herein, "plant genome" refers to a nuclear genome, a mitochondrial genome, or a plastid (e.g., chloroplast) genome of a plant cell. In another aspect, a polynucleotide provided herein is integrated into an artificial chromosome. In one aspect, an artificial chromosome comprising a polynucleotide provided herein is integrated into a plant cell.

In one aspect, a modified plant, seed, plant component, plant cell, or plant genome provided herein comprises one or more transgenes. In one aspect, a transgene provided herein improves nitrogen utilization efficiency in a tobacco plant. As used herein, a "transgene" refers to a polynucleotide that has been transferred into a genome by any method known in the art. In one aspect, a transgene is an exogenous polynucleotide. In one aspect, a transgene is an endogenous polynucleotide that is integrated into a new genomic locus where it is not normally found. Therefore, a transgene can also be a cisgene under appropriate circumstances.

In one aspect, transgenes provided herein comprise a recombinant DNA construct. In one aspect, recombinant DNA constructs or expression cassettes provided herein can comprise a selectable marker gene for the selection of transgenic cells. Selectable marker genes include, but are not limited to, genes encoding antibiotic resistance, such as those encoding neomycin phosphotransferase II (NPTII) and hygromycin phosphotransferase (HPT), as well as genes conferring resistance to herbicidal compounds, such as glufosinate ammonium, bromoxynil, imidazolinones, triazolopyrimidines, sulfonylurea (e.g., chlorsulfuron and sulfometuron methyl), and 2,4-dichlorophenoxyacetate (2,4-D). Additional selectable markers include phenotypic markers such as β-galactosidase and fluorescent proteins such as green fluorescent protein (GFP).

In one aspect, methods and compositions provided herein comprise a vector. As used herein, the terms "vector" or "plasmid" are used interchangeably and refer to a circular, double-stranded DNA molecule that is physically separate from chromosomal DNA. In one aspect, a plasmid or vector used herein is capable of replication in vivo. A "transformation vector," as used herein, is a plasmid that is capable of transforming a plant cell. In an aspect, a plasmid provided herein is a bacterial plasmid. In another aspect, a plasmid provided herein is an *Agrobacterium* Ti plasmid or derived from an *Agrobacterium* Ti plasmid. In still another aspect, a vector provided herein is a viral vector.

In one aspect, a plasmid or vector provided herein is a recombinant vector. As used herein, the term "recombinant vector" refers to a vector formed by laboratory methods of genetic recombination, such as molecular cloning. In another aspect, a plasmid provided herein is a synthetic plasmid. As used herein, a "synthetic plasmid" is an artificially created plasmid that is capable of the same functions (e.g., replication) as a natural plasmid (e.g., Ti plasmid). Without being limited, one skilled in the art can create a synthetic plasmid de novo via synthesizing a plasmid by individual nucleotides, or by splicing together nucleic acid molecules from different pre-existing plasmids.

Vectors are commercially available or can be produced by recombinant DNA techniques routine in the art. In one aspect, a vector provided herein comprises all or part of SEQ ID NO: 65. A vector containing a nucleic acid can have expression elements operably linked to such a nucleic acid, and further can include sequences such as those encoding a selectable marker (e.g., an antibiotic resistance gene). A vector containing a nucleic acid can encode a chimeric or fusion polypeptide (i.e., a polypeptide operatively linked to a heterologous polypeptide, which can be at either the N-terminus or C-terminus of the polypeptide). Representative heterologous polypeptides are those that can be used in purification of the encoded polypeptide (e.g., 6×His tag, glutathione S-transferase (GST)).

Suitable methods of introducing polynucleotides (e.g., transgenes, recombinant vectors, recombinant DNA constructs, expression constructs) into plant cells of the present disclosure include microinjection (Crossway et al. (1986) *Biotechniques* 4:320-334), electroporation (Shillito et al. (1987) *Meth. Enzymol.* 153:313-336; Riggs et al. (1986) *Proc. Natl. Acad. Sci. USA* 83:5602-5606), *Agrobacterium*-mediated transformation (U.S. Pat. Nos. 5,104,310, 5,149, 645, 5,177,010, 5,231,019, 5,463,174, 5,464,763, 5,469,976, 4,762,785, 5,004,863, 5,159,135, 5,563,055, and 5,981, 840), direct gene transfer (Paszkowski et al. (1984) *EMBO J.* 3:2717-2722), and ballistic particle acceleration (see, for example, U.S. Pat. Nos. 4,945,050, 5,141,131, 5,886,244, 5,879,918, and 5,932,782; Tomes et al. (1995) in Plant Cell, Tissue, and Organ Culture Fundamental Methods, ed. Gamborg and Phillips (Springer-Verlag, Berlin); McCabe et al. (1988) *Biotechnology* 6:923-926). Also see Weissinger et al. (1988) *Ann. Rev. Genet.* 22:421-477; Christou et al. (1988) *Plant Physiol.* 87:671-674 (soybean); McCabe et al. (1988) *Bio Technology* 6:923-926 (soybean); Finer and McMullen (1991) *In Vitro Cell Dev. Biol.* 27P: 175-182 (soybean); Singh et al. (1998) *Theor. Appl. Genet.* 96:319-324 (soybean); De Wet et al. (1985) in The Experimental Manipulation of Ovule Tissues, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation). In one aspect, a bacterial cell provided herein comprises a recombinant DNA construct or recombinant vector provided herein. It is appreciated that many different species of bacterial cells can comprise a recombinant DNA construct or recombinant vector, I including, but not limited to, *Agrobacterium tumefaciens*, *Escherichia coli*. Yeast cells (e.g., *Saccharomyces cerevisiae*) comprising a recombinant DNA construct or recombinant vector provided herein are also provided.

In another aspect, recombinant constructs or expression cassettes provided herein may be introduced into plants by contacting plants with a virus or viral nucleic acids. Generally, such methods involve incorporating an expression cassette of the present disclosure within a viral DNA or RNA molecule. It is recognized that promoters for use in the expression cassettes provided herein also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221.

Any plant tissue that can be subsequently propagated using clonal methods, whether by organogenesis or embryogenesis, may be transformed with a recombinant construct or an expression cassette provided herein. By "organogenesis" in intended the process by which shoots and roots are developed sequentially from meristematic centers. By "embryogenesis" is intended the process by which shoots and roots develop together in a concerted fashion (not sequentially), whether from somatic cells or gametes. Exemplary tissues that are suitable for various transformation protocols described herein include, but are not limited to, callus tissue, existing meristematic tissue (e.g., apical meristems, axillary buds, and root meristems) and induced meristem tissue (e.g., cotyledon meristem and hypocotyl meristem), hypocotyls, cotyledons, leaf disks, pollen, embryos, and the like.

As commonly understood in the art, the term "promoter" may generally refer to a DNA sequence that contains an RNA polymerase binding site, transcription start site, and/or TATA box and assists or promotes the transcription and expression of an associated transcribable polynucleotide sequence and/or gene (or transgene). A promoter may be synthetically produced, varied or derived from a known or naturally occurring promoter sequence or other promoter sequence (e.g., as provided herein). A promoter may also include a chimeric promoter comprising a combination of two or more heterologous sequences. A promoter of the present invention may thus include variants of promoter sequences that are similar in composition, but not identical to or complimentary to, other promoter sequence(s) known or provided herein. As used herein, a "heterologous promoter" in the context of a DNA construct refers to either: (i) a promoter that is derived from a source distinct from the operably linked structural gene or coding region or (ii) a promoter derived from the same source as the operably linked structural gene or coding region, where the promoter's sequence is modified from its original form. As used herein, the term "operably linked" refers to a functional linkage between a promoter or other regulatory element and an associated transcribable polynucleotide sequence or coding sequence of a gene (or transgene), such that the promoter, etc., operates to initiate, assist, affect, cause, and/or promote the transcription and expression of the associated coding or transcribable polynucleotide sequence, at least in particular tissue(s), developmental stage(s), and/or under certain condition(s). A "plant expressible promoter" refers to a promoter that may be used to express in a plant, plant cell and/or plant tissue an associated coding sequence, transgene or transcribable polynucleotide sequence that is operably linked to the promoter.

A promoter may be classified according to a variety of criteria relating to the pattern of expression of a coding sequence or gene (including a transgene) operably linked to the promoter, such as constitutive, developmental, tissue-specific, inducible, etc. Promoters that initiate transcription in all or most tissues of the plant are referred to as "constitutive" promoters. Promoters that initiate transcription during certain periods or stages of development are referred to as "developmental" promoters. Promoters whose expression is enhanced in certain tissues of the plant relative to other plant tissues are referred to as "tissue-enhanced" or "tissue-preferred" promoters. Thus, a "tissue-preferred" promoter causes relatively higher or preferential expression in a specific tissue(s) of the plant, but with lower levels of expression in other tissue(s) of the plant. Promoters that express within a specific tissue(s) of the plant, with little or no expression in other plant tissues, are referred to as "tissue-specific" promoters. A promoter that expresses in a certain cell type of the plant is referred to as a "cell type specific" promoter. An "inducible" promoter is a promoter that initiates transcription in response to an environmental stimulus such as cold, drought or light, or other stimuli, such as wounding or chemical application. A promoter may also be classified in terms of its origin, such as being heterologous, homologous, chimeric, synthetic, etc. A "heterologous" promoter is a promoter sequence having a different origin relative to its associated transcribable sequence, coding sequence, or gene (or transgene), and/or not naturally occurring in the plant species to be transformed. The term "heterologous" may refer more broadly to a combination of two or more DNA molecules or sequences when such a combination is not normally found in nature. For example, two or more DNA molecules or sequences would be heterologous with respect to each other if they are normally found in different genomes or at different loci in the same genome, or if they are not identically combined in nature.

Exemplary constitutive promoters include the core promoter of the Rsyn7 promoter and other constitutive promoters disclosed in U.S. Pat. No. 6,072,050; the core CaMV 35S promoter (Odell et al. (1985) Nature 313:810-812); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J 3:2723-2730); ALS promoter (U.S. Pat. No. 5,659,026), and the like.

Exemplary chemical-inducible promoters include the tobacco PR-la promoter, which is activated by salicylic acid. Other chemical-inducible promoters of interest include steroid-responsive promoters (see, for example, the glucocorticoid-inducible promoter in Schena et al. (1991) Proc. Natl. Acad. Sci. USA 88:10421-10425 and McNellis et al. (1998) Plant J. 14(2):247-257) and tetracycline-inducible promoters (see, for example, Gatz et al. (1991) Mol. Gen. Genet. 227:229-237, and U.S. Pat. Nos. 5,814,618 and 5,789,156). Additional exemplary promoters that can be used herein are those responsible for heat-regulated gene expression, light-regulated gene expression (for example, the pea rbcS-3A; the maize rbcS promoter; the chlorophyll alb-binding protein gene found in pea; or the Arabssu promoter), hormone-regulated gene expression (for example, the abscisic acid (ABA) responsive sequences from the Em gene of wheat; the ABA-inducible HVA1 and HVA22, and rd29A promoters of barley and *Arabidopsis*; and wound-induced gene expression (for example, of wun1), organ specific gene expression (for example, of the tuber-specific storage protein gene; the 23-kDa zein gene from maize described by; or the French bean (ß-phaseolin gene), or pathogen-inducible promoters (for example, the PR-1, prp-1, or (ß-1,3 glucanase promoters, the fungal-inducible wirla promoter of wheat, and the nematode-inducible promoters, TobRB7-5A and Hmg-1, of tobacco and parsley, respectively).

As used herein, a "leaf" promoter includes any promoter that initiates, causes, drives, etc., transcription or expression of its associated gene, transgene or transcribable DNA sequence in leaf tissue derived from any part of a plant. Such a "leaf" promoter may be further defined as initiating, causing, driving, etc., transcription or expression of its associated gene/transgene or transcribable DNA sequence in one or more tissue(s) of a plant, such as one or more floral tissue(s). Such a "leaf" promoter may be further defined as a "leaf preferred" promoter that initiates, causes, drives, etc., transcription or expression of its associated gene, transgene or transcribable DNA sequence at least preferentially or mostly, if not exclusively, in leaf tissue derived from any part of a plant (as opposed to floral tissue). However, a "leaf" and a "leaf preferred" promoter may each also permit, allow, cause, drive, etc., transcription or expression of its associated gene, transgene or transcribable DNA sequence during reproductive phase(s) or stage(s) of development in one or more cells or tissues of the plant, such as in one or more vegetative or reproductive tissue(s). In fact, a "leaf" promoter may even initiate, cause, drive, etc., transcription or expression of its associated gene, transgene or transcribable DNA sequence in one or more reproductive or vegetative tissues at a greater level or extent than in leaf tissue(s).

As used herein, a "root" promoter includes any promoter that initiates, causes, drives, etc., transcription or expression of its associated gene, transgene or transcribable DNA sequence in root tissue derived from any part of a plant. Such a "root" promoter may be further defined as initiating, causing, driving, etc., transcription or expression of its associated gene/transgene or transcribable DNA sequence in one or more tissue(s) of a plant, such as one or more floral tissue(s). Such a "root" promoter may be further defined as a "root preferred" promoter that initiates, causes, drives, etc., transcription or expression of its associated gene, transgene or transcribable DNA sequence at least preferentially or mostly, if not exclusively, in root tissue derived from any part of a plant (as opposed to floral tissue). However, a "root" and a "root preferred" promoter may each also permit, allow, cause, drive, etc., transcription or expression of its associated gene, transgene or transcribable DNA sequence during reproductive phase(s) or stage(s) of development in one or more cells or tissues of the plant, such as in one or more vegetative or reproductive tissue(s). In fact, a "root" promoter may even initiate, cause, drive, etc., transcription or expression of its associated gene, transgene or transcribable DNA sequence in one or more reproductive or vegetative tissues at a greater level or extent than in root tissue(s).

Additional exemplary tissue-preferred promoters include those disclosed in Yamamoto et al. (1997) Plant J. 12(2): 255-265; Kawamata et al. (1997) Plant Cell Physiol. 38(7): 792-803; Hansen et al. (1997) Mol. Gen. Genet. 254(3):337-343; Russell et al. (1997) Transgenic Res. 6(2):157-168; Rinehart et al. (1996) Plant Physiol. 112(3):1331-1341; Van Camp et al. (1996) Plant Physiol. 112(2):525-535; Canevascini et al. (1996) Plant Physiol. 112(2):513-524; Yamamoto et al. (1994) Plant Cell Physiol. 35(5):773-778; Lam (1994) Results Probl. Cell Differ. 20:181-196; Orozco et al. (1993) Plant Mol. Biol. 23(6):1129-1138; Matsuoka et al. (1993) Proc Natl. Acad. Sci. USA 90(20):9586-9590; and Guevara-Garcia et al. (1993) Plant J. 4(3):495-505.

As used herein, "operably linked" refers to a functional linkage between two or more elements. For example, an operable linkage between a polynucleotide of interest and a regulatory sequence (e.g., a promoter) is a functional link that allows for expression of the polynucleotide of interest. Operably linked elements may be contiguous or non-contiguous.

As used herein, "heterologous" refers to a sequence that originates from a foreign species, or, if from the same species, is substantially modified from its native form in composition and/or genomic locus by deliberate human intervention. The term also is applicable to nucleic acid constructs, also referred to herein as "polynucleotide constructs" or "nucleotide constructs." In this manner, a "heterologous" nucleic acid construct is intended to mean a construct that originates from a foreign species, or, if from the same species, is substantially modified from its native form in composition and/or genomic locus by deliberate human intervention. Heterologous nucleic acid constructs include, but are not limited to, recombinant nucleotide constructs that have been introduced into a plant or plant part thereof, for example, via transformation methods or subsequent breeding of a transgenic plant with another plant of interest.

In one aspect, inhibition of the expression of one or more polypeptides provided herein may be obtained by RNA interference (RNAi) by expression of a polynucleotide provided herein. In one aspect, RNAi comprises expressing a non-coding RNA. As used herein, a "non-coding RNA" is selected from the group consisting of a microRNA (miRNA), a small interfering RNA (siRNA), a trans-acting siRNA (ta-siRNA), a transfer RNA (tRNA), a ribosomal RNA (rRNA), an intron, a hairpin RNA (hpRNA), an intron-containing hairpin RNA (ihpRNA), and guide RNA. In one aspect, a single non-coding RNA provided herein inhibits the expression of at least 1, at least 2, at least 3, at least 4, at least 5, at least 6, at least 7, at least 8, at least 9, at least 10, or more than 10 polypeptides. In one aspect, a non-coding RNA provided herein is stably transformed into a plant genome. In another aspect, a non-coding RNA provided herein is transiently transformed into a plant genome.

As used herein, the terms "down-regulate," "suppress," "inhibit," "inhibition," and "inhibiting" are defined as any method known in the art or described herein that decreases the expression or function of a gene product of interest (e.g., an mRNA, a protein, a non-coding RNA). "Inhibition" can be in the context of a comparison between two plants, for example, a modified plant versus a control plant. Alternatively, inhibition of expression or function of a target gene product can be in the context of a comparison between plant cells, organelles, organs, tissues, or plant components within the same plant or between different plants, and includes comparisons between developmental or temporal stages within the same plant or plant component or between plants or plant components. "Inhibition" includes any relative decrement of function or production of a gene product of interest, up to and including complete elimination of function or production of that gene product. The term "inhibition" encompasses any method or composition that down-regulates translation and/or transcription of the target gene product or functional activity of the target gene product.

The term "inhibitory sequence" encompasses any polynucleotide or polypeptide sequence capable of inhibiting the expression or function of a gene in a plant, such as full-length polynucleotide or polypeptide sequences, truncated polynucleotide or polypeptide sequences, fragments of polynucleotide or polypeptide sequences, variants of polynucleotide or polypeptide sequences, sense-oriented nucleotide sequences, antisense-oriented nucleotide sequences, the complement of a sense- or antisense-oriented nucleotide sequence, inverted regions of nucleotide sequences, hairpins of nucleotide sequences, double-stranded nucleotide sequences, single-stranded nucleotide sequences, combinations thereof, and the like. The term "polynucleotide sequence" includes sequences of RNA, DNA, chemically modified nucleic acids, nucleic acid analogs, combinations thereof, and the like.

When the phrase "capable of inhibiting" is used in the context of a polynucleotide inhibitory sequence, it is intended to mean that the inhibitory sequence itself exerts the inhibitory effect; or, where the inhibitory sequence encodes an inhibitory nucleotide molecule (for example, hairpin RNA, miRNA, or double-stranded RNA polynucleotides), or encodes an inhibitory polypeptide (e.g., a polypeptide that inhibits expression or function of the target gene product), following its transcription (for example, in the case of an inhibitory sequence encoding a hairpin RNA, miRNA, or double-stranded RNA polynucleotide) or its transcription and translation (in the case of an inhibitory sequence encoding an inhibitory polypeptide), the transcribed or translated product, respectively, exerts the inhibitory effect on the target gene product (e.g., inhibits expression or function of the target gene product).

An inhibitory sequence provided herein can be a sequence triggering gene silencing via any silencing pathway or mechanism known in the art, including, but not limited to, sense suppression/co-suppression, antisense suppression, double-stranded RNA (dsRNA) interference, hairpin RNA interference and intron-containing hairpin RNA interference, amplicon-mediated interference, ribozymes, small interfering RNA, artificial or synthetic microRNA, and artificial trans-acting siRNA. An inhibitory sequence may range from at least 20 nucleotides, at least 50 nucleotides, at least 70 nucleotides, at least 100 nucleotides, at least 150 nucleotides, at least 200 nucleotides, at least 250 nucleotides, at least 300 nucleotides, at least 350 nucleotides, at least 400 nucleotides, and up to the full-length polynucleotide encoding the proteins of the present disclosure, depending upon the desired outcome. In one aspect, an inhibitory sequence can be a fragment of between 50 and 400 nucleotides, between 70 and 350 nucleotides, between 90 and 325 nucleotides, between 90 and 300 nucleotides, between 90 and 275 nucleotides, between 100 and 400 nucleotides, between 100 and 350 nucleotides, between 100 and 325 nucleotides, between 100 and 300 nucleotides, between 125 and 300 nucleotides, or between 125 and 275 nucleotides in length.

MicroRNAs (miRNAs) are non-protein coding RNAs, generally of between 19 to 25 nucleotides (commonly 20 to 24 nucleotides in plants), that guide cleavage in trans of target transcripts, negatively regulating the expression of genes involved in various regulation and development pathways (Bartel (2004) Cell, 116:281-297). In some cases, miRNAs serve to guide in-phase processing of siRNA primary transcripts (see Allen et al. (2005) Cell, 121:207-221).

Many microRNA genes (MIR genes) have been identified and made publicly available in a database ("miRBase", available on line at microrna.sanger.ac.uk/sequences; also see Griffiths-Jones et al. (2003) Nucleic Acids Res., 31:439-441). MIR genes have been reported to occur in intergenic regions, both isolated and in clusters in the genome, but can also be located entirely or partially within introns of other genes (both protein-coding and non-protein-coding). Transcription of MIR genes can be, at least in some cases, under promotional control of a MIR gene's own promoter. The primary transcript, termed a "pri-miRNA", can be quite large (several kilobases) and can be polycistronic, containing one or more pre-miRNAs (fold-back structures containing a stem-loop arrangement that is processed to the mature miRNA) as well as the usual 5' "cap" and polyadenylated tail of an mRNA.

Maturation of a mature miRNA from its corresponding precursors (pri-miRNAs and pre-miRNAs) differs significantly between animals and plants. For example, in plant cells, microRNA precursor molecules are believed to be largely processed to the mature miRNA entirely in the nucleus, whereas in animal cells, the pri-miRNA transcript is processed in the nucleus by the animal-specific enzyme Drosha, followed by export of the pre-miRNA to the cytoplasm where it is further processed to the mature miRNA. Mature miRNAs in plants are typically 21 nucleotides in length.

Transgenic expression of miRNAs (whether a naturally occurring sequence or an artificial sequence) can be employed to regulate expression of the miRNA's target gene or genes. Inclusion of a miRNA recognition site in a transgenically expressed transcript is also useful in regulating expression of the transcript; see, for example, Parizotto et al. (2004) *Genes Dev.,* 18:2237-2242. Recognition sites of miRNAs have been validated in all regions of an mRNA, including the 5' untranslated region, coding region, and 3' untranslated region, indicating that the position of the miRNA target site relative to the coding sequence may not necessarily affect suppression. Because miRNAs are important regulatory elements in eukaryotes, transgenic suppression of miRNAs is useful for manipulating biological pathways and responses. Finally, promoters of MIR genes can have very specific expression patterns (e.g., cell-specific, tissue-specific, temporally specific, or inducible), and thus are useful in recombinant constructs to induce such specific transcription of a DNA sequence to which they are operably linked. Various utilities of miRNAs, their precursors, their recognition sites, and their promoters are known. Non-limiting examples of these utilities include: (1) the expression of a native miRNA or miRNA precursor sequence to suppress a target gene; (2) the expression of an artificial miRNA or miRNA precursor sequence to suppress a target gene; (3) expression of a transgene with a miRNA recognition site, where the transgene is suppressed when the mature miRNA is expressed; (4) expression of a transgene driven by a miRNA promoter.

Designing an artificial miRNA sequence can be as simple as substituting sequence that is complementary to the intended target for nucleotides in the miRNA stem region of the miRNA precursor. One non-limiting example of a general method for determining nucleotide changes in the native miRNA sequence to produce the engineered miRNA precursor includes the following steps: (a) Selecting a unique target sequence of at least 18 nucleotides specific to the target gene, e.g., by using sequence alignment tools such as BLAST© (see, for example, Altschul et al. (1990) J. Mol. Biol., 215:403-410; Altschul et al. (1997) Nucleic Acids Res., 25:3389-3402), for example, of both tobacco cDNA and genomic DNA databases, to identify target transcript orthologues and any potential matches to unrelated genes, thereby avoiding unintentional silencing of non-target sequences; (b) Analyzing the target gene for undesirable sequences (e.g., matches to sequences from non-target species), and score each potential 19-mer segment for GC content, Reynolds score (see Reynolds et al. (2004) Nature Biotechnol., 22:326-330), and functional asymmetry characterized by a negative difference in free energy ("..DELTA..DELTA.G" or "$\Delta\Delta G$"). Preferably 19-mers are selected that have all or most of the following characteristics: (1) a Reynolds score>4, (2) a GC content between 40% to 60%, (3) a negative $\Delta\Delta G$, (4) a terminal adenosine, (5) lack of a consecutive run of 4 or more of the same nucleotide; (6) a location near the 3' terminus of the target gene; (7) minimal differences from the miRNA precursor transcript. Positions at every third nucleotide in an siRNA have been reported to be especially important in influencing RNAi efficacy and an algorithm, "siExplorer" is publicly available at rna.chem.t.u-tokyo.ac.jp/siexplorer.htm; (c) Determining the reverse complement of the selected 19-mers to use in making a modified mature miRNA. The additional nucleotide at position 20 is preferably matched to the selected target sequence, and the nucleotide at position 21 is preferably chosen to either be unpaired to prevent spreading of silencing on the target transcript or paired to the target sequence to promote spreading of silencing on the target transcript; and (d) transforming the artificial miRNA into a plant.

In one aspect, an artificial miRNA provided herein reduces or eliminates RNA transcription or protein translation of a target gene.

In one aspect, a miRNA or an artificial miRNA provided herein is under the control of a tissue specific promoter. In a further aspect, a miRNA or an artificial miRNA provided herein is under the control of a tissue-preferred promoter. In a further aspect, a miRNA or an artificial miRNA provided herein is under the control of a constitutive promoter.

Tobacco material obtained from modified tobacco lines, varieties or hybrids of the present disclosure can be used to make tobacco products. As used herein, "tobacco product" is defined as any product made or derived from tobacco that is intended for human use or consumption. In an aspect, a tobacco product provided herein comprises cured components from a modified tobacco plant provided herein. In another aspect, a tobacco product provided herein comprises cured tobacco leaves from a modified tobacco plant provided herein.

Tobacco products provided herein include, without limitation, cigarette products (e.g., cigarettes, bidi cigarettes, kreteks), cigar products (e.g., cigars, cigar wrapping tobacco, cigarillos), pipe tobacco products, products derived from tobacco, tobacco-derived nicotine products, smokeless tobacco products (e.g., moist snuff, dry snuff, chewing tobacco, moist smokeless tobacco, fine cut chewing tobacco, long cut chewing tobacco, pouched chewing tobacco), films, chewables (e.g., gum), lozenges, dissolving strips, tabs, tablets, shaped parts, gels, consumable units, insoluble matrices, hollow shapes, reconstituted tobacco, expanded tobacco, and the like. See, for example, U.S. Patent Publication No. US 2006/0191548.

As used herein, "cigarette" refers a tobacco product having a "rod" and "filler". The cigarette "rod" includes the cigarette paper, filter, plug wrap (used to contain filtration materials), tipping paper that holds the cigarette paper (including the filler) to the filter, and all glues that hold these components together. The "filler" includes (1) all tobaccos, including but not limited to reconstituted and expanded tobacco, (2) non-tobacco substitutes (including but not limited to herbs, non-tobacco plant materials and other spices that may accompany tobaccos rolled within the cigarette paper), (3) casings, (4) flavorings, and (5) all other additives (that are mixed into tobaccos and substitutes and rolled into the cigarette).

In one aspect, this disclosure provides nicotine derived from and a method of producing nicotine from a modified tobacco plant provided herein for use in a product.

Tobacco products derived from plants of the present disclosure also include cigarettes and other smoking articles, particularly those smoking articles including filter elements, where the rod of smokeable material includes cured tobacco within a tobacco blend. In an aspect, a tobacco product of the present disclosure is selected from the group consisting of a cigarillo, a non-ventilated recess filter cigarette, a vented recess filter cigarette, a bidi cigarette, a cigar, snuff, pipe tobacco, cigar tobacco, cigarette tobacco, chewing tobacco, leaf tobacco, hookah tobacco, shredded tobacco, and cut tobacco. In another aspect, a tobacco product of the present disclosure is a smokeless tobacco product. Smokeless tobacco products are not combusted and include, but not limited to, chewing tobacco, moist smokeless tobacco, snus, and dry snuff. Chewing tobacco is coarsely divided tobacco leaf that is typically packaged in a large pouch-like package and used in a plug or twist. Moist smokeless tobacco is a moist, more finely divided tobacco that is provided in loose form or in pouch form and is typically packaged in round cans and used as a pinch or in a pouch placed between an adult tobacco consumer's cheek and gum. Snus is a heat treated smokeless tobacco. Dry snuff is finely ground tobacco that is placed in the mouth or used nasally. In a further aspect, a tobacco product of the present disclosure is selected from the group consisting of loose leaf chewing tobacco, plug chewing tobacco, moist snuff, and nasal snuff. In yet another aspect, a tobacco product of the present disclosure is selected from the group consisting of an electronically heated cigarette, an e-cigarette, an electronic vaporing device. In one aspect, a method provided herein comprises preparing a tobacco product using a cured tobacco leaf from a modified tobacco plant provided herein.

As used herein, "reconstituted tobacco" refers to a part of tobacco filler made from tobacco dust and other tobacco scrap material, processed into sheet form and cut into strips to resemble tobacco. In addition to the cost savings, reconstituted tobacco is very important for its contribution to cigarette taste from processing flavor development using reactions between ammonia and sugars.

As used herein, "expanded tobacco" refers to a part of tobacco filler which is processed through expansion of suitable gases so that the tobacco is "puffed" resulting in reduced density and greater filling capacity. It reduces the weight of tobacco used in cigarettes.

Also provided herein is cured tobacco material made from tobacco plants or plant components provided herein. "Curing" is the aging process that reduces moisture and brings about the destruction of chlorophyll giving tobacco leaves a golden color and by which starch is converted to sugar. Cured tobacco therefore has a higher reducing sugar content and a lower starch content compared to harvested green leaf. In one aspect, tobacco plants or plant components provided herein can be cured using conventional means, e.g., flue-cured, barn-cured, fire-cured, air-cured or sun-cured. See, for example, Tso (1999, Chapter 1 in Tobacco, Production, Chemistry and Technology, Davis & Nielsen, eds., Blackwell Publishing, Oxford) for a description of different types of curing methods. Cured tobacco is usually aged in a wooden drum (e.g., a hogshead) or cardboard cartons in compressed conditions for several years (e.g., two to five years), at a moisture content ranging from 10% to 25%. See, U.S. Pat. Nos. 4,516,590 and 5,372,149. Cured and aged tobacco then can be further processed. Further processing includes conditioning the tobacco under vacuum with or without the introduction of steam at various temperatures, pasteurization, and fermentation. Fermentation typically is characterized by high initial moisture content, heat generation, and a 10 to 20% loss of dry weight. See, for example, U.S. Pat. Nos. 4,528,993, 4,660,577, 4,848,373, 5,372,149; U.S. Publication No. 2005/0178398; and Tso (1999, Chapter 1 in Tobacco, Production, Chemistry and Technology, Davis & Nielsen, eds., Blackwell Publishing, Oxford). Cured, aged, and fermented tobacco can be further processed (e.g., cut, shredded, expanded, or blended). See, for example, U.S. Pat. Nos. 4,528,993; 4,660,577; and 4,987,907. In one aspect, the cured tobacco material of the present disclosure is flue-cured, sun-cured, air-cured, or fire-cured.

The present disclosure further provides a method manufacturing a tobacco product comprising tobacco material from tobacco plants provided herein. In one aspect, methods provided herein comprise conditioning aged tobacco material made from tobacco plants provided herein to increase its moisture content from between 12.5% and 13.5% to 21%, blending the conditioned tobacco material to produce a desirable blend. In one aspect, the method of manufacturing a tobacco product provided herein further comprises casing or flavoring the blend. Generally, during the casing process, casing or sauce materials are added to blends to enhance their quality by balancing the chemical composition and to develop certain desired flavor characteristics. Further details for the casing process can be found in Tobacco Production, Chemistry and Technology, Edited by L. Davis and M. Nielsen, Blackwell Science, 1999.

Tobacco material provided herein can be also processed using methods including, but not limited to, heat treatment (e.g., cooking, toasting), flavoring, enzyme treatment, expansion and/or curing. Both fermented and non-fermented tobaccos can be processed using these techniques. Examples of suitable processed tobaccos include dark air-cured, dark fire cured, Burley, flue cured, and cigar filler or wrapper, as well as the products from the whole leaf stemming operation. In one aspect, tobacco fibers include up to 70% dark tobacco on a fresh weight basis. For example, tobacco can be conditioned by heating, sweating and/or pasteurizing steps as described in U.S. Publication Nos. 2004/0118422 or 2005/0178398.

Tobacco material provided herein can be subject to fermentation. Fermenting typically is characterized by high initial moisture content, heat generation, and a 10 to 20% loss of dry weight. See, e.g., U.S. Pat. Nos. 4,528,993; 4,660,577; 4,848,373; and 5,372,149. In addition to modifying the aroma of the leaf, fermentation can change either or both the color and texture of a leaf. Also during the fermentation process, evolution gases can be produced, oxygen can be taken up, the pH can change, and the amount of water retained can change. See, for example, U.S. Publication No. 2005/0178398 and Tso (1999, Chapter 1 in Tobacco, Production, Chemistry and Technology, Davis & Nielsen, eds., Blackwell Publishing, Oxford). Cured, or cured and fermented tobacco can be further processed (e.g., cut, expanded, blended, milled or comminuted) prior to incorporation into the oral product. The tobacco, in some cases, is long cut fermented cured moist tobacco having an oven volatiles content of between 48 and 50 weight percent prior to mixing with a copolymer and, optionally, flavorants and other additives.

In one aspect, tobacco material provided herein can be processed to a desired size. In certain aspects, tobacco fibers can be processed to have an average fiber size of less than 200 micrometers. In one aspect, tobacco fibers are between 75 and 125 micrometers. In another aspect, tobacco fibers are processed to have a size of 75 micrometers or less. In one aspect, tobacco fibers include long cut tobacco, which can be cut or shredded into widths of 10 cuts/inch up to 110 cuts/inch and lengths of 0.1 inches up to 1 inch. Double cut tobacco fibers can have a range of particle sizes such that 70% of the double cut tobacco fibers falls between the mesh sizes of −20 mesh and 80 mesh.

Tobacco material provided herein can be processed to have a total oven volatiles content of 10% by weight or greater; 20% by weight or greater; 40% by weight or greater; 15% by weight to 25% by weight; 20% by weight to 30% by weight; 30% by weight to 50% by weight; 45% by weight to 65% by weight; or 50% by weight to 60% by weight. Those of skill in the art will appreciate that "moist" tobacco typically refers to tobacco that has an oven volatiles content of between 40% by weight and 60% by weight (e.g., 45% by weight to 55% by weight, or 50% by weight). As used herein, "oven volatiles" are determined by calculating the percentage of weight loss for a sample after drying the sample in a pre-warmed forced draft oven at 110° C. for 3.25 hours. An oral product can have a different overall oven volatiles content than the oven volatiles content of the tobacco fibers used to make the oral product. The processing steps described herein can reduce or increase the oven volatiles content.

In one aspect, tobacco plants, seeds, plant components, plant cells, and plant genomes provided herein are from a tobacco type selected from the group consisting of flue-cured tobacco, sun-cured tobacco, air-cured tobacco, dark air-cured tobacco, and dark fire-cured tobacco. In another aspect, tobacco plants, seeds, plant components, plant cells, and plant genomes provided herein are from a tobacco type selected from the group consisting of Burley tobacco, Maryland tobacco, bright tobacco, Virginia tobacco, Oriental tobacco, Turkish tobacco, and Galpão tobacco. In one aspect, a tobacco plants or seed provided herein is a hybrid plants or seed. As used herein, a "hybrid" is created by crossing two plants from different varieties or species, such that the progeny comprises genetic material from each parent. Skilled artisans recognize that higher order hybrids can be generated as well. For example, a first hybrid can be made by crossing Variety C with Variety D to create a C×D hybrid, and a second hybrid can be made by crossing Variety E with Variety F to create an E×F hybrid. The first and second hybrids can be further crossed to create the higher order hybrid (C×D)×(E×F) comprising genetic information from all four parent varieties.

Flue-cured tobaccos (also called Virginia of bright tobaccos) amount to approximately 40% of world tobacco production. Flue-cured tobaccos are often also referred to as "bright tobacco" because of the golden-yellow to deep-orange color it reaches during curing. Flue-cured tobaccos have a light, bright aroma and taste. Flue-cured tobaccos are generally high in sugar and low in oils. Major flue-cured tobacco growing countries are Argentina, Brazil, China, India, Tanzania and the U.S. In one aspect, modified tobacco plants or seeds provided herein are in a flue-cured tobacco background selected from the group consisting of CC 13, CC 27, CC 33, CC35, CC 37, CC 65, CC 67, CC 700, GF 318, GL 338, GL 368, GL 939, K 346, K 399, K326, NC 102, NC 196, NC 291, NC 297, NC 299, NC 471, NC 55, NC 606, NC 71, NC 72, NC 92, PVH 1118, PVH 1452, PVH 2110, SPEIGHT 168, SPEIGHT 220, SPEIGHT 225, SPEIGHT 227, SPEIGHT 236, and any variety essentially derived from any one of the foregoing varieties. In another aspect, modified tobacco plants or seeds provided herein are in a flue-cured tobacco background selected from the group consisting of Coker 48, Coker 176, Coker 371-Gold, Coker 319, Coker 347, GL 939, K 149, K326, K 340, K 346, K 358, K 394, K 399, K 730, NC 27NF, NC 37NF, NC 55, NC 60, NC 71, NC 72, NC 82, NC 95, NC 297, NC 606, NC 729, NC 2326, McNair 373, McNair 944, Ox 207, Ox 414 NF, Reams 126, Reams 713, Reams 744, RG 8, RG 11, RG 13, RG 17, RG 22, RG 81, RG H4, RG H51, Speight H-20, Speight G-28, Speight G-58, Speight G-70, Speight G-108, Speight G-111, Speight G-117, Speight 168, Speight 179, Speight NF-3, Va 116, Va 182, and any variety essentially derived from any one of the foregoing varieties. See WO 2004/041006 A1. In further aspects, modified tobacco plants, seeds, hybrids, varieties, or lines provided herein are in any flue cured background selected from the group consisting of K326, K346, and NC196.

Air-cured tobaccos include Burley, Maryland, and dark tobaccos. The common factor is that curing is primarily without artificial sources of heat and humidity. Burley tobaccos are light to dark brown in color, high in oil, and low in sugar. Burley tobaccos are air-cured in barns. Major Burley growing countries are Argentina, Brazil, Italy, Malawi, and the U.S. Maryland tobaccos are extremely fluffy, have good burning properties, low nicotine and a neutral aroma. Major Maryland growing countries include the U.S. and Italy. In one aspect, modified tobacco plants or seeds provided herein are in a Burley tobacco background selected from the group consisting of Clay 402, Clay 403, Clay 502, Ky 14, Ky 907, Ky 910, Ky 8959, NC 2, NC 3, NC 4, NC 5, NC 2000, TN 86, TN 90, TN 97, R 610, R 630, R 711, R 712, NCBH 129, HB4488PLC, PD 7319LC, Bu 21×Ky 10, HB04P, Ky 14×L 8, Kt 200, Newton 98, Pedigo 561, Pf561 and Va 509. In further aspects, modified tobacco plants, seeds, hybrids, varieties, or lines provided herein are in any Burley background selected from the group consisting of TN 90, KT 209, KT 206, KT212, and HB 4488. In another aspect, modified tobacco plants or seeds provided herein are in a Maryland tobacco background selected from the group consisting of Md 10, Md 40, Md 201, Md 609, Md 872 and Md 341.

Dark air-cured tobaccos are distinguished from other types primarily by its curing process which gives dark air-cured tobacco its medium- to dark-brown color and distinct aroma. Dark air-cured tobaccos are mainly used in the production of chewing tobacco and snuff. In one aspect, modified tobacco plants or seeds provided herein are in a dark air-cured tobacco background selected from the group consisting of Sumatra, Jatim, Dominican Cubano, Besuki, One sucker, Green River, Virginia sun-cured, and Paraguan Passado.

Dark fire-cured tobaccos are generally cured with low-burning wood fires on the floors of closed curing barns. Dark fire-cured tobaccos are used for making pipe blends, cigarettes, chewing tobacco, snuff and strong-tasting cigars. Major growing regions for dark fire-cured tobaccos are Tennessee, Kentucky, and Virginia, USA. In one aspect, modified tobacco plants or seeds provided herein are in a dark fire-cured tobacco background selected from the group consisting of Narrow Leaf Madole, Improved Madole, Tom Rosson Madole, Newton's VH Madole, Little Crittenden, Green Wood, Little Wood, Small Stalk Black Mammoth, DT 508, DT 518, DT 592, KY 171, DF 911, DF 485, TN D94, TN D950, VA 309, and VA 359.

Oriental tobaccos are also referred to as Greek, aroma and Turkish tobaccos due to the fact that they are typically grown in eastern Mediterranean regions such as Turkey, Greece, Bulgaria, Macedonia, Syria, Lebanon, Italy, and Romania. The small plant and leaf size, characteristic of today's Oriental varieties, as well as its unique aroma properties are a result of the plant's adaptation to the poor soil and stressful climatic conditions in which it develop over many past centuries. In one aspect, modified tobacco plants or seeds provided herein are in an Oriental tobacco background selected from the group consisting of Izmir, Katerini, Samsun, Basma and Krumovgrad, Trabzon, Thesalian, Tasova, Sinop, Izmit, Hendek, Edirne, Semdinli, Adiyanman, Yayladag, Iskenderun, Duzce, Macedonian, Mavra, Prilep, Bafra, Bursa, Bucak, Bitlis, Balikesir, and any variety essentially derived from any one of the foregoing varieties.

In one aspect, modified tobacco plants, seeds, hybrids, varieties, or lines provided herein are essentially derived from or in the genetic background of BU 64, CC 101, CC 200, CC 13, CC 27, CC 33, CC 35, CC 37, CC 65, CC 67, CC 301, CC 400, CC 500, CC 600, CC 700, CC 800, CC 900, CC 1063, Coker 176, Coker 319, Coker 371 Gold, Coker 48, CU 263, DF911, Galpão, GL 26H, GL 338, GL 350, GL 395, GL 600, GL 737, GL 939, GL 973, GF 157, GF 318, RJR 901, HB 04P, K 149, K 326, K 346, K 358, K394, K 399, K 730, NC 196, NC 37NF, NC 471, NC 55, NC 92, NC2326, NC 95, NC 925, PVH 1118, PVH 1452, PVH 2110, PVH 2254, PVH 2275, VA 116, VA 119, KDH 959, KT 200, KT204LC, KY 10, KY 14, KY 160, KY 17, KY 171, KY 907, KY 907LC, KTY14×L8 LC, Little Crittenden, McNair 373, McNair 944, male sterile KY 14×L8, Narrow Leaf Madole, MS KY171, Narrow Leaf Madole (phph), MS Narrow Leaf Madole, MS TND950, PD 7302LC, PD 7305LC, PD 7309LC, PD 7312LC, PD 7318LC, PD 7319LC, MSTKS 2002, TKF 2002, TKF 6400, TKF 4028, TKF 4024, KT206LC, KT209LC, KT210LC, KT212LC, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, 'Perique', PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN90LC, TN 97, TN97LC, TN D94, TN D950, a TR (Tom Rosson) Madole, VA 309, VA 359, or any commercial tobacco variety according to standard tobacco breeding techniques known in the art.

All foregoing mentioned specific varieties of dark air-cured, Burley, Maryland, dark fire-cured, or Oriental type are only listed for exemplary purposes. Any additional dark air-cured, Burley, Maryland, dark fire-cured, Oriental varieties are also contemplated in the present application.

Also provided herein are populations of tobacco plants described herein. In one aspect, a population of tobacco plants provided herein has a planting density of between 5,000 and 8000, between 5,000 and 7,600, between 5,000 and 7,200, between 5,000 and 6,800, between 5,000 and 6,400, between 5,000 and 6,000, between 5,000 and 5,600, between 5,000 and 5,200, between 5,200 and 8,000, between 5,600 and 8,000, between 6,000 and 8,000, between 6,400 and 8,000, between 6,800 and 8,000, between 7,200 and 8,000, or between 7,600 and 8,000 plants per acre.

Also provided herein are containers of seeds from tobacco plants described herein. A container of tobacco seeds of the present disclosure may contain any number, weight, or volume of seeds. For example, a container can contain at least or greater than 10 seeds; at least or greater than 25 seeds; at least or greater than 50 seeds; at least, or greater than, 100 seeds; at least, or greater than, 200 seeds; at least, or greater than, 300 seeds; at least, or greater than, 400 seeds; at least, or greater than, 500 seeds; at least, or greater than, 600 seeds; at least, or greater than, 700 seeds; at least, or greater than, 800 seeds; at least, or greater than, 900 seeds; at least, or greater than, 1000 seeds; at least, or greater than, 1500 seeds; at least, or greater than, 2000 seeds; at least, or greater than, 2500 seeds; at least, or greater than, 3000 seeds; at least, or greater than, 3500 seeds; at least, or greater than, 4000 seeds; or at least, or greater than 5000 seeds. Alternatively, the container can contain at least, or greater than, 1 ounce of seeds; at least, or greater than, 5 grams of seeds; at least, or greater than, 10 grams of seeds; at least, or greater than, 30 grams of seeds; at least, or greater than, 50 grams of seeds; at least, or greater than, 100 grams of seeds; at least, or greater than, 500 grams of seeds; at least, or greater than, 1 kilogram of seeds; at least, or greater than 1.5 kilograms of seeds; at least, or greater than 2 kilograms of seeds; at least, or greater than, 5 kilograms of seeds; or at least, or greater than, 10 kilograms of seeds. Containers of tobacco seeds may be any container available in the art. By way of non-limiting example, a container may be a box, a bag, a packet, a pouch, a tape roll, a tube, or a bottle.

In one aspect, present disclosure provides cured leaf from a modified tobacco plant comprising a reduced level of one or more TSNAs. In one aspect, reduced one or more TSNAs are selected from the group consisting of N'-nitrosonornicotine (NNN), 4-methylnitrosoamino-1-(3-pyridyl)-1-butanone (NNK), N'-nitrosoanatabine (NAT) N'-nitrosoanabasine (NAB), and any combination thereof. In one aspect, the level of total TSNAs or an individual TSNA is measured based on a freeze-dried cured leaf sample using liquid chromatograph with tandem mass spectrometry (LC/MS/MS).

In one aspect, present disclosure provides cured leaf from a modified tobacco plant comprising a reduced level of one or more alkaloids. In one aspect, reduced one or more alkaloids are selected from the group consisting of nicotine, nornicotine, anabasine, anatabine.

The present disclosure also provides methods for breeding tobacco lines, cultivars, or varieties comprising enhanced nitrogen utilization efficiency. Breeding can be carried out via any known procedures. DNA fingerprinting, SNP mapping, haplotype mapping or similar technologies may be used in a marker-assisted selection (MAS) breeding program to transfer or breed a desirable trait or allele into a tobacco plant. For example, a breeder can create segregating populations in an $F_2$ or backcross generation using $F_1$ hybrid plants provided herein or further crossing the $F_1$ hybrid plants with other donor plants with an agronomically desirable genotype. Plants in the $F_2$ or backcross generations can be screened for a desired agronomic trait or a desirable chemical profile using one of the techniques known in the art or listed herein. Depending on the expected inheritance pattern or the MAS technology used, self-pollination of selected plants before each cycle of backcrossing to aid identification of the desired individual plants can be performed. Backcrossing or other breeding procedure can be repeated until the desired phenotype of the recurrent parent is recovered. In one aspect, a recurrent parent in the present disclosure can be a flue-cured variety, a Burley variety, a dark air-cured variety, a dark fire-cured variety, or an Oriental variety. In another aspect, a recurrent parent can be a modified tobacco plant, line, or variety. In one aspect, a recurrent parent provided herein is TN90. In another aspect, a recurrent parent provided herein is MD609. Other breeding techniques can be found, for example, in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, N.Y., incorporated herein by reference in their entirety.

Results of a plant breeding program using modified tobacco plants described herein includes useful lines, cultivars, varieties, progeny, inbreds, and hybrids of the present disclosure. As used herein, the term "variety" refers to a population of plants that share constant characteristics which separate them from other plants of the same species. A variety is often, although not always, sold commercially. While possessing one or more distinctive traits, a variety is further characterized by a very small overall variation between individuals within that variety. A "pure line" variety may be created by several generations of self-pollination and selection, or vegetative propagation from a single parent using tissue or cell culture techniques. A variety can be essentially derived from another line or variety. As defined by the International Convention for the Protection of New Varieties of Plants (Dec. 2, 1961, as revised at Geneva on Nov. 10, 1972; on Oct. 23, 1978; and on Mar. 19, 1991), a variety is "essentially derived" from an initial variety if: a) it is predominantly derived from the initial variety, or from a variety that is predominantly derived from the initial variety, while retaining the expression of the essential characteristics that result from the genotype or combination of genotypes of the initial variety; b) it is clearly distinguishable from the initial variety; and c) except for the differences which result from the act of derivation, it conforms to the initial variety in the expression of the essential characteristics that result from the genotype or combination of genotypes of the initial variety. Essentially derived varieties can be obtained, for example, by the selection of a natural or induced mutant, a somaclonal variant, a variant individual from plants of the initial variety, backcrossing, or transformation. A first tobacco variety and a second tobacco variety from which the first variety is essentially derived, are considered as having essentially identical genetic background. A "line" as distinguished from a variety most often denotes a group of plants used non-commercially, for example in plant research. A line typically displays little overall variation between individuals for one or more traits of interest, although there may be some variation between individuals for other traits.

In one aspect, the present disclosure provides a method of producing a tobacco plant comprising crossing at least one tobacco plant of a first tobacco variety with at least one tobacco plant of a second tobacco variety, where the at least one tobacco plant of the first tobacco variety exhibits enhanced nitrogen utilization efficiency compared to a control tobacco plant of the same variety grown under comparable conditions; and selecting for progeny tobacco plants that exhibit enhanced nitrogen utilization efficiency compared to a control tobacco plant of the same cross grown under comparable conditions. In one aspect, a first tobacco variety provided herein comprises modified tobacco plants. In another aspect, a second tobacco variety provided herein comprises modified tobacco plants. In one aspect, a first or second tobacco variety is male sterile. In another aspect, a first or second tobacco variety is cytoplasmically male sterile. In another aspect, a first or second tobacco variety is female sterile. In one aspect, a first or second tobacco variety is an elite variety. In another aspect, a first or second tobacco variety is a hybrid.

In one aspect, the present disclosure provides a method of introgressing one or more transgenes into a tobacco variety, the method comprising: (a) crossing a first tobacco variety comprising one or more transgenes with a second tobacco variety without the one or more transgenes to produce one or more progeny tobacco plants; (b) genotyping the one or more progeny tobacco plants for the one or more transgenes; and (c) selecting a progeny tobacco plant comprising the one or more transgenes. In another aspect, these methods further comprise backcrossing the selected progeny tobacco plant with the second tobacco variety. In further aspects, these methods further comprise: (d) crossing the selected progeny plant with itself or with the second tobacco variety to produce one or more further progeny tobacco plants; and (e) selecting a further progeny tobacco plant comprising the one or more transgenes. In one aspect, the second tobacco variety is an elite variety.

In one aspect, the present disclosure provides a method of introgressing one or more mutations into a tobacco variety, the method comprising: (a) crossing a first tobacco variety comprising one or more mutations with a second tobacco variety without the one or more mutations to produce one or more progeny tobacco plants; (b) genotyping the one or more progeny tobacco plants for the one or more mutations; and (c) selecting a progeny tobacco plant comprising the one or more mutations. In another aspect, these methods further comprise backcrossing the selected progeny tobacco plant with the second tobacco variety. In further aspects, these methods further comprise: (d) crossing the selected progeny plant with itself or with the second tobacco variety to produce one or more further progeny tobacco plants; and (e) selecting a further progeny tobacco plant comprising the one or more mutations. In one aspect, the second tobacco variety is an elite variety.

In one aspect, the present disclosure provides a method of growing a population of modified tobacco plants comprising enhanced nitrogen utilization efficiency, where the method comprises planting a population of tobacco seeds comprising one or more mutations, one or more transgenes, or both, where the one or more modified tobacco plants exhibit enhanced nitrogen utilization efficiency compared to control tobacco plants of the same variety when grown under comparable conditions.

In one aspect, this disclosure provides a method for manufacturing a modified seed, comprising introducing a recombinant DNA construct provided herein into a plant cell; screening a population of plant cells for the recombinant DNA construct; selecting one or more plant cells from the population; generating one or more modified plants from the one or more plant cells; and collecting one or more modified seeds from the one or more modified plants.

As used herein, "locus" is a chromosome region where a polymorphic nucleic acid, trait determinant, gene, or marker is located. The loci of this disclosure comprise one or more polymorphisms in a population; e.g., alternative alleles are present in some individuals. As used herein, "allele" refers to an alternative nucleic acid sequence at a particular locus. The length of an allele can be as small as 1 nucleotide base, but is typically larger. For example, a first allele can occur on one chromosome, while a second allele occurs on a second homologous chromosome, e.g., as occurs for different chromosomes of a heterozygous individual, or between different homozygous or heterozygous individuals in a population. As used herein, a chromosome in a diploid plant is "hemizygous" when only one copy of a locus is present. For example, an inserted transgene is hemizygous when it only inserts into one sister chromosome (e.g., the second sister chromosome does not contain the inserted transgene).

In one aspect, a modified plant, seed, plant component, plant cell, or plant genome is homozygous for a transgene provided herein. In another aspect, a modified plant, seed, plant component, plant cell, or plant genome is heterozygous for a transgene provided herein. In one aspect, a modified plant, seed, plant component, plant cell, or plant genome is hemizygous for a transgene provided herein. In one aspect, a modified plant, seed, plant component, plant cell, or plant genome is homozygous for a mutation provided herein. In another aspect, a modified plant, seed, plant component, plant cell, or plant genome is heterozygous for a mutation provided herein. In one aspect, a modified plant, seed, plant component, plant cell, or plant genome is hemizygous for a mutation provided herein.

As used herein, "introgression" or "introgress" refers to the transmission of a desired allele of a genetic locus from one genetic background to another.

As used herein, "crossed" or "cross" means to produce progeny via fertilization (e.g. cells, seeds or plants) and includes crosses between different plants (sexual) and self-fertilization (selfing).

As used herein, "backcross" and "backcrossing" refer to the process whereby a progeny plant is repeatedly crossed back to one of its parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. The initial cross gives rise to the $F_1$ generation. The term "BC1" refers to the second use of the recurrent parent, "BC2" refers to the third use of the recurrent parent, and so on. In one aspect, a backcross is performed repeatedly, with a progeny individual of each successive backcross generation being itself backcrossed to the same parental genotype.

As used herein, "elite variety" means any variety that has resulted from breeding and selection for superior agronomic performance.

As used herein, "selecting" or "selection" in the context of breeding refer to the act of picking or choosing desired individuals, normally from a population, based on certain pre-determined criteria.

In one aspect, tobacco plants provided herein are hybrid plants. Hybrids can be produced by preventing self-pollination of female parent plants (e.g., seed parents) of a first variety, permitting pollen from male parent plants of a second variety to fertilize the female parent plants, and allowing $F_1$ hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by male sterility (MS), or transgenic male sterility where a transgene inhibits microsporogenesis and/or pollen formation, or self-incompatibility. Female parent plants containing MS are particularly useful. In aspects in which the female parent plants are MS, pollen may be harvested from male fertile plants and applied manually to the stigmas of MS female parent plants, and the resulting $F_1$ seed is harvested. Additionally, female sterile plants can also be used to prevent self-fertilization.

Plants can be used to form single-cross tobacco $F_1$ hybrids. Pollen from a male parent plant is manually transferred to an emasculated female parent plant or a female parent plant that is male sterile to form $F_1$ seed. Alternatively, three-way crosses can be carried out where a single-cross $F_1$ hybrid is used as a female parent and is crossed with a different male parent. As another alternative, double-cross hybrids can be created where the $F_1$ progeny of two different single-crosses are themselves crossed. Self-incompatibility can be used to particular advantage to prevent self-pollination of female parents when forming a double-cross hybrid.

In one aspect, a tobacco variety provided herein is male sterile. In another aspect, a tobacco variety provided herein is cytoplasmic male sterile (CMS). Male sterile tobacco plants may be produced by any method known in the art. Methods of producing male sterile tobacco are described in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, N.Y. 761 pp. In another aspect, a tobacco variety provided herein is female sterile. As a non-limiting example, female sterile plants can be made by mutating the STIG1 gene. See, for example, Goldman et al. 1994, *EMBO Journal* 13:2976-2984.

In one aspect, the present disclosure provides for, and includes, a method of determining the NUE of a tobacco line comprising obtaining at least one metabolite from a tobacco plant of a tobacco line, determining the amount of the at least one obtained metabolites, and determining the NUE of the tobacco line based on the amount of the at least one metabolite determined. In a further aspect, the at least one metabolite is obtained from a plant tissue selected from the group consisting of root tissue, leaf tissue, floral tissue, meristem tissue, and stem tissue. In a further aspect of this method, at least two metabolites are obtained. In a further aspect of this method, at least three metabolites are obtained. In a further aspect of this method, at least four metabolites are obtained. In a further aspect of this method, at least five metabolites are obtained. In a further aspect of this method, at least six metabolites are obtained. In a further aspect of this method, at least seven metabolites are obtained. In a further aspect of this method, at least eight metabolites are obtained. In a further aspect of this method, at least nine metabolites are obtained. In a further aspect of this method, at least ten metabolites are obtained. In a further aspect of this method, the amount of at least two metabolites is determined. In a further aspect of this method, the amount of at least three metabolites is determined. In a further aspect of this method, the amount of at least four metabolites is determined. In a further aspect of this method, the amount of at least five metabolites is determined. In a further aspect of this method, the amount of at least six metabolites is determined. In a further aspect of this method, the amount of at least seven metabolites is determined. In a further aspect of this method, the amount of at least eight metabolites is determined. In a further aspect of this method, the amount of at least nine metabolites is determined. In a further aspect of this method, the amount of at least ten metabolites is determined.

In another aspect of a method provided herein, the amount of a metabolite selected from the group consisting of X-2357, N-acetylmuramate, X-23319, X-23852, X-23330, alpha-ketoglutarate, X-21756, 4-hydroxy-2-oxoglutaric acid, D-23937, X-23937, X-23916, 1-methyladenine, 4-guanidinobutanoate, syringaldehyde, thiamin, p-hydroxybenzaldehyde, X-23453, X-11429, X-21796, N'-methylnicotinamide, cotinine, X-23389, N-acetylarginine, X-23366, N-acetylphenylalanine, naringenin, X-23454, X-23580, and X-23852 is determined.

In another aspect of a method provided herein, a tobacco plant with enhanced NUE comprises enhanced NUE as compared to a tobacco plant that comprises a lower amount of at least one metabolite in at least one tissue. In a further aspect, a tobacco plant with enhanced NUE comprises a lower amount of at least two metabolites in at least one tissue. In a further aspect, a tobacco plant with enhanced NUE comprises a lower amount of at least three metabolites in at least one tissue. In a further aspect, a tobacco plant with enhanced NUE comprises a lower amount of at least four metabolites in at least one tissue. In a further aspect, a tobacco plant with enhanced NUE comprises a lower amount of at least five metabolites in at least one tissue. In a further aspect, a tobacco plant with enhanced NUE comprises a lower amount of at least one metabolite in two tissues. In a further aspect, a tobacco plant with enhanced NUE comprises a lower amount of at least two metabolites in at least two tissues. In a further aspect, a tobacco plant with enhanced NUE comprises a lower amount of at least three metabolites in at least two tissues. In a further aspect, a tobacco plant with enhanced NUE comprises a lower amount of at least four metabolites in at least two tissues. In a further aspect, a tobacco plant with enhanced NUE comprises a lower amount of at least five metabolites in at least two tissues. In a further aspect, a tobacco plant with enhanced NUE comprises a lower amount of at least one metabolite in three tissues. In a further aspect, a tobacco plant with enhanced NUE comprises a lower amount of at least two metabolites in at least three tissues. In a further aspect, a tobacco plant with enhanced NUE comprises a lower amount of at least three metabolites in at least three tissues. In a further aspect, a tobacco plant with enhanced NUE comprises a lower amount of at least four metabolites in at least three tissues. In a further aspect, a tobacco plant with enhanced NUE comprises a lower amount of at least five metabolites in at least three tissues. In a further aspect, a tobacco plant with enhanced NUE comprises a lower amount of at least one metabolite in four tissues. In a further aspect, a tobacco plant with enhanced NUE comprises a lower amount of at least two metabolites in at least four tissues. In a further aspect, a tobacco plant with enhanced NUE comprises a lower amount of at least three metabolites in at least four tissues. In a further aspect, a tobacco plant with enhanced NUE comprises a lower amount of at least four metabolites in at least four tissues. In a further aspect, a tobacco plant with enhanced NUE comprises a lower amount of at least five metabolites in at least four tissues. In a further aspect, a tobacco plant with enhanced NUE comprises a lower amount of at least one metabolite in five tissues. In a further aspect, a tobacco plant with enhanced NUE comprises a lower amount of at least two metabolites in at least five tissues. In a further aspect, a tobacco plant with enhanced NUE comprises a lower amount of at least three metabolites in at least five tissues. In a further aspect, a tobacco plant with enhanced NUE comprises a lower amount of at least four metabolites in at least five tissues. In a further aspect, a tobacco plant with enhanced NUE comprises a lower amount of at least five metabolites in at least five tissues.

In another aspect of a method provided herein, a tobacco plant with enhanced NUE comprises enhanced NUE as compared to a tobacco line that comprises a higher amount of at least one metabolite in at least one tissue. In a further aspect, a tobacco plant with enhanced NUE comprises a higher amount of at least two metabolites in at least one tissue. In a further aspect, a tobacco plant with enhanced NUE comprises a higher amount of at least three metabolites in at least one tissue. In a further aspect, a tobacco plant with enhanced NUE comprises a higher amount of at least four metabolites in at least one tissue. In a further aspect, a tobacco plant with enhanced NUE comprises a higher amount of at least five metabolites in at least one tissue. In a further aspect, a tobacco plant with enhanced NUE comprises a higher amount of at least one metabolite in two tissues. In a further aspect, a tobacco plant with enhanced NUE comprises a higher amount of at least two metabolites in at least two tissues. In a further aspect, a tobacco plant with enhanced NUE comprises a higher amount of at least three metabolites in at least two tissues. In a further aspect, a tobacco plant with enhanced NUE comprises a higher amount of at least four metabolites in at least two tissues. In a further aspect, a tobacco plant with enhanced NUE comprises a higher amount of at least five metabolites in at least two tissues. In a further aspect, a tobacco plant with enhanced NUE comprises a higher amount of at least one metabolite in three tissues. In a further aspect, a tobacco plant with enhanced NUE comprises a higher amount of at least two metabolites in at least three tissues. In a further aspect, a tobacco plant with enhanced NUE comprises a higher amount of at least three metabolites in at least three tissues. In a further aspect, a tobacco plant with enhanced NUE comprises a higher amount of at least four metabolites in at least three tissues. In a further aspect, a tobacco plant with enhanced NUE comprises a higher amount of at least five metabolites in at least three tissues. In a further aspect, a tobacco plant with enhanced NUE comprises a higher amount of at least one metabolite in four tissues. In a further aspect, a tobacco plant with enhanced NUE comprises a higher amount of at least two metabolites in at least four tissues. In a further aspect, a tobacco plant with enhanced NUE comprises a higher amount of at least three metabolites in at least four tissues. In a further aspect, a tobacco plant with enhanced NUE comprises a higher amount of at least four metabolites in at least four tissues. In a further aspect, a tobacco plant with enhanced NUE comprises a higher amount of at least five metabolites in at least four tissues. In a further aspect, a tobacco plant with enhanced NUE comprises a higher amount of at least one metabolite in five tissues. In a further aspect, a tobacco plant with enhanced NUE comprises a higher amount of at least two metabolites in at least five tissues. In a further aspect, a tobacco plant with enhanced NUE comprises a higher amount of at least three metabolites in at least five tissues. In a further aspect, a tobacco plant with enhanced NUE comprises a higher amount of at least four metabolites in at least five tissues. In a further aspect, a tobacco plant with enhanced NUE comprises a higher amount of at least five metabolites in at least five tissues.

In another aspect of a method provided herein, a tobacco plant with enhanced NUE comprises enhanced NUE as compared to a tobacco line that comprises an equal amount of at least one metabolite in at least one tissue. In a further aspect, a tobacco plant with enhanced NUE comprises an equal amount of at least two metabolites in at least one tissue. In a further aspect, a tobacco plant with enhanced NUE comprises an equal amount of at least three metabolites in at least one tissue. In a further aspect, a tobacco plant with enhanced NUE comprises an equal amount of at least four metabolites in at least one tissue. In a further aspect, a tobacco plant with enhanced NUE comprises an equal amount of at least five metabolites in at least one tissue. In a further aspect, a tobacco plant with enhanced NUE comprises an equal amount of at least one metabolite in two tissues. In a further aspect, a tobacco plant with enhanced NUE comprises an equal amount of at least two metabolites in at least two tissues. In a further aspect, a tobacco plant with enhanced NUE comprises an equal amount of at least three metabolites in at least two tissues. In a further aspect, a tobacco plant with enhanced NUE comprises an equal amount of at least four metabolites in at least two tissues. In a further aspect, a tobacco plant with enhanced NUE comprises an equal amount of at least five metabolites in at least two tissues. In a further aspect, a tobacco plant with enhanced NUE comprises an equal amount of at least one metabolite in three tissues. In a further aspect, a tobacco plant with enhanced NUE comprises an equal amount of at least two metabolites in at least three tissues. In a further aspect, a tobacco plant with enhanced NUE comprises an equal amount of at least three metabolites in at least three tissues. In a further aspect, a tobacco plant with enhanced NUE comprises an equal amount of at least four metabolites in at least three tissues. In a further aspect, a tobacco plant with enhanced NUE comprises an equal amount of at least five metabolites in at least three tissues. In a further aspect, a tobacco plant with enhanced NUE comprises an equal amount of at least one metabolite in four tissues. In a further aspect, a tobacco plant with enhanced NUE comprises an equal amount of at least two metabolites in at least four tissues. In a further aspect, a tobacco plant with enhanced NUE comprises an equal amount of at least three metabolites in at least four tissues. In a further aspect, a tobacco plant with enhanced NUE comprises an equal amount of at least four metabolites in at least four tissues. In a further aspect, a tobacco plant with enhanced NUE comprises an equal amount of at least five metabolites in at least four tissues. In a further aspect, a tobacco plant with enhanced NUE comprises an equal amount of at least one metabolite in five tissues. In a further aspect, a tobacco plant with enhanced NUE comprises an equal amount of at least two metabolites in at least five tissues. In a further aspect, a tobacco plant with enhanced NUE comprises an equal amount of at least three metabolites in at least five tissues. In a further aspect, a tobacco plant with enhanced NUE comprises an equal amount of at least four metabolites in at least five tissues. In a further aspect, a tobacco plant with enhanced NUE comprises an equal amount of at least five metabolites in at least five tissues.

In another aspect of a method provided herein, a tobacco plant with enhanced NUE comprises decreased NUE as compared to a tobacco line that comprises a lower amount of at least one metabolite in at least one tissue. In a further aspect, a tobacco plant with enhanced NUE comprises a lower amount of at least two metabolites in at least one tissue. In a further aspect, a tobacco plant with enhanced NUE comprises a lower amount of at least three metabolites in at least one tissue. In a further aspect, a tobacco plant with enhanced NUE comprises a lower amount of at least four metabolites in at least one tissue. In a further aspect, a tobacco plant with enhanced NUE comprises a lower amount of at least five metabolites in at least one tissue. In a further aspect, a tobacco plant with enhanced NUE comprises a lower amount of at least one metabolite in two tissues. In a further aspect, a tobacco plant with enhanced NUE comprises a lower amount of at least two metabolites in at least two tissues. In a further aspect, a tobacco plant with enhanced NUE comprises a lower amount of at least three metabolites in at least two tissues. In a further aspect, a tobacco plant with enhanced NUE comprises a lower amount of at least four metabolites in at least two tissues. In a further aspect, a tobacco plant with enhanced NUE comprises a lower amount of at least five metabolites in at least two tissues. In a further aspect, a tobacco plant with enhanced NUE comprises a lower amount of at least one metabolite in three tissues. In a further aspect, a tobacco plant with enhanced NUE comprises a lower amount of at least two metabolites in at least three tissues. In a further aspect, a tobacco plant with enhanced NUE comprises a lower amount of at least three metabolites in at least three tissues. In a further aspect, a tobacco plant with enhanced NUE comprises a lower amount of at least four metabolites in at least three tissues. In a further aspect, a tobacco plant with enhanced NUE comprises a lower amount of at least five metabolites in at least three tissues. In a further aspect, a tobacco plant with enhanced NUE comprises a lower amount of at least one metabolite in four tissues. In a further aspect, a tobacco plant with enhanced NUE comprises a lower amount of at least two metabolites in at least four tissues. In a further aspect, a tobacco plant with enhanced NUE comprises a lower amount of at least three metabolites in at least four tissues. In a further aspect, a tobacco plant with enhanced NUE comprises a lower amount of at least four metabolites in at least four tissues. In a further aspect, a tobacco plant with enhanced NUE comprises a lower amount of at least five metabolites in at least four tissues. In a further aspect, a tobacco plant with enhanced NUE comprises a lower amount of at least one metabolite in five tissues. In a further aspect, a tobacco plant with enhanced NUE comprises a lower amount of at least two metabolites in at least five tissues. In a further aspect, a tobacco plant with enhanced NUE comprises a lower amount of at least three metabolites in at least five tissues. In a further aspect, a tobacco plant with enhanced NUE comprises a lower amount of at least four metabolites in at least five tissues. In a further aspect, a tobacco plant with enhanced NUE comprises a lower amount of at least five metabolites in at least five tissues.

In another aspect of a method provided herein, a tobacco plant with enhanced NUE comprises decreased NUE as compared to a tobacco line that comprises a higher amount of at least one metabolite in at least one tissue. In a further aspect, a tobacco plant with enhanced NUE comprises a higher amount of at least two metabolites in at least one tissue. In a further aspect, a tobacco plant with enhanced NUE comprises a higher amount of at least three metabolites in at least one tissue. In a further aspect, a tobacco plant with enhanced NUE comprises a higher amount of at least four metabolites in at least one tissue. In a further aspect, a tobacco plant with enhanced NUE comprises a higher amount of at least five metabolites in at least one tissue. In a further aspect, a tobacco plant with enhanced NUE comprises a higher amount of at least one metabolite in two tissues. In a further aspect, a tobacco plant with enhanced NUE comprises a higher amount of at least two metabolites in at least two tissues. In a further aspect, a tobacco plant with enhanced NUE comprises a higher amount of at least three metabolites in at least two tissues. In a further aspect, a tobacco plant with enhanced NUE comprises a higher amount of at least four metabolites in at least two tissues. In a further aspect, a tobacco plant with enhanced NUE comprises a higher amount of at least five metabolites in at least two tissues. In a further aspect, a tobacco plant with enhanced NUE comprises a higher amount of at least one metabolite in three tissues. In a further aspect, a tobacco plant with enhanced NUE comprises a higher amount of at least two metabolites in at least three tissues. In a further aspect, a tobacco plant with enhanced NUE comprises a higher amount of at least three metabolites in at least three tissues. In a further aspect, a tobacco plant with enhanced NUE comprises a higher amount of at least four metabolites in at least three tissues. In a further aspect, a tobacco plant with enhanced NUE comprises a higher amount of at least five metabolites in at least three tissues. In a further aspect, a tobacco plant with enhanced NUE comprises a higher amount of at least one metabolite in four tissues. In a further aspect, a tobacco plant with enhanced NUE comprises a higher amount of at least two metabolites in at least four tissues. In a further aspect, a tobacco plant with enhanced NUE comprises a higher amount of at least three metabolites in at least four tissues. In a further aspect, a tobacco plant with enhanced NUE comprises a higher amount of at least four metabolites in at least four tissues. In a further aspect, a tobacco plant with enhanced NUE comprises a higher amount of at least five metabolites in at least four tissues. In a further aspect, a tobacco plant with enhanced NUE comprises a higher amount of at least one metabolite in five tissues. In a further aspect, a tobacco plant with enhanced NUE comprises a higher amount of at least two metabolites in at least five tissues. In a further aspect, a tobacco plant with enhanced NUE comprises a higher amount of at least three metabolites in at least five tissues. In a further aspect, a tobacco plant with enhanced NUE comprises a higher amount of at least four metabolites in at least five tissues. In a further aspect, a tobacco plant with enhanced NUE comprises a higher amount of at least five metabolites in at least five tissues.

In another aspect of a method provided herein, a tobacco plant with enhanced NUE comprises decreased NUE as compared to a tobacco line that comprises an equal amount of at least one metabolite in at least one tissue. In a further aspect, a tobacco plant with enhanced NUE comprises an equal amount of at least two metabolites in at least one tissue. In a further aspect, a tobacco plant with enhanced NUE comprises an equal amount of at least three metabolites in at least one tissue. In a further aspect, a tobacco plant with enhanced NUE comprises an equal amount of at least four metabolites in at least one tissue. In a further aspect, a tobacco plant with enhanced NUE comprises an equal amount of at least five metabolites in at least one tissue. In a further aspect, a tobacco plant with enhanced NUE comprises an equal amount of at least one metabolite in two tissues. In a further aspect, a tobacco plant with enhanced NUE comprises an equal amount of at least two metabolites in at least two tissues. In a further aspect, a tobacco plant with enhanced NUE comprises an equal amount of at least three metabolites in at least two tissues. In a further aspect, a tobacco plant with enhanced NUE comprises an equal amount of at least four metabolites in at least two tissues. In a further aspect, a tobacco plant with enhanced NUE comprises an equal amount of at least five metabolites in at least two tissues. In a further aspect, a tobacco plant with enhanced NUE comprises an equal amount of at least one metabolite in three tissues. In a further aspect, a tobacco plant with enhanced NUE comprises an equal amount of at least two metabolites in at least three tissues. In a further aspect, a tobacco plant with enhanced NUE comprises an equal amount of at least three metabolites in at least three tissues. In a further aspect, a tobacco plant with enhanced NUE comprises an equal amount of at least four metabolites in at least three tissues. In a further aspect, a tobacco plant with enhanced NUE comprises an equal amount of at least five metabolites in at least three tissues. In a further aspect, a tobacco plant with enhanced NUE comprises an equal amount of at least one metabolite in four tissues. In a further aspect, a tobacco plant with enhanced NUE comprises an equal amount of at least two metabolites in at least four tissues. In a further aspect, a tobacco plant with enhanced NUE comprises an equal amount of at least three metabolites in at least four tissues. In a further aspect, a tobacco plant with enhanced NUE comprises an equal amount of at least four metabolites in at least four tissues. In a further aspect, a tobacco plant with enhanced NUE comprises an equal amount of at least five metabolites in at least four tissues. In a further aspect, a tobacco plant with enhanced NUE comprises an equal amount of at least one metabolite in five tissues. In a further aspect, a tobacco plant with enhanced NUE comprises an equal amount of at least two metabolites in at least five tissues. In a further aspect, a tobacco plant with enhanced NUE comprises an equal amount of at least three metabolites in at least five tissues. In a further aspect, a tobacco plant with enhanced NUE comprises an equal amount of at least four metabolites in at least five tissues. In a further aspect, a tobacco plant with enhanced NUE comprises an equal amount of at least five metabolites in at least five tissues.

In another aspect, a method provided herein comprises determining the amount of a metabolite using a method selected from the group consisting of liquid chromatography/mass spectrometry (LC/MS), high-performance liquid chromatography (HPLC), ultra HPLC (UHPLC), mass spectrometry (MS), tandem mass spectrometry (MS/MS), matrix assisted laser desorption/ionization mass spectrometry (MALDI-MS), X-ray fluorescence spectrometry (XRF), ion chromatography (IC), gas chromatography (GC), gas chromatography/mass spectrometry (GC/MS), capillary electrophoresis/mass spectrometry (CE-MS), ion mobility spectrometry/mass spectrometry (IMS/MS), X-ray diffraction, nuclear magnetic resonance (NMR), emission spectral analysis, polarography, ultraviolet-visual spectrometry, infrared spectrometry, and thin-layer chromatography.

In one aspect, the present specification provides for, and includes, a method of determining the NUE of a tobacco line using a metabolite signature comprising isolating a metabolite signature from a tobacco plant of a tobacco line, determining the amount of each metabolite comprising a metabolite signature, and determining the NUE of a tobacco line by comparing the metabolite signature to a control metabolite signature from a control tobacco line comprising a known NUE. In a further aspect of this method, NUE comprises enhanced NUE as compared to a control tobacco line. In another aspect of this method, a metabolite signature is isolated from a plant tissue selected from the group consisting of root tissue, leaf tissue, floral tissue, meristem tissue, and stem tissue.

In an aspect of a method provided herein, a metabolite signature comprises at least two metabolites. In a further aspect, a metabolite signature comprises at least three metabolites. In a further aspect, a metabolite signature comprises at least four metabolites. In a further aspect, a metabolite signature comprises at least five metabolites. In a further aspect, a metabolite signature comprises at least six metabolites. In a further aspect, a metabolite signature comprises at least seven metabolites. In a further aspect, a metabolite signature comprises at least eight metabolites. In a further aspect, a metabolite signature comprises at least nine metabolites. In a further aspect, a metabolite signature comprises at least ten metabolites. In a further aspect, a metabolite signature comprises at least eleven metabolites. In a further aspect, a metabolite signature comprises at least twelve metabolites. In a further aspect, a metabolite signature comprises at least thirteen metabolites. In a further aspect, a metabolite signature comprises at least fourteen metabolites. In a further aspect, a metabolite signature comprises at least fifteen metabolites. In a further aspect, a metabolite signature comprises at least twenty metabolites. In a further aspect, a metabolite signature comprises at least twenty-five metabolites. In a further aspect, a metabolite signature comprises at least thirty metabolites. In a further aspect, a metabolite signature comprises at least thirty-five metabolites. In a further aspect, a metabolite signature comprises at least forty metabolites. In a further aspect, a metabolite signature comprises at least forty-five metabolites. In a further aspect, a metabolite signature comprises at least fifty metabolites. In a further aspect, metabolite signature comprises between two and fifty metabolites. In a further aspect, metabolite signature comprises between three and forty-five metabolites. In a further aspect, metabolite signature comprises between three and forty metabolites. In a further aspect, metabolite signature comprises between four and thirty-five metabolites. In a further aspect, metabolite signature comprises between five and thirty metabolites. In a further aspect, metabolite signature comprises between six and twenty-five metabolites. In a further aspect, metabolite signature comprises between seven and twenty metabolites. In a further aspect, metabolite signature comprises between eight and fifteen metabolites. In a further aspect, metabolite signature comprises between nine and fourteen metabolites. In a further aspect, metabolite signature comprises between ten and thirteen metabolites. In a further aspect, metabolite signature comprises between ten and twelve metabolites.

In one aspect, the current specification provides for, and includes, a method of breeding a tobacco line comprising a metabolite signature associated with enhanced NUE comprising determining the metabolite signature of a first tobacco plant from a first tobacco line, where a first tobacco plant comprises enhanced NUE as compared to a control tobacco plant lacking the metabolite signature, crossing the first plant with a second plant of a second tobacco line, and obtaining at least one progeny seed from the crossing, where a progeny plant grown from at least one progeny seed comprises the metabolite signature, and where the progeny plant comprises enhanced NUE as compared to a control plant lacking the metabolite signature. In a further aspect of this method, a progeny plant is crossed to third plant that is from the first tobacco line. In another aspect, a first tobacco line is selected from the group consisting of MD609, MD601, Banket A1, K326, K346, K358, K394, K399, K730, NC196, NC37NF, NC471, NC55, NC92, NC2326, NC95, NC925. In another aspect, a second tobacco line is selected from the group consisting of TN86, TN86LC, TN90, TN90LC, TN97, TN97LC. In a further aspect, a metabolite signature comprises a leaf metabolite signature. In a further aspect, a metabolite signature comprises a root metabolite signature. In another aspect, a metabolite signature comprises higher amounts of 4-guanidinobutanoate, syringaldehyde, thiamin, p-hydroxybenzaldehyde, X-23454, X-23580, X-23852, or any combination thereof as compared to the metabolite signature of a control tobacco plant. In another aspect, a metabolite signature comprises lower amounts of X-2357, N-acetylmuramate, X-23319, X-23852, X-23330, alpha-ketoglutarate, X-21756, 4-hydroxy-2-oxoglutaric acid, X-23937, X-23916, 1-methyladenine, X-23453, X-11429, X-21796, N'-methylnicotinamide, cotinine, X-23389, N-acetylarginine, N-23366, N-acetylphenylalanine, naringenin, or any combination thereof as compared to the metabolite signature of a control tobacco plant.

In another aspect, a method provided herein comprises tobacco plants comprising enhanced NUE where enhanced NUE comprises an increased partial factor productivity (PFP) compared to a tobacco plant lacking enhanced NUE grown in the same conditions. In a further aspect, enhanced NUE comprises an increased agronomic efficiency (AE) compared to a tobacco plant lacking enhanced NUE grown in the same conditions. In a further aspect, enhanced NUE comprises an increased recovery efficiency (RE) compared to a tobacco plant lacking enhanced NUE grown in the same conditions. In a further aspect, enhanced NUE comprises an increased physiological efficiency (PE) compared to a tobacco plant lacking said enhanced NUE grown in the same conditions. In a further aspect, enhanced NUE comprises an increased internal efficiency (IE) compared to a tobacco plant lacking said enhanced NUE grown in the same conditions.

In one aspect, the present specification provides for, and includes, a method of selecting a tobacco plant comprising obtaining a population of tobacco plants, isolating at least one metabolite associated with enhanced NUE from at least one tobacco plant from the population of tobacco plants, and selecting at least one tobacco plant that comprises a higher amount of at least one metabolite as compared to a control tobacco plant. In a further aspect of this method, a selected tobacco plant comprises enhanced NUE as compared to a control tobacco plant. In a further aspect of this method, at least one metabolite is selected from the group consisting of 4-guanidinobutanoate, syringaldehyde, thiamin, p-hydroxybenzaldehyde, X-23454, X-23580, X-23852, or any combination thereof. In a further aspect of this method, a metabolite is isolated from a plant tissue selected from the group consisting of root tissue, leaf tissue, floral tissue, meristem tissue, and stem tissue.

In one aspect, the present specification provides for, and includes, a method of selecting a tobacco plant comprising obtaining a population of tobacco plants, isolating at least one metabolite associated with enhanced NUE from at least one tobacco plant from the population of tobacco plants, and selecting at least one tobacco plant that comprises a lower amount of at least one metabolite as compared to a control tobacco plant. In a further aspect of this method, a selected tobacco plant comprises a enhanced NUE as compared to a control tobacco plant. In a further aspect of this method, at least one metabolite is selected from the group consisting of X-2357, N-acetylmuramate, X-23319, X-23852, X-23330, alpha-ketoglutarate, X-21756, 4-hydroxy-2-oxoglutaric acid, X-23937, X-23916, 1-methyladenine, X-23453, X-11429, X-21796, N'-methylnicotinamide, cotinine, X-23389, N-acetylarginine, N-23366, N-acetylphenylalanine, naringenin, or any combination thereof. In a further aspect of this method, a metabolite is isolated from a plant tissue selected from the group consisting of root tissue, leaf tissue, floral tissue, meristem tissue, and stem tissue.

In one aspect, the present specification provides for, and includes, a method of screening a tobacco plant for a first metabolite signature associated with enhanced NUE comprising isolating a first metabolite signature from a tobacco plant, determining the amount of at least one metabolite that comprises that first metabolite signature, comparing the first metabolite signature to a second metabolite signature of a control tobacco plant comprising a known NUE, and determining if the first metabolite signature is associated with enhanced NUE.

In one aspect, the present specification provides for, and includes, a modified tobacco seed, or tobacco plant grown therefrom, comprising a cisgenic polynucleotide comprising a heterologous promoter operably linked to a coding region, where the modified tobacco plant comprises enhanced nitrogen utilization efficiency as compared to an unmodified control tobacco plant lacking the cisgenic polynucleotide when grown under the same conditions. In a further aspect, a modified tobacco seed or tobacco plant comprises a heterologous promoter that is selected from the group consisting of a constitutive promoter, an inducible promoter, a tissue-preferred promoter, and a tissue-specific promoter. In another aspect, a heterologous promoter comprises a polynucleotide sequence from a tobacco genome. In another aspect, a heterologous promoter comprises a polynucleotide sequence from a plant genome. In another aspect, a tissue-preferred promoter is a leaf-preferred promoter. In another aspect, a tissue-preferred promoter is a root-preferred promoter. In a further aspect, a modified tobacco seed or tobacco plant is of a Burley variety.

In a further aspect, a modified tobacco seed or tobacco plant of the present specification comprises lower amounts of TSNAs as compared to an unmodified tobacco plant lacking the cisgenic polynucleotide when grown under the same conditions. In a further aspect, a modified tobacco seed or tobacco plant comprises lower amount N'-nitrosonornicotine (NNN) as compared to an unmodified tobacco plant lacking the cisgenic polynucleotide when grown under the same conditions. In a further aspect, a modified tobacco seed or tobacco plant comprises lower amount 4-methylnitrosoamino-1-(3-pyridyl)-1-butanone (NNK) as compared to an unmodified tobacco plant lacking the cisgenic polynucleotide when grown under the same conditions. In a further aspect, a modified tobacco seed or tobacco plant comprises lower amount N'-nitrosoanatabine (NAT) as compared to an unmodified tobacco plant lacking the cisgenic polynucleotide when grown under the same conditions. In a further aspect, a modified tobacco seed or tobacco plant comprises lower amount N'-nitrosoanabasine (NAB) as compared to an unmodified tobacco plant lacking the cisgenic polynucleotide when grown under the same conditions. In a further aspect, a modified tobacco seed or tobacco plant comprises lower amounts of alkaloids as compared to an unmodified tobacco plant lacking the cisgenic polynucleotide when grown under the same conditions. In a further aspect, a modified tobacco seed or tobacco plant comprises lower amounts of nicotine as compared to an unmodified tobacco plant lacking the cisgenic polynucleotide when grown under the same conditions. In a further aspect, a modified tobacco seed or tobacco plant comprises lower amounts of nornicotine as compared to an unmodified tobacco plant lacking the cisgenic polynucleotide when grown under the same conditions. In a further aspect, a modified tobacco seed or tobacco plant comprises lower amounts of anabasine as compared to an unmodified tobacco plant lacking the cisgenic polynucleotide when grown under the same conditions. In a further aspect, a modified tobacco seed or tobacco plant comprises lower amounts of anatabine as compared to an unmodified tobacco plant lacking the cisgenic polynucleotide when grown under the same conditions.

In a further aspect, a modified tobacco seed or tobacco plant of the present specification comprises a coding region encoding a polypeptide that is at least 70% identical or similar to a sequence selected from the group consisting of SEQ ID NOs:1 to 8. In a further aspect, a modified tobacco seed or tobacco plant comprises a coding region encoding a polypeptide that is at least 75% identical or similar to a sequence selected from the group consisting of SEQ ID NOs:1 to 8. In a further aspect, a modified tobacco seed or tobacco plant comprises a coding region encoding a polypeptide that is at least 80% identical or similar to a sequence selected from the group consisting of SEQ ID NOs:1 to 8. In a further aspect, a modified tobacco seed or tobacco plant comprises a coding region encoding a polypeptide that is at least 85% identical or similar to a sequence selected from the group consisting of SEQ ID NOs:1 to 8. In a further aspect, a modified tobacco seed or tobacco plant comprises a coding region encoding a polypeptide that is at least 90% identical or similar to a sequence selected from the group consisting of SEQ ID NOs:1 to 8. In a further aspect, a modified tobacco seed or tobacco plant comprises a coding region encoding a polypeptide that is at least 95% identical or similar to a sequence selected from the group consisting of SEQ ID NOs:1 to 8. In a further aspect, a modified tobacco seed or tobacco plant comprises a coding region encoding a polypeptide that is at least 96% identical or similar to a sequence selected from the group consisting of SEQ ID NOs:1 to 8. In a further aspect, a modified tobacco seed or tobacco plant comprises a coding region encoding a polypeptide that is at least 97% identical or similar to a sequence selected from the group consisting of SEQ ID NOs:1 to 8. In a further aspect, a modified tobacco seed or tobacco plant comprises a coding region encoding a polypeptide that is at least 98% identical or similar to a sequence selected from the group consisting of SEQ ID NOs:1 to 8. In a further aspect, a modified tobacco seed or tobacco plant comprises a coding region encoding a polypeptide that is at least 99% identical or similar to a sequence selected from the group consisting of SEQ ID NOs:1 to 8. In a further aspect, a modified tobacco seed or tobacco plant comprises a coding region encoding a polypeptide that is 100% identical to a sequence selected from the group consisting of SEQ ID NOs:1 to 8.

In a further aspect, a modified tobacco seed or tobacco plant of the present specification comprises a coding region encoding a polynucleotide that is at least 70% identical or similar to a sequence selected from the group consisting of SEQ ID NOs:9 to 16. In a further aspect, a modified tobacco seed or tobacco plant comprises a coding region encoding a polynucleotide that is at least 75% identical or similar to a sequence selected from the group consisting of SEQ ID NOs:9 to 16. In a further aspect, a modified tobacco seed or tobacco plant comprises a coding region encoding a polynucleotide that is at least 80% identical or similar to a sequence selected from the group consisting of SEQ ID NOs:9 to 16. In a further aspect, a modified tobacco seed or tobacco plant comprises a coding region encoding a polynucleotide that is at least 85% identical or similar to a sequence selected from the group consisting of SEQ ID NOs:9 to 16. In a further aspect, a modified tobacco seed or tobacco plant comprises a coding region encoding a polynucleotide that is at least 90% identical or similar to a sequence selected from the group consisting of SEQ ID NOs:9 to 16. In a further aspect, a modified tobacco seed or tobacco plant comprises a coding region encoding a polynucleotide that is at least 95% identical or similar to a sequence selected from the group consisting of SEQ ID NOs:9 to 16. In a further aspect, a modified tobacco seed or tobacco plant comprises a coding region encoding a polynucleotide that is at least 96% identical or similar to a sequence selected from the group consisting of SEQ ID NOs:9 to 16. In a further aspect, a modified tobacco seed or tobacco plant comprises a coding region encoding a polynucleotide that is at least 97% identical or similar to a sequence selected from the group consisting of SEQ ID NOs:9 to 16. In a further aspect, a modified tobacco seed or tobacco plant comprises a coding region encoding a polynucleotide that is at least 98% identical or similar to a sequence selected from the group consisting of SEQ ID NOs:9 to 16. In a further aspect, a modified tobacco seed or tobacco plant comprises a coding region encoding a polynucleotide that is at least 99% identical or similar to a sequence selected from the group consisting of SEQ ID NOs:9 to 16. In a further aspect, a modified tobacco seed or tobacco plant comprises a coding region encoding a polynucleotide that is identical to a sequence selected from the group consisting of SEQ ID NOs:9 to 16.

In a further aspect, a modified tobacco seed or tobacco plant comprises a leaf-preferred promoter that is encoded by a sequence at least 70% identical to a sequence selected from the group consisting of SEQ ID NOs:17 to 19, or a functional fragment thereof. In a further aspect, a leaf-preferred promoter is encoded by a sequence at least 75% identical to a sequence selected from the group consisting of SEQ ID NOs:17 to 19, or a functional fragment thereof. In a further aspect, a leaf-preferred promoter is encoded by a sequence at least 80% identical to a sequence selected from the group consisting of SEQ ID NOs:17 to 19, or a functional fragment thereof. In a further aspect, a leaf-preferred promoter is encoded by a sequence at least 85% identical to a sequence selected from the group consisting of SEQ ID NOs:17 to 19, or a functional fragment thereof. In a further aspect, a leaf-preferred promoter is encoded by a sequence at least 90% identical to a sequence selected from the group consisting of SEQ ID NOs:17 to 19, or a functional fragment thereof. In a further aspect, a leaf-preferred promoter is encoded by a sequence at least 95% identical to a sequence selected from the group consisting of SEQ ID NOs:17 to 19, or a functional fragment thereof. In a further aspect, a leaf-preferred promoter is encoded by a sequence at least 96% identical to a sequence selected from the group consisting of SEQ ID NOs:17 to 19, or a functional fragment thereof. In a further aspect, a leaf-preferred promoter is encoded by a sequence at least 97% identical to a sequence selected from the group consisting of SEQ ID NOs:17 to 19, or a functional fragment thereof. In a further aspect, a leaf-preferred promoter is encoded by a sequence at least 98% identical to a sequence selected from the group consisting of SEQ ID NOs:17 to 19, or a functional fragment thereof. In a further aspect, a leaf-preferred promoter is encoded by a sequence at least 99% identical to a sequence selected from the group consisting of SEQ ID NOs:17 to 19, or a functional fragment thereof. In a further aspect, a leaf-preferred promoter is encoded by to a sequence selected from the group consisting of SEQ ID NOs:17 to 19, or a functional fragment thereof.

In a further aspect, a modified tobacco seed or tobacco plant comprises a root-preferred promoter that is encoded by a sequence at least 70% identical to a sequence selected from the group consisting of SEQ ID NOs:20 to 24, or a functional fragment thereof. In a further aspect, a leaf-preferred promoter is encoded by a sequence at least 75% identical to a sequence selected from the group consisting of SEQ ID NOs:20 to 24, or a functional fragment thereof. In a further aspect, a leaf-preferred promoter is encoded by a sequence at least 80% identical to a sequence selected from the group consisting of SEQ ID NOs:20 to 24, or a functional fragment thereof. In a further aspect, a leaf-preferred promoter is encoded by a sequence at least 85% identical to a sequence selected from the group consisting of SEQ ID NOs:20 to 24, or a functional fragment thereof. In a further aspect, a leaf-preferred promoter is encoded by a sequence at least 90% identical to a sequence selected from the group consisting of SEQ ID NOs:20 to 24, or a functional fragment thereof. In a further aspect, a leaf-preferred promoter is encoded by a sequence at least 95% identical to a sequence selected from the group consisting of SEQ ID NOs:20 to 24, or a functional fragment thereof. In a further aspect, a leaf-preferred promoter is encoded by a sequence at least 96% identical to a sequence selected from the group consisting of SEQ ID NOs:20 to 24, or a functional fragment thereof. In a further aspect, a leaf-preferred promoter is encoded by a sequence at least 97% identical to a sequence selected from the group consisting of SEQ ID NOs:20 to 24, or a functional fragment thereof. In a further aspect, a leaf-preferred promoter is encoded by a sequence at least 98% identical to a sequence selected from the group consisting of SEQ ID NOs:20 to 24, or a functional fragment thereof. In a further aspect, a leaf-preferred promoter is encoded by a sequence at least 99% identical to a sequence selected from the group consisting of SEQ ID NOs:20 to 24, or a functional fragment thereof. In a further aspect, a leaf-preferred promoter is encoded by to a sequence selected from the group consisting of SEQ ID NOs:20 to 24, or a functional fragment thereof.

In a further aspect, a modified tobacco plant of the present specification comprising a cisgenic polynucleotide comprises higher levels of a metabolite selected from the group consisting of 4-guanidinobutanoate, syringaldehyde, thiamin, and p-hydroxybenzaldehyde in root tissue as compared to an unmodified tobacco plant lacking the cisgenic polynucleotide when grown under the same conditions.

In a further aspect, a modified tobacco plant of the present specification comprising a cisgenic polynucleotide comprises higher levels of a metabolite selected from the group consisting of 4-guanidinobutanoate, X-23454, X-23580, and X-23852 in leaf tissue as compared to an unmodified tobacco plant lacking the cisgenic polynucleotide when grown under the same conditions.

In a further aspect, a modified tobacco plant of the present specification comprising a cisgenic polynucleotide comprises lower levels of a metabolite selected from the group consisting of X-2357, N-acetylmuramate, X-23319, X-23852, X-23330, alpha-ketoglutarate, X-21756, 4-hydroxy-2-oxoglutaric acid, X-23937, X-23916, and 1-methyladenine in root tissue as compared to an unmodified tobacco plant lacking the cisgenic polynucleotide when grown under the same conditions.

In a further aspect, a modified tobacco plant of the present specification comprising a cisgenic polynucleotide comprises lower levels of a metabolite selected from the group consisting of X-23453, X-21756, X-11429, X-21796, N'-methylnicotinamide, cotinine, X-23389, N-acetylarginine, N-23366, N-acetylphenylalanine, and naringenin in leaf tissue as compared to an unmodified tobacco plant lacking the cisgenic polynucleotide when grown under the same conditions.

In one aspect, the present specification provides for, and includes, a recombinant DNA construct comprising a heterologous promoter operably linked to a polynucleotide encoding a polypeptide at least 70% identical or similar to a polypeptide selected from the group consisting of SEQ ID NOs:1 to 8. In a further aspect, a recombinant DNA construct comprises a polynucleotide encoding a polypeptide at least 75% identical or similar to a polypeptide selected from the group consisting of SEQ ID NOs:1 to 8. In a further aspect, a recombinant DNA construct comprises a polynucleotide encoding a polypeptide at least 80% identical or similar to a polypeptide selected from the group consisting of SEQ ID NOs:1 to 8. In a further aspect, a recombinant DNA construct comprises a polynucleotide encoding a polypeptide at least 85% identical or similar to a polypeptide selected from the group consisting of SEQ ID NOs:1 to 8. In a further aspect, a recombinant DNA construct comprises a polynucleotide encoding a polypeptide at least 90% identical or similar to a polypeptide selected from the group consisting of SEQ ID NOs:1 to 8. In a further aspect, a recombinant DNA construct comprises a polynucleotide encoding a polypeptide at least 95% identical or similar to a polypeptide selected from the group consisting of SEQ ID NOs:1 to 8. In a further aspect, a recombinant DNA construct comprises a polynucleotide encoding a polypeptide at least 96% identical or similar to a polypeptide selected from the group consisting of SEQ ID NOs:1 to 8. In a further aspect, a recombinant DNA construct comprises a polynucleotide encoding a polypeptide at least 97% identical or similar to a polypeptide selected from the group consisting of SEQ ID NOs:1 to 8. In a further aspect, a recombinant DNA construct comprises a polynucleotide encoding a polypeptide at least 98% identical or similar to a polypeptide selected from the group consisting of SEQ ID NOs:1 to 8. In a further aspect, a recombinant DNA construct comprises a polynucleotide encoding a polypeptide at least 99% identical or similar to a polypeptide selected from the group consisting of SEQ ID NOs:1 to 8. In a further aspect, a recombinant DNA construct comprises a polynucleotide encoding a polypeptide 100% identical to a polypeptide selected from the group consisting of SEQ ID NOs:1 to 8.

In one aspect, the present specification provides for, and includes, cured tobacco material, or a tobacco product comprising the cured tobacco material, where the cured tobacco material is made from a tobacco plant comprising a cisgenic polynucleotide comprising a heterologous promoter operably linked to a coding region, where the modified tobacco plant comprises enhanced nitrogen utilization efficiency as compared to an unmodified control tobacco plant lacking the cisgenic polynucleotide when grown under the same conditions.

In one aspect, the present specification provides for, and includes, a greenhouse, growth chamber, or field comprising the modified tobacco seed or plant disclosed herein. In one aspect, the present specification provides for, and includes, a method to grow tobacco plants of the present specification in a greenhouse, growth chamber, or field.

In one aspect, the present specification provides for, and includes, a modified tobacco seed, or tobacco plant grown therefrom, comprising at least one mutation in an endogenous locus encoding a polypeptide selected from the group consisting of SEQ ID NOs: 25 to 40, and where a modified tobacco seed or tobacco plant comprises enhanced nitrogen utilization efficiency as compared to an unmodified control tobacco plant lacking at least one mutation when grown under the same conditions. In a further aspect, a mutation in an endogenous locus is selected from the group consisting of an insertion, a deletion, a substitution, and an inversion. In another aspect, a mutation in an endogenous locus is a silent mutation, a non-silent mutation, or a null mutation. In a further aspect, a modified tobacco seed or modified tobacco plant is of a Burley variety.

In a further aspect, a modified tobacco plant comprises higher levels of a metabolite selected from the group consisting of 4-guanidinobutanoate, syringaldehyde, thiamin, and p-hydroxybenzaldehyde in root tissue as compared to an unmodified tobacco plant when grown under the same conditions. In a further aspect, a modified tobacco plant comprises higher levels of a metabolite selected from the group consisting of 4-guanidinobutanoate, X-23454, X-23580, and X-23852 in leaf tissue as compared to an unmodified tobacco plant when grown under the same conditions. In a further aspect, a modified tobacco plant comprises lower levels of a metabolite selected from the group consisting of X-2357, N-acetylmuramate, X-23319, X-23852, X-23330, alpha-ketoglutarate, X-21756, 4-hydroxy-2-oxoglutaric acid, X-23937, X-23916, and 1-methyladenine in root tissue as compared to an unmodified tobacco plant lacking when grown under the same conditions. In a further aspect, a modified tobacco plant comprises lower levels of a metabolite selected from the group consisting of X-23453, X-21756, X-11429, X-21796, N'-methylnicotinamide, cotinine, X-23389, N-acetylarginine, N-23366, N-acetylphenylalanine, and naringenin in leaf tissue as compared to an unmodified tobacco plant when grown under the same conditions.

In one aspect, the present specification provides for, and includes, a recombinant DNA construct comprising a heterologous promoter operably linked to a guide RNA comprising at least 18 contiguous nucleotides identical or complementary to a polynucleotide encoding a polypeptide selected from the group consisting of SEQ ID NOs:25 to 40. In a further aspect, a guide RNA comprises at least 19 contiguous nucleotides identical or complementary to a polynucleotide encoding a polypeptide selected from the group consisting of SEQ ID NOs:25 to 40. In a further aspect, a guide RNA comprises at least 20 contiguous nucleotides identical or complementary to a polynucleotide encoding a polypeptide selected from the group consisting of SEQ ID NOs:25 to 40. In a further aspect, a guide RNA comprises at least 21 contiguous nucleotides identical or complementary to a polynucleotide encoding a polypeptide selected from the group consisting of SEQ ID NOs:25 to 40. In a further aspect, a guide RNA comprises at least 22 contiguous nucleotides identical or complementary to a polynucleotide encoding a polypeptide selected from the group consisting of SEQ ID NOs:25 to 40. In a further aspect, a guide RNA comprises at least 23 contiguous nucleotides identical or complementary to a polynucleotide encoding a polypeptide selected from the group consisting of SEQ ID NOs:25 to 40. In a further aspect, a guide RNA comprises at least 24 contiguous nucleotides identical or complementary to a polynucleotide encoding a polypeptide selected from the group consisting of SEQ ID NOs:25 to 40. In a further aspect, a guide RNA comprises at least 25 contiguous nucleotides identical or complementary to a polynucleotide encoding a polypeptide selected from the group consisting of SEQ ID NOs:25 to 40. In a further aspect, a guide RNA comprises at least 26 contiguous nucleotides identical or complementary to a polynucleotide encoding a polypeptide selected from the group consisting of SEQ ID NOs:25 to 40. In a further aspect, a guide RNA comprises at least 27 contiguous nucleotides identical or complementary to a polynucleotide encoding a polypeptide selected from the group consisting of SEQ ID NOs:25 to 40. In a further aspect, a guide RNA comprises at least 28 contiguous nucleotides 100% identical or complementary to a polynucleotide encoding a polypeptide selected from the group consisting of SEQ ID NOs:25 to 40.

In one aspect, the present specification provides for, and includes, cured tobacco material, or a tobacco product comprising the cured tobacco material, where the cured tobacco material is made from a tobacco plant comprising at least one mutation in an endogenous locus encoding a polypeptide selected from the group consisting of SEQ ID NOs:25 to 40, and where the modified tobacco seed or tobacco plant comprises enhanced NUE as compared to an unmodified control tobacco plant lacking at least one mutation when grown under the same conditions. In a further aspect, a tobacco plant comprises at least two mutations in an endogenous locus encoding a polypeptide selected from the group consisting of SEQ ID NOs:25 to 40. In a further aspect, a tobacco plant comprises at least three mutations in an endogenous locus encoding a polypeptide selected from the group consisting of SEQ ID NOs:25 to 40. In a further aspect, a tobacco plant comprises at least four mutations in an endogenous locus encoding a polypeptide selected from the group consisting of SEQ ID NOs:25 to 40. In a further aspect, a tobacco plant comprises at least five mutations in an endogenous locus encoding a polypeptide selected from the group consisting of SEQ ID NOs:25 to 40. In a further aspect, a tobacco plant comprises at least six mutations in an endogenous locus encoding a polypeptide selected from the group consisting of SEQ ID NOs:25 to 40. In a further aspect, a tobacco plant comprises at least seven mutations in an endogenous locus encoding a polypeptide selected from the group consisting of SEQ ID NOs:25 to 40. In a further aspect, a tobacco plant comprises at least eight mutations in an endogenous locus encoding a polypeptide selected from the group consisting of SEQ ID NOs:25 to 40. In a further aspect, a tobacco plant comprises at least nine mutations in an endogenous locus encoding a polypeptide selected from the group consisting of SEQ ID NOs:25 to 40. In a further aspect, a tobacco plant comprises at least ten mutations in an endogenous locus encoding a polypeptide selected from the group consisting of SEQ ID NOs:25 to 40.

In one aspect, the present specification provides for, and includes, a modified tobacco seed, or tobacco plant grown therefrom, comprising a cisgenic polynucleotide comprising a heterologous promoter operably linked to a polynucleotide encoding a small RNA (sRNA) at least 85% identical or complementary to a polynucleotide selected from the group consisting of SEQ ID NOs:41 to 56, and where the modified tobacco seed or tobacco plant comprises enhanced NUE as compared to an unmodified control tobacco plant lacking the cisgenic polynucleotide when grown under the same conditions. In a further aspect, a cisgenic polynucleotide comprises a polynucleotide encoding a sRNA at least 90% identical or complementary to a polynucleotide selected from the group consisting of SEQ ID NOs:41 to 56. In a further aspect, a cisgenic polynucleotide comprises a polynucleotide encoding a sRNA at least 91% identical or complementary to a polynucleotide selected from the group consisting of SEQ ID NOs:41 to 56. In a further aspect, a cisgenic polynucleotide comprises a polynucleotide encoding a sRNA at least 92% identical or complementary to a polynucleotide selected from the group consisting of SEQ ID NOs:41 to 56. In a further aspect, a cisgenic polynucleotide comprises a polynucleotide encoding a sRNA at least 93% identical or complementary to a polynucleotide selected from the group consisting of SEQ ID NOs:41 to 56. In a further aspect, a cisgenic polynucleotide comprises a polynucleotide encoding a sRNA at least 94% identical or complementary to a polynucleotide selected from the group consisting of SEQ ID NOs:41 to 56. In a further aspect, a cisgenic polynucleotide comprises a polynucleotide encoding a sRNA at least 95% identical or complementary to a polynucleotide selected from the group consisting of SEQ ID NOs:41 to 56. In a further aspect, a cisgenic polynucleotide comprises a polynucleotide encoding a sRNA at least 96% identical or complementary to a polynucleotide selected from the group consisting of SEQ ID NOs:41 to 56. In a further aspect, a cisgenic polynucleotide comprises a polynucleotide encoding a sRNA at least 97% identical or complementary to a polynucleotide selected from the group consisting of SEQ ID NOs:41 to 56. In a further aspect, a cisgenic polynucleotide comprises a polynucleotide encoding a sRNA at least 98% identical or complementary to a polynucleotide selected from the group consisting of SEQ ID NOs:41 to 56. In a further aspect, a cisgenic polynucleotide comprises a polynucleotide encoding a sRNA at least 99% identical or complementary to a polynucleotide selected from the group consisting of SEQ ID NOs:41 to 56. In a further aspect, a cisgenic polynucleotide comprises a polynucleotide encoding a sRNA 100% identical or complementary to a polynucleotide selected from the group consisting of SEQ ID NOs:41 to 56. In a further aspect, a heterologous promoter is selected from the group consisting of a constitutive promoter, an inducible promoter, a tissue-preferred promoter, and a tissue-specific promoter. In a further aspect, a tissue-preferred promoter is a leaf-preferred promoter. In a further aspect, a tissue-preferred promoter is a root-preferred promoter.

In a further aspect, a sRNA having at least 18 nucleotides. In a further aspect, a sRNA comprises at least 19 nucleotides. In a further aspect, a sRNA comprises at least 20 nucleotides. In a further aspect, a sRNA comprises at least 21 nucleotides. In a further aspect, a sRNA comprises at least 22 nucleotides. In a further aspect, a sRNA comprises at least 23 nucleotides. In a further aspect, a sRNA comprises at least 24 nucleotides. In a further aspect, a sRNA comprises at least 25 nucleotides. In a further aspect, a sRNA comprises at least 26 nucleotides. In a further aspect, a sRNA comprises at least 27 nucleotides. In a further aspect, a sRNA comprises at least 28 nucleotides. In a further aspect, a sRNA is selected from the group consisting of a microRNA, a small-interfering RNA (siRNA), a trans-acting siRNA, and precursors thereof. In a further aspect, a sRNA down-regulates the expression or translation of a polynucleotide selected from the group consisting of SEQ ID NOs:41 to 56.

In one aspect, the present specification provides for, and includes, a recombinant DNA construct comprising a heterologous promoter operably linked to a polynucleotide encoding a small RNA (sRNA) at least 85% identical or complementary to a polynucleotide selected from the group consisting of SEQ ID NOs:41 to 56. In a further aspect, a recombinant DNA construct comprises a polynucleotide encoding a sRNA at least 90% identical or complementary to a polynucleotide selected from the group consisting of SEQ ID NOs:41 to 56. In a further aspect, a recombinant DNA construct comprises a polynucleotide encoding a sRNA at least 91% identical or complementary to a polynucleotide selected from the group consisting of SEQ ID NOs:41 to 56. In a further aspect, a recombinant DNA construct comprises a polynucleotide encoding a sRNA at least 92% identical or complementary to a polynucleotide selected from the group consisting of SEQ ID NOs:41 to 56. In a further aspect, a recombinant DNA construct comprises a polynucleotide encoding a sRNA at least 93% identical or complementary to a polynucleotide selected from the group consisting of SEQ ID NOs:41 to 56. In a further aspect, a recombinant DNA construct comprises a polynucleotide encoding a sRNA at least 94% identical or complementary to a polynucleotide selected from the group consisting of SEQ ID NOs:41 to 56. In a further aspect, a recombinant DNA construct comprises a polynucleotide encoding a sRNA at least 95% identical or complementary to a polynucleotide selected from the group consisting of SEQ ID NOs:41 to 56. In a further aspect, a recombinant DNA construct comprises a polynucleotide encoding a sRNA at least 96% identical or complementary to a polynucleotide selected from the group consisting of SEQ ID NOs:41 to 56. In a further aspect, a recombinant DNA construct comprises a polynucleotide encoding a sRNA at least 97% identical or complementary to a polynucleotide selected from the group consisting of SEQ ID NOs:41 to 56. In a further aspect, a recombinant DNA construct comprises a polynucleotide encoding a sRNA at least 98% identical or complementary to a polynucleotide selected from the group consisting of SEQ ID NOs:41 to 56. In a further aspect, a recombinant DNA construct comprises a polynucleotide encoding a sRNA at least 99% identical or complementary to a polynucleotide selected from the group consisting of SEQ ID NOs:41 to 56. In a further aspect, a recombinant DNA construct comprises a polynucleotide encoding a sRNA 100% identical or complementary to a polynucleotide selected from the group consisting of SEQ ID NOs:41 to 56.

In one aspect, the present specification provides for, and includes, cured tobacco material, or a tobacco product comprising the cured tobacco material, where the cured tobacco material is made from a tobacco plant comprising a cisgenic polynucleotide comprising a heterologous promoter operably linked to a polynucleotide encoding a sRNA at least 85% identical or complementary to a polynucleotide selected from the group consisting of SEQ ID NOs:41 to 56, and where the modified tobacco seed or tobacco plant comprises enhanced NUE as compared to an unmodified control tobacco plant lacking the cisgenic polynucleotide when grown under the same conditions. In a further aspect, a cisgenic polynucleotide encodes a sRNA at least 90% identical or complementary to a polynucleotide selected from the group consisting of SEQ ID NOs:41 to 56. In a further aspect, a cisgenic polynucleotide encodes a sRNA at least 91% identical or complementary to a polynucleotide selected from the group consisting of SEQ ID NOs:41 to 56. In a further aspect, a cisgenic polynucleotide encodes a sRNA at least 92% identical or complementary to a polynucleotide selected from the group consisting of SEQ ID NOs:41 to 56. In a further aspect, a cisgenic polynucleotide encodes a sRNA at least 93% identical or complementary to a polynucleotide selected from the group consisting of SEQ ID NOs:41 to 56. In a further aspect, a cisgenic polynucleotide encodes a sRNA at least 94% identical or complementary to a polynucleotide selected from the group consisting of SEQ ID NOs:41 to 56. In a further aspect, a cisgenic polynucleotide encodes a sRNA at least 95% identical or complementary to a polynucleotide selected from the group consisting of SEQ ID NOs:41 to 56. In a further aspect, a cisgenic polynucleotide encodes a sRNA at least 96% identical or complementary to a polynucleotide selected from the group consisting of SEQ ID NOs:41 to 56. In a further aspect, a cisgenic polynucleotide encodes a sRNA at least 97% identical or complementary to a polynucleotide selected from the group consisting of SEQ ID NOs:41 to 56. In a further aspect, a cisgenic polynucleotide encodes a sRNA at least 98% identical or complementary to a polynucleotide selected from the group consisting of SEQ ID NOs:41 to 56. In a further aspect, a cisgenic polynucleotide encodes a sRNA at least 99% identical or complementary to a polynucleotide selected from the group consisting of SEQ ID NOs:41 to 56. In a further aspect, a cisgenic polynucleotide encodes a sRNA 100% identical or complementary to a polynucleotide selected from the group consisting of SEQ ID NOs:41 to 56.

In one aspect, the present specification provides for, and includes, a method of enhancing the NUE of a tobacco plant comprising introducing a cisgenic nucleic acid molecule into a tobacco cell, and regenerating a modified tobacco plant from that tobacco cell where the modified tobacco plant comprises enhanced NUE as compared to a tobacco plant lacking the cisgenic nucleic acid molecule. In another aspect, the method further comprises crossing the modified tobacco plant with a second tobacco plant or self-pollinating the modified tobacco plant.

In one aspect, the present specification provides for, and includes, a method of enhancing the NUE of a tobacco plant comprising introducing a modification to a nucleic acid molecule encoding a gene having a sequence selected from the group consisting of SEQ ID NOs:41 to 56 in a tobacco cell and regenerating a modified tobacco plant from the tobacco cell, where the modified tobacco plant comprises enhanced NUE as compared to a tobacco plant lacking the modification. In another aspect, the method further comprises crossing the modified tobacco plant with a second tobacco plant or self-pollinating the modified tobacco plant. In a further aspect, a modification is introducing via a method comprising the use of an RNA-guided nuclease. In a further aspect, a RNA-guided nuclease is selected from the group consisting of a Cas9 nuclease, a Cpf1 nuclease, a CasX nuclease, a CasY nuclease, and functional homologues thereof. In a further aspect, the modification is selected from the group consisting of an insertion, a substitution, an inversion, and a deletion In one aspect, the present specification provides for, and includes, a method of enhancing the NUE of a tobacco plant comprising introducing a nucleic acid encoding a small RNA (sRNA) homologous to at least 18 contiguous nucleic acids of a nucleic acid molecule encoding a gene having a sequence selected from the group consisting of SEQ ID NOs.41 to 56 in a tobacco cell, and regenerating a modified tobacco plant from the tobacco cell, where the modified tobacco plant comprises enhanced NUE as compared to a tobacco plant lacking the sRNA. In another aspect, the method further comprises crossing the modified tobacco plant with a second tobacco plant or self-pollinating the modified tobacco plant. In a further aspect, the method comprises introducing a sRNA selected from the group consisting of a microRNA, a small-interfering RNA (siRNA), a trans-acting siRNA, and precursors thereof.

In one aspect, the present specification provides for, and includes, a method comprising providing a first population of tobacco plants comprising enhanced NUE, genotyping a first population of tobacco plants for the presence of a molecular marker within 20 cM of an enhanced NUE locus; and selecting one or more tobacco plants genotyped and found to comprise the molecular marker. In a further aspect, a method disclosed herein comprises genotyping a first population of tobacco plants for the presence of a molecular marker within 15 cM of an enhanced NUE locus. In a further aspect, a method disclosed herein comprises genotyping a first population of tobacco plants for the presence of a molecular marker within 10 cM of an enhanced NUE locus. In a further aspect, a method disclosed herein comprises genotyping a first population of tobacco plants for the presence of a molecular marker within 9 cM of an enhanced NUE locus. In a further aspect, a method disclosed herein comprises genotyping a first population of tobacco plants for the presence of a molecular marker within 8 cM of an enhanced NUE locus. In a further aspect, a method disclosed herein comprises genotyping a first population of tobacco plants for the presence of a molecular marker within 7 cM of an enhanced NUE locus. In a further aspect, a method disclosed herein comprises genotyping a first population of tobacco plants for the presence of a molecular marker within 6 cM of an enhanced NUE locus. In a further aspect, a method disclosed herein comprises genotyping a first population of tobacco plants for the presence of a molecular marker within 5 cM of an enhanced NUE locus. In a further aspect, a method disclosed herein comprises genotyping a first population of tobacco plants for the presence of a molecular marker within 4 cM of an enhanced NUE locus. In a further aspect, a method disclosed herein comprises genotyping a first population of tobacco plants for the presence of a molecular marker within 3 cM of an enhanced NUE locus. In a further aspect, a method disclosed herein comprises genotyping a first population of tobacco plants for the presence of a molecular marker within 2 cM of an enhanced NUE locus. In a further aspect, a method disclosed herein comprises genotyping a first population of tobacco plants for the presence of a molecular marker within 1 cM of an enhanced NUE locus. In a further aspect, a method disclosed herein comprises genotyping a first population of tobacco plants for the presence of a molecular marker within 0.5 cM of an enhanced NUE locus. In a further aspect, the method comprises crossing one or more selected tobacco plants to a second tobacco plant; and obtaining progeny seed from that cross. In a further aspect, a molecular marker is selected from the group consisting of a SNP marker, an INDEL marker, an RFLP marker, an SSR marker, an AFLP marker, and a RAPD marker.

In a further aspect, a method provided herein comprises a tobacco plant comprising an enhanced NUE locus comprising a polynucleotide encoding a polypeptide at least 70% identical or similar to a polypeptide selected from the group consisting of SEQ ID NOs:1 to 8. In a further aspect, a polynucleotide encodes a polypeptide at least 75% identical or similar to a polypeptide selected from the group consisting of SEQ ID NOs:1 to 8. In a further aspect, a polynucleotide encodes a polypeptide at least 80% identical or similar to a polypeptide selected from the group consisting of SEQ ID NOs:1 to 8. In a further aspect, a polynucleotide encodes a polypeptide at least 85% identical or similar to a polypeptide selected from the group consisting of SEQ ID NOs:1 to 8. In a further aspect, a polynucleotide encodes a polypeptide at least 90% identical or similar to a polypeptide selected from the group consisting of SEQ ID NOs:1 to 8. In a further aspect, a polynucleotide encodes a polypeptide at least 95% identical or similar to a polypeptide selected from the group consisting of SEQ ID NOs:1 to 8. In a further aspect, a polynucleotide encodes a polypeptide at least 96% identical or similar to a polypeptide selected from the group consisting of SEQ ID NOs:1 to 8. In a further aspect, a polynucleotide encodes a polypeptide at least 97% identical or similar to a polypeptide selected from the group consisting of SEQ ID NOs:1 to 8. In a further aspect, a polynucleotide encodes a polypeptide at least 98% identical or similar to a polypeptide selected from the group consisting of SEQ ID NOs:1 to 8. In a further aspect, a polynucleotide encodes a polypeptide at least 99% identical or similar to a polypeptide selected from the group consisting of SEQ ID NOs:1 to 8. In a further aspect, a polynucleotide encodes a polypeptide 100% identical to a polypeptide selected from the group consisting of SEQ ID NOs:1 to 8. In a further aspect, an enhanced NUE locus is genetically linked to a polynucleotide sequence selected from the group consisting of SEQ ID NOs:57 to 64. In another aspect, an enhanced NUE locus is genetically linked to a G nucleotide at position 57 of SEQ ID NOs: 58. In another aspect, an enhanced NUE locus is genetically linked to a C nucleotide at position 117 of SEQ ID NOs: 58. In another aspect, an enhanced NUE locus is genetically linked to a G nucleotide at position 57 and a C nucleotide at position 117 of SEQ ID NOs: 58. In another aspect, an enhanced NUE locus is genetically linked to a T nucleotide at position 147 of SEQ ID NO:57. In another aspect, an enhanced NUE locus is genetically linked to a G nucleotide at position 162 of SEQ ID NO:59. In another aspect, an enhanced NUE locus is genetically linked to a C nucleotide at position 36 of SEQ ID NO:60. In another aspect, an enhanced NUE locus is genetically linked to a T nucleotide at position 36 of SEQ ID NO:61. In another aspect, an enhanced NUE locus is genetically linked to a T nucleotide at position 36 of SEQ ID NO:62. In another aspect, an enhanced NUE locus is genetically linked to a G nucleotide at position 36 of SEQ ID NO:63. In another aspect, an enhanced NUE locus is genetically linked to a T nucleotide at position 36 of SEQ ID NO:64.

In a further aspect of a method provided herein, a first population of tobacco plants is of a Maryland variety. In a further aspect, a method provided herein comprises a first population of tobacco plants of a variety selected from the group consisting of MD609, MD601, Banket A1, K326, K346, K358, K394, K399, K730, NC196, NC37NF, NC471, NC55, NC92, NC2326, NC95, NC925. In a further aspect, a method provided herein comprises a second population of tobacco plants of the Burley variety In a further aspect, a method provided herein comprises a second population of tobacco plants of a variety selected from the group consisting of TN86, TN86LC, TN90, TN90LC, TN97, TN97LC.

In a further aspect, a method provided herein comprises progeny seed comprising molecular markers. In a further aspect, a method provided herein comprises progeny seed comprising enhanced NUE. In a further aspect, a method provided herein comprises progeny seed comprising a molecular marker within 20 cM of an enhanced NUE efficiency locus provided herein. In a further aspect, a method provided herein comprises progeny seed comprising a molecular marker within 15 cM of an enhanced NUE efficiency locus provided herein. In a further aspect, a method provided herein comprises progeny seed comprising a molecular marker within 10 cM of an enhanced NUE efficiency locus provided herein. In a further aspect, a method provided herein comprises progeny seed comprising a molecular marker within 9 cM of an enhanced NUE efficiency locus provided herein. In a further aspect, a method provided herein comprises progeny seed comprising a molecular marker within 8 cM of an enhanced NUE efficiency locus provided herein. In a further aspect, a method provided herein comprises progeny seed comprising a molecular marker within 7 cM of an enhanced NUE efficiency locus provided herein. In a further aspect, a method provided herein comprises progeny seed comprising a molecular marker within 6 cM of an enhanced NUE efficiency locus provided herein. In a further aspect, a method provided herein comprises progeny seed comprising a molecular marker within 5 cM of an enhanced NUE efficiency locus provided herein. In a further aspect, a method provided herein comprises progeny seed comprising a molecular marker within 4 cM of an enhanced NUE efficiency locus provided herein. In a further aspect, a method provided herein comprises progeny seed comprising a molecular marker within 3 cM of an enhanced NUE efficiency locus provided herein. In a further aspect, a method provided herein comprises progeny seed comprising a molecular marker within 2 cM of an enhanced NUE efficiency locus provided herein. In a further aspect, a method provided herein comprises progeny seed comprising a molecular marker within 1 cM of an enhanced NUE efficiency locus provided herein. In a further aspect, a method provided herein comprises progeny seed comprising a molecular marker within 0.5 cM of an enhanced NUE efficiency locus provided herein.

In one aspect, the present specification provides for, and includes, a method comprising providing a first population of tobacco plants, genotyping the first population of tobacco plants for the presence of an enhanced NUE allele of a locus encoded by a sequence selected from the group consisting of SEQ ID NOs:9 to 16; and selecting one or more genotyped tobacco plants that comprise an enhanced NUE allele. In a further aspect, the method further comprises crossing the one or more selected tobacco plants to a second tobacco plant; and obtaining progeny seed from the cross.

In one aspect, the present specification provides for, and includes, a method of introgressing an enhanced NUE trait into a tobacco variety comprising crossing a first tobacco variety comprising an enhanced nitrogen utilization efficiency trait with a second tobacco variety lacking the enhanced nitrogen utilization efficiency trait, obtaining progeny seed from the cross, genotyping at least one progeny seed for a molecular marker linked to an enhanced nitrogen utilization efficiency trait, where the molecular marker is within 20 cM of a locus having a sequence selected from the group consisting of SEQ ID NOs:9 to 16;

and selecting a progeny seed comprising an enhanced nitrogen utilization efficiency trait.

In one aspect, the present specification provides for, and includes, a method of selecting a tobacco plant with an enhanced NUE trait comprising isolating nucleic acids from a collection of tobacco germplasm, assaying the isolated nucleic acids for one or more markers located within 20 cM of a locus having a sequence selected from the group consisting of SEQ ID NOs:9 to 16, and selecting a tobacco plant comprising an enhanced NUE trait. In a further aspect, the method further comprises crossing the one or more selected tobacco plants to a second tobacco plant; and obtaining progeny seed from the cross.

In one aspect, the present specification provides for, and includes, a method of selecting a tobacco plant with an enhanced NUE trait comprising isolating nucleic acids from a collection of tobacco germplasm, assaying the isolated nucleic acids for one or more markers located within 20 cM of a marker selected from the group consisting of SEQ ID NOs:57 to 64, and selecting a tobacco plant comprising an enhanced NUE trait. In a further aspect, a method disclosed herein comprises assaying isolated nucleic acids for one or more markers located within 15 cM of a marker selected from the group consisting of SEQ ID NOs: 58. In a further aspect, a method disclosed herein comprises assaying isolated nucleic acids for one or more markers located within 10 cM of a marker selected from the group consisting of SEQ ID NOs:57 to 64. In a further aspect, a method disclosed herein comprises assaying isolated nucleic acids for one or more markers located within 9 cM of a marker selected from the group consisting of SEQ ID NOs:57 to 64. In a further aspect, a method disclosed herein comprises assaying isolated nucleic acids for one or more markers located within 8 cM of a marker selected from the group consisting of SEQ ID NOs:57 to 64. In a further aspect, a method disclosed herein comprises assaying isolated nucleic acids for one or more markers located within 7 cM of a marker selected from the group consisting of SEQ ID NOs:57 to 64. In a further aspect, a method disclosed herein comprises assaying isolated nucleic acids for one or more markers located within 6 cM of a marker selected from the group consisting of SEQ ID NOs:57 to 64. In a further aspect, a method disclosed herein comprises assaying isolated nucleic acids for one or more markers located within 5 cM of a marker selected from the group consisting of SEQ ID NOs:57 to 64. In a further aspect, a method disclosed herein comprises assaying isolated nucleic acids for one or more markers located within 4 cM of a marker selected from the group consisting of SEQ ID NOs:57 to 64. In a further aspect, a method disclosed herein comprises assaying isolated nucleic acids for one or more markers located within 3 cM of a marker selected from the group consisting of SEQ ID NOs:57 to 64. In a further aspect, a method disclosed herein comprises assaying isolated nucleic acids for one or more markers located within 2 cM of a marker selected from the group consisting of SEQ ID NOs:57 to 64. In a further aspect, a method disclosed herein comprises assaying isolated nucleic acids for one or more markers located within 1 cM of a marker selected from the group consisting of SEQ ID NOs:57 to 64. In a further aspect, a method disclosed herein comprises assaying isolated nucleic acids for one or more markers located within 0.5 cM of a marker selected from the group consisting of SEQ ID NOs:57 to 64. In a further aspect, a method disclosed herein comprises assaying isolated nucleic acids for a marker selected from the group consisting of SEQ ID NOs:57 to 64. In another aspect, an allele associated with enhanced NUE comprises a G nucleotide at position 57 of SEQ ID NO:58. In another aspect an allele associated with enhanced NUE comprises a C nucleotide at position 117 of SEQ ID NO:58. In another aspect, an allele associated with enhanced NUE comprises a G nucleotide at position 57 and a C nucleotide at position 117 of SEQ ID NO:58. In another aspect, an allele associated with enhanced NUE comprises a T nucleotide at position 147 of SEQ ID NO:57. In another aspect, an allele associated with enhanced NUE comprises a G nucleotide at position 162 of SEQ ID NO:59. In another aspect, an allele associated with enhanced NUE comprises a C nucleotide at position 36 of SEQ ID NO:60. In another aspect, an allele associated with enhanced NUE comprises a T nucleotide at position 36 of SEQ ID NO:61. In another aspect, an allele associated with enhanced NUE comprises a T nucleotide at position 36 of SEQ ID NO:62. In another aspect, an allele associated with enhanced NUE comprises a G nucleotide at position 36 of SEQ ID NO:63. In another aspect, an allele associated with enhanced NUE comprises a T nucleotide at position 36 of SEQ ID NO:64. In a further aspect, a tobacco plant can be selected comprising any combination of alleles associated with enhanced NUE disclosed herein.

The following are exemplary embodiments

Embodiment 1. A method of determining the nitrogen utilization efficiency (NUE) of a tobacco line comprising:
 a. obtaining at least one metabolite from a tobacco plant of said tobacco line;
 b. determining the amount of said at least one metabolite; and
 c. determining the nitrogen utilization efficiency of said tobacco line based on the amount of said at least one metabolite identified in step (b).

Embodiment 2. The method of embodiment 1, wherein said at least one metabolite is obtained from a plant tissue selected from the group consisting of root tissue, leaf tissue, floral tissue, meristem tissue, and stem tissue.

Embodiment 3. The method of embodiment 1 or 2, wherein said plant tissue comprises leaf tissue.

Embodiment 4. The method of any one of embodiments 1 to 3, wherein said plant tissue comprises root tissue.

Embodiment 5. The method of any one of embodiments 1 to 4, wherein said at least one metabolite is selected from the group consisting of X-2357, N-acetylmuramate, X-23319, X-23852, X-23330, alpha-ketoglutarate, X-21756, 4-hydroxy-2-oxoglutaric acid, D-23937, X-23937, X-23916, 1-methyladenine, 4-guanidinobutanoate, syringaldehyde, thiamin, p-hydroxybenzaldehyde, X-23453, X-11429, X-21796, N'-methylnicotinamide, cotinine, X-23389, N-acetylarginine, X-23366, N-acetylphenylalanine, naringenin, X-23454, X-23580, and X-23852.

Embodiment 6. The method of any one of embodiments 1 to 5, wherein said NUE comprises enhanced NUE as compared to a tobacco line that comprises a lower amount of said at least one metabolite in said at least one tissue.

Embodiment 7. The method of any one of embodiments 1 to 6, wherein said NUE comprises enhanced NUE as compared to a tobacco line that comprises an equal amount of said at least one metabolite in said at least one tissue.

Embodiment 8. The method of any one of embodiments 1 to 7, wherein said NUE comprises enhanced NUE as compared to a tobacco line that comprises an equal amount of said at least one metabolite in said at least one tissue.

Embodiment 9. The method of any one of embodiments 1 to 8, wherein said NUE comprises decreased NUE as compared to a tobacco line that comprises a lower amount of said at least one metabolite in said at least one tissue.

Embodiment 10. The method of any one of embodiments 1 to 9, wherein said NUE comprises decreased NUE as compared to a tobacco line that comprises an equal amount of said at least one metabolite in said at least one tissue.

Embodiment 11. The method of any one of embodiments 1 to 10, wherein said NUE comprises decreased NUE as compared to a tobacco line that comprises an equal amount of said at least one metabolite in said at least one tissue.

Embodiment 12. The method of any one of embodiments 1 to 11, wherein said determining the amount of said at least one metabolite comprises a method selected from the group consisting of liquid chromatography/mass spectrometry (LC/MS), high-performance liquid chromatography (HPLC), ultra HPLC (UHPLC), mass spectrometry (MS), tandem mass spectrometry (MS/MS), matrix assisted laser desorption/ionization mass spectrometry (MALDI-MS), X-ray fluorescence spectrometry (XRF), ion chromatography (IC), gas chromatography (GC), gas chromatography/mass spectrometry (GC/MS), capillary electrophoresis/mass spectrometry (CE-MS), ion mobility spectrometry/mass spectrometry (IMS/MS), X-ray diffraction, nuclear magnetic resonance (NMR), emission spectral analysis, polarography, ultraviolet-visual spectrometry, infrared spectrometry, thin-layer chromatography.

Embodiment 13. The method of any one of embodiments 1 to 12, wherein said at least one metabolite comprises at least two metabolites.

Embodiment 14. The method of any one of embodiments 1 to 13, wherein said at least one metabolite comprises at least five metabolites.

Embodiment 15. The method of any one of embodiments 1 to 14, wherein said at least one metabolite comprises at least ten metabolites.

Embodiment 16. A method of determining the nitrogen utilization efficiency (NUE) of a tobacco line using a metabolite signature comprising:
  a. isolating said metabolite signature from a tobacco plant of said tobacco line;
  b. determining the amount of each metabolite comprising said metabolite signature;
  c. determining said NUE of said tobacco line by comparing said metabolite signature to a control metabolite signature from a control tobacco line comprising a known NUE.

Embodiment 17. The method of embodiment 16, wherein said metabolite signature comprises at least 2, at least 3, at least 4, at least 5, at least 6, at least 7, at least 8, at least 9, at least 10, at least 11, at least 12, at least 13, at least 14, at least 15, at least 20, at least 25, at least 30, at least 35, at least 40, at least 45, or at least 50 metabolites.

Embodiment 18. The method of embodiments 16 or 17, wherein said NUE comprises enhanced NUE as compared to said control tobacco line.

Embodiment 19. The method of any one of embodiments 16 to 18, wherein said NUE comprises reduced NUE as compared to said control tobacco line.

Embodiment 20. The method of any one of embodiments 16 to 19, wherein said metabolite signature is isolated from a plant tissue selected from the group consisting of root tissue, leaf tissue, floral tissue, meristem tissue, and stem tissue.

Embodiment 21. A method of breeding a tobacco line comprising a metabolite signature associated with enhanced nitrogen utilization efficiency (NUE) comprising:
  a. determining the metabolite signature of a first tobacco plant from a first tobacco line, wherein said first tobacco plant comprises enhanced NUE as compared to a control tobacco plant lacking said metabolite signature;
  b. crossing said first plant with a second plant of a second tobacco line; and
  c. obtaining at least one progeny seed from the crossing of step (a), wherein a progeny plant grown from said at least one progeny seed comprises said metabolite signature, and wherein said progeny plant comprises enhanced NUE as compared to a control plant lacking said metabolite signature.

Embodiment 22. The method of embodiment 21, wherein said method further comprises:
  d. crossing said progeny plant to a tobacco plant from said first tobacco line.

Embodiment 23. The method of embodiments 21 or 22, wherein said first tobacco line is selected from the group consisting of MD609, MD601, Banket A1, K326, K346, K358, K394, K399, K730, NC196, NC37NF, NC471, NC55, NC92, NC2326, NC95, NC925.

Embodiment 24. The method of any one of embodiments 21 to 23, wherein said second tobacco line is selected from the group consisting of TN86, TN86LC, TN90, TN90LC, TN97, TN97LC.

Embodiment 25. The method of any one of embodiments 21 to 24, wherein said metabolite signature comprises a leaf metabolite signature.

Embodiment 26. The method of any one of embodiments 21 to 25, wherein said metabolite signature comprises a root metabolite signature.

Embodiment 27. The method of any one of embodiments 21 to 26, wherein said enhanced NUE comprises an increased partial factor productivity (PFP) compared to a tobacco plant lacking said enhanced NUE grown in the same conditions.

Embodiment 28. The method of any one of embodiments 21 to 27, wherein said enhanced NUE comprises an increased agronomic efficiency (AE) compared to a tobacco plant lacking said enhanced NUE grown in the same conditions.

Embodiment 29. The method of any one of embodiments 21 to 28, wherein said enhanced NUE comprises an increased recovery efficiency (RE) compared to a tobacco plant lacking said enhanced NUE grown in the same conditions.

Embodiment 30. The method of any one of embodiments 21 to 29, wherein said enhanced NUE comprises an increased physiological efficiency (PE) compared to a tobacco plant lacking said enhanced NUE grown in the same conditions.

Embodiment 31. The method of any one of embodiments 21 to 30, wherein said enhanced NUE comprises an increased internal efficiency (IE) compared to a tobacco plant lacking said enhanced NUE grown in the same conditions.

Embodiment 32. The method of any one of embodiments 21 to 31, wherein said metabolite signature comprises equal amounts of 4-guanidinobutanoate, syringaldehyde, thiamin, p-hydroxybenzaldehyde, X-23454, X-23580, X-23852, or any combination thereof as compared to the metabolite signature of said control tobacco plant.

Embodiment 33. The method of any one of embodiments 21 to 32, wherein said metabolite signature comprises lower amounts of X-2357, N-acetylmuramate, X-23319, X-23852, X-23330, alpha-ketoglutarate, X-21756, 4-hydroxy-2-oxoglutaric acid, X-23937, X-23916, 1-methyladenine, X-23453, X-11429, X-21796, N'-methylnicotinamide, cotinine, X-23389, N-acetylarginine, N-23366, N-acetylphenylalanine, naringenin, or any combination thereof as compared to the metabolite signature of said control tobacco plant.

Embodiment 34. The method of any one of embodiments 21 to 33, wherein said metabolite signature comprises at least 2, at least 3, at least 4, at least 5, at least 6, at least 7, at least 8, at least 9, at least 10, at least 11, at least 12, at least 13, at least 14, at least 15, at least 20, at least 25, at least 30, at least 35, at least 40, at least 45, or at least 50 metabolites.

Embodiment 35. A method of selecting a tobacco plant comprising:
  a. obtaining a population of tobacco plants;
  b. isolating at least one metabolite associated with enhanced nitrogen utilization efficiency (NUE) from at least one tobacco plant of said population of tobacco plants;
  c. selecting at least one tobacco plant that comprises a equal amount of said at least one metabolite as compared to a control tobacco plant.

Embodiment 36. The method of embodiment 35, wherein said tobacco plant selected in step (c) comprises a equal NUE as compared to said control tobacco plant.

Embodiment 37. The method of embodiment 35 or 36, wherein said enhanced NUE comprises an increased partial factor productivity (PFP) compared to a tobacco plant lacking said enhanced NUE grown in the same conditions.

Embodiment 38. The method of any one of embodiments 35 to 37, wherein said enhanced NUE comprises an increased agronomic efficiency (AE) compared to a tobacco plant lacking said enhanced NUE grown in the same conditions.

Embodiment 39. The method of any one of embodiments 35 to 38, wherein said enhanced NUE comprises an increased recovery efficiency (RE) compared to a tobacco plant lacking said enhanced NUE grown in the same conditions.

Embodiment 40. The method of any one of embodiments 35 to 39, wherein said enhanced NUE comprises an increased physiological efficiency (PE) compared to a tobacco plant lacking said enhanced NUE grown in the same conditions.

Embodiment 41. The method of any one of embodiments 35 to 40, wherein said enhanced NUE comprises an increased internal efficiency (IE) compared to a tobacco plant lacking said enhanced NUE grown in the same conditions.

Embodiment 42. The method of any one of embodiments 35 to 41, wherein said at least one metabolite is selected from the group consisting of 4-guanidinobutanoate, syringaldehyde, thiamin, p-hydroxybenzaldehyde, X-23454, X-23580, X-23852, or any combination thereof.

Embodiment 43. The method of any one of embodiments 35 to 42, wherein said at least one metabolite is isolated from leaf tissue or root tissue.

Embodiment 44. The method of any one of embodiments 35 to 43, wherein said at least one metabolite is isolated from a plant tissue selected from the group consisting of root tissue, leaf tissue, floral tissue, meristem tissue, and stem tissue.

Embodiment 45. A method of selecting a tobacco plant comprising:
  a. obtaining a population of tobacco plants;
  b. isolating at least one metabolite associated with enhanced nitrogen utilization efficiency (NUE) from at least one tobacco plant of said population of tobacco plants;
  c. selecting at least one tobacco plant that comprises a lower amount of said at least one metabolite as compared to a control tobacco plant.

Embodiment 46. The method of embodiment 45, wherein said tobacco plant selected in step (c) comprises a equal NUE as compared to said control tobacco plant.

Embodiment 47. The method of embodiment 45 or 46, wherein said enhanced NUE comprises an increased partial factor productivity (PFP) compared to a tobacco plant lacking said enhanced NUE grown in the same conditions.

Embodiment 48. The method of any one of embodiments 45 to 47, wherein said enhanced NUE comprises an increased agronomic efficiency (AE) compared to a tobacco plant lacking said enhanced NUE grown in the same conditions.

Embodiment 49. The method of any one of embodiments 45 to 48, wherein said enhanced NUE comprises an increased recovery efficiency (RE) compared to a tobacco plant lacking said enhanced NUE grown in the same conditions.

Embodiment 50. The method of any one of embodiments 45 to 49, wherein said enhanced NUE comprises an increased physiological efficiency (PE) compared to a tobacco plant lacking said enhanced NUE grown in the same conditions.

Embodiment 51. The method of any one of embodiments 45 to 50, wherein said enhanced NUE comprises an increased internal efficiency (IE) compared to a tobacco plant lacking said enhanced NUE grown in the same conditions.

Embodiment 52. The method of any one of embodiments 45 to 51, wherein said at least one metabolite is selected from the group consisting of X-2357, N-acetylmuramate, X-23319, X-23852, X-23330, alpha-ketoglutarate, X-21756, 4-hydroxy-2-oxoglutaric acid, X-23937, X-23916, 1-methyladenine, X-23453, X-11429, X-21796, N'-methylnicotinamide, cotinine, X-23389, N-acetylarginine, N-23366, N-acetylphenylalanine, naringenin, or any combination thereof.

Embodiment 53. The method of any one of embodiments 45 to 52, wherein said at least one metabolite is isolated from leaf tissue or root tissue.

Embodiment 54. The method of any one of embodiments 45 to 53, wherein said at least one metabolite is isolated from a plant tissue selected from the group consisting of root tissue, leaf tissue, floral tissue, meristem tissue, and stem tissue.

Embodiment 55. A method of screening a tobacco plant for a metabolite signature associated with enhanced nitrogen utilization efficiency (NUE) comprising:
  a. isolating a first metabolite signature associated with enhanced NUE from said tobacco plant;
  b. determining the amount of at least one metabolite comprising said first metabolite signature;
  c. comparing said first metabolite signature to a second metabolite signature of a control tobacco plant that comprises a known NUE; and
  d. determining if said first metabolite signature is associated with enhanced NUE.

Embodiment 56. The method of embodiment 55, wherein said enhanced NUE comprises an increased partial factor productivity (PFP) compared to a tobacco plant lacking said enhanced NUE grown in the same conditions.

Embodiment 57. The method of embodiment 55 or 56, wherein said enhanced NUE comprises an increased agronomic efficiency (AE) compared to a tobacco plant lacking said enhanced NUE grown in the same conditions.

Embodiment 58. The method of any one of embodiments 55 to 57, wherein said enhanced NUE comprises an increased recovery efficiency (RE) compared to a tobacco plant lacking said enhanced NUE grown in the same conditions.

Embodiment 59. The method of any one of embodiments 55 to 58, wherein said enhanced NUE comprises an increased physiological efficiency (PE) compared to a tobacco plant lacking said enhanced NUE grown in the same conditions.

Embodiment 60. The method of any one of embodiments 55 to 59, wherein said enhanced NUE comprises an increased internal efficiency (IE) compared to a tobacco plant lacking said enhanced NUE grown in the same conditions.

Embodiment 61. A modified tobacco seed, or tobacco plant grown therefrom, comprising a cisgenic polynucleotide comprising a heterologous promoter operably linked to a coding region, wherein said modified tobacco plant comprises enhanced nitrogen utilization efficiency as compared to an unmodified control tobacco plant lacking said cisgenic polynucleotide when grown under the same conditions.

Embodiment 62. The modified tobacco seed or tobacco plant of embodiment 61, wherein said coding region encodes a polypeptide at least 70% identical or similar to a sequence selected from the group consisting of SEQ ID NOs:1 to 8.

Embodiment 63. The modified tobacco seed or tobacco plant of embodiment 61 or 62, wherein said coding region comprises a polynucleotide sequence at least 70% identical or complementary to a polynucleotide sequence selected from the group consisting of SEQ ID NOs:9 to 16.

Embodiment 64. The modified tobacco seed or tobacco plant of any one of embodiments 61 to 63, wherein said heterologous promoter is selected from the group consisting of a constitutive promoter, an inducible promoter, a tissue-preferred promoter, and a tissue-specific promoter.

Embodiment 65. The modified tobacco seed or tobacco plant of any one of embodiments 61 to 64, wherein said heterologous promoter comprises a polynucleotide sequence from a tobacco genome.

Embodiment 66. The modified tobacco seed or tobacco plant of any one of embodiments 61 to 65, wherein said heterologous promoter comprises a polynucleotide sequence from a plant genome.

Embodiment 67. The modified tobacco seed or tobacco plant of any one of embodiments 61 to 66, wherein said tissue-preferred promoter is a leaf-preferred promoter.

Embodiment 68. The modified tobacco seed or tobacco plant of any one of embodiments 61 to 67, wherein said tissue-preferred promoter is a root-preferred promoter.

Embodiment 69. The modified tobacco seed or tobacco plant of any one of embodiments 61 to 68, wherein said leaf-preferred promoter is encoded by a sequence at least 70% identical or complementary to a sequence selected from the group consisting of SEQ ID NOs:17 to 19, or a functional fragment thereof.

Embodiment 70. The modified tobacco seed or tobacco plant of any one of embodiments 61 to 69, wherein said root-preferred promoter is encoded by a sequence at least 70% identical or complementary to a sequence selected from the group consisting of SEQ ID NOs:20 to 24, or a functional fragment thereof.

Embodiment 71. The modified tobacco plant of any one of embodiments 61 to 70, wherein said modified tobacco plant comprises equal levels of a metabolite selected from the group consisting of 4-guanidinobutanoate, syringaldehyde, thiamin, and p-hydroxybenzaldehyde in root tissue as compared to an unmodified tobacco plant lacking said cisgenic polynucleotide when grown under the same conditions.

Embodiment 72. The modified tobacco plant of any one of embodiments 61 to 71, wherein said modified tobacco plant comprises equal levels of a metabolite selected from the group consisting of 4-guanidinobutanoate, X-23454, X-23580, and X-23852 in leaf tissue as compared to an unmodified tobacco plant lacking said cisgenic polynucleotide when grown under the same conditions.

Embodiment 73. The modified tobacco plant of any one of embodiments 61 to 72, wherein said modified tobacco plant comprises lower levels of a metabolite selected from the group consisting of X-2357, N-acetylmuramate, X-23319, X-23852, X-23330, alpha-ketoglutarate, X-21756, 4-hydroxy-2-oxoglutaric acid, X-23937, X-23916, and 1-methyladenine in root tissue as compared to an unmodified tobacco plant lacking said cisgenic polynucleotide when grown under the same conditions.

Embodiment 74. The modified tobacco plant of any one of embodiments 61 to 73, wherein said modified tobacco plant comprises lower levels of a metabolite selected from the group consisting of X-23453, X-21756, X-11429, X-21796, N'-methylnicotinamide, cotinine, X-23389, N-acetylarginine, N-23366, N-acetylphenylalanine, and naringenin in leaf tissue as compared to an unmodified tobacco plant lacking said cisgenic polynucleotide when grown under the same conditions.

Embodiment 75. The modified tobacco seed or plant of any one of embodiments 61 to 74, wherein said modified tobacco seed or plant is of a Burley variety.

Embodiment 76. The modified tobacco seed or plant of any one of embodiments 61 to 75, wherein said modified tobacco seed or plant comprises lower amounts of TSNAs as compared to an unmodified tobacco plant lacking said cisgenic polynucleotide when grown under the same conditions.

Embodiment 77. A recombinant DNA construct comprising a heterologous promoter operably linked to a polynucleotide encoding a polypeptide at least 70% identical or similar to a polypeptide selected from the group consisting of SEQ ID NOs:1 to 8.

Embodiment 78. Cured tobacco material, or a tobacco product comprising said cured tobacco material, wherein said cured tobacco material is made from a tobacco plant comprising a cisgenic polynucleotide comprising a heterologous promoter operably linked to a coding region, wherein said modified tobacco plant comprises enhanced nitrogen utilization efficiency as compared to an unmodified control tobacco plant lacking said cisgenic polynucleotide when grown under the same conditions.

Embodiment 79. A greenhouse, growth chamber, or field comprising the modified tobacco seed or plant of any one of embodiments 61 to 76.

Embodiment 80. A modified tobacco seed, or tobacco plant grown therefrom, comprising at least one mutation in an endogenous locus encoding a polypeptide selected from the group consisting of SEQ ID NOs:25 to 40, and wherein said modified tobacco seed or tobacco plant comprises enhanced nitrogen utilization efficiency as compared to an unmodified control tobacco plant lacking said at least one mutation when grown under the same conditions.

Embodiment 81. The modified tobacco seed or tobacco plant of embodiment 80, wherein said at least one mutation is selected from the group consisting of an insertion, a deletion, a substitution, and an inversion.

Embodiment 82. The modified tobacco seed or tobacco plant of embodiment 80 or 81, wherein said at least one mutation is a null mutation.

Embodiment 83. The modified tobacco plant of any one of embodiments 80 to 82, wherein said modified tobacco plant comprises equal levels of a metabolite selected from the group consisting of 4-guanidinobutanoate, syringaldehyde, thiamin, and p-hydroxybenzaldehyde in root tissue as compared to an unmodified tobacco plant lacking said at least one mutation when grown under the same conditions.

Embodiment 84. The modified tobacco plant of any one of embodiments 80 to 83, wherein said modified tobacco plant comprises equal levels of a metabolite selected from the group consisting of 4-guanidinobutanoate, X-23454, X-23580, and X-23852 in leaf tissue as compared to an unmodified tobacco plant lacking said at least one mutation when grown under the same conditions.

Embodiment 85. The modified tobacco plant of any one of embodiments 80 to 84, wherein said modified tobacco plant comprises lower levels of a metabolite selected from the group consisting of X-2357, N-acetylmuramate, X-23319, X-23852, X-23330, alpha-ketoglutarate, X-21756, 4-hydroxy-2-oxoglutaric acid, X-23937, X-23916, and 1-methyladenine in root tissue as compared to an unmodified tobacco plant lacking said at least one mutation when grown under the same conditions.

Embodiment 86. The modified tobacco plant of any one of embodiments 80 to 85, wherein said modified tobacco plant comprises lower levels of a metabolite selected from the group consisting of X-23453, X-21756, X-11429, X-21796, N'-methylnicotinamide, cotinine, X-23389, N-acetylarginine, N-23366, N-acetylphenylalanine, and naringenin in leaf tissue as compared to an unmodified tobacco plant lacking said at least one mutation when grown under the same conditions.

Embodiment 87. The modified tobacco seed or plant of any one of embodiments 80 to 86, wherein said modified tobacco seed or plant is of a Burley variety.

Embodiment 88. The modified tobacco seed or plant of any one of embodiments 80 to 87, wherein said modified tobacco seed or plant comprises lower amounts of TSNAs as compared to an unmodified tobacco plant lacking said at least one mutation when grown under the same conditions.

Embodiment 89. A recombinant DNA construct comprising a heterologous promoter operably linked to a guide RNA comprising at least 18, at least 19, at least 20, at least 21, at least 22, at least 23, at least 24, at least 25, at least 26, at least 27, or at least 28 contiguous nucleotides identical or complementary to a polynucleotide encoding a polypeptide selected from the group consisting of SEQ ID NOs:25 to 40.

Embodiment 90. Cured tobacco material, or a tobacco product comprising said cured tobacco material, wherein said cured tobacco material is made from a tobacco plant comprising at least one mutation in an endogenous locus encoding a polypeptide selected from the group consisting of SEQ ID NOs:25 to 40, and wherein said modified tobacco seed or tobacco plant comprises enhanced nitrogen utilization efficiency as compared to an unmodified control tobacco plant lacking said at least one mutation when grown under the same conditions.

Embodiment 91. A modified tobacco seed, or tobacco plant grown therefrom, comprising a cisgenic polynucleotide comprising a heterologous promoter operably linked to a polynucleotide encoding a small RNA (sRNA) at least 85% identical or complementary to a polynucleotide selected from the group consisting of SEQ ID NOs:41 to 56, and wherein said modified tobacco seed or tobacco plant comprises enhanced nitrogen utilization efficiency as compared to an unmodified control tobacco plant lacking said cisgenic polynucleotide when grown under the same conditions.

Embodiment 92. The modified tobacco seed or tobacco plant of embodiment 91, wherein said sRNA comprises at least 18, at least 19, at least 20, at least 21, at least 22, at least 23, at least 24, at least 25, at least 26, at least 27, or at least 28 nucleotides.

Embodiment 93. The modified tobacco seed or tobacco plant of embodiment 91 or 92, wherein said sRNA is selected from the group consisting of a microRNA, a small-interfering RNA (siRNA), a trans-acting siRNA, and precursors thereof.

Embodiment 94. The modified tobacco seed or tobacco plant of any one of embodiments 91 to 93, wherein said sRNA down-regulates the expression or translation of a polynucleotide selected from the group consisting of SEQ ID NOs:41 to 56.

Embodiment 95. The modified tobacco seed or tobacco plant of any one of embodiments 91 to 94, wherein said heterologous promoter is selected from the group consisting of a constitutive promoter, an inducible promoter, a tissue-preferred promoter, and a tissue-specific promoter.

Embodiment 96. The modified tobacco seed or tobacco plant of any one of embodiments 91 to 95, wherein said tissue-preferred promoter is a leaf-preferred promoter.

Embodiment 97. The modified tobacco seed or tobacco plant of any one of embodiments 91 to 96, wherein said tissue-preferred promoter is a root-preferred promoter.

Embodiment 98. The modified tobacco seed or tobacco plant of any one of embodiments 91 to 97, wherein said leaf-preferred promoter is encoded by a sequence at least 70% identical or complementary to a sequence selected from the group consisting of SEQ ID NOs:17 to 19, or a functional fragment thereof.

Embodiment 99. The modified tobacco seed or tobacco plant of any one of embodiments 91 to 98, wherein said root-preferred promoter is encoded by a sequence at least 70% identical or complementary to a sequence selected from the group consisting of SEQ ID NOs:20 to 24, or a functional fragment thereof.

Embodiment 100. The modified tobacco seed or tobacco plant of any one of embodiments 91 to 99, wherein said heterologous promoter comprises a polynucleotide sequence from a tobacco genome.

Embodiment 101. The modified tobacco seed or tobacco plant of any one of embodiments 91 to 100, wherein said heterologous promoter comprises a polynucleotide sequence from a plant genome.

Embodiment 102. The modified tobacco plant of any one of embodiments 91 to 101, wherein said modified tobacco plant comprises equal levels of a metabolite selected from the group consisting of 4-guanidinobutanoate, syringaldehyde, thiamin, and p-hydroxybenzaldehyde in root tissue as compared to an unmodified tobacco plant lacking said cisgenic polynucleotide when grown under the same conditions.

Embodiment 103. The modified tobacco plant of any one of embodiments 91 to 102, wherein said modified tobacco plant comprises equal levels of a metabolite selected from the group consisting of 4-guanidinobutanoate, X-23454, X-23580, and X-23852 in leaf tissue as compared to an unmodified tobacco plant lacking said cisgenic polynucleotide when grown under the same conditions.

Embodiment 104. The modified tobacco plant of any one of embodiments 91 to 103, wherein said modified tobacco plant comprises lower levels of a metabolite selected from the group consisting of X-2357, N-acetylmuramate, X-23319, X-23852, X-23330, alpha-ketoglutarate, X-21756, 4-hydroxy-2-oxoglutaric acid, X-23937, X-23916, and 1-methyladenine in root tissue as compared to an unmodified tobacco plant lacking said cisgenic polynucleotide when grown under the same conditions.

Embodiment 105. The modified tobacco plant of any one of embodiments 91 to 104, wherein said modified tobacco plant comprises lower levels of a metabolite selected from the group consisting of X-23453, X-21756, X-11429, X-21796, N'-methylnicotinamide, cotinine, X-23389, N-acetylarginine, N-23366, N-acetylphenylalanine, and naringenin in leaf tissue as compared to an unmodified tobacco plant lacking said cisgenic polynucleotide when grown under the same conditions.

Embodiment 106. The modified tobacco seed or plant of any one of embodiments 91 to 105, wherein said modified tobacco seed or plant is of a Burley variety.

Embodiment 107. The modified tobacco seed or plant of any one of embodiments 91 to 106, wherein said modified tobacco seed or plant comprises lower amounts of TSNAs as compared to an unmodified tobacco plant lacking said cisgenic polynucleotide when grown under the same conditions.

Embodiment 108. A recombinant DNA construct comprising a heterologous promoter operably linked to a polynucleotide encoding a small RNA (sRNA) at least 85% identical or complementary to a polynucleotide selected from the group consisting of SEQ ID NOs:41 to 56.

Embodiment 109. Cured tobacco material, or a tobacco product comprising said cured tobacco material, wherein said cured tobacco material is made from a tobacco plant comprising a cisgenic polynucleotide comprising a heterologous promoter operably linked to a polynucleotide encoding a small RNA (sRNA) at least 85% identical or complementary to a polynucleotide selected from the group consisting of SEQ ID NOs:41 to 56, and wherein said modified tobacco seed or tobacco plant comprises enhanced nitrogen utilization efficiency as compared to an unmodified control tobacco plant lacking said cisgenic polynucleotide when grown under the same conditions.

Embodiment 110. A method of enhancing the nitrogen utilization efficiency (NUE) of a tobacco plant comprising:
a. introducing a cisgenic nucleic acid molecule into a tobacco cell; and
b. regenerating a modified tobacco plant from said tobacco cell, wherein said modified tobacco plant comprises enhanced NUE as compared to a tobacco plant lacking said cisgenic nucleic acid molecule.

Embodiment 111. The method of embodiment 110, wherein said method further comprises:
c. crossing said modified tobacco plant with a second tobacco plant or self-pollinating said modified tobacco plant.

Embodiment 112. The method of embodiment 110 or 111, wherein said enhanced NUE comprises an increased partial factor productivity (PFP) compared to a tobacco plant lacking said enhanced NUE grown in the same conditions.

Embodiment 113. The method of any one of embodiments 110 to 112, wherein said enhanced NUE comprises an increased agronomic efficiency (AE) compared to a tobacco plant lacking said enhanced NUE grown in the same conditions.

Embodiment 114. The method of any one of embodiments 110 to 113, wherein said enhanced NUE comprises an increased recovery efficiency (RE) compared to a tobacco plant lacking said enhanced NUE grown in the same conditions.

Embodiment 115. The method of any one of embodiments 110 to 114, wherein said enhanced NUE comprises an increased physiological efficiency (PE) compared to a tobacco plant lacking said enhanced NUE grown in the same conditions.

Embodiment 116. The method of any one of embodiments 110 to 115, wherein said enhanced NUE comprises an increased internal efficiency (IE) compared to a tobacco plant lacking said enhanced NUE grown in the same conditions.

Embodiment 117. A method of enhancing the nitrogen utilization efficiency (NUE) of a tobacco plant comprising:
a. introducing a modification to a nucleic acid molecule encoding a gene having sequence selected from the group consisting of SEQ ID NOs:41 to 56 in a tobacco cell;
b. regenerating a modified tobacco plant from said tobacco cell, wherein said modified tobacco plant comprises enhanced NUE as compared to a tobacco plant lacking said modification.

Embodiment 118. The method of embodiment 117, wherein said introduction comprises the use of an RNA-guided nuclease.

Embodiment 119. The method of embodiment 117 or 118, wherein said RNA-guided nuclease is selected from the group consisting of a Cas9 nuclease, a Cpf1 nuclease, a CasX nuclease, a CasY nuclease, and functional homologues thereof.

Embodiment 120. The method of any one of embodiments 117 to 119, wherein said modification is selected from the group consisting of an insertion, a substitution, an inversion, and a deletion.

Embodiment 121. The method of any one of embodiments 117 to 120, wherein said enhanced NUE comprises an increased partial factor productivity (PFP) compared to a tobacco plant lacking said enhanced NUE grown in the same conditions.

Embodiment 122. The method of any one of embodiments 117 to 121, wherein said enhanced NUE comprises an increased agronomic efficiency (AE) compared to a tobacco plant lacking said enhanced NUE grown in the same conditions.

Embodiment 123. The method of any one of embodiments 117 to 122, wherein said enhanced NUE comprises an increased recovery efficiency (RE) compared to a tobacco plant lacking said enhanced NUE grown in the same conditions.

Embodiment 124. The method of any one of embodiments 117 to 123, wherein said enhanced NUE comprises an increased physiological efficiency (PE) compared to a tobacco plant lacking said enhanced NUE grown in the same conditions.

Embodiment 125. The method of any one of embodiments 117 to 124, wherein said enhanced NUE comprises an increased internal efficiency (IE) compared to a tobacco plant lacking said enhanced NUE grown in the same conditions.

Embodiment 126. The method of any one of embodiments 117 to 125, wherein said method further comprises:
c. crossing said modified tobacco plant with a second tobacco plant or self-pollinating said modified tobacco plant.

Embodiment 127. A method of enhancing the nitrogen utilization efficiency (NUE) of a tobacco plant comprising:

a. introducing a nucleic acid encoding a small RNA (sRNA) homologous to at least 18 contiguous nucleic acids of a nucleic acid molecule encoding a gene having sequence selected from the group consisting of SEQ ID NOs:41 to 56 in a tobacco cell;

b. regenerating a modified tobacco plant from said tobacco cell, wherein said modified tobacco plant comprises enhanced NUE as compared to a tobacco plant lacking said sRNA.

Embodiment 128. The method of embodiment 127, wherein said sRNA is selected from the group consisting of a microRNA, a small-interfering RNA (siRNA), a trans-acting siRNA, and precursors thereof.

Embodiment 129. The method of embodiment 127 or 128, wherein said enhanced NUE comprises an increased partial factor productivity (PFP) compared to a tobacco plant lacking said enhanced NUE grown in the same conditions.

Embodiment 130. The method of any one of embodiments 127 to 129, wherein said enhanced NUE comprises an increased agronomic efficiency (AE) compared to a tobacco plant lacking said enhanced NUE grown in the same conditions.

Embodiment 131. The method of any one of embodiments 127 to 130, wherein said enhanced NUE comprises an increased recovery efficiency (RE) compared to a tobacco plant lacking said enhanced NUE grown in the same conditions.

Embodiment 132. The method of any one of embodiments 127 to 131, wherein said enhanced NUE comprises an increased physiological efficiency (PE) compared to a tobacco plant lacking said enhanced NUE grown in the same conditions.

Embodiment 133. The method of any one of embodiments 127 to 132, wherein said enhanced NUE comprises an increased internal efficiency (IE) compared to a tobacco plant lacking said enhanced NUE grown in the same conditions.

Embodiment 134. The method of any one of embodiments 127 to 133, wherein said method further comprises:

c. crossing said modified tobacco plant with a second tobacco plant or self-pollinating said modified tobacco plant.

Embodiment 135. A method comprising:

a. providing a first population of tobacco plants comprising enhanced nitrogen utilization efficiency;

b. genotyping said first population of tobacco plants for the presence of a molecular marker within 20 cM of an enhanced nitrogen utilization efficiency locus; and c. selecting one or more tobacco plants genotyped in step (b) that comprise said molecular marker.

Embodiment 136. The method of embodiment 135, wherein said method further comprises:

d. crossing one or more tobacco plants selected in step (c) to a second tobacco plant; and e. obtaining progeny seed from the cross of step (d).

Embodiment 137. The method of embodiment 135 or 136, wherein said molecular marker is selected from the group consisting of a SNP marker, an INDEL marker, an RFLP marker, an SSR marker, an AFLP marker, and a RAPD marker.

Embodiment 138. The method of any one of embodiments 135 to 137, wherein said enhanced nitrogen utilization efficiency locus comprises a polynucleotide encoding a polypeptide at least 70% identical or similar to a polypeptide selected from the group consisting of SEQ ID NOs:1 to 8.

Embodiment 139. The method of any one of embodiments 135 to 138, wherein said enhanced nitrogen utilization efficiency locus comprises a polynucleotide sequence selected from the group consisting of SEQ ID NOs:9 to 16.

Embodiment 140. The method of any one of embodiments 135 to 139, wherein said molecular marker is selected from the group consisting of SEQ ID NOs:57 to 64.

Embodiment 141. The method of any one of embodiments 135 to 140, wherein said molecular marker comprises a G nucleotide at position 57 of SEQ ID NO:58.

Embodiment 142. The method of any one of embodiments 135 to 141, wherein said molecular marker comprises a C nucleotide at position 117 of SEQ ID NO:58.

Embodiment 143. The method of any one of embodiments 135 to 142, wherein said molecular marker comprises a G nucleotide at position 57 and a C nucleotide at position 117 of SEQ ID NO:58.

Embodiment 144. The method of any one of embodiments 135 to 143, wherein said molecular marker comprises a T nucleotide at position 14 of SEQ ID NO:57.

Embodiment 145. The method of any one of embodiments 135 to 144, wherein said molecular marker comprises a G nucleotide at position 162 of SEQ ID NO:59.

Embodiment 146. The method of any one of embodiments 135 to 145, wherein said molecular marker comprises a C nucleotide at position 36 of SEQ ID NO:60.

Embodiment 147. The method of any one of embodiments 135 to 146, wherein said molecular marker comprises a T nucleotide at position 36 of SEQ ID NO:61.

Embodiment 148. The method of any one of embodiments 135 to 147, wherein said molecular marker comprises a T nucleotide at position 36 of SEQ ID NO:62.

Embodiment 149. The method of any one of embodiments 135 to 148, wherein said molecular marker comprises a G nucleotide at position 36 of SEQ ID NO:63.

Embodiment 150. The method of any one of embodiments 135 to 149, wherein said molecular marker comprises a T nucleotide at position 36 of SEQ ID NO:64.

Embodiment 151. The method of any one of embodiments 135 to 150, wherein said first population of tobacco plants is of a Maryland variety.

Embodiment 152. The method of any one of embodiments 135 to 151, wherein said first population of tobacco plants is of a variety selected from the group consisting of MD609, MD601, Banket A1, K326, K346, K358, K394, K399, K730, NC196, NC37NF, NC471, NC55, NC92, NC2326, NC95, NC925.

Embodiment 153. The method of any one of embodiments 135 to 152, wherein said second tobacco plant is of a variety selected from the group consisting of TN86, TN86LC, TN90, TN90LC, TN97, TN97LC.

Embodiment 154. The method of any one of embodiments 135 to 153, wherein said progeny seed comprises said molecular marker.

Embodiment 155. The method of any one of embodiments 135 to 154, wherein said progeny seed comprises said enhanced nitrogen utilization efficiency.

Embodiment 156. The method of any one of embodiments 135 to 155, wherein said molecular marker is within 15 cM of said enhanced nitrogen utilization efficiency locus.

Embodiment 157. The method of any one of embodiments 135 to 156, wherein said molecular marker is within 10 cM of said enhanced nitrogen utilization efficiency locus.

Embodiment 158. The method of any one of embodiments 135 to 157, wherein said molecular marker is within 5 cM of said enhanced nitrogen utilization efficiency locus.

Embodiment 159. The method of any one of embodiments 135 to 158, wherein said molecular marker is within 2 cM of said enhanced nitrogen utilization efficiency locus.

Embodiment 160. The method of any one of embodiments 135 to 159, wherein said molecular marker is within 1 cM of said enhanced nitrogen utilization efficiency locus.

Embodiment 161. The method of any one of embodiments 135 to 160, wherein said molecular marker is within 0.5 cM of said enhanced nitrogen utilization efficiency locus.

Embodiment 162. A method comprising:
a. providing a first population of tobacco plants;
b. genotyping said first population of tobacco plants for the presence of an enhanced nitrogen utilization efficiency allele of a locus encoded by a sequence selected from the group consisting of SEQ ID NOs:9 to 16; and
c. selecting one or more tobacco plants genotyped in step (b) that comprise said enhanced nitrogen utilization efficiency allele.

Embodiment 163. The method of embodiment 161 or 162, wherein said method further comprises:
d. crossing the one or more tobacco plants selected in step (c) to a second tobacco plant; and
e. obtaining progeny seed from the crossing of step (d).

Embodiment 164. The method of any one of embodiments 161 to 163, wherein said first population of tobacco plants is of a Maryland variety.

Embodiment 165. The method of any one of embodiments 161 to 164, wherein said first population of tobacco plants is of a variety selected from the group consisting of MD609, MD601, Banket A1, K326, K346, K358, K394, K399, K730, NC196, NC37NF, NC471, NC55, NC92, NC2326, NC95, NC925.

Embodiment 166. The method of any one of embodiments 161 to 165, wherein said second tobacco plant is of a variety selected from the group consisting of TN86, TN86LC, TN90, TN90LC, TN97, TN97LC.

Embodiment 167. The method of any one of embodiments 161 to 166, wherein said progeny seed comprises said molecular marker.

Embodiment 168. The method of any one of embodiments 161 to 167, wherein said progeny seed comprises said enhanced nitrogen utilization efficiency.

Embodiment 169. A method of introgressing an enhanced nitrogen utilization efficiency trait into a tobacco variety comprising:
a. crossing a first tobacco variety comprising said enhanced nitrogen utilization efficiency trait with a second tobacco variety lacking said enhanced nitrogen utilization efficiency trait;
b. obtaining progeny seed from the cross of step (a);
c. genotyping at least one of said progeny seed obtained in step (b) for a molecular marker linked to said enhanced nitrogen utilization efficiency trait, wherein said molecular marker is within 20 cM of a locus selected from the group consisting of SEQ ID NOs:9 to 16; and
d. selecting a progeny seed comprising said enhanced nitrogen utilization efficiency trait.

Embodiment 170. The method of embodiment 169, wherein said first tobacco variety is a Maryland tobacco variety.

Embodiment 171. The method of embodiment 169 or 170, wherein said first tobacco variety is selected from the group consisting of MD609, MD601, Banket A1, K326, K346, K358, K394, K399, K730, NC196, NC37NF, NC471, NC55, NC92, NC2326, NC95, NC925.

Embodiment 172. The method of any one of embodiments 169 to 171, wherein said second tobacco variety is a Burley tobacco variety.

Embodiment 173. The method of any one of embodiments 169 to 172, wherein said second tobacco variety is selected from the group consisting of TN86, TN86LC, TN90, TN90LC, TN97, TN97LC.

Embodiment 174. The method of any one of embodiments 169 to 173, wherein said enhanced NUE comprises an increased partial factor productivity (PFP) compared to a tobacco plant lacking said enhanced NUE grown in the same conditions.

Embodiment 175. The method of any one of embodiments 169 to 174, wherein said enhanced NUE comprises an increased agronomic efficiency (AE) compared to a tobacco plant lacking said enhanced NUE grown in the same conditions.

Embodiment 176. The method of any one of embodiments 169 to 175, wherein said enhanced NUE comprises an increased recovery efficiency (RE) compared to a tobacco plant lacking said enhanced NUE grown in the same conditions.

Embodiment 177. The method of any one of embodiments 169 to 176, wherein said enhanced NUE comprises an increased physiological efficiency (PE) compared to a tobacco plant lacking said enhanced NUE grown in the same conditions.

Embodiment 178. The method of any one of embodiments 169 to 177, wherein said enhanced NUE comprises an increased internal efficiency (IE) compared to a tobacco plant lacking said enhanced NUE grown in the same conditions.

Embodiment 179. The method of any one of embodiments 169 to 178, wherein said molecular marker is within 15 cM of said locus.

Embodiment 180. The method of any one of embodiments 169 to 179, wherein said molecular marker is within 10 cM of said locus.

Embodiment 181. The method of any one of embodiments 169 to 180, wherein said molecular marker is within 5 cM of said locus.

Embodiment 182. The method of any one of embodiments 169 to 181, wherein said molecular marker is within 2 cM of said locus.

Embodiment 183. The method of any one of embodiments 169 to 182, wherein said molecular marker is within 1 cM of said locus.

Embodiment 184. The method of any one of embodiments 169 to 183, wherein said molecular marker is within 0.5 cM of said locus.

Embodiment 185. A method of selecting a tobacco plant comprising an enhanced nitrogen utilization efficiency trait comprising:
a. isolating nucleic acids from a collection of tobacco germplasm;
b. assaying said nucleic acids for one or more markers located within 20 cM of a locus selected from the group consisting of SEQ ID NOs:9 to 16; and
c. selecting said tobacco plant comprising said enhanced nitrogen utilization efficiency trait.

Embodiment 186. The method of embodiment 185, wherein said method further comprises:
d. crossing said tobacco plant selected in step (c) with a second tobacco plant; and
e. obtaining progeny seed from the cross of step (d).

Embodiment 187. The method of embodiment 185 or 186, wherein said molecular marker is within 15 cM of said locus.

Embodiment 188. The method of any one of embodiments 185 to 187, wherein said molecular marker is within 10 cM of said locus.

Embodiment 189. The method of any one of embodiments 185 to 188, wherein said molecular marker is within 5 cM of said locus.

Embodiment 190. The method of any one of embodiments 185 to 189, wherein said molecular marker is within 2 cM of said locus.

Embodiment 191. The method of any one of embodiments 185 to 190, wherein said molecular marker is within 1 cM of said locus.

Embodiment 192. The method of any one of embodiments 185 to 191, wherein said molecular marker is within 0.5 cM of said locus.

Embodiment 193. A method of selecting a tobacco plant comprising an enhanced nitrogen utilization efficiency trait comprising:
 a. isolating nucleic acids from a collection of tobacco germplasm;
 b. assaying said nucleic acids for one or more markers located within 20 cM of SNP marker selected from the group consisting of SEQ ID NOs:57 to 64; and
 c. selecting said tobacco plant comprising said enhanced nitrogen utilization efficiency trait.

Embodiment 194. The method of embodiment 193, wherein said assaying comprises assaying for a G nucleotide at position 57 of SEQ ID NO:58.

Embodiment 195. The method of embodiment 193 or 194, wherein said assaying comprises assaying for a C nucleotide at position 117 of SEQ ID NO:58.

Embodiment 196. The method of any one of embodiments 193 to 195, wherein said assaying comprises assaying for a G nucleotide at position 57 and a C nucleotide at position 117 of SEQ ID NO:58.

Embodiment 197. The method of embodiment 193 to 196, wherein said assaying comprises assaying for a T nucleotide at position 14 of SEQ ID NO:57.

Embodiment 198. The method of any one of embodiments 193 to 197, wherein said assaying comprises assaying for a G nucleotide at position 162 of SEQ ID NO:59.

Embodiment 199. The method of any one of embodiments 193 to 198, wherein said assaying comprises assaying for a C nucleotide at position 36 of SEQ ID NO:60.

Embodiment 200. The method of any one of embodiments 193 to 199, wherein said assaying comprises assaying for a T nucleotide at position 36 of SEQ ID NO:61.

Embodiment 201. The method of any one of embodiments 193 to 200, wherein said assaying comprises assaying for a T nucleotide at position 36 of SEQ ID NO:62.

Embodiment 202. The method of any one of embodiments 193 to 201, wherein said assaying comprises assaying for a G nucleotide at position 36 of SEQ ID NO:63.

Embodiment 203. The method of any one of embodiments 193 to 202, wherein said assaying comprises assaying for a T nucleotide at position 36 of SEQ ID NO:64.

EXAMPLES

Example 1. Field Production Practices

Field grown tobacco plants are generated using standard field production practices. Each test plot comprises up to 40 rows of transplanted seedlings. Seedlings are germinated in a greenhouse before transplantation. For testing NUE traits, a test plot receives a nitrogen rate of 60 pounds of nitrogen per acre. Plants are topped using standard procedures when 50% of the plants in a test plot reach the elongated button stage. Pesticide application follows standard protocols. Leaves are harvested at maturity and sorted into 3 sticks per plot with 5 plants per stick for curing. Leaves are sampled from the sticks at the takedown/stripping stage. Five leaves are harvested from three different sticks per experimental variety for 15 leaves per sample. Half of the lamina from the fourth leaf from the top of each plant is harvested for sampling. Analytical analysis of alkaloids, TSNA and $NO_3$ are conducted using routine methods known in the art.

Example 2. Identification of Metabolites Associated with Enhanced Nitrogen Utilization Efficiency Maryland tobacco varieties require approximately 25% less nitrogen fertilizer input as compared to Burley tobacco varieties. In order to identify metabolites associated with high nitrogen efficiency (Maryland) and low nitrogen efficiency (Burley) tobacco varieties, differences in metabolite levels were examined in the Maryland tobacco variety MD609 and the Burley tobacco variety TN90.

MD609 and TN90 seedlings were germinated from seed and grown without the addition of nitrogen for six weeks. After six weeks, the seedlings from each variety were split into two groups: Group A comprised plants that were provided with 100 parts per million nitrogen or the normal greenhouse fertilization; and Group B comprised plants that were provided with 25 ppm or 25% of the normal greenhouse fertilization rate. Metabolites were extracted using methanol from root leaf tissue at 10 and 14 weeks after seeding.

The isolated metabolites were analyzed using three different LC/MS approaches (UHPLC-MS/MS (+ESI), UHPLC-MS/MS (−ESI), and GC-MS (+EI)) to separate and identify individual metabolites. Metabolites were identified by comparing the obtained mass spectra to standard spectral databases (Metabolon Inc, Morrisville, NC). Peaks were quantified using area-under-the-curve. Each compound was scaled by registering the medians to equal one (1.00) and normalizing each data point proportionately (termed the "block correction"). The molecular mass of unknown metabolites is provided in Table 1. Discriminant metabolites are shown below in Tables 2 to 5, along with scaled measured values for each sample. Discriminant metabolites were determined by Student's t-test comparisons between TN90 and MD609 taking into account all time points. Metabolites with a p-value less than 0.01 were included in the analysis.

TABLE 1 molecular mass in kiloDaltons for unknown metabolite compounds.

| Metabolite | Mass |
|---|---|
| X-21756 | 247.0918 |
| X-21796 | 138.0566 |
| X-23319 | 299.0771 |
| X-23330 | 251.1136 |
| X-23366 | 189.1023 |
| X-23389 | 157.0762 |
| X-23453 | 161.0818 |
| X-23454 | 319.0933 |
| X-23576 | 267.1237 |
| X-23580 | 311.1136 |
| X-23852 | 374.144 |
| X-23916 | 395.0291 |
| X-23937 | 161.0819 |

TABLE 2

Metabolites negatively correlated with enhanced nitrogen efficiency
identified in root tissue when comparing MD609 and TN90 tobacco lines
at week 10 and week 14 after seeding.

| | TN90 | | | | MD609 | | | |
| --- | --- | --- | --- | --- | --- | --- | --- | --- |
| | 25% Nitrogen | | 100% Nitrogen | | 25% Nitrogen | | 100% Nitrogen | |
| Metabolite | W10 | W14 | W10 | W14 | W10 | W14 | W10 | W14 |
| X-23576 | 4.6 | 3.6 | 1.2 | 8.4 | 2.5 | 1.2 | 1 | 2.3 |
| N-acetylmuramate | 0.3 | 0.4 | 2.5 | 4 | 0.1 | 0.2 | 0.3 | 0.6 |
| X-23319 | 0.5 | 0.5 | 3.2 | 2.9 | 0.3 | 0.3 | 0.4 | 1.2 |
| X-23852 | 0.8 | 1.0 | 2.2 | 3.1 | 0.1 | 1.0 | 0.9 | 0.4 |
| X-23330 | 0.7 | 0.5 | 3.5 | 2.4 | 0.4 | 0.6 | 0.9 | 1.0 |
| Alpha-ketoglutarate | 2.1 | 1.5 | 1.5 | 0.9 | 0.8 | 0.6 | 0.8 | 0.5 |
| X-21756 | 0.6 | 0.4 | 1.9 | 1.3 | 0.2 | 0.3 | 1.0 | 0.5 |
| 4-hydroxy-2-oxoglutaric acid | 0.9 | 0.4 | 1.1 | 1.2 | 0.5 | 0.4 | 0.5 | 0.6 |
| X-23937 | 0.2 | 0.2 | 0.7 | 1.1 | 0.1 | 0.2 | 0.1 | 0.4 |
| X-23916 | 0.6 | 0.6 | 0.5 | 1.0 | 0.3 | 0.3 | 0.2 | 0.3 |
| 1-methyladenine | 1.2 | 0.9 | 1.2 | 1.1 | 1.0 | 0.8 | 0.8 | 0.7 |

TABLE 3

Metabolites positively correlated with enhanced nitrogen efficiency
identified in root tissue when comparing MD609 and TN90 tobacco lines.

| | TN90 | | | | MD609 | | | |
| --- | --- | --- | --- | --- | --- | --- | --- | --- |
| | 25% Nitrogen | | 100% Nitrogen | | 25% Nitrogen | | 100% Nitrogen | |
| Metabolite | W10 | W14 | W10 | W14 | W10 | W14 | W10 | W14 |
| 4-guanidinobutanoate | 0.7 | 0.7 | 0.7 | 0.6 | 1.0 | 1.1 | 0.8 | 0.7 |
| Syringaldehyde | 0.5 | 0.6 | 0.4 | 0.3 | 0.9 | 1.0 | 0.6 | 0.4 |
| Thiamin | 0.2 | 0.1 | 0.7 | 0.7 | 0.7 | 1.1 | 0.7 | 1.1 |
| p-hydroxybenzaldehyde | 0.4 | 1.0 | 0.8 | 0.9 | 0.6 | 1.6 | 1.4 | 1.5 |

TABLE 4

Metabolites negatively correlated with enhanced nitrogen efficiency
identified in leaf tissue when comparing MD609 and TN90 tobacco lines.

| | TN90 | | | | MD609 | | | |
| --- | --- | --- | --- | --- | --- | --- | --- | --- |
| | 25% Nitrogen | | 100% Nitrogen | | 25% Nitrogen | | 100% Nitrogen | |
| Metabolite | W10 | W14 | W10 | W14 | W10 | W14 | W10 | W14 |
| X-23453 | 1.2 | 4.9 | 2.2 | 3.9 | 0.9 | 1.3 | 1.3 | 1.9 |
| X-21756 | 1.6 | 0.8 | 2.3 | 2.5 | 0.8 | 0.3 | 1.0 | 0.8 |
| X-11429 | 1.3 | 0.6 | 2.7 | 2.4 | 0.7 | 0.2 | 1.0 | 1.0 |
| X-21796 | 0.7 | 2.0 | 0.7 | 2.0 | 0.2 | 0.6 | 0.2 | 0.5 |
| N'-methylnicotinamide | 0.7 | 1.0 | 1.9 | 1.1 | 0.9 | 0.1 | 0.1 | 0.2 |
| Cotinine | 0.5 | 1.4 | 0.3 | 1.7 | 0.4 | 0.4 | 0.1 | 0.3 |
| X-23389 | 0.9 | 1.2 | 0.4 | 1.2 | 0.5 | 0.3 | 0.1 | 0.2 |
| N-acetylarginine | 1.0 | 0.7 | 0.8 | 1.9 | 0.6 | 0.3 | 0.7 | 0.8 |
| X-23366 | 0.6 | 0.9 | 0.1 | 0.8 | 0.3 | 0.2 | 0.1 | 0.1 |
| N-acetylphenylalanine | 1.0 | 1.0 | 1.2 | 1.0 | 0.9 | 0.4 | 0.7 | 0.5 |
| Naringenin | 0.4 | 0.8 | 0.3 | 0.8 | 0.2 | 0.2 | 0.1 | 0.4 |

TABLE 5

Metabolites positively correlated with enhanced nitrogen efficiency identified in leaf tissue when comparing MD609 and TN90 tobacco lines.

| | TN90 | | | | MD609 | | | |
|---|---|---|---|---|---|---|---|---|
| | 25% Nitrogen | | 100% Nitrogen | | 25% Nitrogen | | 100% Nitrogen | |
| Metabolite | W10 | W14 | W10 | W14 | W10 | W14 | W10 | W14 |
| 4-guanidinobutanoate | 0.6 | 0.8 | 1.0 | 1.1 | 1.3 | 0.9 | 1.6 | 1.6 |
| X-23454 | 0.1 | 0.1 | 0.5 | 0.1 | 0.8 | 0.1 | 1.5 | 1.5 |
| X-23580 | 1.1 | 3.6 | 1.8 | 1.5 | 4.9 | 6.0 | 3.5 | 5.3 |
| X-23852 | 0.9 | 7.7 | 3.6 | 2.1 | 9.8 | 13.2 | 7.6 | 11.0 |

Example 3. Identification of Gene Expression Associated with Enhanced Nitrogen Utilization Efficiency The same plants used in Example 1 are also subjected to RNA extraction to be used for RNAseq. RNA is extracted from leaf and root tissue at 10 weeks and 14 weeks after seeding and used for Illumina sequencing. The RNAseq data were analyzed according to methods standard in the art. Candidate genes are subsequently verified.

Seventeen genes (Tables 6 and 7) were found to negatively correlate with the enhanced nitrogen utilization efficiency phenotype of MD609, and seven genes (Tables 8 and 9) were found to positively correlate with the enhanced nitrogen utilization efficiency phenotype of MD609. The negatively correlated genes are candidates for down-regulation in Burley tobacco varieties (via mutagenesis, cisgenic transformation, or transgenic transformation), and the positively correlated genes are candidates for over-expression in Burley tobacco varieties to improve nitrogen utilization efficiency. Single nucleotide polymorphism (SNP) markers associated are provided for tracking the each candidate gene (Tables 6 to 10). The polymorphism associated with the MD609 alleles, and therefore favorable for enhanced NUE is provided (Table 10).

Figure 2:
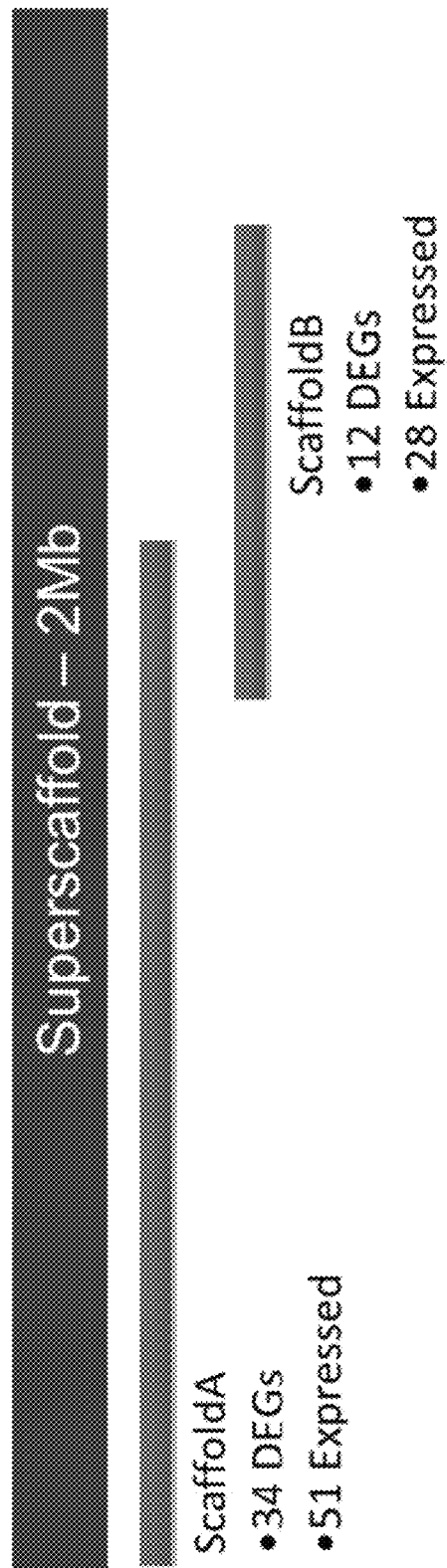
FIG. 2 depicts a 2 megabase region of tobacco chromosome 11 that is covered by superscaffold 1. Superscaffold1 is a contig of scaffolds A and B. Of the 79 expressed genes located in this region, 56 genes are differentially expressed.

Identification of the genomic location for each of the correlated genes identifies four clusters of genes associated with enhanced NUE in the tobacco genome (FIG. 1). Seven genes are similarly located on chromosome 1, four genes are similarly located on chromosome 11, three genes are similarly located on chromosome 14, and five genes are similarly located on chromosome 20 (FIG. 1). These four locations are also hotspots for genes differentially expressed between low and normal nitrogen conditions (FIG. 1). SNP markers are created to identify MD609 specific and therefore enhanced NUE polymorphisms for each of these locations (Tables 6 to 10). The area on chromosome 11 is further characterized and contains 79 total expressed genes and 46 of these genes are differentially expressed genes under low nitrogen conditions (FIG. 2).

TABLE 6

Genes identified as negatively correlated with enhanced nitrogen utilization efficiency in root tissue.

| Gene Identifier | SEQ ID NO | Gene Description | SNP marker SEQ ID NO: |
|---|---|---|---|
| G38453 | 25 | Putative vacuolar proton ATPase subunit E | 57 |
| G64360 | 26 | Clathrin interactor epsin 1-like | 63 |
| G26157 | 27 | Serine/threonine-protein kinase PBS1 | 59 |

TABLE 6-continued

Genes identified as negatively correlated with enhanced nitrogen utilization efficiency in root tissue.

| Gene Identifier | SEQ ID NO | Gene Description | SNP marker SEQ ID NO: |
|---|---|---|---|
| G54692 | 28 | ATPase family AAA domain-containing protein 1-a-like | 57 |
| G32111 | 29 | Uncharacterized protein | 57 |
| G49619 | 30 | Coatomer subunit gamma | 61 |
| G19982 | 31 | Uncharacterized protein | 60 |
| G39737 | 32 | Uncharacterized protein | 58 |
| G28894 | 33 | Putative quinolinate phosphoribosyltransferase | 60 |
| G30288 | 38 | Probable acyl-activating enzyme chloroplastic-like | 59 |
| G39762 | 39 | Alpha-l-fucosidase | 58 |
| G39442 | 40 | Uncharacterized protein | 57 |

TABLE 7

Genes identified as negatively correlated with enhanced nitrogen utilization efficiency in leaf tissue.

| Gene Identifier | SEQ ID NO | Gene Description | SNP Marker SEQ ID NO: |
|---|---|---|---|
| G41803 | 34 | ABC transporter F-family member 3-like | 57 |
| G46356 | 35 | Uncharacterized protein | 57 |
| G56420 | 36 | WD repeat-containing protein 26-like | 58 |
| G59801 | 37 | Protein phosphatase 2A | 60 |
| G30288 | 38 | Probable acyl-activating enzyme chloroplastic-like | 59 |
| G39762 | 39 | Alpha-l-fucosidase | 58 |
| G39442 | 40 | Uncharacterized protein | 57 |

TABLE 8

Genes identified as positively correlated with enhanced nitrogen utilization efficiency in root tissue.

| Gene Identifier | SEQ ID NO | Gene Description | SNP Marker SEQ ID NO: |
|---|---|---|---|
| G59318 | 1 | PR-10 type pathogenesis-related protein | 57 |
| G20580 | 2 | Uncharacterized amino acid permease | 60 |
| G30999 | 3 | TBZ17 | 62 |

TABLE 8-continued

Genes identified as positively correlated with enhanced nitrogen utilization efficiency in root tissue.

| Gene Identifier | SEQ ID NO | Gene Description | SNP Marker SEQ ID NO: |
|---|---|---|---|
| G29260 | 4 | BTB/POZ domain-containing protein (AT5G48800-like) | 64 |
| G41446 | 8 | 3-isopropylmalate dehydratase small subunit | 57 |

TABLE 9

Genes identified as positively correlated with enhanced nitrogen utilization efficiency in leaf tissue.

| Gene Identifier | SEQ ID NO | Gene Description | SNP Marker SEQ ID NO: |
|---|---|---|---|
| G41343 | 5 | Glucose-6-phosphate 1-epimerase-like | 57 |
| G53261 | 6 | Probable nitrite transporter (AT1G68570-like) | 60 |
| G42290 | 7 | Phospho-2-dehydro-3-deoxyheptonate aldolase | 58 |
| G41446 | 8 | 3-isopropylmalate dehydratase small subunit | 61 |

TABLE 10

SNP markers comprising polymorphisms associated with enhanced NUE.

| SNP marker SEQ ID NO | Positon of polymorphism | Allele associated with NUE |
|---|---|---|
| 57 | 147 | T |
| 58 | 57 | G |
|  | 117 | C |
| 59 | 162 | G |
| 60 | 36 | C |
| 61 | 36 | T |
| 62 | 36 | T |
| 63 | 36 | G |
| 64 | 36 | T |

Example 4. Identifying Tobacco Leaf- and Root-Preferred Promoters

RNA samples from 4 week old TN90 tobacco plants are obtained from 10 tissue types (axillary buds before topping; axillary buds 2 hours after topping; axillary buds 6 hours after topping; axillary buds 24 hours after topping; axillary buds 72 hours after topping; roots before topping; roots 24 hours after topping; roots 72 hours after topping; young leaf at the time of topping; and shoot apical meristem). The resulting RNA samples (three independently collected samples for each tissue type) are used as starting material for Illumina 1×100 bp sequencing.

Illumina reads are mapped and used to identify a list of candidate genes exhibiting high root or leaf expression. Tables 11 and 12 provide RPKM expression values for genes identified as having leaf-preferred or root-preferred expression. These genes are candidates for possessing leaf-preferred promoters or root-preferred promoters, respectively.

TABLE 11

Genes with leaf-preferred expression

| Promoter | Gene Description | SEQ ID NO: | Axillary Bud | | | | | Root | | | SAM | Leaf |
|---|---|---|---|---|---|---|---|---|---|---|---|---|
| | | | 0 hr | 2 hr | 6 hr | 24 hr | 72 hr | 0 hr | 24 hr | 72 hr | | |
| P16098 | Carbonic anhydrase | 17 | 4.88 | 5.94 | 7.49 | 4.67 | 16.12 | 0.45 | 0.41 | 0.52 | 2.89 | 1002.14 |
| P42207 | CP12 | 18 | 0.41 | 0.99 | 1.24 | 0.52 | 1.83 | 0.05 | 0.02 | 0.07 | 0.13 | 34.34 |
| P47582 | Chloroplast sedoheptulose-1,7-bisphosphatase | 19 | 0.32 | 0.68 | 0.91 | 0.68 | 1.96 | 0.03 | 0.03 | 0.06 | 0.06 | 96.69 |

TABLE 12

Genes with root-preferred expression

| Promoter | Gene Description | SEQ ID NO: | Axillary Bud | | | | | Root | | | SAM | Leaf |
|---|---|---|---|---|---|---|---|---|---|---|---|---|
| | | | 0 hr | 2 hr | 6 hr | 24 hr | 72 hr | 0 hr | 24 hr | 72 hr | | |
| P2862 | Putative PLA2 | 20 | 0.65 | 0.78 | 0.58 | 0.38 | 0.38 | 336.69 | 391.95 | 511.86 | 0.36 | 0.43 |
| P57190 | Uncharacterized protein | 21 | 0.38 | 0.45 | 0.29 | 0.39 | 0.35 | 198.00 | 416.84 | 384.52 | 0.47 | 0.26 |
| P49330 | Glutathione S-transferase parC | 22 | 0.35 | 0.35 | 0.27 | 0.75 | 0.38 | 196.29 | 269.39 | 417.71 | 0.23 | 0.22 |
| P3788 | PR-10 type pathogenesis-related protein | 23 | 0.29 | 0.36 | 0.45 | 0.15 | 0.23 | 192.16 | 88.51 | 193.35 | 0.26 | 0.16 |
| P77628 | Cytochrome P450 | 24 | 0.39 | 0.71 | 0.53 | 0.39 | 0.44 | 144.99 | 333.54 | 386.32 | 0.52 | 0.50 |

Example 5. Development of Modified Plants

An expression vector, p45-2-7 (SEQ ID NO: 65), is used as a backbone to generate multiple transformation vectors (See Examples X-Y). p45-2-7 contains a CsVMV promoter, a NOS terminator, and a cassette comprising a kanamycin selection marker (NPT II) operably linked to an Actin2 promoter and a NOS terminator. Nucleic acid vectors comprising transgenes of interest are introduced into tobacco leaf discs via *Agrobacterium* transformation. See, for example, Mayo et al., 2006, *Nat Protoc.* 1:1105-11 and Horsch et al., 1985, *Science* 227:1229-1231.

TN90 tobacco plants are grown in Magenta™ GA-7 boxes and leaf discs are cut and placed into Petri plates. *Agrobacterium tumefaciens* cells comprising a transformation vector are collected by centrifuging a 20 mL cell suspension in a 50 mL centrifuge tube at 3500 RPM for 10 minutes. The supernatant is removed and the *Agrobacterium tumefaciens* cell pellet is resuspended in 40 mL liquid re-suspension medium. Tobacco leaves, avoiding the midrib, are cut into eight 0.6 cm discs with a #15 razor blade and placed upside down in a Petri plate. A thin layer of Murashige & Skoog with B5 vitamins liquid re-suspension medium is added to the Petri plate and the leaf discs are poked uniformly with a fine point needle. Approximately 25 mL of the *Agrobacterium tumefaciens* suspension is added to the Petri plate and the leaf discs are incubated in the suspension for 10 minutes.

Leaf discs are transferred to co-cultivation Petri plates (½ MS medium) and discs are placed upside down in contact with filter paper overlaid on the co-cultivation TOM medium (MS medium with 20 g/L sucrose; 1 mg/L indole-3-acetic acid; and 2.5 mg/L 6-benzyl aminopurine (BAP)). The Petri plate is sealed with parafilm prior to incubation in dim light (60-80 mE/ms) with 18 hours on, 6 hours off photoperiods at 24 degrees Celsius for three days. After incubation, leaf discs are transferred to regeneration/selection TOM K medium Petri plates (TOM medium plus 300 mg/L kanamycin). Leaf discs are sub-cultured bi-weekly to fresh TOM K medium in dim light with 18 hours on, 6 hours off photoperiods at 24 degrees Celsius until shoots become excisable. Shoots from leaves are removed with forceps and inserted in MS basal medium with 100 mg/L kanamycin. Shoots on MS basal medium with 100 mg/L kanamycin are incubated at 24 degrees Celsius with 18 hours on, 6 hours off photoperiods with high intensity lighting (6080 mE/ms) to induce rooting.

When plantlets containing both shoots and roots grow large enough (e.g., reach approximately half the height of a Magenta™ GA-7 box), they are transferred to soil. Established seedlings are transferred to a greenhouse for further analysis and to set seed. Evaluation of enhanced nitrogen utilization efficiency phenotypes is conducted by growing modified plants ($T_0$, $T_1$, $T_2$, or later generations) and control plants. Control plants are either NLM plants that have not been transformed or NLM plants that have been transformed with an empty p45-2-7 vector.

Phenotypic screening for enhanced nitrogen utilization efficiency is conducted in a greenhouse using zero parts per million (ppm) nitrogen (no nitrogen), 25 ppm nitrogen (low nitrogen), and 100 ppm nitrogen (normal nitrogen). Initial screening is undertaken in the greenhouse with $T_1$ plants. Homozygous $T_2$ populations are then evaluated in the field using 60 pounds per acre fertilizer (~25% of the recommended rate for Burley tobacco. Seedling growth, chlorophyll loss, and final yield are measured and compared to control plants grown at normal nitrogen levels.

Figure 5:
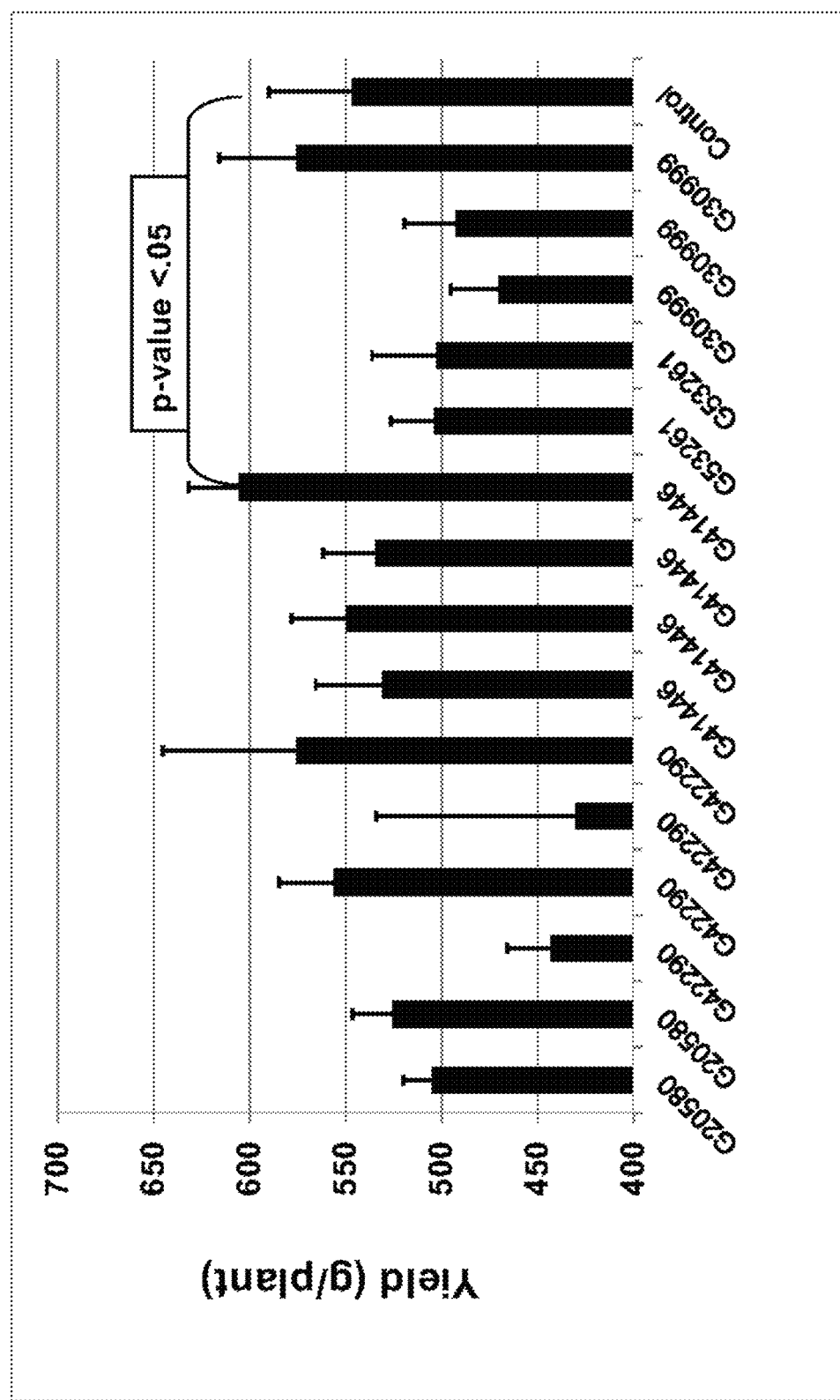
FIG. 5 depicts yield in grams fresh weight per plant of greenhouse grown $T_1$ plants overexpressing genes positively correlated with increased yield under nitrogen stress. The mean and standard deviation based on 9 plants per sample is displayed.

In the $T_1$ generation, plants overexpressing G20580 (2 independent transformants), G42290 (4 independent transformants), G41446 (4 independent transformants), G53261 (2 independent transformants), and G30999 (3 independent transformants) are grown in the greenhouse along with controls under nitrogen limiting conditions equivalent to 60 pounds of Nitrogen per acre. Nine plants per transformant are sampled and one of the lines overexpressing G41446 show a statistically significant increase in yield (grams fresh weight per plant) compared to the control (See FIG. 5).

Example 6. Creating a Cisgenic Tobacco Plant with Enhanced Nitrogen Utilization Efficiency Nitrogen utilization efficiency can be improved by modifying the expression of genes involving the genes that were identified as differentially expressed in Example 2. Similarly, genes involved in the biosynthesis or degradation of the metabolites identified in Example 1 can be modulated to improve nitrogen utilization efficiency. Genes that are positively associated with enhanced nitrogen utilization efficiency can be over-expressed using a general over-expression promoter or a tissue-preferred promoter to over-express the gene in desired tissues.

Transformation vectors are created to overexpress proteins that are positively associated with enhanced nitrogen utilization efficiency. Separate transformation vectors comprising one of SEQ ID NOs:9 to 16 are incorporated into p45-2-7 transformation vectors. Additionally transformation vectors are created comprising one of SEQ ID NOs:9 to 16.

Modified tobacco plants are generated using these transformation vectors according to Example 4. Modified tobacco plants ($T_1$ generation) and control tobacco plants are then phenotypically evaluated as described in Example 4. The modified tobacco plants exhibit enhanced nitrogen utilization efficiency as compared to control tobacco plants grown under the same conditions.

Example 7. Creating a Transgenic Tobacco Plant with Enhanced Nitrogen Utilization Efficiency Nitrogen utilization efficiency can also be enhanced by down-regulating the expression of genes identified as being negatively associated with nitrogen utilization efficiency in Example 2.

Transformation vectors comprising RNAi constructs are designed to inhibit tobacco genes whose expression is negatively associated with nitrogen utilization efficiency in Example 2. Separate transformation vectors comprise one of SEQ ID NOs:41 to 56, which are incorporated into p45-2-7 transformation vectors. Additional transformation vectors are created comprising one of SEQ ID NOs:41 to 56.

Modified tobacco plants are generated using these transformation vectors according to Example 4. Modified tobacco plants (T1 generation) and control tobacco plants are then phenotypically evaluated as described in Example 4. The modified tobacco plants exhibit enhanced nitrogen utilization efficiency as compared to control tobacco plants grown under the same conditions.

Example 8. Additional Methods of Improving Nitrogen Utilization Efficiency Using Gene Editing Technologies Gene editing technologies such as CRISPR/Cas9, CRISPR/Cpf1, CRISPR/CasX, CRISPR/CasY, CRISPR/Csm1, zinc-finger nucleases (ZFN), and transcription activator-like effector nucleases (TALENs) are used to modify the coding region of a gene negatively associated with enhanced nitrogen utilization efficiency so that the gene encodes a non-functional protein or a lower-functioning protein. These gene editing technologies are also used to edit or replace an endogenous promoter sequence to drive its cognate protein expression in either leaf or root tissue to improve nitrogen utilization efficiency. For example, an endogenous G64360 is edited or replaced so the gene is only expressed in leaf tissue, where it can function to improve nitrogen utilization efficiency of the plant.

Separate CRISPR/Cas9 or CRISPR/Cpf1 guide RNAs are constructed to recognize and hybridize to the promoter sequence of each one of SEQ ID NOs:9 to 40. The engineered guide RNA and a donor polynucleotide comprising a promoter selected from the group consisting of SEQ ID NOs: 17 to 24 are provided to a tobacco plant, allowing the selected promoter to replace the endogenous promoter of the selected genes and restrict expression of endogenous to either leaf or root tissue as desired. The edited tobacco plants exhibit enhanced nitrogen utilization efficiency compared to control tobacco plants grown under similar conditions.

Example 9. Development of Novel Mutations to Improve Nitrogen Utilization Efficiency Via Random Mutagenesis Random mutagenesis of tobacco plants are performed using ethyl methanesulfonate (EMS) mutagenesis or fast neutron bombardment. EMS mutagenesis consists of chemically inducing random point mutations. Fast neutron mutagenesis consists of exposing seeds to neutron bombardment which causes large deletions through double stranded DNA breakage.

For EMS mutagenesis, one gram (approximately 10,000 seeds) of the Burley tobacco variety TN90 seeds are washed in 0.1% Tween for fifteen minutes and then soaked in 30 mL of ddH$_2$O for two hours. One hundred fifty (150) μL of 0.5% EMS (Sigma, Catalogue No. M-0880) is then mixed into the seed/ddH$_2$O solution and incubated for 8-12 hours (rotating at 30 R.P.M.) under a hood at room temperature (RT; approximately 20° C.). The liquid then is removed from the seeds and mixed into 1 M NaOH overnight for decontamination and disposal. The seeds are then washed twice with 100 mL ddH$_2$O for 2-4 hours. The washed seeds are then suspended in 0.1% agar solution.

The EMS-treated seeds in the agar solution are evenly spread onto water-soaked Carolina's Choice Tobacco Mix (Carolina Soil Company, Kinston, NC) in flats at ~2000 seeds/flat. The flats are then covered with plastic wrap and placed in a growth chamber. Once the seedlings emerge from the soil, the plastic wrap is punctured to allow humidity to decline gradually. The plastic wrap is completely removed after two weeks. Flats are moved to a greenhouse and fertilized with NPK fertilizer. The seedlings are replugged into a float tray and grown until transplanting size. The plants are subsequently transplanted into a field. During growth, the plants self-pollinate to form M1 seeds. At the mature stage, five capsules are harvested from each plant and individual designations are given to the set of seeds from each plant. This forms the M1 population. A composite of M1 seed from each M0 plant are grown, and plants are phenotypically evaluated for enhanced nitrogen efficiency as described in Example 4. M1 plants exhibiting enhanced nitrogen efficiency are selected and screened for mutations using DNA sequencing and gene mapping techniques known in the art.

Example 10. Using Breeding to Create a Tobacco Plant with Enhanced Nitrogen Utilization Efficiency Traditional breeding techniques can be used to introduce NUE favorable alleles provided herein into any tobacco variety to enhance NUE. A population of tobacco plants can be created by crossing a tobacco plant with at least one favorable NUE allele (See Table 10) to a tobacco plant lacking that favorable allele. Marker assisted selection, or other techniques known in the art (e.g. direct sequencing) can be used to track introgression of a favorable allele in the F$_1$ generation and can be used to determine heterozygosity or homozygosity in subsequent generations. Enhanced NUE of progeny plants can be determined using methods known in the art or described above. Multiple different NUE favorable alleles can be combined into a single line. A molecular phenotype as determined by metabolite signature can be used to track enhanced NUE during breeding. The metabolite signatures of progeny plants can be determined using methods described above. Progeny plants with metabolite signatures of parental plants with enhanced NUE are crossed to create subsequent populations of tobacco plants with enhanced NUE.

Figure 3:
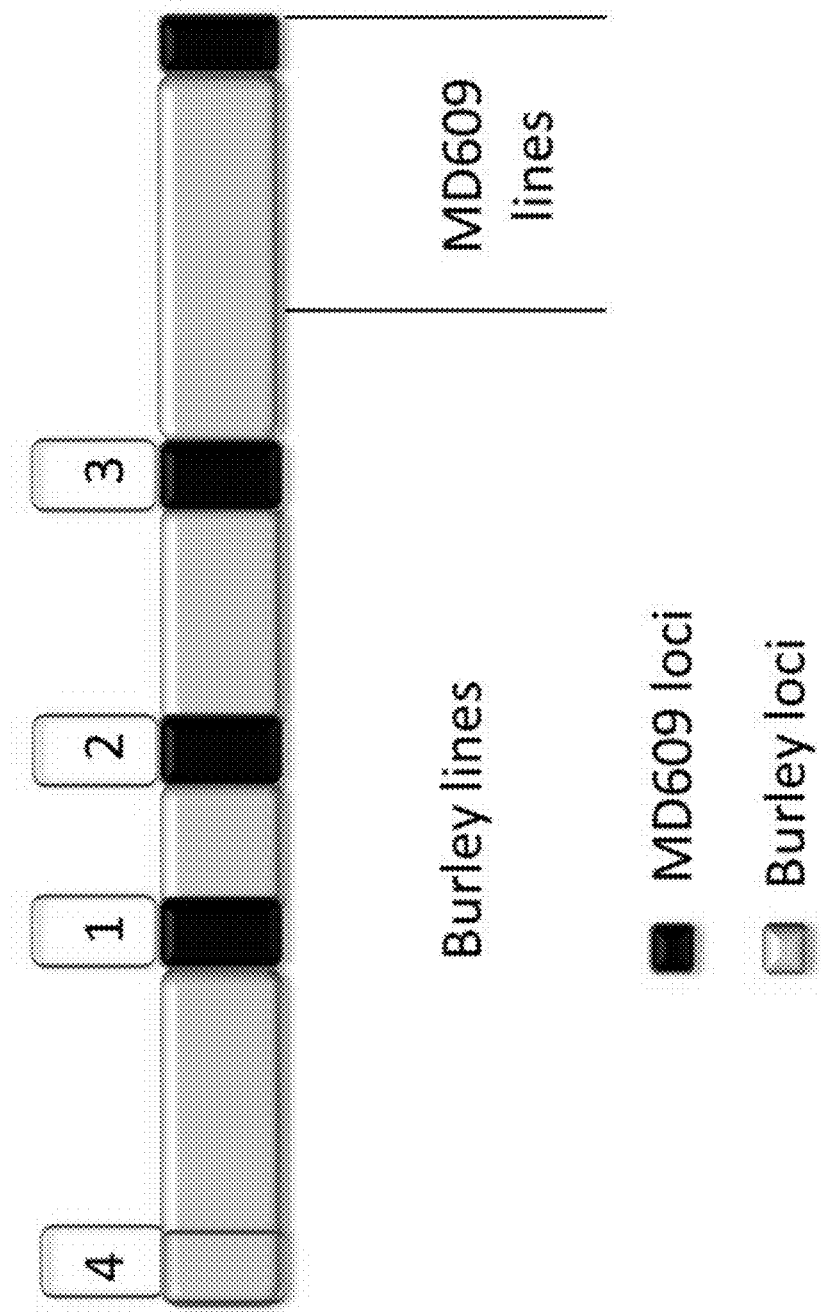
FIG. 3 depicts the allelic constitution for 23 Burley and 6 Maryland varieties at a genetic locus correlated with NUE on tobacco chromosome 11. Lines 1, 2, and 3 are Burley lines that contain a favorable Maryland allele at SEQ ID NO:58, and line 4 is a standard Burley line that contains an unfavorable Burley allele at SEQ ID NO:58.
Figure 4:
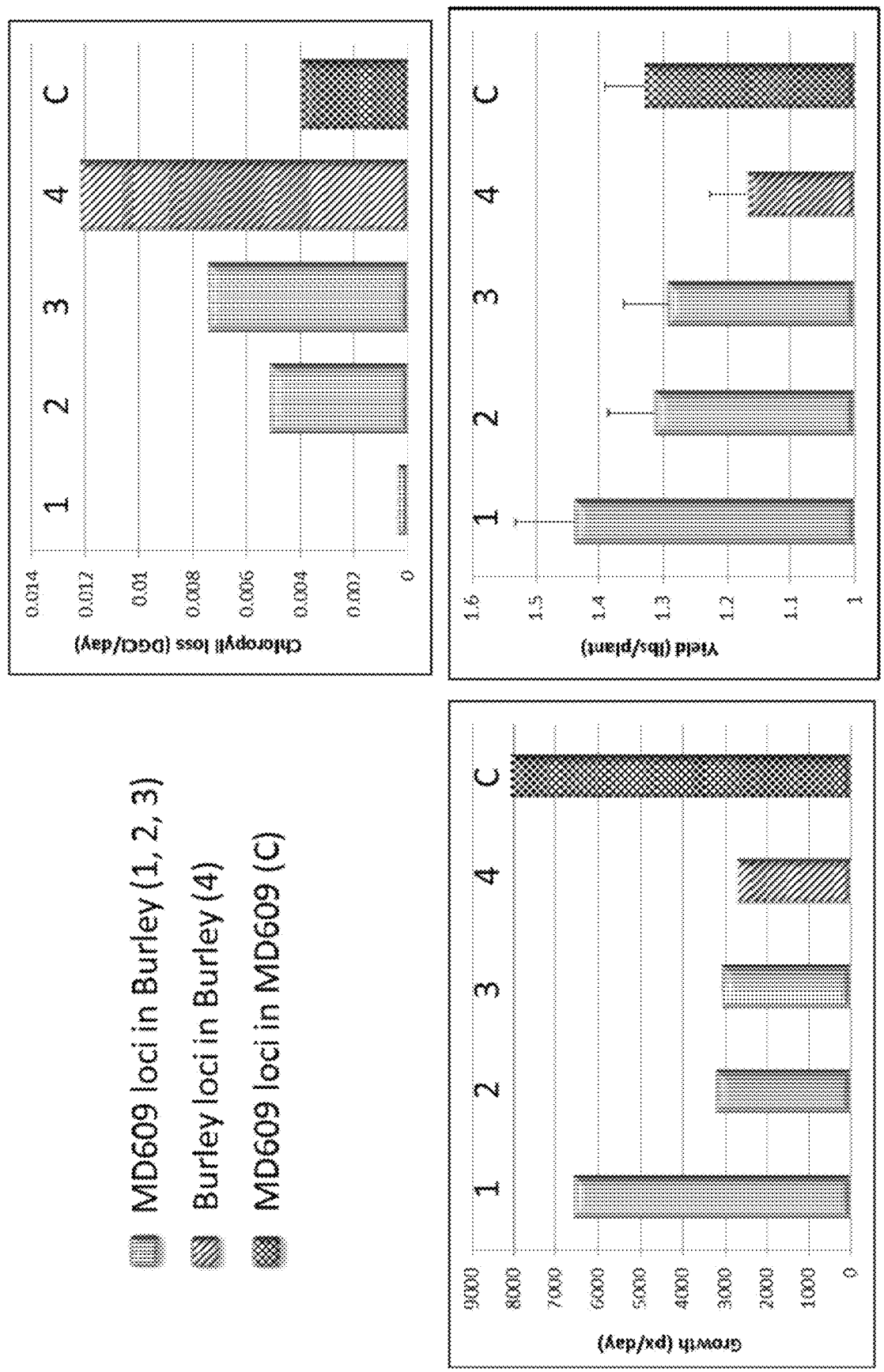
FIG. 4 depicts chlorophyll loss, growth, and yield for Lines 1 to 4 as described in FIG. 3 and a MD609 control (C). Lines 1, 2, and 3 are Burley lines that contain a favorable Maryland allele at SEQ ID NO:58 and line 4 is a standard Burley line that contains an unfavorable Burley allele at SEQ ID NO:58.

Introduction of Maryland609 loci into commercially available Burley varieties can be performed as described to develop Burley lines with enhanced NUE. Screening of 23 Burley and 6 MD609 lines identified 3 Burley lines containing the MD609 allele at SNP marker S451 (SEQ ID NO:58) (FIG. 3). The three Burley lines with the MD609 allele were tested for chlorophyll loss, growth, and yield under nitrogen limiting conditions and compared to a control TN90 Burley line and a control MD609 line (MD609 with the MD609 allele at SNP marker S451) (FIG. 4). The Burley lines with the MD609 allele exhibit chlorophyll lose, growth, and yield more similar to the Maryland control (FIG. 4). The TN90 Burley control exhibits increased chlorophyll lose, decreased growth, and decreased yield compared to the MD609 control (FIG. 4). These results indicate that introduction of the MD609 allele at SNP marker S451 can enhance NUE.

Figure 6:
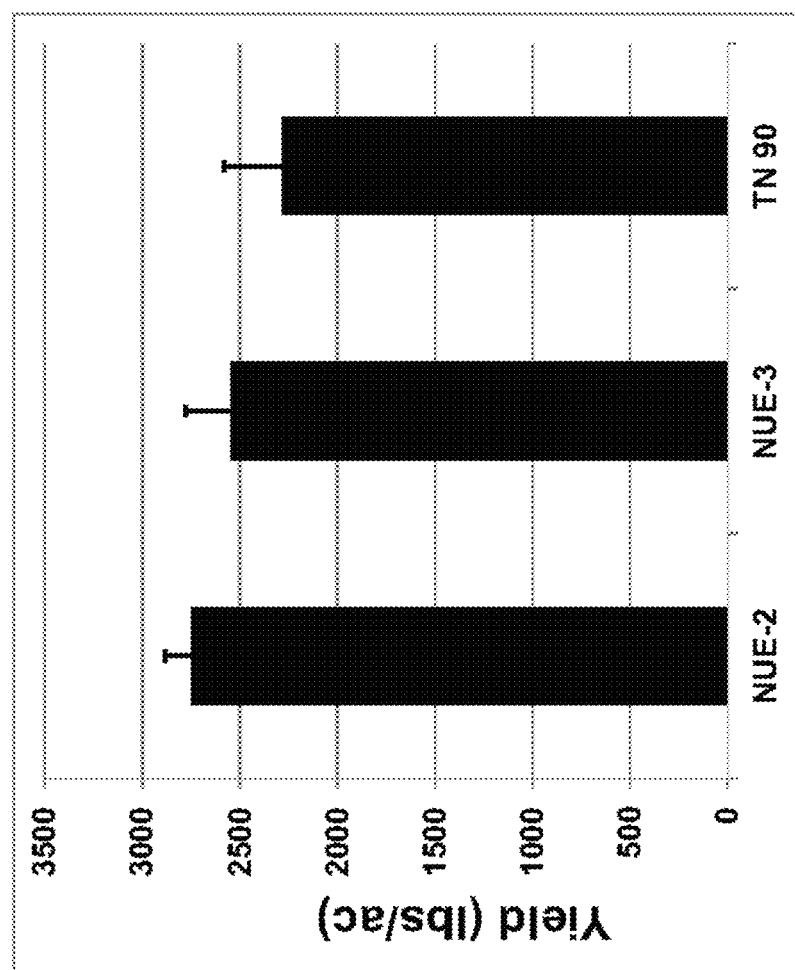
FIG. 6 depicts yield in pounds per acre after harvest for two independent field grown $F_4$ lines, NUE-2 and NUE-3. The test lines are generated from crosses of MD609 to Burley TN90 as described. The mean and standard deviation is provided in comparison to control TN90 Burley tobacco.

In order to introduce MD609 alleles into Burley, MD609 was crossed with Burley. F$_1$ progeny from this cross were selected and subsequently selfed to produce F$_2$ seed. F$_2$ and F$_3$ plants were grown and selfed to generate F$_4$ seed. Bulked F$_4$ seed from two independent crossing schemes, identified as the NUE-2 and NUE-3 lines, are grown and harvested in the field. The genotypes of the SNP markers S451, S317, S12385, S238, S3894, and S2237 are determined for F$_4$ seed of both NUE-2 and NUE-3 lines (See Table 13). F$_4$ plants are grown using reduced nitrogen production practices described in Example 1. Both NUE-2 and NUE-3 lines demonstrate an increased yield in pounds per acre compared to the Burley control TN90 (See FIG. 6).

Alternatively, a modified tobacco plant comprising an enhanced NUE phenotype can be created using the methods described herein and crossed to a unmodified tobacco plant to propagate the modification in subsequent generations. Selection for the genetic modification can be tracked using appropriate techniques known in the art. Enhanced NUE of progeny plants can be determined using methods known in the art or described above.

TABLE 13

Genotypes of field grown plants from F$_4$ NUE-2 and NUE-3 lines and TN90. MD represents a MD609 allele, Burley represents a Burley allele, and HET represents a heterozygous MD609/Burley.

| | S451 | S317 | S12835 | S238 | S3894 | S2237 |
|---|---|---|---|---|---|---|
| NUE-2 | MD | HET | MD | Burley | Burley | MD |
| NUE-3 | MD | HET | MD | Burley | Burley | MD |
| TN90 | Burley | Burley | Burley | Burley | Burley | Burley |

What is claimed is:

1. A method of producing a *Nicotiana tabacum* plant comprising an enhanced nitrogen utilization efficiency (NUE) trait, said method comprising:
   a) selecting a *Nicotiana tabacum* plant comprising at least one favorable NUE allele comprising a T nucleotide at a position corresponding to position 36 of SEQ ID NO: 61 or a T nucleotide at a position corresponding to position 36 of SEQ ID NO: 64;
   b) crossing said *Nicotiana tabacum* plant selected in step a) with a second *Nicotiana tabacum* plant; and
   c) obtaining progeny seed from a cross of step b) wherein a plant grown from said progeny seed comprises said enhanced NUE trait and said at least one favorable NUE allele.

2. The method of claim 1, wherein said enhanced NUE trait is selected from the group consisting of an increased partial factor productivity (PFP), an increased agronomic efficiency (AE), an increased recovery efficiency (RE), an increased physiological efficiency (PE), and an increased internal efficiency (IE), when compared to a *Nicotiana tabacum* plant lacking said enhanced NUE trait when grown in the same conditions.

3. The method of claim 1, wherein said *Nicotiana tabacum* plant is of a variety selected from the group consisting of MD609, MD601, Banket A1, K326, K346, K358, K394, K399, K730, NC196, NC37NF, NC471, NC55, NC92, NC2326, NC95, and NC925.

4. The method of claim 1, wherein said second *Nicotiana tabacum* plant is a Burley tobacco variety.

5. The method of claim 4, wherein said Burley tobacco variety is selected from the group consisting of TN86, TN86LC, TN90, TN90LC, TN97, and TN97LC.

6. A method of introgressing an enhanced nitrogen utilization efficiency (NUE) trait into a *Nicotiana tabacum* variety, said method comprising the steps of:
   a) crossing a tobacco plant from a first *Nicotiana tabacum* variety comprising an enhanced NUE trait with a tobacco plant from a second *Nicotiana tabacum* variety lacking said enhanced NUE trait;
   b) obtaining progeny seed from the cross of step a); and
   c) selecting at least one progeny seed comprising at least one favorable NUE allele comprising a T nucleotide at a position corresponding to position 36 of SEQ ID NO: 61 or a T nucleotide at a position corresponding to position 36 of SEQ ID NO: 64 and wherein a plant grown from said at least one progeny seed further comprises said enhanced NUE trait.

7. The method of claim 6, wherein said second *Nicotiana tabacum* variety is a Burley tobacco variety.

8. The method of claim 7, wherein said Burley tobacco variety is selected from the group consisting of TN86, TN86LC, TN90, TN90LC, TN97, and TN97LC.

9. The method of claim 6, wherein said enhanced NUE trait is selected from the group consisting of an increased partial factor productivity (PFP), an increased agronomic efficiency (AE), an increased recovery efficiency (RE), an increased physiological efficiency (PE), and an increased internal efficiency (IE), when compared to a *Nicotiana tabacum* plant lacking said enhanced NUE trait when grown in the same conditions.

10. The method of claim 6, wherein said first *Nicotiana tabacum* variety is selected from the group consisting of MD609, MD601, Banket A1, K326, K346, K358, K394, K399, K730, NC196, NC37NF, NC471, NC55, NC92, NC2326, NC95, and NC925.

* * * * *

SEQUENCE LISTING

```
Sequence total quantity: 65
SEQ ID NO: 1              moltype = AA  length = 128
FEATURE                   Location/Qualifiers
source                    1..128
                          mol_type = protein
                          organism = Nicotiana tabacum
SEQUENCE: 1
MGLKGKLISQ MEMKCAGDLL HEHFKSNPHQ TSTMSPDKIT NFTLHEGQLG NTGSVVSWKY   60
VLGGKERHAK QALHIDDAKK SITFNFLEGY MNELYKSMTP QYRINNNLEC HKSRNHPMQV  120
TSPNHTQI                                                          128

SEQ ID NO: 2              moltype = AA  length = 540
FEATURE                   Location/Qualifiers
source                    1..540
                          mol_type = protein
                          organism = Nicotiana tabacum
SEQUENCE: 2
MKAEGSALSS AGSYHRLAYH EVINDDNQNK IFTSDDSRLR QLGYKQELYR GLSFIANFSF   60
TFAIVSVLTG ISTLYNQALT FGGPITLVYG WPIVSLMTLI VGLAMAEICS AYPTSAGLYY  120
WSAKLSGNYF GPFASWITGW FNIVGQWAVT ASIDFSLAQL VQVMILLSTG GLNGGGYQAS  180
KYVVIALHGG ILLLHAILNS LPISWLSFFG QLAAAWNVLG VFLLMILIPM VSTERASAKF  240
VFTNFNTDNG DGINNNLYIF VGLLMSQYT LTGYDASAHM TEETKNADKN GPKGIVSAIG   300
ISVLAGWAYI LGITFAVTDI PHLLNKNNDS GGYAIAQIFY DAFKNRYGSG VGGIICLGVI  360
AIAVFFCGMS SLTSNSRMAY AFSRDGAMPY SSFWHKVNKQ EVPLNAVWMS AFIAFCMALT  420
SLGSLVAFQA MTSIATIGLY IAYALPILFR VTLARKSFTP GPFNLGSYGL VVGWVAIFWV  480
ALISVLFSLP VAYPITDQTL NYTPVAVGGL LILVVSSWIF SAIHWFKGPI TNLGNSSEEA  540

SEQ ID NO: 3              moltype = AA  length = 145
FEATURE                   Location/Qualifiers
source                    1..145
                          mol_type = protein
                          organism = Nicotiana tabacum
SEQUENCE: 3
MASTQQAVSS GSDADQRYAK FDERKRKRME SNRESARRSR MRKQQRLGEL MSETTQLQNQ   60
NSICRERIDS VERNYCAIDA ENNVLRAQIA ELTERLNSLN SLTQFWADAT GFPVDLPEIP  120
DTLLEPWQLP CPIQPIDASS DMLLF                                       145

SEQ ID NO: 4              moltype = AA  length = 654
FEATURE                   Location/Qualifiers
source                    1..654
                          mol_type = protein
                          organism = Nicotiana tabacum
SEQUENCE: 4
MPGVYLETAS LPKGRGLECQ ESQAVRYFFR GRNKVDDSLT IEIFNLFPWI FFTILAMDKH   60
HHQLPLTKST SRQRYNEWVF RDVPSDITIE VDGGIFSLHK FPLVSRSGRI RRLVAEHRDS  120
DISRIELVSL PGGTESFELA AKFCYGVNPE ITAANVAQLC CVSDYLEMSE DYSKNNLGSR  180
AEEYLDSIVC KNLEMCVEVL RQCENLLPLA DELKVVSRCI DAVASKACVE QIASSFSRLE  240
YSISGGRLHM SKQANCELDW WIEDISMLRI DLYQRVITAM KFRGVRPESI AASLVNYAQK  300
ELIQKTLSGS NIQEKLVVET IVSLMPVEKF VVPLTFLFGL LRSAVMLDCT VACRLDLERR  360
IGSQLDTATL DDILIPSFRH AGDTLFDVDT VHRILVNFSQ QEGDSDDDME DVSVFESDSP  420
TTTPSQTALF KVSKLVDNYL AEIALDANLK LNKFIAVAET LPAHARTVHD GLYRAIDLYL  480
KAHQTLSDPD KRRLCKLIDF QKLSQEAGAQ AAQNERLPLZ SIQVVLYFEQ LRLRNALFCS  540
YPDDDIKPTH QSWRINSGAL SAAMSPKDNY ASLRRENREL KLELARMRMR LNDLEKDHVC  600
MKRNMQKSSS RRFMKSFSKR IGKKFNIFGH NFSRDCSSPS SQSERTESKI TERT        654

SEQ ID NO: 5              moltype = AA  length = 303
FEATURE                   Location/Qualifiers
source                    1..303
                          mol_type = protein
                          organism = Nicotiana tabacum
SEQUENCE: 5
MEHSAADRDP KAVEFAKDKN GVGQVLLRNP RGASVRVSLH GGQVLSWKND HGEELLFISS   60
KATFKPPTAV RGGIPICFPQ FGNRGSLEQH GFARNRMWII DDNPPPLHPN DSNGKAFTDL  120
LLKSSDDDLK VWPHGFEFRL RVTLAVDGSL TLISRIRNVN CKPFSFSIAY HTYFALSDIS  180
EVRVEGLETL DYLDNLCNRE RFTEQGDALT FETEVDRVYL SSSDVIAIFD HEKKRTFVIK  240
REGLPDVVVW NPWEKKSKTI ADFGDDEYRH MLCVDGAAIE KPITLKPGEE WTGRLELSVM  300
PSS                                                                303

SEQ ID NO: 6              moltype = AA  length = 578
FEATURE                   Location/Qualifiers
source                    1..578
                          mol_type = protein
                          organism = Nicotiana tabacum
SEQUENCE: 6
MEVMKKKENT SRKMKGGMIT MPFIFANEIC EKLAVVGFGA NMIIYLTNEL HLPLTKAANT   60
LTNFGGTASL TPLLGAFIAD TFAGRFWTIT IASIIYQIGM IILTVSAILP QLRPPSCKGD  120
EFCKEANSGQ LAILYISLLL TAFGSGGIRP CVVAFGAEQF DETDPNQKTQ TWKFFNWYYF  180
SMGFSMLIAV TVIVYIQDNI GWGIGFGVPT IAMLISIIVF IFGYPLYRNL DPAGSPFTRL  240
```

```
LQVCVAAYKK RKLDMVSDPS FLYQNEELDS AISTAGKLVH TKQMKFLDRA AIVTEEDNRK    300
SPNLWRLNTV HRVEELKSII RMGPIWASGI ILITAYAQQH TFSVQQAKTM DRHLINSFEI    360
PAASMTVFTL TAMLCTICFY DRVFVPIARK FTGLERGISF LSRMAIGFSI SVLATLVAGF    420
IEVKRKEAAL THGLIDKGKA IVPISVFWLV PQYCLHGVVA FMSIGHLEFF YDQAPESMRS    480
TATALFWTSI SAGNYLSTLL VSLVHKFTSG SGGSNWLPDN NLNKGKLEYF YWLITILQVV    540
NLIYYLFCAK FYTFKPIQVH KTEDLDSKKD SIELVNNV                            578

SEQ ID NO: 7           moltype = AA  length = 517
FEATURE                Location/Qualifiers
source                 1..517
                       mol_type = protein
                       organism = Nicotiana tabacum
SEQUENCE: 7
MALSNTLSLS SSKSLVQSHL LHNPSLPQPR IPVFHNPQHG RRHPISAVHA AEPAKTATAS     60
QPLKKTQWSL DSWKSKKALQ LPEYPDEKEL ESVLETLESN PPLVFAGEAR NLEERLGEAA    120
LGKAFLLQGG DCAESFKEFN ANNIRDTFRI LLQMSVVLMF GGQVPVIKVG RMAGQFAKPR    180
SDPFEEIDGV KLPSYKGDNI NGDTFDEKSR IPDPHRLIRA YMQSAATLNL LRAFATGGYA    240
AMQRVTEWNL DFVENSEQGD RYQELAHRVD EALGFMAAAG LTVDHPIMAT TDFWTSHECL    300
LLPYEQALTR EDSTSGLFYD CSAHMIWVGE RTRQLDGAHV EFLRGVANPL GIKVSQKMDP    360
NELVKLIDIL NPTNKPGRIT VIVRMGAENM RVKLCHLIRA VRGAGQIVTW VCDPMHGNTI    420
KAPCGLKTRA FDSILAEVRA FFDVHEQEGS HPGGIHLEMT GQNVTECIGG SRTVTYDDLG    480
SRYHTHCDPR LNASQSLELS FIVAERLRKR RMASQRL                             517

SEQ ID NO: 8           moltype = AA  length = 254
FEATURE                Location/Qualifiers
source                 1..254
                       mol_type = protein
                       organism = Nicotiana tabacum
SEQUENCE: 8
MAASSTLSSS ITTFKLSPCQ PRASSTTASV KIPSIPPITL SILLISHFGP TPKNPTVAPL     60
RCSATSTTPE TTTTTSTPFH DLCYVVGDNI DNDQIIPAKY LTLVSSNPDE YKKLGSYALC    120
GLPLSYQTRF VDPDEFSSKY SIIIGGENFG CGSSREHAPV ALGAAGVAES YARIFFRNSV    180
ATGEVYPLES EVRICEECKT GDVVAVELAE SRLINHMTGK EYKLKSIGDV GPVIEAGGIF    240
AYARKAGMIP SREA                                                      254

SEQ ID NO: 9           moltype = DNA  length = 386
FEATURE                Location/Qualifiers
source                 1..386
                       mol_type = genomic DNA
                       organism = Nicotiana tabacum
SEQUENCE: 9
atgggtctca aaggcaagtt gatctctcaa atggagatga agtgtgctgg agatttgctt     60
catgaacact tcaaatcaaa tccacaccaa acctccacca tgtctcctga taagataaca    120
aatttcacgt tacatgaggg tcagttgggg aatactggtt ctgttgtcag ctggaagtat    180
gttctcggag aaaagagag gcatgcgaag caggccctac acatagatga tgcaaaaaaa    240
tcaatcacct tcaattttct tgaaggttat atgaatgaat tatacaagtc catgacacca    300
caatatagaa tcaataataa tctagaatgc cataagtctc gaaaccatcc aatgcaagtt    360
acaagtccta accatacgca aatctg                                         386

SEQ ID NO: 10          moltype = DNA  length = 1622
FEATURE                Location/Qualifiers
source                 1..1622
                       mol_type = genomic DNA
                       organism = Nicotiana tabacum
SEQUENCE: 10
atgaaagcag aaggctcagc attatcatca gctggttctt atcatcgact tgcttatcat     60
gaagttatta atgatgataa tcaaaacaaa attttacaa gtgatgactc tcgtctcaga    120
caattgggtt acaaacaaga actctatcgt ggcctttcgt tcattgcgaa cttctcattt    180
acattcgcca ttgtatcagt tcttacgggc atatccacat tgtataatca ggccttaact    240
tttggtggc ctataactct tgtttacggt tggcccatag ttagcttaat gacacttatt    300
gtgggcctgg ccatgctga aatatgttca gcttatccaa cttcagctgg gctttactat    360
tggagtgcta aattgtctgg aaattacttc ggcccatttg cttcttggat tactggctgg    420
tttaacattg ttggtcagtg ggctgtcacg gcaagtatag attttccctt ggcgcagtta    480
gttcaggtga tgattctcct tagcactggt ggattaaatg gaggtggata ccaagcctct    540
aaatacgttg ttatcgcact ccacggtgga attctgcttt tacatgctat attaaacagt    600
cttcctatct catggttgtc cttctttgga caactagccg ctgcatgaa tgttttaggt    660
gtctttcttc ttatgatttt gatcccaatg gtctcaacag aaagagccag cgctaaattt    720
tgtttacta atttcaatac tgacaatggg gatggaatta acaataacct ctacatcttc    780
gtcctcggac ttcttatgag ccagtatacg ttgacaggtt atgacgcttc tgctcatatg    840
acagaagaaa cgaaaaatgc agataagaat gggccaaaag gaatagtaag tgctattggc    900
atatcagttc ttgctggctg gcttatata cttggtataa ccttcgcagt tacagatatc    960
ccgcatctat tgaataaaaa caatgattct ggggtatg ctattgctca aatctttac     1020
gatgcattca agaatagata cggcagtggt gttggtggaa tcatttgctt aggtgtaatt    1080
gctattgccg tattctttg tggtatgagc tcactaacta gcaactcgag gatgcgttat    1140
gcattctcca gagatggagc gatgccatat tcgtcgttct ggcataaagt aaacaagcaa    1200
gaggttccac taaatgcagt ctggatgcg gcctttatag cattttgcat ggcattgacg    1260
tctcttggaa gcttggtagc atttcaagcc atgacatcga tagcaacaat tgggtctat    1320
attgcttatg ccttgccaat cctatttcga gtgactctag ctcgaaagtc tttcactcca    1380
ggtcctttta acttgggaag ctatgggctc gttgtaggtt gggttgcaat attttgggtt   1440
```

```
gcactcattt ctgtactctt ctctttgcct gttgcatacc ctattacaga tcaaactctc    1500
aactatactc ctgtcgcggt cggtggcctt ctcattcttg ttgtttcttc ttggatcttc    1560
agtgctatac attggtttaa aggtcctatt accaatttag gaaactctag tgaggaagca    1620
ta                                                                   1622

SEQ ID NO: 11         moltype = DNA   length = 437
FEATURE               Location/Qualifiers
source                1..437
                      mol_type = genomic DNA
                      organism = Nicotiana tabacum
SEQUENCE: 11
atggcttcta ctcagcaagc ggtgagttct ggttctgatg cagaccagcg gtatgcaaag    60
tttgatgaac ggaaaaggaa gagaatggaa tccaaccgtg agtctgctcg taggtcacgg    120
atgaggaagc agcagcgatt gggggagttg atgagcgaaa caacacagct acagaaccag    180
aacagtatct gccgcgagag gattgattct gttgaaagaa attattgtgc catcgatgca    240
gagaacaatg tgttgagggc tcagattgct gaattgactg aacgtttgaa ttcactgaac    300
tcgctcactc aattttgggc tgatgctact ggatttcctg ttgacctccc tgaaattccc    360
gacactttgc ttgagccatg gcagctgcct tgccctattc aacctatcga tgcttcttct    420
gatatgttgc tgttttg                                                   437

SEQ ID NO: 12         moltype = DNA   length = 1965
FEATURE               Location/Qualifiers
source                1..1965
                      mol_type = genomic DNA
                      organism = Nicotiana tabacum
SEQUENCE: 12
atgccggggg tctatttgga aacagcctct ctacccaagg gtaggggtct ggaatgtcaa    60
gaatcacaag ctgttaggta tttctttcga gggagaaata aagtcgatga ttcattgact    120
attgagattt tcaatctttt cccttggatt ttcttcacca tattggccat ggacaagcac    180
caccatcaac tacctctaac caagtctact tcgcgccagc gttataacga atgggtattt    240
cgagatgttc ctagtgatat aacaatagaa gtggatggtg gcatattttc actccacaag    300
tttcccccttg tttcgagaag cggacgaatc cggaggctag tagcagagca cagagattct    360
gatatatcaa gaattgagct tgttagttta ccaggtggaa cagaatcatt cgagctagca    420
gccaaattct gttatggtgt caactttgag atcacagcag caaatgttgc tcagctttgt    480
tgcgtatccg attatctcga gatgtcagag gactactcga aaaacaatct cggttcaaga    540
gctgaagaat atcttgacag cattgtttgc aagaatcttg aaatgtgtgt tgaagtcttg    600
agacaatgtg aaaacttact tccacttgct gatgagctga agttgttag ccggtgtatc    660
gatgctgtag catcgaaagc ttgtgtcgag caaatcgcct caagtttctc gcgattggag    720
tatagtatct caggtggaag actacatatg agtaaacaag ccaattgcga attggactgg    780
tggattgagg atatttcaat gcttcgtatc gacttgtacc aacgtgtcat aaccgcgatg    840
aagtttcgtg gggttaggcc tgagagtatt gctgcatcac tagtgaacta tgcacagaag    900
gaattgatac aaaagaccct ttctggttca aatatccaag aaaaactagt ggttgagacg    960
atcgtgagcc tgatgccagt tgaaaaattc gtcgtgaatc tgaccttttct tttggattg    1020
ttgcgaagtg cagtgatgtt agattgcacg gttgcttgta ggcttgatct cgagaggcgg    1080
ataggatctc aattggatac ggctaccctg gacgatatac tgattccttc ctttcgacat    1140
gctggtgata cattgtttga tgttgacaca gtgcatcgaa tattgggttaa cttttcacag    1200
caagaggcgg atagcgatga tgatatggaa gatgtatcgt ttttgaatc gcatagccct    1260
actacgacgc catcacaaac tgcattgttc aaagtatcaa agttggttga caattaccta    1320
gctgaaattg cactagatgc aaatctaaag ctgaacaagt tcattgctgt tgcagaaaca    1380
ttaccagcac atgcgcgtac tgtccacgat ggactttatc gagcaatcga cctttacctc    1440
aaggctcatc aaactttatc agatccagac aagaggaac tatgcaaatt gattgatttc    1500
caaaagctct cacaggaagc tggtgcacag gctgcacaaa atgagcgcct tcccctccaa    1560
tcaatcgttc aagttcttta tttgcagcaa ttgaggctac gaaacgcctt gttttgttcg    1620
taccctgatg atgacattaa gccaacgcac cagtcttgga ggatcaatag tggtgctctt    1680
agtgctgcaa tgtctcccaa ggacaattat gcttcgttga gacgagaaaa tagagagcta    1740
aaacttgaac tagcgcggat gaggatgaga ttaaatgacc tggaaaaaga tcatgtttgt    1800
atgaagagga atatgcaaaaa atctagctcg agacgattca tgaaatcctt ctccaaaagg    1860
attggcaaaa agttcaatat tttcggacat aattttttcca gggattgtag ttctccctca    1920
agtcagtcag aaagaactga atctaaaata actgaaagaa cttga                    1965

SEQ ID NO: 13         moltype = DNA   length = 911
FEATURE               Location/Qualifiers
source                1..911
                      mol_type = genomic DNA
                      organism = Nicotiana tabacum
SEQUENCE: 13
atggagcatt ctgcagcaga tagggatcct aaagctgtag aatttgcaaa ggataagaat    60
ggagttggtc aagttttgct tcgaaatcca cgtggcgcct ctgttcgagt tagcctgcat    120
ggaggacagg ttctttcttg gaagaatgac catggtgaag aattacttt tataagcgat    180
aaggcaactt ttaagccgcc aacagctgtg agaggaggaa ttccaattg ttttccacag    240
tttgaaaacc ggggctccct cgagcaacat ggatttgcca gaaataggat gtggatcatt    300
gatgataatc ctcctcctct acaccctaat gattccaatg caaagcatt caccgattta    360
ctacttaaat catctgatga tgatcttaaa gtctggcctc atggttttga atttcggctg    420
agagtaactt tggctgttga tggatctctt accctgatat cacgcatcag aaatgtcaac    480
tgcaagccgc ttagtttctc cattgcatac catacatatt ttgctctctc agatatcagt    540
gaagtgagag tggaaggctt ggagactctt gactaccttg caacttgtg caacagagaa    600
cgtttcactg agcaaggaga tgccttaaca tttgaaaccg aggtggatcg agtttatctt    660
agttcatcag atgtgatagc aattttttgat cacgagaaaa agcggacttt tgtgataaag    720
agggaagggc ttcctgatgt tgtggtttgg aatccatggg agaagaaatc taaaaccata    780
```

```
gcagattttg gagatgacga gtacagacat atgctttgtg tagacggagc agcaattgag    840
aaaccaatca ccttgaagcc aggtgaagaa tggactggaa ggttggaact gtccgtcatg    900
ccttcaagtt g                                                         911

SEQ ID NO: 14          moltype = DNA   length = 1736
FEATURE                Location/Qualifiers
source                 1..1736
                       mol_type = genomic DNA
                       organism = Nicotiana tabacum
SEQUENCE: 14
atggaagtaa tgaagaagaa agaaaacacc tctagaaaaa tgaagggtgg aatgattacc     60
atgcccttca tatttgcaaa tgagatatgt gagaagttgg cagtggtggg atttggtgca    120
aatatgataa tatacttgac aaatgagctc catcttccat tgactaaagc agctaatact    180
cttacaaact ttggtggcac tgcaagtttg actccattac ttggagcttt cattgctgat    240
acctttgcag gaaggttttg gaccataaca attgcttcta tcatctacca aatcggtatg    300
atcattttaa cagtatcagc aatacttcct caactaaggc caccttcttg caaaggtgat    360
gaattttgca agaagcaaa ttctggccaa ctagccattc tctatatatc attactccta    420
acagcatttg gatcaggagg aattaggcct tgtgttgtga catttggagc agaacaattt    480
gatgaaactg atccaaatca aaaaacacaa acatggaaat tcttcaattg gtattatttc    540
agtatgggat tttccatgct aatagctgtg acagtaattg tttatatcca agataatatt    600
ggatggggta taggatttgg agtcccaact attgctatgc ttatttcaat tattgttttc    660
ataattggat accctttata tagaaacttg gatcctgctg gtagtccttt tactaggcta    720
ttgcaagttt gtgttgctgc ttacaagaaa agaaaattgg acatggtttc tgatcctagt    780
ttcttgtacc aaaatgaaga gcttgattct gctatttcta ctgctggcaa gcttgttcac    840
actaagcaaa tgaagttctt ggacagagca gcaatagtga cagaggaaga caatcgaaaa    900
tctccgaatc tatggaggct aaaacacagtt catcgcgtag aagagctaga atcgatcata    960
agaatgggac caatatgggc atctggaata attctaatca cagcatatgc tcaacaacac   1020
acattctcag ttcaacaggc aaaaacaatg gacagacact taataaattc ttcgaaatc    1080
ccagctgcat caatgacagt cttcacatta acagcaatgt tatgcaccat ttgcttctat   1140
gaccgcgtat ttgtgcctat agcacgtaaa ttcactggtc tagaacgagg catatcgttt   1200
cttagcagaa tggctattgg gttctctatt tcagttctag ccacattagt agctggattt   1260
atagaagtta aacgaaaaga agcagcctta actcatggac tgatcgataa aggtaaggcg   1320
attgttccca tttcagtatt ttggcttgtg cctcagtatt gttacatgg tgtggtggca    1380
tttatgtcaa ttggacatct tgaatttttc tatgatcaag caccagagag tgagaagt    1440
acagctactg cattattttg gacatcaatt tcagctggga attatttgag tacacttttg   1500
gtttcattag tgcataaatt tacttcagga tctggaggat caaattggtt acctgataat   1560
aatttgaata agggaaaatt agagtatttt tattggttaa tcacaattct acaagtggtt   1620
aacttgatttt actatctgtt ttgtgcaaaa ttctatactt ttaagcctat tcaggtacac   1680
aagacagaag atttggactc taaaaaagat agtattgaac ttgtaaataa tgttta       1736

SEQ ID NO: 15          moltype = DNA   length = 1553
FEATURE                Location/Qualifiers
source                 1..1553
                       mol_type = genomic DNA
                       organism = Nicotiana tabacum
SEQUENCE: 15
atggcttat caaacacctt atcattgtca tcatcaaaat cccttgttca atctcacctt     60
ctccacaatc cctccttacc ccagcctcgt attcccgttt tcacaaccc ccaacatggg    120
cggcgccacc ccatctccgc cgtacacgcg gcggagcccg ccaaaacagc aactgcttca    180
cagccgttga aaaaaaccca atggagtctt gattcttgga aaagcaaaaa ggcttttgcaa   240
ttacctgaat acccagatga aaaagaactt gaatctgtcc ttgaaacttc tgaatctaat   300
cctccacttg tgtttgctgg tgaagctagg aatttagaag agagacttgg tgaagctgct   360
ttaggaaaag cttttttatt acaaggtggt gattgtgctg agagttttaa ggaatttaat   420
gctaataata ttcgtgatac ttttaggatt cttcttcaga tgagtgttgt tcttatgttt   480
ggtggtcaag ttcctgtgat taaggttgga agaatggcag gtcagtttgc gaaaccaaga    540
tcagatccgt ttgaggagat tgatggagtg aagctgccaa gttacaaggg tgataacatt    600
aatggcgata catttgatga gaagtcaaga attccagacc ctcataggct tattagggct    660
tacatgcaat ctgctgcgac tcttaacctt cttagggctt ttgctactgg aggttatgct    720
gcaatgcaga gggtcaccga atggaatctt gattttgtgg agaacagtga gcaaggagat    780
aggtatcaag aactagctca cagagtcgat gaagccttgc gattcatggc tgctgctgga    840
ctcacagtag accaccctat catggcaaca actgattttt ggacatctca cgagtgcttg    900
cttcttcctt atgaacaagc acttacaagg gaggattcaa cttctggtct tttctatgat    960
tgttccgctc acatgatttg ggttgggaa cgaaccaggc aacttgacgg tgctcatgtt   1020
gagttcttga gaggagtagc aaacccactt ggcataaggt tagcccaaaa gatgaatcca   1080
aatgagctcg ttaaactcat tgacatcctg aacccaacca ataagccgg aagaattact   1140
gtaattgtga gaatgggtgc tgagaatatg agagtgaagc tttgccactt gatcagggca   1200
gttcgaggag ctgggacagat tgttacctgg gtttgtgacc cgatgcacgg caacaccata   1260
aaggcaccat gcggactcaa aacccgtgct ttcgattcaa tcctggctga ggtccgagct   1320
ttcttcgatg tgcatgagca agaagggagc cacccttggtg gtatccatct agaaatgaca   1380
gggcaaaatg tgactgaatg cattggcgga tcacgaacag taacctacga cgatttgggc   1440
tctcgctacc acacacattg tgacccaaga ttgaacgctt ctcaatctct agaacttcc    1500
ttcatcgtag ctgaacgact aagaaaacga agaatggcct ctcaacgtct gta          1553

SEQ ID NO: 16          moltype = DNA   length = 764
FEATURE                Location/Qualifiers
source                 1..764
                       mol_type = genomic DNA
                       organism = Nicotiana tabacum
SEQUENCE: 16
```

```
atggcggctt catcaactct ttccagttcc atcaccacct tcaaactgtc tccgtgccaa    60
ccacgcgcct cctctactac cgcctccgtc aaaatccctt caattcctcc aataacccct    120
tcaatccttt taatttctca ttttggccca actcccaaaa accctaccgt cgcaccactc    180
cgttgttccg ctacctccac cacaccagaa actaccacac gacttccac  accattccac    240
gacctttgct acgtcgtcgg ggacaacatc gacaatgacc aaatcatccc tgcaaaatac    300
ctaaccctag tttcgtcaaa cccagacgag tacaaaaaac tcgggtccta cgcgctgtgc    360
ggactccctt tatcatacca aacccgtttc gtcgacccag atgaattctc atccaagtac    420
tccatcatca taggcggtga aaacttcggg tgcgggtcgt cgcgggagca cgcgccggtt    480
gctttaggag ctgcgggtgt ggcggagtcg tacgcgagga tattcttcag gaactcggtt    540
gcgactggcg aagtttatcc ccttgaatca gaagtgagga tttgtgagga gtgtaagacg    600
ggtgatgtgg tggctgttga actagcagag agtaggttga ttaatcatat gactgggaaa    660
gagtataaat tgaagtcaat tggtgatgtt ggtcctgtca ttgaagctgg tggcattttt    720
gcttatgcaa gaaaggctgg aatgattcct tcccgagaag ctta                     764

SEQ ID NO: 17           moltype = DNA  length = 2500
FEATURE                 Location/Qualifiers
source                  1..2500
                        mol_type = genomic DNA
                        organism = Nicotiana tabacum
SEQUENCE: 17
tctgacatat ctatagcatt tcatttcact acaagtcact tcatgtcgtc accgtttaat    60
gtgcttaata tgtcgaaacc atgactagtg atatagacat tctcaaattt cttaaagagg    120
cataaggaac ttttgcatgg attgaaagag agcatatata atttatttct agcatccatt    180
gcctaaaatg agatgactct ctctccactt taatttccat acaatctcaa ggaagacatt    240
ggatagtaga tatataagct ccatttttgtg aactcctgta agatcattgc ctcatgtgct    300
atattgcacg gactttccga aatgctgttg tattcatgtc agatcctcta aaaatatatt    360
acttttggag aatctgacac acatctagag acatttttcg gaaaatctgag caatgtagct    420
ctagtgtgcc ggagaaagca taggtcaatt agtcttgcaa ttgactaatt gcaatctgct    480
aatagaagta tatatgtaag agtacatcga catggtaagc actaaactat cagataggct    540
atctttttc atatacctaa gtcttggtgc acaaactcgt tacttatgct ggtgagaagt    600
aatacctatc cagtgaaata gtcgaggtgc cggaaaatca gtctacgcac tacttagtta    660
aaaaagttct aaatcatcta aaggagcag  gagcttttgg gaaagaaaca ggtataaggc    720
aatgtgcaat ggtgactgtc gacaacatta attatgcaaa ggtgagaaat atcatctctt    780
tattgtaaat ataaagtgac acacacgagc agtatgaaaa atctaataaa gttgatgct    840
gtgcaacaaa ttcatttgga atttctttgg tgaattattc ttttggttgt caatgtgtaa    900
gtgtttagag tagacatgaa ttgataactg aagaaaagtt tgagtaactt gttggaccct    960
gccaaattat tgtgaatgtg taagtatttc cacaatgtca ctgatcatac tgttgcagat   1020
acacatacg  ccagaattca ataatagcaa taactaaaaa tttctaccaa actgaaaatg   1080
caaaattgag gcagataaaa tttgtaagat tgtggtatgg ggcgtgaagt tgttgactta   1140
tagccactgg tgcaattgat ttaagatagg accttatctc ttctcatcca ctaccttttt   1200
cgtttgcctt tcatttacct tgctccatc  attttcttta tgtatatcca gattttttaa   1260
tttgaatttg cagttcgttt aagtataact tcagcagctg ctgacacatg tcacgttagt   1320
tacctctttt atttgtggga tgtggcgagc agtgatctga taagggatat ttgacctta    1380
tcgaacacat gacatgaaaa aaaaaaggtt aattgattta gttgaagata agtgaagctc   1440
taaaggcaat tgaaggaatt taaatttact aaaatccaaa aacacgatat taattatatg   1500
ttccgtgcat gcttaactca cgcgtactag agatttaat  ccttctaatt ctattacgtt   1560
tattctaata cttgcattgg attttacta gccaaaactc gacgcagatt gatctcctta   1620
ttctcactaa agataagagg agccaaaagt ggagtaagaa atctttacaa actaaagggg   1680
ttagatgaaa aggaagaatc caatacttcg gattcaacat gttaacaaaa gcaattttt   1740
aaccgacttt gtcactacag ggaaaaaaa  tattttaca ctattcaggc agtctaaatt   1800
ttcaacgaac ggaattcaat taaactctct acgtcacatc tacatctgtg atcagcaata   1860
attgttgagt tgatttggaa ttaagtaaat tagttctgat cactccggaa gtgaaactgc   1920
aaatgtgcaa taacacgaac aaaagactat gattccatgg tttcaacata gcccacaaac   1980
aagctaattg agattatggc gattaataga agatcattag gtttaatttg gcgaggcgaa   2040
tagccattgc atgtatagtc caaaccatga aaatgacaca acaaaccata cgacaaccta   2100
aaaaagaatg caaatatagg tggaacttga tattgaggat taaataactg ccccacaaga   2160
aaaaacaaca tgccccatat tcaaccataa cgatcactcg tatttaatta ttctctcctt   2220
taattcaaat aaaaaaaaat cttaggttct tggcttctta gccatatgct tttagttcca   2280
ggcaaaagta ctgcaacatt caatctccaa cgtacaaact ctcatctaca atggattgaa   2340
gctctcattt gcttagcaat cactttcaac tctgttataa tactgttata tgtaagagac   2400
ccgacccatg atcaagaccc attccacaac tatataatat atactagtga gtgaggagta   2460
ataaaagcaa gcaaaagcta aaaggaagtt cttgagccaa                         2500

SEQ ID NO: 18           moltype = DNA  length = 1406
FEATURE                 Location/Qualifiers
source                  1..1406
                        mol_type = genomic DNA
                        organism = Nicotiana tabacum
SEQUENCE: 18
ccttatagaa attgtctgct tctttcttct cgaaactcaa aaccccgatc gaaaaattag    60
tttttggggt tagaacatgg atgggattga gtttaaaaac gtaaagatca tagagcctag   120
agggaaaaga atctgatgtc atgtcgtaaa ggaaaaggaa agcaaataac agtgtccagc   180
ctcgaggcaa aggaagaaaa gatgccccgg aacaggaaga gctttaggct caaattaagc   240
acactcaatt cactcctctg tttaattaga atttccatgt ttcctccttc cgccggacaa   300
cccatcttag tttcttccac aacatttata attcaatgtc ctaaatttgg aagcgacata   360
ttgcattata cctctagtaa tcagttggat tagccgatta ggtaaacgta agagatacac   420
tatgtaagta tattcttcaa ggtatatgag aatatgttta cgtaacagaa tgatttaaat   480
gaactgatta ttgattctgt attatcatgc ttatgctttc gatgattaat tagccacatc   540
tagctaaaact ttttcttcca tatctttttt ttttttttttg tgatttacaa gaatagatcg   600
```

```
tgtcatttgt tttcttaaag tacctatgtc aacatcatgg atgacatgga ataacaagtg    660
catggaggtc gataagaaaa aaacaagcag ctccttggat ttttcgaagt ttggactttt    720
tagagcctca attttgctga aatatcgaaa tttggagacg tgagattcac ccagtcaccg    780
cttacgattt aatttatata cactgacaag tataaataaa ttataatatt ataaatttaa    840
tttgacagtt atatcatgtt atatgctttt tttttcgagt aactccttca acttattgtg    900
agcattacct atggttattt tgaatttaag gtattacatt gacgctttaa agttctatta    960
cacagtagtg tatagaagtt aaactcagac tgttttcacc ctttgttcac actccaattt   1020
tgaaaaacta ttaacaagg actatccaac ttctatttaa gaagaaacta atccttgttt   1080
gatttaatca atcttgaatt tctgtgaacg gtacaaattc cgtgaccaaa ctggaccatc   1140
atctaaactc caactaacgc acggaataat atcaagcttt atgctttaga ttttgtattt   1200
tctaacataa agatcctaga gaaacagacc acataaaaga catttacga cgtgcatgtc    1260
cagcagtggc tataaaaatg ataagaaatg tgcgctcaat agtcgttcca tgctctgttt   1320
atatatatgt accttctcat acattaaaca tcatatcata caaagatca ctaaaacaga    1380
aggaaaaaag aaaagatctt cagaat                                        1406

SEQ ID NO: 19           moltype = DNA   length = 2500
FEATURE                 Location/Qualifiers
source                  1..2500
                        mol_type = genomic DNA
                        organism = Nicotiana tabacum
SEQUENCE: 19
gcgcaatatc caggacggtg gtcttgcacc gcatcccacc cgggagggat caactcgacg     60
tgatcgggaa ggccgtattt agccttaagc tctaataaat cagcctcctt cattgccgac    120
ttaaaggttt cgggttcgac ttcaggcaat tttgagaaat cggacctgga tcgtacgagg    180
aactatctct tccatcgtca ggaagcttct gtcctcaaca gcagtgggaa tgctctcagc    240
atgaggagga aaaactatcg ctagaggac cgggtcactt ccctcgctgg actcagaagg     300
tacattagac atgttttaaa cgaaagagag gaaggtatca aacaacggag gattaaaaac    360
gatgaggatc gctggaacaa agggaaaaga tgcacaacaa tggaaaagga agaagaagat    420
ataaggtttc gatgtaggaa gtctgtaaag tttgggatta caccctcata tccctattta    480
taggaattca ggcgccagaa ccaagaaatt ggctcatcat tcctagcat cggaattgaa     540
gtggcaggac caatcaggag ccccatgcaa aataaagcga cgcatcggga atacgcatca    600
tgatgatgca cgaggtcatg acgtcacctt gattcatgga caacacaact ccaaaatttg    660
cagctcacga agggccactt ttctagctcg cctcaatcat cacgagccga tcagctcgtc    720
taatcgtttt gaccgtaatg aacataattc gctcatcgag cccgcctgag gtcggcctca    780
ataagcggag gggctaactg tatgggtcaa aatctgtcct aaaatattta agataagata    840
atactaaaga aagaattctc gagccgtcgt tagtcgaggt ggactaggaa gggagcgaaac   900
ttatagtcga agaatcgacg agagccatgg tcgagatgtc aataatggtc gaagtcgagc    960
accgttgata aagctgtaac aactagtttt cgaaatagga tattaaagag aatattctag   1020
tggattctct gcacttgtac tattaaggtt tactaggaat atgtctcata taaatagaaa   1080
aagagacaat gatatgaggc atgtgatatt catttgtaac aagatacttt gacaaaaaag   1140
attctctctc tctctctctc tctcactaag atacaaacac caccttttca ctaagattct   1200
tgtctgtatt attccatact ttttcatcag atccgagaat aattcaagca ttcaaggatt   1260
tgtgtgtcac tcatcattgt caagaggaac aaccatccg ttcatcctt attgggtgaa     1320
tcattcctcc tatttactta agtgtcattt attgttattc attgccatta aatgccacat   1380
tattattcat gattttttgga atagttattg catactgtta tcactattcg accaaatcta   1440
tgtgacttta tcacaccctt ggaagctacg tctagaaata ttattgttaa ctaattttaa   1500
cccataatca cataaatttg attatttgaa ccgagagtca tttttttggt caaacatata   1560
ctttattaat aagttatcat aatcgctttg ttttttaaagg attgcacgcc gaaatttgtc   1620
gctaataatt gacatatcta aaacgttgtg tccccgttgc actcaaattc cgggtccgcc   1680
tctagaccta ctaacatttt taccactata gtgagtatct tgcatgtttc acgtacattt   1740
tgtgcatctg cacactcact aatctttctt aaaatatgtg agacaaata cattctttct    1800
tagaagcttg aagacagcag gatttctctg agataaaatg aaactaaaga aaaagaaaaa   1860
gcaatgcttt gggcttaggc tcattcgaaa tatagagtca gtaaattcaa aatgaatatg   1920
atcttaatac atttattatt ttaattattt tagaacatac gtaaacaata tataataa     1980
gttcaattga actaagaaaa cttgtctctc tatttgtgta tgccaatatt gaacgagact   2040
accatcatga aataaaaaaa tccagtccac tcgtatgtcg tatgactatt taactctaat   2100
gcttcttttc atagatattc atatgattca tgtcgaaaat ataatgttcg atcggttgaa   2160
ttcttagctg acaatagcag acatttgaaa atgtatactc cccttagtta ttccaacttc   2220
caaaagtcac taaactctaa tagcatgaca ggaagcgtaa catgccatg ccaaaatcca    2280
aattgcctag taggagtaaa aacaaaatga aatgggtcac cattcatcgg caattaggta   2340
accatatctc ttttgatatt tgagccacaa atatacgagt gatactcatt attttaatct   2400
catccacgtg gcaccatccc attaactgct tatctcaggc tgaaaccta gtatcttgca    2460
tattttcttc ttcctcagtg taaaacctta attcacaata                         2500

SEQ ID NO: 20           moltype = DNA   length = 2500
FEATURE                 Location/Qualifiers
source                  1..2500
                        mol_type = genomic DNA
                        organism = Nicotiana tabacum
SEQUENCE: 20
gaacacatct aaacaacttg gaatcacctc aaatatcgca cagaagttgc aaatgacata     60
acaaacctat tttaactcct agaacaataa tccaaactcg ataacatcaa agtcaactcc    120
cgatcaaacc tatgaacttt tcaaaccttc aaattgccaa cttttaccaa ttatagccaa    180
aaccttctag aaatattcaa atgtaaatct gggcatacat ccaagtccaa aattgccata    240
cggacctacc agaaccatca aaactcagat ccatggtcaa atacataaaa gtcaaacttg    300
gtcaattctt ccgacttaaa actttctatc taagaatcat tctctcgaat caattccgaa    360
ccgcttaaaa actaaaatcg acgatatccg taggtcataa taaatcatac gaagctactc    420
gtgccctcaa accaccgaac gaagcacaaa tgctcaaaat cactacttgg gtcgttacat    480
ttttgagttg gtcacactat ttatttttgt acttgttgaa ttgatgaaac tatataggtt    540
```

```
atagcaagtt ttacttatat ttgttgcctc ttttacctcg ccgagggtag ttatgatact    600
tgctgagtac gttgggtcgg ttgtactgat actacactct gcacttaatt gtacaaatcc    660
aggtgtcaga cccagacatt agtagctgag gctagcagaa gagttgattg ctgagcgacg    720
aggtagaact gcattcttga tcgcagtctt ggcgtctctt ttcttaatta ctgttgtctt    780
tatttcagac agtattgtac ttggtcattt cagacttttat ttccgtatta gagcttatga    840
ctctgtattt accagtttct acgggatata tcatgtatta gcggtatttt gctatattga    900
agttttagac atatgttatt tctataaatt atgttatttt ggttctttat tgttatgtcc    960
ggcttgccta gcaaatgtgt taggcgtcat catgactggt tgggattttg ggtcgtgaca   1020
catatcttct ctaaatgcta tcaccgtaat gtatacatgt cttttattca tatcttctct   1080
atatgttgct ttacatgatg aaataattca cggtatatat cttctctata tattaatctg   1140
tattacctga cttatttatc catgcatatc ttttctatat gcaactgttg actggttctt   1200
tgaactgtta gtttgtttac aatgcttgtg catgtcttgt ctatatatat cgatggcctt   1260
acttgtactt catgcttaga ttttgttatt gttcttgtgc acatgtacat tcatgaacat   1320
ttcaggtttc ataaaattag tatcttttga cttaaattct cattactact tcactgagat   1380
tagtcaagag atttactaag tacatgtggt tagttatact catactatac ttttgcacct   1440
tgcgtgcaga tttcagagtt gagctgctgt gatgatgaag gccagcattg aagaggtacc   1500
ggtgttctag atacaagttg tcacttgttc atggttgttt acgttttata ttatatttat   1560
gtaaattta aatagatgct gtaatctctg ttcatattag agttgcactc gtaatcttgt   1620
tcttaatcgt tcatgacttg tactaccagt ccttgggata attatgtgaa ttttctcaat   1680
cttatttatt atttattgat aatctttcat tcgagttgtg ttatttgttg tttggcttac   1740
ctagcatacc atagttaggt gccagtactc gtaacatttg ttcttacttt ctagactttt   1800
agtgtatatt aaaaatattt attttatgt actgcttttgc attagtaaga ggatcttta    1860
ggtataatgc tctttcttac ttttaataac tatcgtcttg tattaataaa attttcttgc   1920
aaatttaaa agcaatgaca tattaatgga gaaattatac acaatataaa gataaatca    1980
atttaaaaaa gcaacatgta aaagttgta gacgagataa gatgcctatt atttatattt   2040
ggtacatgaa tgtcattttc catgaaagtt tttcaaaacc aataatttgt atatgttagt   2100
tgaaatgtca cttttgtttt gttcaatcag aaccagtaat ttgtatttaa taatactaat   2160
gtcatttta tccgactcaa ttaactactc cctcttttac aacaaggaaa gaaaagcttg    2220
ttactctccc tataagtttt tcacgaaggc aatacaattg ttgcaacttc ttttcataa    2280
tcgtagtttt tcttcattga tcataatggg tggaaagagt tctccaacga tgtttttgtt   2340
ggttctagcc ttcttacttt atgcatctat ttagtataat tttattatat ataaatgttc   2400
ggattttct ctcactactt tctcccccctt acttcaaccc aactatcaaa agagattatt    2460
tttagatatc aaaataatta acacaaactt tattacaaat                         2500
```

SEQ ID NO: 21          moltype = DNA   length = 2500
FEATURE                Location/Qualifiers
source                 1..2500
                       mol_type = genomic DNA
                       organism = Nicotiana tabacum
SEQUENCE: 21

```
caaaatactc tataatgaaa taatgagga gaaagaaaga gaagagtgaa aagtcttgaa      60
ttggtgtgtt tactaatgag gagaaactcc tctatttata gcaagaaatc cttagcctaa    120
taatggatat tatgtcatgc aaatgtcatg atctacaaat ttgttataat ggatattatg    180
tcatggcaaa tgtcatggac caaaatttgt tataatggat attatgtcat ggcaaatgtc    240
atgaaccaca aatttgttat aatggtatta tatcatggca aatgtcatga aaatttggcc    300
atattacata ggatcacttt tcgaagacaa acacaattat atggataata caaatgatgt    360
aaattcatcg tgtttaaagc atattccatt tcggatgcct ccaaatctga aaatatgtaa    420
cgccaaatat tgtttattt aaaaaatgcc aattatacaa ggctctatcc atgcaaagta    480
acttatccac acgtaaaagc aatacaacgt taattaggcc aagaattagc ataagttagt    540
gcaattttaa agttttgtac tcaccttta tgcctcaaat atctgtccaa ataaagtagt     600
aaaatttaac aaattgatat cacagagaaa caaagaaatt atttggaatc attctagtgt    660
actttcaaat attcactaaa tttatctcga agttatgcat aatttgcgca ccttgagcta    720
aataattga tttgtttcta ttatatacgt ttatacatta ccagtgcttt ttgttttttt     780
ggtctacttg ttcggcacaa ttattacact taacaatgca ataataattg agaatacggt    840
aaagggccaa aattatccct agactattcg atttggtata aaattgtcct ccgttcatct    900
attgagtcaa aaatgtctat attgttattt tagtggctca ataatgcctt tattactaac    960
cgacttattt gaaaaaaata attaataaat atccacgtgt caccgtccat ggctaaata   1020
aaatacttac taaactttta aaaagaatc accataaccct aggttttgat tggcgccgca   1080
cgattataaa cctgtaatcc aaatctttta ttcttaatag acaatgtaac ttattcttct   1140
tcctctttta attaagttca gttctgcaaa tgggagaatt tatgtcacca caacaacaag   1200
aaaagtaaca atttaagcaa gaaatgttg atttttgggaa taaatgaagt gggtatggga   1260
ataaaatttc ggatcttgac ttaggaagta attcaattaa atgagagtaa attcattaat   1320
gaaacaaat gggtatgaca tgggtgaaaa taattcatta tctcctcctc taattcgatt    1380
tcatggagat gggagaagaa agagggagtt ggcagctagg cgggtcctt ttgggggcgg    1440
tccgatgaaa acccaggtta tggttttctt ctttttttaaa aaaatataaa ttggtaagga   1500
tttatattta gaccaatggg acggtgatat gtggatatta attaatttt ttagataagt    1560
tcgttggtaa taaggacata attgaaccac taaataacgg taaggacatt tctagctcaa   1620
taggtagacg gggatatttt tgcaccaaat cgaatagtgt agggtagttt tgacccttct   1680
ccgtactaga agcaaggaga ttagtaacat agcaaaatta ttttgttaat accaaatcaa   1740
acaaagcgac caacatcaca gttgaggacc acgcgcctt agttcatcat attctatgat    1800
gataactgtt ttaatactaa taaataagta tgattataat tgtttaaaca ataaagaaaa   1860
ccaagaatat gtccagttac gttataatga taagactcta ccaacaaca catgtcaact   1920
tcatcgctaa tttgaattgc tcatagctaa caaaattttt gataatttat cgtaaatcta   1980
taactaattt ggattagcga cgatttttgtt cagctacaaa attgtccgt agctaattcc    2040
tgtttttttag tagtaaaaact agcctagtac aactttgttg gttgtgtgac ataaaaaata   2100
aaattctcg tattcaacta attaatcaca ttccaaattc ttcataaata ctaaatagat    2160
tctcttttc cataactgaa gcaccaatta ctcgagaaaa gaaaattaaa gtaaatatgg    2220
gttccgaaac tatcaagctt cctaatatag acttctccaa tgtgacctaa agccaggcac   2280
acttgtatgg aaccaagtga aaagccaagt ccacaaagct ctagtaaact atggcgtttt   2340
```

```
gaagcatcat ttgataaaat cctatacacc ttcgaaaatc ctttttgaat ccttaaaaga   2400
gcttttcgat ctcccttac  aaaccaaaat aagaaacatt tcaaccaaac ctttccatgg   2460
ctacgttgga cagtatccag cagttccact ctatgaaagt                         2500

SEQ ID NO: 22          moltype = DNA   length = 2500
FEATURE                Location/Qualifiers
source                 1..2500
                       mol_type = genomic DNA
                       organism = Nicotiana tabacum
SEQUENCE: 22
ttaaggatat gttttaaata attccttaaa aaaaatactc tgagcattat tggtacttta    60
agcttacaaa aaattatact tttatttttc atcaaatatt taacaaacgc tatttgtcga   120
aattgtgggg ggaaaaaaag aatttaacta gtaacgctag aaaagttcca taaaatttca   180
gaaactacag tgcaaaattg cactagacac aaaaaggtaa actaaaaata gcaaaacttg   240
catctcataa attgcaccaa attctagaaa atagaccaaa aatagaagaa ctgtaaaaat   300
tgtaccttta aatgtgagtt ctagctaaat tctttgtatt tcacagttcc ctcaaagacg   360
gagtttgttt actatttgac aatgaaagaa aatagtaaaa atagtacgat atagtcagtt   420
ttcggactgg tcattcaaaa atagtcagcg tttaccaagt caataaaaat agccactatt   480
ttgctgcaaa agagaccgat ccagcataat atactggagt tcggtgcacc tgtgtatgaa   540
ctccagcata ttatgctgga ccgatatact ttgctggctc cagtataata tactggagac   600
tggagcaccg tgctccaaa  ctccagtata ttatgatgga ccggtatact tgctggaact   660
ccagtatatt atgctggagt tctagtgtac ttatgttgga actccatcat attatgctgg   720
agttccggca tacttatctc ggaactccag tataatatgc tggagttcaa gtatacttat   780
gctggaactc cagcataata tactgacgta ttttccgggt tttgaacagt attttcgctc   840
agatttatct ttacatgaaa agtggctaaa tttcgattac ttttgaaact gggctatttt   900
tgaaccgacca gttgtaaatc tggctatttt tgaatttctc ccaagaaaat atcctaacctt  960
aaataacaaa aaatgctcga aaggtatatt tgaagtacta cttttttgaa cctattccaa   1020
acttacaagt aggggtgtac aaacggaacc ggaaaatcgc accaaactga aaagtcaaac   1080
caaaccgatt aaaagaccccg actaggtttg gtttgatttg gttggtatt gagtaaaaaa    1140
atcataacca aactgacata taaatatata gtttttatat atactttaa gattttatat    1200
aaaattttct ttaagaata  tctaaaatat ttgggattct cttgtgggat ataaatttta   1260
atatgatcca taattattaa ccttaaataa tgggttatat gatcgcgttc tcatcaagtg   1320
ttactgaaat gcgtcaatct ctatgtccgt ccatattcat atcatatgtt aagatctatt   1380
atattcttat atctttttc  gaatgtgaag tgataattag tattatttag gtatcatatt   1440
ggttttata  tttaattact aattcggtta accttgaaaa tatatatcaa caaaaatta    1500
ttgtcaaacg aataaaaaaa ataactatta tgtgttacta agaaaattct cccttaaaaa   1560
tattttaata gataatttgt caattttta  tatttttact aaacatatat ttacttatca   1620
aaaatttaat aaagtaaaat taaaataata tttaattaac aaaaaacctg aaaaatcgaa   1680
aaaatccgac aaaacaaaat caatccaaac cgatagggtt gggttggtac accccctact   1740
acaagctcat ctctattatt ttctcaagtt tgtattgaag gttcaaattt caaggattat   1800
aattataatg attgcaaaac gacaatctta atataggtga ttaattctga tatggacaaa   1860
attttgcgtc gtatccatga tcgaccaact accaataatt ttcaaatgct caagggtttc   1920
aagtgctgt  ttatgttctg aaattgtagc tagttggata tattccatca aatcttgtaa   1980
agctaataat gtttcttgac cttttttaaat atactagtga tccttttcatg agatattgag   2040
atcagttttt tctatctgct tggaattgaa taatatagaa tataaacata tgatattattg   2100
ggggcaaata cggacataaa atttaaagtg agtcacttac tttatatgtt aaactatgtc   2160
aagattaatg accacaatcc gaagccgaag gaatataata cgaacgatga atttttgttta   2220
cgattaggtg gaatgattga tattaaaaaa gaatgtaaaa gcaaataaga aaaggtgaat   2280
aatgcatatt aacaatctat attttatacg attaggtagg aagataatat gattgatatt   2340
taaacgtaaa tatttaaag  tacgttgctg tctttgtgac ccctctggcc ataccattac   2400
ccattattta tattccctcg tatcaacatt cagtagcaag taaaaagaga taatttttgt   2460
tgattatttg ttgttgaact tgataaattt tgctgaaaaa                         2500

SEQ ID NO: 23          moltype = DNA   length = 2500
FEATURE                Location/Qualifiers
source                 1..2500
                       mol_type = genomic DNA
                       organism = Nicotiana tabacum
SEQUENCE: 23
gagacgcata ttgtaagaag aagaaagagg ggataagata ggtgggtcga ggaccgggag    60
actgcatatg taagctttca attttctta  agtattataa tttactttta taaaattta    120
aatactattt aatttaaaat aatataggt cgctaccaaa gtaacgtgga ggaattcatc    180
gtagtcacca gctggtgaat cgggtgagcc aacccaacct tcggacgagg atgctgaaag   240
aatatggttg gagtctgttg gcggtccaaa atggggaagg tatacgggct tcctactaaa   300
aattccatcg ctataagtgt ggaatgcagg aatagggact tcctgcaggc gagaacttaa   360
tagggagagc ctctcgctat gcgggagaca gtacaaagct acatcgagct agaagcggcc   420
aaggaaagag aaaggcttag agatgctcaa ttccttggca tgcaagctca gatcagaact   480
ctcctatcta tggagctttt ccgttgcccg tctcgtgagt catcccaggg tcgactccac   540
gtgatcgttc ctcctccttg tgatcgttcc tccgtcctcc ccgtgatcgt ttcccgtcct   600
ccacaagaat tctctatacg tcttgtagat gaaagttcat cagatggtga tgatgttgta   660
gaaaatacccc cttgaccaat actttgatat acttgaact  agactaatag aactgttttg   720
aattagattg aacaatttg  aacttgttgt aattagtttt tgcttggttt tggattgtga   780
ggttcaagtg aactttaatt tgttagtttt aaggtattaa ttggatgttt ggttgttgtt   840
gttggatttg tagttagatt tgtggtgaat taggggttgg atatggtaa ttagggggtta   900
ttagatgtga attgggggta ttggtatgct gttttattt  gacaggtggt atagctacca   960
aaacaggcat tttctgccaa aattaaaccc agaaaaccga ccaacatttg tcagtaacta   1020
aaaaaaaaaa attaaattgc acattcacaa ccaatgttgg ttggttaatg tacaatgaat   1080
ttccagaaat tcaacattac cgaccgaatt tagtcggctt gttgcctgcc ctgtccagtt   1140
taccgaccaa ttttggtcgg tattttaaa  ttttaattat ttataaaaaa aatatatttt   1200
```

```
ccaataccga ccaaagttgg tcggtatttt taaattttaa ttatttataa aaataatata 1260
ttttccaata ctgaccaaag gcaaaattaa taaatttaat acaccgacca agtttggttg 1320
gtaaaattaa attaataaat aatattccga ctaattttga tcggtaagtc aattaaattg 1380
tcagatagtc gtgtagagca taccgaccaa cattggtcgg taatttccga gtaactttgg 1440
tcgctatgcc cttccgatct tcaaaatact gttcacacgt gaatgatcgc gttttgaacg 1500
gttattgacc tttaccgact tactttgatc gttttttttgg acgatatttt tcgaatttct 1560
aatagtgact gtcatctatt tcttttttgaa aaagaaaaa aagaatcaaa cttgagcttg 1620
gaagcacggg ggaaataaca tggcgatttc ttttgtcata aaagaagaca acaaacaact 1680
cctcgaattc tgcttttaac tttttaagtt gacttcccaa atcccaacta ctcaggaaac 1740
agttgagctt gtttgcctag atctaacaca atatataatg catacgaccc cataacaaaa 1800
tctgtatttt cacgtttatt acactgaaaa aaaaaagata aaacattata tagcagacaa 1860
gataaaacct tctttgtcaa aacaaaatac aaaatatgta ctaagagaaa atcaccaaca 1920
tatcgttacg gattcacttg tttgataaag atgatcttct tttgtggata tttacataaa 1980
taattgatcg aatttattgt ttatacataa attatacact gattatataa gggtatataa 2040
ctattataca tccgtcgact agttcgtttc agcaattagt tgaacaacta cttaaattaa 2100
ttctttttttt aatataagta ttgaaattca attgtcttca ttctttttata acagtaaaat 2160
taatgctcat aattttgtga gccttacatt aattaaggac cgcgtagtcg taaaccaact 2220
ataaaatgaa tataataagc tgtaaatttta tctacagcat ttttagttag cgtgcgtacg 2280
taaaaattca aatcgagaga caaacttata acttactaca acctaattat atacgaaatg 2340
aactaacact aaccttcgtc cccactaatt aaaaatcgtg gatcatgttt tatactagct 2400
ttgcatacag ctaattaaaa tctatataga ctacaacttt tgaacatttt ctcacaccac 2460
tttcttttca caacttttag ctactccgaa aaaagtaatt 2500

SEQ ID NO: 24          moltype = DNA  length = 2500
FEATURE                Location/Qualifiers
source                 1..2500
                       mol_type = genomic DNA
                       organism = Nicotiana tabacum
SEQUENCE: 24
ctgaccataa aagttttcta atgcacactat tccataaact caagaccaga accaacttaa 60
attacattgt aattttacgg atgattattc aacttttact ttgttacatc gaagtcacta 120
aattttttgaa actttgctac tttcttcctc ctttattcga ggtagaagaa gacagtgcaa 180
tagttgactt attagacagc tttactcata tcacgagagc ttaaaggagc tttgtctaat 240
tccatgatct taatctgtcc atatgtcctt gtatttgatt ttcaagaaag gaattccttt 300
tatttcagag gcggatccag aattttaatt ttatggattc aggattatat tagagcctat 360
tttagtaata cagttagagt ctgcagtacc atttgaaaag tctcatttta aggcttttca 420
cttttgaaatt cctttatccca ttttttcaagt ttttgcttct ggagccactc cttttctgag 480
cctgcaagtt caagtgagcg ttactgcagt tcaagaatga caaaaaaggg ttgtgataag 540
ctgcaatgga ttgaagtgaa cgtcaaataa ttaatgctgt gactattgca acttttgcag 600
cttctttagg ctttgtctga agtgaatgtc ttcattcgaa atgaatagac ttcagcaagc 660
tatgttgcta agattctccg aaaatgtcac gaggtccatg tcagatccct caaaagtaat 720
gcattttttga aggatctgat acgggtgcgg caacattttg gagagtacgc gcaacatagc 780
cagccaacaa gtcgatactt acggtctaat agtttgaaga tctcctatcc aaccaagatt 840
attgaacatg tttcgattgc catttagctc aaatgacaaa atgaatgaat atttcctttt 900
taagtacacg tctctaatac atttatatag tcactccgga aaccctgtta catatattag 960
tatctacata taggttaatt ggaagccact gaaacaacct taatactttta aaagctaata 1020
aatctagaaa aaagagctaa aactacccct aacctattcg cttaggttta aaaatatcct 1080
tcgtccacct attttgtaaa aattgcccct aacatcaact tttcggccca ctcatacct 1140
agaaactaac gaccccatttt gattaagat aattttttta ttacttatta tgtgtcaatt 1200
tcctaatggc ttaaattaaa acctcattcc acatcctatt agcccgctcc ataacccaaa 1260
atatccatac tcgacccatg accggctttt taaaatgcct taacttcacc tctcatcttc 1320
tcctctttca tccctaccct cccactctat attttctcta atcatcctcc tccatggcca 1380
aagtacaata actcgccatt ggtaactgag gactaccgtc ggcttcaact ttaagatctt 1440
caccccttcaa cacccacgga tcttcctctc ccactcagat ttttcggcct taatttaatt 1500
tttaaattaa tattttttttg ttaaatcaat tttttgaggtt aaatctggta ttcttttggaa 1560
ttaaattaat ggttcattta aagatttatt ggtttaataa gttatgtttc cgccaaagtt 1620
atatttttttg taccaccatg tagcttttttt ggagttcgac ggcggtgatt tggttaggaa 1680
actgttggcg gagattaagt tgggaaagaa aaacagggaa agggataagg taccaaataa 1740
taaattaata aaaagaaaaa tatgaaattt tgatatatga aaccaaaata acgattggat 1800
catgagtccg gtatggaatc gggtgtttga ggggctaaaa agggattaac gagttggaac 1860
gactaagatg gattgcgagt ggcttattta cggatcagtt ctgggttaga gtgagatttt 1920
taatttttgac caataagcaa ttgccacatc atatataacc aaaaaaattt tattcagcaa 1980
aggtccgtca gaaataaggg catgaatgag ccaaattttt aacgatgaag acagtttta 2040
caaaataggt ggacagatgg tattttttaaa cccaaacgaa taggttaggg gcagttttgg 2100
cccttttttg ataaatctaa tatcactcca gtaatgacaa agctagaatc tacatatatc 2160
tgtctttatt ttcaacatat agattcctta cacatcattg tcacaaatct tgcttaaatg 2220
gaatctcaga gttaaataga gatagatttc actcaattat cagatcataa ctaaactacc 2280
taaagatgga tttaggagga attatcttaa tcttccttttt cagtacccctc tgcctctatc 2340
tccttggac aatcattaaa ctcctttatt taatactggtg gatgccactt caaatacaaa 2400
atagaatgag ttttcaggga atcaaaggcc cccttatag ctttccccat gggaatacca 2460
aagaaatctc actaatgaga agccaaacta tggacaacct 2500

SEQ ID NO: 25          moltype = AA  length = 318
FEATURE                Location/Qualifiers
source                 1..318
                       mol_type = protein
                       organism = Nicotiana tabacum
SEQUENCE: 25
MCVYSNCNKK RGRGRERGVV IQGKTAVGNN KTTNYYLYFL IFAPSLTSTA HRFSDPKKVA 60
```

```
KMNDADVSKQ IQQMVRFIRQ EAEEKAYGFP SPPKKYWPIS YSIDQLALVR LILSNNVRIE    120
EEFNIEKLQL VELEKKKIRQ EYERKEKQVD VRKKIEYSMQ LNASRIKVLQ AQDDLVNSMK    180
EAASKELLNV SHHQNHHIYK KLLQDLIVQS LLRLKEPCVL LRCREDDVSL VEGVLDAAKE    240
EYAEKAQVHS PEVIIDQIYL PSAPSHHNAH GSSCYGGVVL ASRDGKIVCE NTLDARLEVV    300
FRKKLPEIRK CLFGQVAA                                                 318

SEQ ID NO: 26           moltype = AA  length = 659
FEATURE                 Location/Qualifiers
source                  1..659
                        mol_type = protein
                        organism = Nicotiana tabacum
SEQUENCE: 26
MITPKLSLLC IQNPGTQTRS PSGYANESHT TGSENLTQLR LLLSGMGKPR IMHNSREGNE     60
VAHLLAKKTI NQSNMDHLVY LAISPSLVET KVLSDKDGES SLKFVVDDAC RMSNMDFMKV    120
FDQTVREIKR EVNLKVLKVP EIEQKVLDAT DDEPWGPHGT ALAEIAQATK KFSECQMVMN    180
VLWTRLTETG KNWRYVYKSL AVVEYLVAHG SERAVDEIVE HTYQISSLTS FEYVEPNGKD    240
MGINVRKKAE NIVALLNNKE KIEDARNKAA ANRDKYFGLS SSGVTFKSSS ASLNSSSNFQ    300
SGDRYGGFGN KSDGDSFKDS YREKDRYGED KFDQFKSKKG SSRYGSNVQD TVSSSGSKTS    360
KRVGKPDKAT SNPPHSAAVS SSKYEEDFDD FDPRGTSSTK PSTEKSDQVD LFGQNLIGDL    420
LDVPTPVPAD NSTVSSHPSE VDLFADANFA LAKPQSEISV DLFASQPASS SAAPSTIDFF    480
SAPDPVVQSD IRSPKSDKIN ATTVDPFAAV PLNTFDSSDP FGTFVSHADP VSVASENANR    540
GGNQEETPSK LDKSSVEAKP APKKDDFQVR SGIWADSLSR GLIDLNISAP KKVNLADIGI    600
VGGLTDGSDV KEKGPTTFYM GRAMGQGTGL GQSGFTSTST GGDDFFSSHQ NYQFGSFQK     659

SEQ ID NO: 27           moltype = AA  length = 284
FEATURE                 Location/Qualifiers
source                  1..284
                        mol_type = protein
                        organism = Nicotiana tabacum
SEQUENCE: 27
MAMDDNFHRQ RLGAHAPPGY FVRLENGRAK DDLYLRKGGR MRKWLCCTCQ VEESDPSHEN     60
ELHKSPKNNF DGYQKGSKAS VPAKAEVQKA IPTIEVPALS LDELKEETDN FGSKALIGEG    120
SYGRVYANL NNGKAVAVKK LDVSSEPETN VDFLSQVSMV SRLKHVNLVD LLGYCVEGNL     180
RVLAYEKGVQ GAQPGPTLDW MQRVKIAVDA ARGLEYLHEK VQPPIIHRDI RSSNVLLFED    240
YKAKLLILIC QISLLTWLLA FILHEFWEHL VIMHQSNVLH LTLL                     284

SEQ ID NO: 28           moltype = AA  length = 485
FEATURE                 Location/Qualifiers
source                  1..485
                        mol_type = protein
                        organism = Nicotiana tabacum
SEQUENCE: 28
MPPPPSTISD DDSSYFHVST LLPLYRARLR KKLNLRRLRN GTCRAEFAND APIAVAIGAC     60
IFSSLVFPTT YTEDDDGDSV IDSADARFAV MGIISFIPYF NWMSWVFAWL DTGKQRYAVY    120
ALVYLAPYLR TNLSLSPEDS WLPIASILLC IFHIQLEVSI KNGDFQALNK FTGTGEELSS    180
VSRKKDDSIS EEDMIAGDVV NPDHIDVGFD SIGGLGGIKD TLFQLAILPL RRPELFCHGK    240
LLGPMKGVLL YGPPGTGKTM LAKAIAKESG AVFINVKVST LMSKWFGDAQ KLVAAIFGLA    300
YKLQPAIIFI DEVDSFLGQR RASETEMLTS MKTEFMALWD GFTTDQNARV MVLAATNRPT    360
DLDEAILRRF SQSFEIGKPS LSDRTKIFKV VLKGERIEDN VDFDRLAGLC EGYTGSDILE    420
ACKLAAFIPL REYLQDEKKG KQSQAPRPLS QSDLETALAQ SKKTKITARK PAVVSFRLDD    480
YEDLD                                                                485

SEQ ID NO: 29           moltype = AA  length = 444
FEATURE                 Location/Qualifiers
source                  1..444
                        mol_type = protein
                        organism = Nicotiana tabacum
SEQUENCE: 29
MSSHDIRRPF KRPAISDQQR RRELSLLRQC QNRRDAQLQA RRLASTVLSL QPTQDDDYKS     60
ASEEQQLDIE VASVPEVDSF PDETDADFGH PRDAHDIRQA TKLRGPEARQ WFAKQLMLPE    120
WMIDVPDNLN TDWYVFARPA GKRCFVVSSN GTTISRLRNG IRLHRFPSAL PNGARINNSK    180
SAQSYCILDC IFHESDETYY VIDGVCWAGL SLYECTAEFR FFWLNSKLAE TGACDAPSTY    240
HRYKFSTLPV YNCDKEGLHT AYVGQVPYVK DGLLFYNKHA HYQTGNTPLT LVWKDENCSQ    300
YVIDTDNRGQ VPSQQQVVLE LLDDSRLATS DDPPVIFGCL LGEFIQKTEL QRGDLIKFAI    360
GEGGLVFVDS KLEKADLQYL GKSNRARAFA DSYSKVLFQY AARHSPLRIE HLFASISSCV    420
EDGRSNSRCR YGWLKCHARE TFFN                                          444

SEQ ID NO: 30           moltype = AA  length = 829
FEATURE                 Location/Qualifiers
source                  1..829
                        mol_type = protein
                        organism = Nicotiana tabacum
SEQUENCE: 30
MAQPLLKKDD DRDDEAEYSP FMGIEKGAVL QEARVFNDPQ LDARRCSQVI TKLLYLLNQG     60
ETFTKVEATE VFFAVTKLFQ SKDLGLRRMV YLMIKELSPS ADEVIIVTSS LMKDMNSSTD    120
MYRANAIRVL CRITDGTLLT QIERYLKQAI VDKNPVVASA ALVSGIHLLQ TNPEIVKRWS    180
NEVQEAVQSR AALVQFHALA LLHQIRQNDR LAVSKLVTSL TRGTVRSPLA QCLLIRYTSQ    240
VIREAAMSNQ TGDRPFYDYL EGCLRHKAEM VIFEAARAIT ELSGVTSREL TPAITVLQLF    300
LSSSKPVLRF AAVRTLNKVA MTHPMAVTNC NIDMESLISD QNRSIATLAI TTLLKTGNES    360
```

```
SVDRLMKQIT NFMSDIGDEF KIVVVEAIRS LCLKFPLKYR SLMNFLSNIL REEGGFEYKK    420
AIVDSIVILI RDIPDAKESG LLLHLCEFIED CEFTYLSTQI LHFLGNEGPK TSDPSKYIRY    480
IYNRVILENA TVRASAVSTL AKFGALVDSL KPRIFVLLKR CLFDGDDEVR DRATLYLNTL    540
GGDGAVVETD DEVKEFLFGS LGVPLTNLET SLKNYEPSEE AFDIFSVPKE VKSQPLAEKK    600
APGKKPTGLG APPVGPTSTV DSYERLLSSI PEFASYGKLF KSSAPVELTE AETEYAVNVV    660
KHIFDSHVVF QYNCTNTIPE QLLENGRHLW LLRRKPEGVPA VGKFSNTLRF IVKEVDPTTG    720
EAEDDGVEDE YQLEDLEVVT ADYMLKLGVS NFRNAWESLG PDCERGTEVV PSNSRSHTCL    780
LSGVYIGSVK VLVRLSFGLD GAKEVAMKLA VRSEDISVSD AIHEVVASG              829

SEQ ID NO: 31           moltype = AA  length = 566
FEATURE                 Location/Qualifiers
source                  1..566
                        mol_type = protein
                        organism = Nicotiana tabacum
SEQUENCE: 31
MKMRGYSFFT ATLILVAVSI FLSSIHTDAL PRDTFKSILG EGNLESWKNG VLDSAGMAQA     60
PGPADGHVGT LVLAGNRTRR PDFLSGFHKY RGGWDIANKH YWASVGFTGL AGIILALLWF    120
ISFGLALVVH YCCGWKFNIR GREWHFSQNI CLGVLIVLTC AAAIGCVLLS VGQDDFPHAEA   180
LDTLKYVVNQ SDYTVQTLRN VTQYLLLAKT VNVAQIFLPS DVKDDIDHLN GDLDSAADKL    240
EDKTNENSGK IRRVFNAVRS ALITIAIVML LISILGLCLS ILGHQHAIHI FIISGWLLVA    300
VTFVLYGVFV IINSAISDTC MAMGEWVDNP HAESALSNIL PCVDPRTTNR TLFKSKQVTV    360
DLVNIVNGFI DTYANSNPSN HANSNYYNQS GPVMPHLCYP YDSQLQDLPC PADQVSMANS    420
SMVWQNFTCN VSAAAICTSV GRLTPDMYGO LVATVNISYA LEHYAPPLLN LQNCDFVRDT    480
FRNITVNHCP PLEHHRLVVN AGLAVISVGV MLSLALWIVY ANRPQREEVF AKLSSRIKSS    540
CNGKNISCSN SNIDLSSRGT TPKTGV                                        566

SEQ ID NO: 32           moltype = AA  length = 280
FEATURE                 Location/Qualifiers
source                  1..280
                        mol_type = protein
                        organism = Nicotiana tabacum
SEQUENCE: 32
MLDASAVAYI QIASIAIADQ VARGQIELAK NVRQRLTSPS VAAPPLSTGK QKGGSSSCCK     60
LAASTSSAQM LTSVLSSLVA EEAASLSSGL KSAGFSSSLP FASPEKRLKL DKPMTFSDMN    120
SSEGGNSTYF TSSQQPITSI PLAPSSGLQS SNQIQAPFPP PPPPPPPLPP ANSPGSQLGQ    180
SAAMMMGMMP YGYSAGSLQP PQIAMGLRPP PPLPQQAQQL HLQTQQPQSQ QQPANGGFYR    240
PLVLDSMDRP ISRQHQQHPG SKSLWNREHM LHCTLIVKVD                         280

SEQ ID NO: 33           moltype = AA  length = 225
FEATURE                 Location/Qualifiers
source                  1..225
                        mol_type = protein
                        organism = Nicotiana tabacum
SEQUENCE: 33
MESDAHFLAK EDGIIAGIAL AEMIFAEVDP SLKEMADAAH PAYILETRKT APGLRLVDKW     60
AVLIGGGKNH RMGLFDMVMI KDNHISAAGG VGKALKSVDQ YLEQNKLQIG VEVETRTIEE    120
VREVLDYASQ TKTSLTRIML DNMVVPLSNG DIDVSMLKEA VELINGRFDT EASGNVTLET    180
VHKIGQTGVT YISSGALTHS VKALDISLKI DTELALEVGR RTKRA                   225

SEQ ID NO: 34           moltype = AA  length = 717
FEATURE                 Location/Qualifiers
source                  1..717
                        mol_type = protein
                        organism = Nicotiana tabacum
SEQUENCE: 34
MTEVATSNVV HDVLGRRAED VDQPIIDYII NVLADEDFDF GLDGEGAFEA LGELLVDSGC     60
VADFPECRAV CSKLSEKLEK HGLVKPQPTV RSLKMPLRMY DGMDEEEAPK NKKPEPVDGP    120
LLTERDKIKI ERRKRKDERL REAEYQAHLK EVEEVKAGMP LVCVNHDGQG DGPTVKDIRM    180
ENFNISVAGR DLIVDGSVTL SFGRHYGLIG RNGTGKTTLL RHMAMHAIDG IPKNCQILHV    240
EQEVVGDDTS VLQCILNTDM ERTQLLEEEG RLLELQREID LEGEAGKSDK LNGEIDKNAL    300
AKRLEEIYKR LDFIDAYSAE SRAATILSGL SFTTEMQKRA TKTFSGGWRM RIALARALFI    360
EPDLLLLDEP TNHLDLHAVL WLETYLVKWP KTFIVVSHAR EFLNTVVTDI IHLQNQKLST    420
YKGDYDTFER TRDEQVKNQQ KAFEANERTR AHMQTFIDKF RYNAKRASLV QSRIKALERI    480
GRVDEVINDP DYKFEFPSPD DRPGAPIISF SDASFGYPGG PLLFKNLNFG ILDLDSRVAMV   540
GPNGIGKSTI LKLISGELQP TSGTVFRSAK VRIAVFSQHH VDGLDLSSNP LLYMMRCFPG    600
VPEQKLRGHL GSFGITGNLA LQPMYTLSGG QKSRVAFAKI TFKKPHILLL DEPSNHLDLD    660
AVEALIQGLV LFQGGVLMVS HDEHLISGSV DQLWAVSEGR VTPFDGTFQD YKKILQS      717

SEQ ID NO: 35           moltype = AA  length = 384
FEATURE                 Location/Qualifiers
source                  1..384
                        mol_type = protein
                        organism = Nicotiana tabacum
SEQUENCE: 35
MGAQISVSKL ANLSFVPRIR VPVPNISVPS PSISSGFVSN LSCSAIGISS VLVNFYQSAS     60
LAKSANPSTY TYTVPSSPSE VLYRWHLPEP NVVDISGNYD CSSVKSRTVV VLLGWLGAKQ    120
KHLKRYAEWY ASAGYHVITF TFPMSEILSY QVGGKAEQDI ELLVNHLVDW LEEEHGKNLV    180
FHTFSNTGWL TYGVILEKFQ KQDPVLMTRI KGCIVDSAPV AAPDPQVWAS GFSAAFLKKN    240
SVATKHIMTI NNKDADVTIE TKTSSDATPA VTEAALLVVL EKFFEVVLSL PAVNRRLSDV    300
```

```
LDLLTSQQPS CPQLYIYSSA DRVIPAISVE SFVEEQRRIG RNVRACNFIS TPHVDHFRND    360
PELYTLQLTQ FLEDSVLSSC KQSS                                           384

SEQ ID NO: 36           moltype = AA   length = 547
FEATURE                 Location/Qualifiers
source                  1..547
                        mol_type = protein
                        organism = Nicotiana tabacum
SEQUENCE: 36
MGGAEDAEPP SKRVKVSSGK PGDLSNGTFP RDPASCSLND LMARPLVCQG DDEVVGTKGV     60
IKKVEFVRIL AEALYSLGYN KTGAHLEEES GIPLQSAVVK LFMQQVLDGK WDESVATLRK    120
IGLVDEKVVQ LASFLILEQK FFELLDEKKV MDALKTLSTE IGPLCINTDR VRELSLCILS    180
PLQQVRAVVS GQVVVRAKPR RKLLEELQKL LPPTVIIPEQ RLIRLVEQAL DLQLDACRFH    240
NSLVGEMSLL TDHQCGRDQI PSQTLQVKLD GLFCMKHQFS GHQKPVSYMS WSPDDHQLLT    300
CGVEEVVRRW DIESGECTHI YEKNGLGLIS CGWAPDGKRI LCGVTDKSIS MWDLEGKELE    360
CWKGHRTIRI SDLGITSDGQ HIVSVCKDNM ILLFGWESKA EKVIQEDQTI TSFVLSMDSK    420
YLLVSLWNQE IHLWNIEGTV KLISKYKGHK RSRFVVRSCF GGLGQAFVAS GSEDSQVYIW    480
HRSSGELIET LAGHSGTVNC VSWNPANPHM LASASDDHTI RIWGMNQVNM KHYDTVSNGV    540
HYCNGGT                                                              547

SEQ ID NO: 37           moltype = AA   length = 587
FEATURE                 Location/Qualifiers
source                  1..587
                        mol_type = protein
                        organism = Nicotiana tabacum
SEQUENCE: 37
MAMVDEPLYP IAVLIDELKN DDIQLRLNSI RRLSTIARAL GEERTRKELI PFLSENNDDD     60
DEVLLAMAEE LGVFIPYVGG VEHAHVLLPP LETLCTVEET CVRDKAVESL CRIGSQMRES    120
DLVDWFVPLV KRLAAGEWFT ARVSACGLFH IAYSSAPEML KAELRSIYSQ LCQDDMPMVR    180
RSAATNLGKF AATVESTYLK SDIMSIFDDL TQDDQDSPYL LAVEGCAALG KLLEPQDCVA    240
HILPVIVNFS QDKSWRVRYM VANQLYELCE AVGPEPTRTD LVPAYVRLLR DNEAEVRIAA    300
AGKVTKFCRI LSPELAIQHI LPCVKELSSD SSQHVRSALA SVIMGMAPVL GKDATIEHLL    360
PIFLSLLKDE FPDVRLNIIS KLDQVNQVIG IDLLSQSLLP AIVELAEDRH WRVRLAIIEY    420
IPLLASQLGI GFFDDKLGAL CMQWLQDKVY SIRDAAANNL KRLAEEFGPE WAMQHIIPQV    480
LDMTTSPHYL YRMTILRAIS LLAPVMGSEI TCSKLLPVVI TATKDRVPNI KFNVAKVLQS    540
LIPIVDHSVV EKTIRPSLVE LAEDPDVDVR FYANQALQSI DNVMMSG                  587

SEQ ID NO: 38           moltype = AA   length = 621
FEATURE                 Location/Qualifiers
source                  1..621
                        mol_type = protein
                        organism = Nicotiana tabacum
SEQUENCE: 38
MGFIESCSQT AEMEIRKCSP FLESELLSGN GGLPLTEWRT VPDIWRTSAE KFGDRVAVVD     60
PYHDPPTTMT YKQLYQEIVD FSEGLRVVGL NPNEKIALFA DNSCRWLVAD QGTMASGAIN    120
VVRGSRSSNQ ELLQLYSHSE SVALAIDNPE MYNRISDTFG SHTAVRFAIL LWGEKSSLGR    180
EAVQGYPVYT YKEIIELGHK SRVDLLDSED ARKQYSFEAI NSDDVATIVY TSGTTGNPKG    240
VMLTHKNLLH QILNLGEIVP AVPGDRFLSM LPPWHAYERA CEYFIFTHGT EQVYTTVKNL    300
KPHYLISVPL VYETLYSGIL KQINSNSAAS KLIALLFLRI SMTYMEAKRI YEAGVSGGGS    360
LSSHVDKFFE AIGIKIQNGY GLTESSPVIS ARHLACNVLG SVGHPIRHVE VKIVNAETDE    420
VLPPGSRGIV KARGPLVMKG YYKNPLATKH AIDENGWLPD GDLGWIAPDH SVGRSRKSGG    480
VIVLEGRAKD TIVLSTGENV EPSEIEEAAM GSSLIQQIVV IGQDQRRLGA IIVPNKEEVL    540
LAAKKSAIVD SETTEVSKEK AVGILYEELR KWTSGCSFQV GPILIVDEPF TIDSGLLTPT    600
MKIKRDKIAA LYKEQIENLY K                                              621

SEQ ID NO: 39           moltype = AA   length = 869
FEATURE                 Location/Qualifiers
source                  1..869
                        mol_type = protein
                        organism = Nicotiana tabacum
SEQUENCE: 39
MGGDETKKTT IMVLKVDLQC SSCYKKVKKV LCKFPRCGVI KSIEIKEPPK PKAPEKPKEP     60
VKPEPEKPK QPEKPKEPEK PKQPEKTTVV VIEKPKEPEK PKAPEKSKEP EKPKEPEKPK    120
EVEKPKPKEP EKPKEAPKPN PVAPPSQPPP PPAPEPIMVQ QYPQPPLGYC CGQCYEGHIG    180
GPCYQWYGRP VLPAPCYDNY GYNYGPGPGP GPYGYGRGCY VSRCDQYFSE ENATGCSIIK    240
WEPNIVASKA KEVYSAWVVR LLQLPTEFYD RIVLSRIGNS IGRLLRIDAC TSSTLRRRYA    300
RLCVQVQMDQ LVQTTIQIGS HIQQLVYEGE KFLCKACGRL GNTTSTCSHT LLDFQKQQQE    360
EPCPNSTGFI GKERQLKSND KPSPSPKVTS QKEAQPMDLK IKLKRHLQVS MSIFLMRHQP    420
ILTSNKFESL LNDSSITFPE IIESQMELDG QNSNLSPDSK LSFSPRNHSS SLLPPLSPRG    480
QKATCNSNKP HKTAGPSTNP LPCTPLPTLM TPITTENPIT DLSLTTCQLA MQLNSPILAS    540
LRLHVKNRTM HTKFLLTDFQ SLPHENQSPS SPSSSPTHYE STPLLPSNEN PSKITLTPPS    600
FLNTVQNEPP TPGYKPSDLH HQCPLTGPPT NAMVGTRTSG PSGFLHSQYP KSRSPVCSTE    660
PTGPSSINLG GYEASNVELH QPPLVDKCSR AHSPTLAPAL LHNMQAHWNP PHHFNPLQNM    720
QLFYQLPFFA PQDQNTPPLI HAWQPIPQHY PAPMDFHHTH SHPHHSAPVP GEQEMETQNQ    780
TIPPLNITSY TENSNLPHEVK ILLFQAMEEK KYVRKCPTEL YKCSLDIRPP LNAAVGNFAV    840
ILSPSLNGLP VPPMGSQFNV TPQPTPIND                                      869

SEQ ID NO: 40           moltype = AA   length = 369
FEATURE                 Location/Qualifiers
```

```
source                  1..369
                        mol_type = protein
                        organism = Nicotiana tabacum
SEQUENCE: 40
MHILYTCPLI LFMALLFAYA AATAADLETN GAEKAGADAG ILSSNSSVNE NLDLINMNRK        60
KDGHLDNDSS NVGDQNKSND SSAKKGDDRE GLKEAEVEKK RIDSGSKRDD RKEETKEAEQ       120
QDKAKDISSE KQGEMEKILP DGIQSREEIL PTRKESFHGE ECDSSYSCTI EEKAVVACLR       180
VPGNESPDLS LLVQNNGKGT VNILIKAPEF VQLEKEKIEL QGKENQRMKV SIRNAGNDNN       240
IILKAGDGQC TLDFRGLIDN ADKTSQFKYG FLSFAIMCLA AIALVATVLM YPKRRLLVSS       300
GHKYQKLDMD LPVSSGRKTE TLSTDGWDNS WDDDWDDEEA PKAPSVPVTP SFSSKSITSR       360
RSSKESWKD                                                              369

SEQ ID NO: 41           moltype = DNA  length = 957
FEATURE                 Location/Qualifiers
source                  1..957
                        mol_type = genomic DNA
                        organism = Nicotiana tabacum
SEQUENCE: 41
atgtgtgtgt actccaattg taacaaaaaa cgtgggagag ggagagagag aggagtcgtg        60
attcaaggga agacagcagt tggcaataat aagactacaa attactatct ctactttctg       120
attttcgctc cttcactcac atccacagca catcgcttct ccgatccaaa aaagttgcg        180
aagatgaacg acgcagatgt atcgaagcag atccagcaga tggtcagatt catccgccag       240
gaagccgaag aaaaagccta tggatttccg tctccgccga agaagtattg gcctatttct       300
tattctattg atcaattagc tttagttaga ctaattttga gtaataatgt gcgcattgaa       360
gaagaattca acatcgagaa gttgcagcta gtggaactgg agaagaagaa gatcaggcag       420
gaatacgagc gtaaggagaa acaagtcgat gttcgcaaaa aattgagta ctccatgcaa        480
ctcaacgcct ctcgaatcaa ggttcttcaa gctcaggatg acttggtcaa ctccatgaag       540
gaggcagcat caaggagct tttaaacgtc agccatcacc agaaccacca tatttataag        600
aagcttctgc aggatcttat tgttcagagt ttgctcagac ttaaagagcc ttgcgtccta       660
ctacgttgtc gggaagatga tgtttccttg gtagaaggg tcttgatgc agcaaaagag        720
gagtatgcag aaaaagctca ggttcactca ccggaggtca taattgacca aatctacctt       780
ccatcagctc catcacatca caatgctcat ggctcttctt gctatggagg agtagttttg       840
gcttctcgag atgggaaaat tgtatgtgaa aatacacttg atgccagatt ggaagttgtg       900
ttccgtaaga aactaccgga gattcgcaag tgtctatttg tcaggttgc tgcctaa          957

SEQ ID NO: 42           moltype = DNA  length = 1980
FEATURE                 Location/Qualifiers
source                  1..1980
                        mol_type = genomic DNA
                        organism = Nicotiana tabacum
SEQUENCE: 42
atgattactc caaagctatc tctcctttgc atacaaaatc ctggcactca gacaaggtct        60
ccaagtggct atgcaaatga atctcatacc accggaagtg aaaatttgac tcaactgagg       120
ttattactgt ccggaatggg gaagccaagg attatgcata actccaggga aggaaatgaa       180
gtagcccacc tactggctaa gaagacaatc aatcaatcta acatggatca tctcgtctat       240
ctggcaattt ctccttctct tgttgagacc aaggtgttgt cagacaaaga tggagaatct       300
tctctaaaat ttgttgtaga cgatgcttgt aggatgatt catgaaggta                   360
ttcgatcaaa cagttcgcga aataaagagg gaggtgaatt tgaaagtgtt gaaggttcct       420
gagattgagc agaaggtatt ggacgctacg gatgatgaac cttggggccc catggtact        480
gcattggctg agatagctca ggctacaaaa aaattctctg agtgtcagat ggttatgaat       540
gtcctgtgaa caagattgac tgaaacagga aagaattgac gttatgttta taagtcttta       600
gctgttgttg agtatttggt ggctcacgga tctgaacgcg ctgttgatga gatcgtagaa       660
cataccatc agatatcttc tctcacaagt ttcgagtatg ttgaacccaa tgggaaagat       720
atggggatca atgtgaggaa gaaagcagaa atattgtgg cactattgaa taacaaggaa        780
aagatcgaag acgctagaaa taaagctgct gcaaatgcag acaagtactt tggattgtca       840
tcttctggag taacatttaa atcgagctct gcctccctaa atagcagcag caactttcag       900
agtggtgatc gatatggagg ttttggaaat aaaagtgatg gcgattcatt taaggatagt       960
tacagggaaa aggatcggta tggtgaagat aaatttgacc agtttaaatc aaagaaggg       1020
tcttctcgtt atggaagcaa tgttcaagac actgtttcat aaagacgtca                 1080
aagagggtag gtaaacctga taagctact tctaatcctc cacatagtgc agctgtgatca      1140
tcaagcaaat atgaggaaga ttttgatgat tttgatcctc gagggacttc aagtactaag      1200
ccttccaccg aaaaatctga ccaagtagat ctatttggac aaaatttgat tggtgacctc      1260
ttggatgtac aacacctgt tccagctgat aattctactg tctccagtca tccatcagag       1320
gttgatttat ttgctgaatgc caattttgca ttggcgaaac caatctga gataagtgta       1380
gatctgtttg cttctcagcc tgcctcttca tctgcagctc cttcaaccat agatttttt      1440
tctgcaccag atcctgttgt acaatccgat atcagatctc ctaaatcaga caagataaat      1500
gctactacgg ttgatccgtt tgctgcagtt ccactaaata ccttttgatag ttctgatccc     1560
tttggtacat ttgtttctca tgctgatcct gtatcagtag ccagtgaaaa tgctaatcgt      1620
ggtgggaatc aggaggagac tcctagcaaa ttagataaat cttctgtcga agctaagcc       1680
gcaccaaaga aggatgattt tcaagtcagg tctggaatat gggctgattc attgagccgt      1740
ggactgattg atctgaatat ctctgcaccc aaaaagtca accttgcaga cataggcatc       1800
gtgggtggat tgaccgatgg gtcagatgtg aagaaaaag gcctactac attttacatg        1860
ggcagagcca tgggtcaagg aaccgggctt ggccaatccg ggttcacgtc cacatcaacg      1920
ggtggagatg actttttttc aagtcaccag aactatcaat ttggcagctt ccaaaagtga      1980

SEQ ID NO: 43           moltype = DNA  length = 855
FEATURE                 Location/Qualifiers
source                  1..855
                        mol_type = genomic DNA
```

```
                        organism = Nicotiana tabacum
SEQUENCE: 43
atggcgatgg atgacaattt ccataggcaa cgactagggg cacatgcacc tccgggttac   60
tttgtccgct tggagaacgg aagggctaaa gacgatcttt acttgagaaa gggaggaagg  120
atgagaaagt ggctctgctg cacctgccaa gtagaggagt ctgacccatc gcatgaaaac  180
gagctccaca aaagcCCCaa gaacaatttt gatggatatc agaaagggtc aaaagcatca  240
gttcctgcca aggctgaagt gcaaaaggca ataccaacta tagagggccc tgcattgtct  300
ttggatgaac tgaaagagga aactgacaat tttggatcga aggcattaat tggtgaagga  360
tcttacggaa gagtatacta tgctaatcta aacaatggca aagccgttgc tgtaaaaaag  420
cttgatgttt catctgagcc tgagactaat gttgacttcc tgagccaggt ctctatggtt  480
tcaagattga agcatgtaaa tctggttgat ttgcttggtt actgtgtgga agggaacctt  540
cgtgtattag cttatgagaa aggagtacaa ggagcacaac ctggacctac acttgattgg  600
atgcaacggg taaaaattgc tgttgatgct gcaaggggcc ttgagtattt gcatgagaag  660
gtccagcctc caataataca cagggatatc agatcaagca atgtccttct ctttgaagac  720
tacaaagcaa aattgctgat tttaatctgt caaatcagtc tcctgacatg gctgctcgcc  780
ttcattctac acgagttttg ggaacatttg gttatcatgc accagagtaa tgtcttgcac  840
cttactcttc tttga                                                    855

SEQ ID NO: 44          moltype = DNA   length = 1458
FEATURE                Location/Qualifiers
source                 1..1458
                       mol_type = genomic DNA
                       organism = Nicotiana tabacum
SEQUENCE: 44
atgccaccgc cgccgtccac catctccgac gatgattcct cttacttcca cgtcagcact   60
cttctacctc tatatcgagc tcgcctccgc aaaaaactta atctgagaag gttgagaaat  120
ggaacttgta gggcagagtt tgcaaacgac gcgccaatcg ccgtcgctat cggtgcttgc  180
attttcagct cgttggtttt tccgactact tacacggagg atgatgacgg ggactccgtg  240
attgattctg ctgatgcgag gtttgctgtt atgggaatta tcagcttcat tccgtatttt  300
aattggatga gttgggtttt cgcgtggttg gatactggga agcagcgtta cgctgtttat  360
gctcttgtgt atttggctcc atatttaaga accaatctgt ctctttctcc tgaagacagc  420
tggctaccaa ttgctagcat cctcttgtgc atcttccaca ttcaactaga agtaagtatc  480
aaaaatggag attttcaggc attgaacaaa tttactggga ctggagagga actatcatca  540
gtttctagga agaaagataa tagcatctct gaagaggata tgattgctgg ggatgtcgtg  600
aatccagacc acatagatgt gggggtttgat tcgattgggg ggctggtgg gattaaggat  660
actttgtttc agctggccat tttacctctg cgaaggcctg aattgttttg tcatgggaaa  720
ttgcttggtc caatgaaagg ggttctgttg tatggaccac ctgggacagg aagacaatg   780
cttgctaaag ccattgctaa agagtctggt gctgtgttca ttaatgtgaa ggtttctact  840
ctcatgagca gtggtttgg tgatgcgcaa agcttgttg ctgctatttt tggttttggcc  900
tataagctcc agcctgctat aatatttatt gatgaagttg acagcttttt gggccagcgt  960
cgtgcaagtg agactgaaat gctgactagc atgaaaactg agttcatggc cttatgggat 1020
ggttttacta ctgatcagaa tgctagagtt atggtcctgg cagcaaccaa tcgcccaact 1080
gaccttgatg aggcaatact taggcgcttt tctcagtcat ttgagattgg gaaaccttcc 1140
cttagtgata gaacaaagat atttaaggta gtattgaagg gtgagagaat tgaagataac 1200
gttgactttg atcgacttgc tggcttgtgt gagggataca ctggttcaga cattctcgag 1260
gcctgcaagc tagctgcctt tattcctctt agggagtatt gcaagatgaa gaagaaagga 1320
aagcaatcac aggctccaag gccattgtca cagtctgatc tagagacagc tttggctcaa 1380
tcaaagaaga ccaagattac tgctaggaaa cctgctgtag tgagctttcg gttggatgat 1440
tatgaggatt tagactga                                               1458

SEQ ID NO: 45          moltype = DNA   length = 1335
FEATURE                Location/Qualifiers
source                 1..1335
                       mol_type = genomic DNA
                       organism = Nicotiana tabacum
SEQUENCE: 45
atgagctcac acgatatacg ccgcccgttc aaacggccgg cgatctcaga ccaacaaaga   60
cgccgagaac tttcattgct ccggcagtgc caaaaccgcc gcgacgctca gttacaagcc  120
cgtcgtttag cttccacagt cctctctctt caacccacgc aagacgatga ctacaagtcc  180
gcttccgaag agcaacagct ggatatagaa gttgcttccg tccccgaagt tgattccttt  240
ccggatgaaa ccgacgccga ttttggacat cctagggacg cacatgatat tcgtcaagct  300
actaagctca gaggacctga agctcgtcag tggttcgcca agcagcttat gcttcctgaa  360
tggatgattg atgttcctga taacttgaac acggattggt atgtatttgc taggccagct  420
ggaaagagat gttttgttgt ttcttcaaac ggaacaacaa tcagtagact gcgaagtgat  480
attcgcttgc accgtttttcc ttctgctcta cctaacggtg ccagaattaa taacagtaaa  540
tctgctcaat catactgtat tctcgattgc atatttcacg agtctgatga acatattat   600
gtcattgacg tgtatgttg ggcgggactt tcgttatatg agtgcacggc ggaattcaga  660
ttcttttggt taaacagcaa gcttgctgag acgggggctt gtgatgctcc ctctacttat  720
catagatata aatttagtac acttcctgtc tacaactgtc acaaagaagg actacacaca  780
gcttatgtag acaagttcc atatgtcaag gatggattac tgttttacaa caagcatgca  840
cattaccaaa caggaaatac accgttaaca ttggttggga aggatgagaa ctgtagccag  900
tatgtcattg atacagataa tagaggacaa gttccaagtc aacaacaggt agttttggag  960
ctcctagatg atagcagact ggctacatct gatgatcctc ctgtcatatt tggttgcttg 1020
cttggggaat tcatacaaaa gacagaactt cagcgtgtgga atcttataaa gtttgctata 1080
ggtgaaggcg gattagtttt tgttgacagt aaactggaga aagctgatct acaatacttg 1140
ggcaaatcca atcgtgctcg tgcttttgct gatagttact cgaaggtctt gttccagtac 1200
gctgctcgac attctcctct gagaattgaa catcttttg catcaatcag ttcatgtgtc 1260
gaagatggaa gatcaaactc aagatgcaga tatggctggt taaagtgcca tgcacgggaa 1320
acttttttca actaa                                                  1335
```

```
SEQ ID NO: 46          moltype = DNA   length = 2490
FEATURE                Location/Qualifiers
source                 1..2490
                       mol_type = genomic DNA
                       organism = Nicotiana tabacum
SEQUENCE: 46
atggctcagc ctctcctgaa gaaagacgac gatcgcgatg acgaagcgga gtactctccg    60
tttatgggga ttgagaaggg ggctgtgctt caggaagcta gggttttcaa tgatccgcaa   120
ttggatgcac gcagatgctc acaggtcatt acaaagcttc tgtatcttct gaatcagggt   180
gagacgttta caaaggttga agctacgaag tgttctttg ctgtcacaaa actctttcag   240
tcaaaggatc ttggtctaag gagaatggta tacttgatga taaagagct ttctccctca   300
gctgatgagg taatcatcgt tactagctct cttatgaagg acatgaatag cagtacagat   360
atgtatcgtg caaatgctat tcgagtcctc tgccgaatca cagatgggac tcttctcaca   420
caaattgaga gatacttgaa acaagcgatt gttgacaaaa accctgttgt tgcaagtgct   480
gcccttgtta gtggaatcca tttgcttcag acaaacccgg agattgtgaa agatggagc    540
aatgaggtcc aagaagctgt tcagtcaagg gcagctctcg ttcaattcca tgcactggcg   600
ctgctgcacc agataaggca aaatgaccgt ttagctgtga gcaagcttgt taccagttgg   660
acaagaggaa ctgttcgctc acctctagct caatgcctct tgattcgtta tactagtcag   720
gttataagag aggctgccat gagtaatcaa acaggggata ggccattcta tgactatcta   780
gagggttgcc tacgtcacaa agcagaaatg gttattttg aagctgccag ggcaatcaca   840
gagcttagtg gtgtgactag tcgagaatta actcctgcaa tcactgttct acagctcttt   900
ttaagctctt ccaagccagt tcttaggttt gctgctgttc gaaccttgaa taaggtggca   960
atgcacacatc ctatgctgt gacaaactgc aacatagata tggagagctt gatttctgat  1020
cagaatagga gcatagcaac tcttgccata acgactcttc ttaagaccgg caatgaatca  1080
agtgttgatc gtttgatgaa gcagataact aattttatgt ccgacattgt tgatgagttc  1140
aagattgttg tggtgaagc cattagatca ttgtgtttga agtttcccct gaagtacaga   1200
tctttgatga atttcttaag caatatttg agggaagaag gaggatttga gtacaaaaag   1260
gctattgttg actcaattgt gatcctgatc agagacattc cagatgctaa agaaagtggg  1320
ctgcttcact tgtgtgaatt tattgaggac tgtgaattta catacctttc tactcagata  1380
ctacattttc ttggaaatga aggacctaag acatcagacc ccagtaagta catacgatat  1440
atatacaata gagttatact tgagaatgca acagttcggg ccagtgcagt gagcacctta  1500
gctaagtttg gtgccttggt tgattcattg aagccccgta tatttgtgct attgaaacgt  1560
tgcctattcg acggtagtga tgaggttcgc gataggcaca cactgtattt gaatacccct  1620
ggaggtgatg gtgcagttgt tgaaactgat gatgaggtga aagagttcct attcggtca   1680
ctcggtgtcc ctctaaccaa tctgagaca agtttaaaga actatgagcc atcagaggag  1740
gcgtttgata ttttttctgt tcccaaggaa gttaaatctc agcctttggc agagaagaaa  1800
gcaccgggta aaaagccaac tggtttgggt gctccacctg tcggcccac ctctactgtt   1860
gattcatatg aaagattact gtcctctatc ccagaattcc ctagctatgg gaagcttttc  1920
aagtcatcgg cgccagtgga gctcacagaa gctgaaacag agtatgcagt taatgtcgtg  1980
aagcacattt tgatagtca tgtagtgttc cagtacaact gcaccaatac cattcctgag   2040
caattgttgg aaaatggcag acatttgtgg cttttgaaa aacctgaagg agtccctgct  2100
gttgggaaat tctcgaacac actaagattc attgttaaag agttgatcc aaccactgat  2160
gaggctgaag atgatggtgt tgaagatgaa taccaactag aagaccttga ggttgtcact  2220
gcagattaca tgctgaaatt gggagtctcc aatttagga atgcatggga gagcttggga  2280
ccagattgtg aacgcggcac tgaggtagtc ccaagcaact caagatcgca cacatgttta  2340
ttatctggtg tatacattgg cagcgtaaag gtacttgttc ggttatcatt tggattggat  2400
ggggcaaagg aggttgcaat gaagctggct gttaggtcag aagatatatc tgtaagtgat  2460
gcaattcatg aagttgttgc aagcggctag                                    2490

SEQ ID NO: 47          moltype = DNA   length = 1701
FEATURE                Location/Qualifiers
source                 1..1701
                       mol_type = genomic DNA
                       organism = Nicotiana tabacum
SEQUENCE: 47
atgaaaatga gggctattc attcttact gctactctca ttcttgttgc tgtttctatt    60
tttcttagct caatccatac tgatgcttta ccaagagata ctttcaagtc tattttaggg   120
gagggaaatc tggaatcatg gaagaatgga tattggact cagcaggtat ggcacaagcg   180
ccaggtcctg ccgatgggca tgttggcacg cttgtgctag cgggaaacag gacgaggaga   240
ccggactttc tttctggttt ccacaaatac agaggtggat gggatattgc aataaaacac   300
tactgggctt ctgttggttt tacaggcctt gctggtatca tacttgctct gctttggttt   360
atttcatttg gcttggctct cgtcgtgcat tattgctgcg gatggaaatt caatatcaga   420
ggcagagaat ggcatttttc acagaatatt tgcctgagtc tgtttattgt cttgacatgt   480
gctgcagcga ttggatgcgt cctactttct gttggacaag atgactttca tgctgaagca   540
ttggacactt taaaatatgt tgtaaatcag tcagattata ctgtgcagac attgagaaat   600
gtaacgcaat acttgttact cgcaaaaact gtaaatgtgg cccagatttt cctcccttca   660
gatgtaaaag atgatatcga tcacctaaat ggcgatctag attctgcagc ggataaaactt  720
gaggataaaa caaatgaaaa ctcaggaaag atacgaaggg tcttcaatgc tgtgcgttca   780
gctttgatca ctattgccat cgtcatgctc ctcatctcta tcttggtgct ttgcctctct   840
atccttggcc atcaacacgc aattcacata tttatcatta gtggatggtt actggtggca   900
gttacattcg ttctctatgg agttttttgtc atcataaaca gtgcaatttc agatacttgt   960
atggcgatgg agagtgggt ggacaatccg catgctgaaa gtgctcttag caacatcctt  1020
ccatgtgttg acccgagaac tacaaaccgg acgtgttca agagcaaaca agtcactgtt  1080
gatcttgtaa atattgtcaa cggatttatc gacacatatg caaattccaa tccatctaat  1140
catgccaatt caaattacta taatcagtca ggacccgtta tgccacatct ctgctatcca  1200
tatgactccc aattgcaaga tcttccgtgc cctgctgatc aagttctat ggcaaattct   1260
tcaatggttt ggcagaactt tacttgcaac gtatctgcag ctgcaatatg cactagtgtc  1320
gggaggctga ctccctgacat gtacggacag ttggtggcga cggtcaacat tagctatgca  1380
```

```
cttgaacatt atgcaccacc gttgcttaat ctccagaact gtgatttcgt tcgtgataca   1440
tttaggaaca tcacggtcaa ccactgccct ccgttggaac accatcttcg ggttgttaat   1500
gcaggattag ctgtcatatc agtcggagtc atgctaagtc tcgcattgtg gatagtatat   1560
gcaaaccgcc cccaaaggga ggaagtgttt gcgaagctct cttcgcgaat aaagagcagc   1620
tgtaacggca agaatattag ctgcagtaat agtaatattg atttgtcatc aagaggtaca   1680
actccaaaga ctggagtgta g                                             1701

SEQ ID NO: 48          moltype = DNA   length = 843
FEATURE                Location/Qualifiers
source                 1..843
                       mol_type = genomic DNA
                       organism = Nicotiana tabacum
SEQUENCE: 48
atgttggacg cgtcagcagt agcatatatt cagattgcta gcattgccat agcagaccag   60
gttgcacgtg gtcagatcga actagcaaaa aatgtaagac agaggctgac atctcccagt   120
gttgctgctc caccattgag tactggaaag caaaagggcg gcagcagctc ttgctgcaaa   180
cttgctgctt caacatcttc tgctcaaatg ttgacctctg ttctttcgtc tcttgttgct   240
gaagaagctg cgtcactgag cagtggattg aaatcagctg gtttttcttc tagcttacct   300
tttgcatctc cagagaaacg gctcaagtta gacaagccaa tgacttttc tgatatgaac   360
agttccgaag ggggtaattc cacttacttc acttcatcac agcaaccgat tactagcatt   420
cctcttgccc cttcctcagg cttacaatcg tcaaaccaga tacaagctcc gtttccacca   480
cctcacctc caccaccacc tttacctcca gcaaattccc ctggaagtca gttaggtcag   540
tctgcagcta tgatgatggg gatgatgccc tatggatata gtgccggcag ccttcagcca   600
cctcaaattg caatgggact gaggccacct ccaccactac cccagcaagc acaacagctg   660
catctcccaga ctcagcagcc acaatctcaa cagcagcctg ccaatggtgg atttatcgt    720
cctctggtat tggattctat ggacagaccc atcagcagac aacaccagca gcacccaggc   780
agtaaatccc tttggaatag ggagcacatg ttacattgta cattaatagt aaaagtagac   840
tag                                                                 843

SEQ ID NO: 49          moltype = DNA   length = 678
FEATURE                Location/Qualifiers
source                 1..678
                       mol_type = genomic DNA
                       organism = Nicotiana tabacum
SEQUENCE: 49
atggaatccg atgctcattt tctagcaaag gaagacggga tcatagcagg aattgcactt   60
gctgagatga tattcgcgga agttgatcct tcattaaagg aaatggcaga tgctgcacac   120
cctgcttaca tcttggagac taggaaaact gctcctggat tacgtttggt ggataaatgg   180
gcggtatttga tcggtggggg gaagaatcac agaatggcct tatttgatat ggtaatgata   240
aaagacaatc acatatctgc tgctggaggt gtcggcaaag ctctaaaatc tgtggatcag   300
tatttggagc aaaataaact tcaaataggg gttgaggttg aaaccaggac aattgaagaa   360
gtacgtgagg ttctagacta tgcatctcaa acaaagactt cgttgactag gataatgctg   420
gacaatatgg ttgttccatt atctaacgga gatattgatg tatccatgct taaggaggct   480
gtagaattga tcaatgggag gtttgatacg gaggcttcag gaaatgttac ccttgaaaca   540
gtacacaaga ttggacaaac tggtgttacc tacatttcta gtggtgccct gacgcattcc   600
gtgaaagcac ttgacatttc cctgaagatc gatacagagc tcgcccttga agttggaagg   660
cgtacaaaac gagcatga                                                 678

SEQ ID NO: 50          moltype = DNA   length = 2154
FEATURE                Location/Qualifiers
source                 1..2154
                       mol_type = genomic DNA
                       organism = Nicotiana tabacum
SEQUENCE: 50
atgacggaag tggcgacgag caacgttgtg cacgcacgtct tagggcgacg agctgaagat   60
gtagatcagc cgattattga ctatataatc aatgttctag ccgatgaaga tttcgatttt   120
ggacttgacg gtgaaggtgc ttttgaagcc ctcggcgaat tactcgtaga ttctggttgc   180
gttgctgact cccccgaatg tcgtgcggtt tgtagcaagt gtctgagaa gttagagaag   240
catggattgg ttaaacctca accaactgtg agaagcttaa aaatgccgct gagaatgtat   300
gatgaatgg atgaagagga agctccaaag aataaaaagc cagaaccagt tgatggtcct   360
ttgctcacag aacgtgacaa gattaagatc gaaaggagga agaggaaaga tgaacgcctg   420
agagaggcag aataccaagc acacttgaaa gaagtggaag aagtgaaagc tggtatgccg   480
ttagtgtgtg tgaatcatga tggtcagggt gatggaccaa ctgttaagga tatccgtatg   540
gaaaatttca atatatctgt tgctggtcgt gaccttatcg tcgatggtte tgttacgctt   600
tcttttggaa gacactatgg ccttattgga agaaacggta cggggaaaac aactctccta   660
agacacatgg ctatgcacgc tattgatggt attcccaaga actgccagat attgcatgtt   720
gagcaagaag tggttggtga tgataccttca gttttgcaat gtattcttaa cactgatatg   780
gagagaaccc aacttctgga agaagaggt cgtctgcttg aattacagag agaaattgac   840
ctagaaggcg aagctggaaa gagtgataag ttgaatggag agatcgacaa aaatgccctc   900
gcgaaaggc ttgaagagat atacaaaaga cttgatttca ttgatgctta ctcggctgag   960
tcacgtgcag caactatact ttcgggttttg agcttcacta cagaaatgca aaagagagca   1020
actaaaacat tttctggagg atggagaatg agaatagctc ttgctcgggc gttgttcatt   1080
gaacctgatc tattgttgct tgatgaaccc acgaatcatc ttgatctaca tgctgtctta   1140
tggctggaaa cttacctggt gaagtggcg aagacattta tagttgtctc tcatgctgaa   1200
gagttcttga atactgtagt cacagacatt atccatctac aaaatcagaa attgagtacc   1260
tacaaaggag actatgatac attcgaaagg cacgagatg aacaagttaa gaatcaacag   1320
aaggcgttcg aggcgaatga acgtacaagg gcccacatgc agacctttat tgataagttc   1380
cggtacaatg caaagcgtgc atctcttgtt caatctagaa ttaaggcact ggaacgaatt   1440
ggtcgtgtgg atgaagtcat caatgatcct gactacaagt ttgagttccc ttctcctgat   1500
```

```
gatagacctg gtgctcctat tataagcttc agtgatgcat cctttggata tcctgggggc   1560
ccattattgt tcaaaaattt gaattttgga atagatctgg atagccgagt agcaatggtt   1620
ggtcctaatg gtattggaaa gtcaacaata cttaagctta tttctgggga gcttcaacca   1680
acttcaggaa ctgttttccg ctctgctaag gtccgaattg ctgtatttag tcagcatcat   1740
gttgatgggc tggatctgtc ctcaaatccc ctcttataca atgatgcgtt gctttccagga   1800
gtgcctgaac aaaaattacg tggtcatcta ggttcatttg gtatcactgg aaatcttgct   1860
cttcagccca tgtacacttt gtctggtggc caaaaaagca gagttgcatt tgcaaagata   1920
accttcaaga agcctcacat attgcttctt gatgagccat caaatcactt ggatcttgac   1980
gctgtggagg ctctgataca aggtcttgtc ttgttccaag gaggcgtact gatggtcagt   2040
cacgatgaac atttaatatc tggtagtgtt gatcaactct gggccgtctc tgagggcagg   2100
gtgacgcctt tcgacgggac attccaggat tacaagaaaa ttctgcaatc ataa          2154

SEQ ID NO: 51           moltype = DNA   length = 1155
FEATURE                 Location/Qualifiers
source                  1..1155
                        mol_type = genomic DNA
                        organism = Nicotiana tabacum
SEQUENCE: 51
atgggtgctc agatatccgt atctaagctt gccaatttgt cctttgtccc cagaatacgc   60
gttcctgtgc ctaacataag tgttccaagt cccagcatca gttctggttt tgtttcaaat   120
cttcgtgtt ctgccatagg catttcttcc gtgttggtca attttatca atcagcatca    180
ttggctaagt cggcaaatcc atcaacatat acttatacag ttccttcttc gccttcaaga   240
gtgttgtata gatggcattt accagagcca aatgtcgttg atatatcagg gaattatgat   300
tgttcatcag taaagtctag gactgtggta gtactgttgg gatggttagg tgcaaaacag   360
aagcatctaa agagatatgc agagtggtat gcctcagcag gatatcatgt cattacattt   420
actttcccaa tgtctgagat tcttagctat caagtcgggg gaaaggcaga gcaggatata   480
gaactgcttg tgaaccatct tgttgattgg ttggaagaag agcatgcgaaa gaacttggtc   540
ttccacactt tcagtaacac gggatggtta acttatggtg tcattttgga gaagtttcag   600
aaacaagatc ctgttttaat gacaaggatc aaaggttgta ttgttgattc tgctcctgta   660
gctgctcccg atccacaggt atgggcttct ggattcctg ctgcctttt gaagaagaat    720
agtgttgcaa ccaaacacat catgactata aacaacaaag atgcagatgt gacaatagaa   780
accaaaactt cttcggatgc tacacctgca gtaactgaag cagcttttgct agtagtactg   840
gagaagttct tgaggtggt tttgagcctt cccgccgtaa ataggagact ttctgatgtt    900
ctagatctat tgcatcccca gcaaccaagt tgcccacaat tgtacatata cagcagtgca   960
gacagagtga ttcctgcgat ttctgttgag tcctttgtag aggagcaacg aagaattggt   1020
cgcaacgtta gagcttgcaa cttcattttct acacctcatg ttgatcattt cagaaatgac   1080
ccagaattat atactttaca gcttacccaa tttcttgagg actccgttct aagctcttgc   1140
aaacagtctt cctga                                                    1155

SEQ ID NO: 52           moltype = DNA   length = 1644
FEATURE                 Location/Qualifiers
source                  1..1644
                        mol_type = genomic DNA
                        organism = Nicotiana tabacum
SEQUENCE: 52
atgggaggtg cagaggatgc tgaaccacca tccaaacgtg tgaaagtatc ctctgggaaa   60
ccaggagatc tttcaaacgg cacatttcct agagatctga caagttgctc attgaatgac   120
ttgatggctc gccccctggt ttgtcaaggg gacgatgagg ttgttggtac aaaaggggtc   180
atcaagaaag ttgaatttgt gcgaatttta gctgaggcat tatattctct tggttataac   240
aaaactgggg cacatctaga agaagagtct gggatacctt tgcaatctgc tgtggtaaag   300
ttatttatgc agcaagtcct tgatggtaaa tgggatgaaa gtgtagccac attacgtaaa   360
atcggtctag tggatgaaaa ggttgttcaa ttggcatcat ttctgatatt ggaacagaag   420
ttttttgaac tgttggatga aaaaaaagtc atggatgctt tgaagacatt gagcactgag   480
attggacctc tttgcataaa cactgataga gtccgtgagc tttctttgtg cattttatca   540
cctttgcagc aggttcgtgc tgtggtgtca ggtcaagttg ttgtgagagc aaagccacga   600
agaaagctac tagaggaatt gcaaaaattg cttcccccaa cagttataat tcctgaacaa   660
agattgatca gtcttgttga acaggctctt gacttgcaac tagatgcttg taggtttcac   720
aactctttgg taggtgagat gtctttgctc actgatcatc agtgcggaag ggatcaaatt   780
cctctcaaa ctttgcaggt gaaattggat ggttttgtc gcatgaagca ccagtttttct   840
ggtcaccaga aacctgtctc ctatatgtca tggagtcctg atgaccatca gcttctcact   900
tgtggagtag aggaagttgt cagacggtgg gatattgaat caggtgaatg tacacatatt   960
tatgagaaaa atggtcttgg tctgatctca tgtggatggg ctcctgatgg caaaaggata   1020
ttatgcggtg ttacggacaa gagcattagc atgtgggatc tggaagggaa agagttggag   1080
tgttggaaag gccatcgaac tattagaata tctgacttgg ataaactag tgatgggcag   1140
catatagtct ctgttttgcaa agataatatg atattactat ttggatggga atcaaaagca   1200
gagaaagtaa ttcaggagga tcaaacaata acttcatttg tattgccat ggacagtaag    1260
tatttattgg ttagtctttg gaatcaagaa atccatctgt ggaatataga gggaactgta   1320
aagctcatat ccaaatataa agggcataaa cgttcacgct ttgttgtaag gtcttgcttt   1380
ggcggactgg gtcaagcatt tgttgccagt ggaagtgagg actcacaggt ttatatatgg   1440
catagaagct caggagaact cattgagaca ttggctggac attctggtac agtaaactgt   1500
gttagctgga acccagcaaa tcctcatatg ttggcatctg caagtgatga tcatactatt   1560
cgcatatggg gcatgaatca agtaaacatg aaacactatg acacagttag taatggcgtg   1620
cattactgca atggcggaac ttag                                          1644

SEQ ID NO: 53           moltype = DNA   length = 1764
FEATURE                 Location/Qualifiers
source                  1..1764
                        mol_type = genomic DNA
                        organism = Nicotiana tabacum
```

```
SEQUENCE: 53
atggcaatgg tagatgagcc attgtacccc atagccgtgt taatagatga acttaagaac   60
gatgatatac aattacggtt gaattcaatt aggaggttat cgactattgc acgtgccctt  120
ggtgaggaaa gaactcgaaa ggaattgatc ccttttttga gtgaaaacaa tgatgatgat  180
gatgagtgt  tattggcaat ggctgaagag cttggtgtgt ttatcccta tgttggaggt  240
gtagagcatg ctcatgtttt gctcccgccg ttggagacgc tttgtactgt tgaggagacc  300
tgtgtgaggg ataaagctgt tgaatcgttc tgtaggattg gatctcagat gagggagagt  360
gatttggttg attggttcgt ccctcttgtg aagaggctgg cagctggtga atggttcaca  420
gctagagttt ctgcctgtgg actctttcat attgcttact caagtgcccc agagatgttg  480
aaggcagaac ttcggtctat ttacagtcaa ttgtgtcaag acgacatgcc tatggtgcga  540
agatcagctg ccacaaactt ggggaagttt gctgctactg ttgaatctac ttacctcaag  600
agtgacatca tgtcaatatt tgatgatctt acacaggatg atcaggattc tgtacgctta  660
ttagctgttg agggctgtgc tgcacttggc aagctgttga agcccagga ttgtgttgca  720
cacatcctgc ctgtcattgt caacttctct caggacaagt cttggcgcgt ccgctacatg  780
gttgctaacc agttgtacga actatgtgaa gctgtagggc ctgagcccac taggacggat  840
ttggtgcctg cctatgtccg tttgcttcga gataatgaag ctgaagttcg catagctgct  900
gcagggaaag tcaccaaatt ctgtcggatt cttagtcccg agctgctat  tcagcatatt  960
cttccctgtg tgaaggaatt atcatcagac tcttcacagc atgtcagatc tgctttggct 1020
tctgttataa tggggatggc tcctgttttg ggaaaggatg caaccattga gcatcttctt 1080
ccaatatttc tttcccttct gaaggacgag tttcctgatg tgcgcctgaa catcattagc 1140
aagcttgatc aagtcaatca ggtgattgga attgatttat tatcccaatc tttgttgcca 1200
gctattgttg agctagcaga ggacaggcat tggcgagtcc gtcttgcaat aatagaatac 1260
atacctctat tggcaagtca attgggcata ggatttttg atgataagct tggtgccctt 1320
tgtatgcaat ggttacagga caaggtttat tcaatcagag atgctgctgc taataaccta 1380
aagcgtcttg cagaagaatt tggtccagag tgggcaatgc agcatataat tcctcaggtc 1440
ttggatatga ctaccagtcc acattatttg tatagaagga caattcttag agcaatttca 1500
ttgcttgcac ctgtaatggg ctctgaaata acttgttcta aattgctgcc tgtggttatt 1560
actgcaacaa aggatagagt gcccaacatt aaatttaatg tggcaaaggt gttgcaatcc 1620
cttatacctg ttgttgacca ctcggtggtg gagaaaacca ttcgccctag tttagtagag 1680
ctagctgaag accctgatgt tgatgttcgc ttttatgcca atcaagcact tcagtcaatt 1740
gataacgtca tgatgtcagg ctag                                        1764

SEQ ID NO: 54         moltype = DNA  length = 1866
FEATURE               Location/Qualifiers
source                1..1866
                      mol_type = genomic DNA
                      organism = Nicotiana tabacum
SEQUENCE: 54
atgggattca tcgaatcatg ttcccagact gcagaaatgg aaatcaggaa gtgctcgcct   60
tttctggaaa gtgaattgtt gtccggtaat ggtgggttgc ccttgacaga gtggagaact  120
gttcccgaca tttggcggac ttcggcagag aagtttggtg accgtgtagc agttgtggac  180
ccatatcatg atcctcctac aaccatgact tataaacagc tttatcagga gattgtggat  240
ttctctgaag gtttgagagt tgttgggcta aacccaacta agaagattgc gcttttttgt  300
gataattcat gtcgatggct tgttgcagat caaggtacga tggcgagtgg ggctatcaac  360
gttgtgaggg gttcaaggtc atcaaatcaa gagctattgc aattatacag ccactctgaa  420
agtgtcgctc ttgctattga caatcctgag atgtacaacc ggatttcaga cacctttggt  480
tcccacacag ctgtacgatt tgctatttta cttttgggcg agaaatcaag ccttggaaga  540
gaagccgtgc agggatatcc tgtatatact tataaggaga ttatagaatt gggtcacaag  600
agtcgtgtgg atctgcttga ttctgaagat gccaggaaac aatattcatt tgaggcaatc  660
aactctgatg atgtggctac aattgtctat accagtggaa ccaccggtaa tccaaaaggt  720
gtcatgctta cgcataaaaa tctgcttcac cagatttga atctggggga gatttgtct  780
gctgtacctg gggacagatt tctaagcatg cttccgcctt ggcatgcata tgagcgtgct  840
tgtgaatatt tcatattcac acatggaaca gagcaagtgt acacaactgt gaaaaattg   900
aagccacatt acttgataag tgttcctta gtttatgaga cattatacag tggaattcta  960
aagcagatca attcaaactc tgctgctagt aaactcaattg ccctattatt tttaaggatc 1020
agtatgactt acatggaggc aaaaaggat tacgaggctg gcgtaagtgg aggtgggagt 1080
ctttcttcac atgttgacaa gttctttgag gcaattggca taagattca gaatggatat 1140
ggtctgactg agtcatctcc cgtgatttct gcccgtcatc ttgcgtgtaa tgtacttggc 1200
tcagttgggc atcccattcg gcatgtagaa gtaaaaattg taaatgctga aacagatgag 1260
gtccttcctc ctggctcaag gggcattgtc aaagccagag ggccactagt aatgaagggc 1320
tactataaga atccgttggc aacaaaaacac gctattgatg agaatggatg gctgaacact 1380
ggtgatcttg gttggattgc gcctgatcat tctgtagggc gaagtcgtaa aagtgggggt 1440
gtaatagtcc ttgaaggccg tgcaaaggat accatagtcc tttcaactgg cgagaatgtt 1500
gaaccatcag agattgaaga agctgcaatg ggaagtagtc tgatccagca gattgtgtc  1560
attggccagg atcaacgacg tcttggagct ataattgtac caaataagga ggaggttctg 1620
ttagcagcta aaaatcagc tattgtggat tctgaaacca ctgaagttag caaggaaaaa 1680
gcagttggca tattatatga ggagttaaga aaatggactt caggttgctc atttcaagtt 1740
ggacctatcc ttattgtcga tgaaccttc acgattgata tgtggcttact aacaccaacc 1800
atgaaaatca agagagacaa aattgcagct ctatacaaag agcaaattga gaacttgtac 1860
aaatga                                                            1866

SEQ ID NO: 55         moltype = DNA  length = 2610
FEATURE               Location/Qualifiers
source                1..2610
                      mol_type = genomic DNA
                      organism = Nicotiana tabacum
SEQUENCE: 55
atgggtggtg acgaaactaa aaagaccact ataatggtgc tcaaggttga tcttcagtgc   60
tccagctgct ataagaaggt caaaaaagtt ctctgtaaat tccctcgatg tggagtaatt  120
```

```
aagagcattg aaatcaaaga acctccaaag cccaaagctc ctgaaaagcc caaggagcct   180
gtgaaaccaa aagaacccga gaagcccaaa caaccggaga agcccaaaga gcccgaaaag   240
cctaaacaac ctgagaagac tacggttgtc gtcattgaaa agcccaagga gcccgagaag   300
cctaaggcac cggaaaagtc aaaagagccc gagaagccca agaaccagaa aaagccgaaa   360
gaagttgaaa agcccaagcc caaagagccc gaaaagccca agaagctcc taaacctaat    420
ccagtggctc caccatcaca accaccacca ccgccagcac cagagccaat aatggttcaa   480
caataccctc agccaccact aggatattgt tgtggacaat gctacgaggg tcatatcggg   540
ggcccatgtt atcaatggta cggaagacct gtccttccgg ccccatgtta cgataactat   600
gggtataact atgggcctgg gcctgggcct gggccgtatg gctacggaag gggttgttat   660
gtgagtagat gtgaccaata cttagtgaa gaaaatgcca caggatgctc aattataaag    720
tgggagccaa atattgtggc tagcaaagct aaagaagtct actccgccgt ttgggttcgc   780
ctcctccaat tacccacaga attctatgat agaattgtcc ttagtagaat tggaaactca   840
attggccgac tactacgcat agatgcttgt acaagttcaa cgcttagaag gaggtacgcg   900
cgactgtgtg tgcaagtgca aatggaccaa ctagtccaaa caacaatcca gattggctcc   960
catatacaac aactggtata tgaaggagaa aaatttcttt gtaaggcctg tgggcgactg  1020
ggaaacacga catcaacatg ctcccacact ctacttgact tccaaaagca caacaagaa   1080
gagccatgtc ctaactcgac tggcttcata ggcaaggaaa ggcaattgaa gagcaatgac  1140
aaaccgtctc cttcccaa ggtaacaagc caaaaagagg cacaaccaat ggatctcaaa    1200
ataaaactca agcgacacct ccaggtatca atgtcaatat ttttgatgcg gcatcagccc  1260
atccttacat ctaataaatt cgaatcactt cttaatgata gcagtattac attcccggaa   1320
ataattgaat cccaaatgga attggatggg caaaactcta acctctcccc agactctaaa  1380
ctgtcgttct ctccaagaaa ccattcctct tccctgctcc ctcctctctc tccacgtggc   1440
caaaaggcta catgcaactc caataaacca cacaaaacag cgggcccatc cactaatcct  1500
ctaccatgca cgccacttcc cacactaatg acacctatta ccactgaaaa ccctataact    1560
gacttgtcac ttaccacctg ccaattggcc atgcaactca actctccaat actggctagt  1620
ctaaggttgc acgttaaaaa tcgaaccatg cacacaaata ttctactaac agattttcaa   1680
tcattacctc acgaaaacca atccccctca tcccctttcat cttctcctac acactatgaa  1740
tctactccac tcctcccatc aaacgaaaat ccctctaaaa taactctcac accaccatcg   1800
ttcctcaata ctgtccagaa tgaaccaccc actcctggat acaaaccttc cgatctacat    1860
caccaatgcc ctctcactgg accaccaacc aacgccatgg ttggaacaag gacttcaggt  1920
ccaagtggct tcttcactc tcaatatcca aaatcacgac gtcctgtttg ttctacagaa    1980
cccacaggtc ctagctcaat taatctcgga gggtatgagg ctagcaatgt cgaactatac   2040
caaccacctt tagttgacaa atgttctaga gcccatagcc ccaccctagc accagccctt   2100
cttcacaaca tgcaagccca ctggaatcca ccacatcact tcaatcccct acaaaacatg  2160
caactttttt accaacttcc cttttttgct ccacaggatc aaaacacccc acccttgatc   2220
catgcatggc aacccatccc tcaacactac ccagctccga tggatttca ccacacacat    2280
tcccatcccc atcacagtgc acctgtacca ggagagcaag aaatggaaac ccaaaatcaa  2340
accatcccac cactaaatat aacatcgtac acagaaaatt caaacctaca cgaggtcaaa  2400
atcttgttat tccaagcgat ggaagaaaag aagtatgtcc gcaaatgtcc cacagagcta  2460
tacaaatgct ccctcgacat aaggccccca ctcaatgcag cagtaggcaa tttcgccgta  2520
atactcagtc catcattgaa tggtcttcct gttccaccaa tggggagcca gttcaatgtc  2580
acccccccagc caacacccat caatgactag                                     2610

SEQ ID NO: 56           moltype = DNA   length = 1110
FEATURE                 Location/Qualifiers
source                  1..1110
                        mol_type = genomic DNA
                        organism = Nicotiana tabacum
SEQUENCE: 56
atgcatatat tgtatacttg tccgctgatt ctgtttatgg ctttactctt tgcttatgct     60
gctgctactg ctgctgattt agagaccaat ggagctgaaa aggcgggtgc ggatgcagga   120
atttgagta gtaatagcag tgtgaatgag aatttagacc tgataaatat gaatagaaaa    180
aaggatggtc atttggataa cgatagttcg aatgttgggg atcaaaacaa gtccaatgat   240
agtagtgcga aaaagggtga cgacagagaa gggttgaaag aagctgaggt ggaaaagaaa   300
agaattgata gtggttctaa gagagatgac aggaaggagg agacgaaaga agctgaacag  360
caagacaaag caaaagatat tagttccgag aagcaggtg agatggaaaa gattctgccg     420
gatgaattc agtcgagaga ggagattttg cctacaagaa aggagagttt ccatggtgaa    480
gaatgcgatt catcttatag ttgcacgata gaggaaaaag cagtggttgc atgtcttaga   540
gttccgggca atgaatctcc agaccttcta cttttggtc aaaacaattgg aaaaggaact    600
gtcaatattt tgattaaggc tcctgagttt gtacaactgg agaaagagaa gattgaactg   660
caaggaaagg aaatcagag gatgaaggtt tctataagga atgcaggaaa tgacaacaat    720
atcattctaa aggccgggga tggccaatgc actcttgatt tcaggggtct gattgacaat    780
gctgataaaa catctcaatt caagtatggt ttcctatctt ttgcaataat gtgtttggct   840
gctattgcat tagttgccac agtcttgatg tactttaaac ggaggcttct agtaagtagc   900
ggccacaagt atcaaaagtt ggacatggat ttaccagttt ccagtggcag aaagacggag   960
acactctcaa ctgatggatg ggacaatagc tgggatgacg attgggatga tgaggaggcg  1020
cccaaagcac catccgtgcc agtcactcct tccttctcgt ctaaaagcat acctcacga   1080
cggtctagta aggaaagctg gaaagactag                                        1110

SEQ ID NO: 57           moltype = DNA   length = 314
FEATURE                 Location/Qualifiers
source                  1..314
                        mol_type = genomic DNA
                        organism = Nicotiana tabacum
SEQUENCE: 57
cttttctcaa gaaacatatt tattaaataa tttcttttc gttacattca tttttataat     60
ctattccttt atgttctctt agagaaaagt atactattct aaaatacatt tatcccaaaa    120
aatagaaaaa tgaatgtagt attcatktac tcaagcgtgt tatattttgt caataaaatg    180
tctcccaaaa tattcaaatc ttgttcaata ccacatttcg tgataatcct tcctgtatat   240
```

```
taattaaaat ctattttacc ccagaattgt actaaaaaag tcagctaggt gtactaccta    300
tttcgcattc atgc                                                     314

SEQ ID NO: 58         moltype = DNA  length = 160
FEATURE               Location/Qualifiers
source                1..160
                      mol_type = genomic DNA
                      organism = Nicotiana tabacum
SEQUENCE: 58
agcccgattt gtcgtgagga tttgatatgt ctccctccaa aggtagcagc tagttttrgga    60
aatatcggtc ctcttgtgat ctgcaccaaa gtgagcaaca atattgcttt attagayccg   120
tttactctga ggcattgttt cttggatgct gatcagtact                         160

SEQ ID NO: 59         moltype = DNA  length = 322
FEATURE               Location/Qualifiers
source                1..322
                      mol_type = genomic DNA
                      organism = Nicotiana tabacum
SEQUENCE: 59
aaaagtgcga tctaaaacga tgcagtaacc aaaccgaagg ggcctgttgc ccatatccac    60
caagtttcag gacgtgttta acatttagct aacaaattct ctcatgagat ttaactgag   120
ttagagcttc aacctgcatg ggcataagtg tacaatacat crggtatgtt actggtgacc   180
aagagtttaa gactgaaaaa ttggagggcg acaataagag tactataccg tttgcaggca   240
ccacaaccac aaatttcaga catgtcatga aagatgcgta gcctcctact gtggcagagg   300
aaagcatgca tggttaattt gg                                           322

SEQ ID NO: 60         moltype = DNA  length = 71
FEATURE               Location/Qualifiers
source                1..71
                      mol_type = genomic DNA
                      organism = Nicotiana tabacum
SEQUENCE: 60
cataaatttt gtccaacatg gaagtatata ggtcamgttg tagttgattt caaacacttg    60
ttagaaaagt a                                                        71

SEQ ID NO: 61         moltype = DNA  length = 71
FEATURE               Location/Qualifiers
source                1..71
                      mol_type = genomic DNA
                      organism = Nicotiana tabacum
SEQUENCE: 61
tttccgctg gggatttcag ttgtattcct ctctgytgtt tctttacttc gggctcgact     60
tgtggtcttc c                                                        71

SEQ ID NO: 62         moltype = DNA  length = 71
FEATURE               Location/Qualifiers
source                1..71
                      mol_type = genomic DNA
                      organism = Nicotiana tabacum
SEQUENCE: 62
acagtaaatt ttctcactct tgattctgca tcaaayacac ttcttgtgct gttaagattc    60
ttcatagttg t                                                        71

SEQ ID NO: 63         moltype = DNA  length = 71
FEATURE               Location/Qualifiers
source                1..71
                      mol_type = genomic DNA
                      organism = Nicotiana tabacum
SEQUENCE: 63
cgcctgtgca taatgaggcg catatggtgg gtatgstta ttttagaaag gaatatgaga     60
gttcatctgg a                                                        71

SEQ ID NO: 64         moltype = DNA  length = 71
FEATURE               Location/Qualifiers
source                1..71
                      mol_type = genomic DNA
                      organism = Nicotiana tabacum
SEQUENCE: 64
ttgtaattat tatgatagaa ttagtattgc tttatwtatt gtattttat cccttttaaaa    60
gtcaactgct g                                                        71

SEQ ID NO: 65         moltype = DNA  length = 11801
FEATURE               Location/Qualifiers
misc_feature          1..11801
                      note = Description of Artificial Sequence: Synthetic
                       polynucleotide
source                1..11801
                      mol_type = other DNA
                      organism = synthetic construct
```

```
SEQUENCE: 65
tgagcgtcgc aaaggcgctc ggtcttgcct tgctcgtcgg tgatgtactt caccagctcc    60
gcgaagtcgc tcttcttgat ggagcgcatg gggacgtgct tggcaatcac gcgcaccccc   120
cggccgtttt agcggctaaa aaagtcatgg ctctgccctc gggcggacca cgcccatcat   180
gaccttgcca agctcgtcct gcttctcttc gatcttcgcc agcagggcga ggatcgtggc   240
atcaccgaac cgcgccgtgc gcgggtcgtc ggtgagccag agtttcagca ggccgcccag   300
gcggccaggt cgccattga tgcgggccag ctcgcggacg tgctcatagt ccacgacgcc   360
cgtgattttg tagccctggc cgacggccag caggtaggcc gacaggctca tgccggccgc   420
cgccgccttt tcctcaatcg ctcttcgttc gtctggaagg cagtacacct tgataggtga   480
gctgcccttc ctggttggct tggtttcatc agccatccgc ttgccctcat ctgttacgcc   540
ggcggtagcc ggccagcctc gcagagcagg attcccgttg agcaccgcca ggtgcgaata   600
agggacagtg aagaaggaac acccgctcgc gggtgggcct acttcaccta tcctgcccgg   660
ctgacgccgt tggatacacc aaggaaagtc tacacgaacc ctttggcaaa atcctgtata   720
tcgtgcgaaa aaggatggat ataccgaaaa aatcgctata atgaccccga agcagggtta   780
tgcagcggaa aagcgccacg cttcccgaag ggagaaaggc ggacaggtat ccggtaagcg   840
gcagggtcgg aacaggagag cgcacgaggg agcttccagg gggaaacgcc tggtatcttt   900
atagtcctgt cgggtttcgc cacctctgac ttgagcgtcg attttgtga tgctcgtcag    960
gggggcggag cctatggaaa aacgccagca acgcggcctt tttacggttc ctggcctttt  1020
gctggccttt tgctcacatg ttctttcctg cgttatcccc tgattctgtg gataaccgta  1080
ttaccgcctt tgagtgagct gataccgctc gccgcagccg aacgaccgag cgcagcgagt  1140
cagtgagcga ggaagcggaa gagcgccaga aggccgccag agaggccgag cgcggccgtg  1200
aggcttggac gctagggcag ggcatgaaaa agcccgtagc gggcgtctga                1260
cgcggtggaa agggggaggg gatgttgtct acatggctct gctgtagtga gtgggttgcg  1320
ctccggcagc ggtcctgatc aatcgtcacc ctttctcggt ccttcaacgt tcctgacaac  1380
gagcctcctt ttcgccaatc catcgacaat caccgcgagt ccctgctcga acgctgcgtc  1440
cggaccggct tcgtcaagg cgtctatcgc ggcccgcaac agggcgaga gcggagcctg   1500
ttcaacggtg ccgccgcgct cgccggcatc gctgtcgccg gctgctcct caagcacggc   1560
cccaacagtg aagtagctga ttgtcatcag cgcattgacg cgctgcccgg ccgaaaaacc  1620
cgcctcgcag aggaagcgaa gctgcgcgtc ggccgtttcc atctgcggtg cgcccggtcg  1680
cgtgccggca tggatgcgcg cgccatcgcg gtaggcgagc agcgcctgcc tgaagctgga  1740
ggcattcccg atcagaaatg agcgccagtc gtcgtcggct ctcggcaccg aatgcgtatg  1800
attctccgcc agcatggctt cggccagtgc gtcgagcagc gcccgcttgt tcctgaagtg  1860
ccagtaaagc gccggctgct gaaccccccaa ccgttccgcc agtttgcgtg tcgtcagacc  1920
gtctacgccg acctcgttca acaggtccag ggcggcacgg atcactgtat ggctgcaa    1980
ctttgtcatg cttgacactt tatcactgat aaacataata tgtccaccaa cttatcagtg  2040
ataaagaatc cgcgcgttca atcggaccag cggaggctgg tccggaggcc agacgtgaaa  2100
cccaacatac ccctgatcgt aattctgagc actgtcgcgc tcgacgctgt cggcatcggc  2160
ctgattatgc cggtgctgcc gggcctcctg cgcgatctgg ttcactcgaa cgacgtcacc  2220
gcccactatg gcattctgct ggcgctctat gcgttggtgc aattgcctg cgccacctgt  2280
ctgggcgcgc tgtcgatcg tttcgggcgg cggccaatct tgctcgtctc gctggccggc  2340
gccagatctg gggaaccctg tggttggcat gcacatacaa atggacgaac ggataaaacct  2400
tttcacgccc tttaaatat ccgattattc taataaacgc tcttttctct taggtttacc  2460
cgccaatata tcctgtcaaa cactgatagt ttaaactgaa ggcgggaaac gaagcttcca  2520
gaaggtaatt atccaagatg tagcatcaag aatccaatgt ttacgggaaa aactatgaa   2580
gtattatgtg agctcagcaa gaagcagatc aatatgcggc acatatgcaa cctatgttca  2640
aaaatgaaga atgtacagat acaagatcct atactgccag aatacgaaga gaatacgta   2700
gaaattgaaa aagaagaacc aggcgaagaa aagaatcttg aacgtaag cactgacgac   2760
aacaatgaaa agaagaagat aaggtcggtg attgtgaaag agacatagag gacacatgta  2820
aggtggaaaa tgtaagggcg aaagtaacc ttatcacaaa ggaatcttat ccccactac    2880
ttatccttt atattttcc gtgtcatttt tgcccttgag ttttcctata taggaacca   2940
agttcggcat ttgtgaaaac aagaaaaaat ttggtgtaag ctattttctt tgaagtactg  3000
aggatacaac ttcagagaaa tttgtaagtt tgtggatcct gcaggctagc gtgcactcta  3060
gactcgacga actgacgagc tcgaatttcc ccgatcgttc aaacatttgg caataaagtt  3120
tcttaagatt gaatcctgtt gccggtcttg cgatgattat catataatt ctgttgaatt   3180
acgttaagca tgtaataatt aacatgtaat gcatgacgtt atttatgaga tgggttttta  3240
tgattagagt cccgcaatta tacatttaat acgcgataga aaacaaaata tagcgcgcaa  3300
actatgataa attatcgcgc gcggtgtcat ctatgttact agatcgggaa ttcctcgagc  3360
aactattttt atgtatgcaa gagtcagcat atgtataatt gattcagaat cgttttgacg  3420
agttcggatg tagtagtagc cattatttaa tgtacatact aatcgtgaat agtgaatatg  3480
atgaaacatt gtatcttatt gtataaatat ccataaacac atcatgaaag acactttctt  3540
tcacggtctg aattaattat gatacaattc taatagaaaa cgaattaaat tacgttgaat  3600
tgtatgaaat ctaattgaac aagccaacca cgacgacgac taacgttgcc tggattgact  3660
cggtttaagt taaccactaa aaaaacggag ctgtcatgta acacgcggat cgagcaggtc  3720
acagtcatga agccatcaaa gcaaaagaac taatccaagg gctgagatga ttaattagtt  3780
taaaaattag ttaacacgag ggaaaaggct gtctgacacag caggtcacgt tatctttacc  3840
tgtggtcgaa atgattcgtg tctgtcgatt ttaattattt ttttgaaagg ccgaaaataa  3900
agttgtaaga gataaacccg cctatataa ttcatatatt ttcctctccg ctttgaattg   3960
tctcgttgtc ctcctcactt tcatcagccg ttttgaatct ccggcgactt gacagagaag  4020
aacaaggaag aagactaaga gagaaagtaa gagatatca ttctccgttt                4080
tgaatcttcc tcaatctcat cttcttccgc tcttttcttc caaggtaata ggaactttct  4140
ggatctactt tatttgctgg atctcgatct tgttttctca atttccttga gatctggaat  4200
tcgtttaatt tggatctgtg aacctccact aaatcttttg gttttactag aatcgatcta  4260
agttgaccga tcagttagct cgattatagc taccagaatt tggcttgacc ttgatggaga  4320
gatccatgtt catgttacct gggaaatgat ttgtatatgt ggttgaaat ctgaactgtt   4380
gaagttagat tgaatctgaa cactgtcaat gttagattga atctgaacac tgtttaaggt  4440
tagatgaagt ttgtgtatag attcttcgaa actttaggat ttgtagtgtc gtacgttgaa  4500
cagaaagcta tttctgattc aatcagggtt tatttgactg tattgaactc tttttgtgtg  4560
tttgcagctc ataaaaggta ccaaacaatg attgaacaag atggattgca cgcaggttct  4620
ccggccgctt gggtggagag gctattcggc tatgactggg cacaacagac aatcggctgc  4680
```

```
tctgatgccg ccgtgttccg gctgtcagcg caggggcgcc cggttctttt tgtcaagacc   4740
gacctgtccg gtgccctgaa tgaactgcag gacgaggcag cgcggctatc gtggctggcc   4800
acgacgggcg ttccttgcgc agctgtgctc gacgttgtca ctgaagcggg aagggactgg   4860
ctgctattgg gcgaagtgcc ggggcaggat ctcctgtcat ctcaccttgc tcctgccgag   4920
aaagtatcca tcatggctga tgcaatgcgg cggctgcata cgcttgatcc ggctacctgc   4980
ccattcgacc accaagcgaa acatcgcatc gagcgagcac gtactcggat ggaagccggt   5040
cttgtcgatc aggatgatct ggacgaagag catcaggggc tcgcgccagc cgaactgttc   5100
gccaggctca aggcgcgcat gcccgacggc gaggatctcg tcgtgaccca tggcgatgcc   5160
tgcttgccga atatcatggt ggaaaatggc cgcttttctg gattcatcga ctgtggccgg   5220
ctgggtgtgg cggaccgcta tcaggacata gcgttggcta cccgtgatat tgctgaagag   5280
cttggcggcg aatgggctga ccgcttcctc gtgctttacg gtatcgccgc tcccgattcg   5340
cagcgcatcg ccttctatcg ccttcttgac gagttctttt gagcgggact ctggcgatcg   5400
ccccgatcgt tcaaacattt ggcaataaag tttcttaaga ttgaatcctg ttgccggtct   5460
tgcgatgatt atcatataat ttctgttgaa ttacgttaaa catgtaataa ttaacatgta   5520
atgcatgacg ttatttatga gatgggtttt tatgattaga gtcccgcaat tatacattta   5580
atacgcgata gaaaacaaaa tatagcgcgc aaactaggat aaattatcgc gcgcggtgtc   5640
atctatgtta ctagatcggg actagtttac accacaatat atcctgccac cagccagcca   5700
acagctcccc gaccggcagc tcggcacaaa atcaccactc gatacaggca gcccatcagt   5760
ccggacggc gtcagcggga gagccgttgt aaggcggcag actttgctca tgttaccgat   5820
gctattcgga agaacggcaa ctaagctgcc gggtttgaaa cacggatgat ctcgcggagg   5880
gtagcatgtt gattgtaacg atgacagagc gttgctgcct gtgatcaaat atcatctccc   5940
tcgcagagat ccgaattatc agccttctta ttcatttctc gcttaaccgt gacaggctgt   6000
cgatcttgag aactatgccg acataatagg aaatcgctgg ataaagccgc tgaggaagct   6060
gagtggcgct atttctttag aagtgaacgt tgacgatatc aactcccctt tccattgctc   6120
accgaatggt acaggtcggg gacccgaagt tccgactgtc ggcctgatgc atccccggct   6180
gatcgacccc agatctgggg ctgagaaagc ccagtaagga aacaactgta ggttcgagtc   6240
gcgagatccc ccggaaccaa aggaagtagg ttaaacccgc tccgatcagg ccgagccacg   6300
ccaggccgag aacattggtt cctgtaggca tcgggattgg cggatcaaac actaaagcta   6360
ctggaacgag cagaagtcct ccggccgcca gttgccaggc ggtaaaggtg agcagaggca   6420
cgggaggttg ccacttgcgg gtcagcacgg ttccgaacgc catggaaacc gccccgcca   6480
ggcccgctgc gacgccgaca ggatctagcg ctgcgtttgg tgtcaacacc aacagcgcca   6540
cgcccgcagt tccgcaaata gccccagga ccgccatcaa tcgtatcggg ctacctagca   6600
gagcggcaga gatgaacacg accatcagcg gctgcacagc gcctaccgtc gccgcgaccc   6660
cgcccggcag gcggtagacc gaaataaaca acaagctcca gaatagcgaa atattaagtg   6720
cgccgaggat gaagatgcgc atccaccaga ttcccgttgg aatctgtcgg acgatcatca   6780
cgagcaataa acccgccggc aacgcccgca gcagcatacc ggcgaccct cggcctcgct   6840
gttcgggctc cacgaaaacg ccggacagat gcgcttgtg agcgtccttg gggccgtcct   6900
cctgtttgaa gaccgacagc ccaatgatct cgccgtcgat gtaggcgccg aatgccacgg   6960
catctcgcaa ccgttcagcg aacgcctcca tgggcttttt ctcctcgtgc tcgtaaacgg   7020
acccgaacat ctctggagct ttcttcaggg ccgacaatgc gatctcgcgg aaatcctgca   7080
cgtcggccgc tccaagccgt cgaatctgag ccttaatcac aattgtcaat tttaatcctc   7140
tgtttatcgg cagttcgtag agcgcgccgt gcgtcccgag cgatactgag cgaagcaagt   7200
gcgtcgagca gtgcccgctt gttcctgaaa tgccagtaaa gcgctggctg ctgaacccgc   7260
agccggaact gaccccacaa ggccctagcg tttgcaatgc accaggtcat cattgaccca   7320
ggcgtgttcc accaggccgc tgcctcgcaa ctcttcgcag gcttcgccga cctgctcgcg   7380
ccacttcttc acgcgggtgg aatccgatcc gcacatgagg cggaaggttt ccagcttgag   7440
cgggtacggc tcccggtgcg agctgaaata gtcgaacatc cgtcgggccg tcggcgacag   7500
cttgcggtac ttctcccata tgaatttcgt gtagtggtcg ccagcaaaca gcacgacgat   7560
ttcctcgtcg atcaggacct ggcaacggga cgttttcttg ccacggtcca ggacgcggaa   7620
gcggtgcagc agcgacaccg attccaggtg cccaacgcgg tcggacgtga agcccatcgc   7680
cgtcgcctgt aggcgcgaca ggcattcctc ggccttcgtc taataccggc cattgatcga   7740
ccagcccagg tcctggcaaa gctcgtagaa cgtgaaggtg atcggctcgc cgatagggt   7800
gcgcttcgcg tactccaaca cctgctgcca caccagttcg tcatcgtcgg cccgcagctc   7860
gacgccggtg taggtgatct tcacgtcctt gttgacgtgg aaaatgacct tgttttgcag   7920
cgcctcgcgc gggattttct tgttgcgcgt ggtgaacagg gcagagcggg ccgtgtcgtt   7980
tggcatcgct cgcatcgtgt ccggccacgg cgcaatatcg aacaaggaaa gctgcatttc   8040
cttgatctgc tgcttcgtgt gtttcagcaa cgcggcctgc ttggcctcgc tgacctgttt   8100
tgccaggtcc tcgccggcgg ttttttcgct tcttggtcgtc atagttcctc gcgtgtcgat   8160
ggtcatcgac ttcgccaaac ctgccgcctc ctgttcgaga cgacgcgaac gctccacggc   8220
ggccggcgac gcgggcaggg cagggggagc cagttgcacg ctgtcgcgct cgatcttggc   8280
cgtagcttgc tggaccatcg agccgacgga ctggaaggtt tcgcggggcg cacgcatgac   8340
ggtgcggctt gcgatggttt cggcatcctc ggcggaaaac cccgcgtcga tcagttcttg   8400
cctgtatgcc ttccggtcaa acgtccgatt cattcaccct ccttgcggga ttgccccgac   8460
tcacgccggg gcaatgtgcc cttattcctg atttgacccg tggtgtccag   8520
ataatccacc ttatcggcaa tgaagtcggt cccgtagacc gtctggccgt ccttctcgta   8580
cttggtattc cgaatcttgc cctgcacgaa taccagcgac cccttgccca aatacttgcc   8640
gtgggcctcg gcctgagagc caaaacactt gatgcggaag aagtcggtgc gctcctgctt   8700
gtcgccggca tcgttgcgcc acatctaggt actaaaacaa ttcatccagt aaaatataat   8760
atttatttt ctcccaatca ggcttgatcc ccagtaagtc aaaaaatagc tcgacatact   8820
gttcttcccc gatatcctcc ctgatcgacc ggacgcagaa ggcaatgtca taccacttgt   8880
ccgccctgcc gcttctccca agatcaataa agccacttac tttgcatctt tcacaaagat   8940
tgttgctgtc tcccaggtcg ccgtgggaaa agacaagttc ctcttcgggc ttttccgtct   9000
ttaaaaaatc atacagctcg gcggatctt taaatggagt gtcttcttcc cagttttcgc   9060
aatccacatc gcgataacatc ttattcagta atccggctaag cggctgtcta   9120
agctattcgt atagggacaa tccgatatgt cgatggagtg aaagagcctg atgcactccg   9180
catacagctc gataatcttt tcagggcttt gttcatcttc atactcttcc gagcaaagga   9240
cgccatcggc ctcactcatg agcagattgc tccagccatc atgccgttca aagtgcagga   9300
cctttggaac aggcagcttt ccttccagcc atagcatcat gtccttttcc cgttccacat   9360
cataggtggt cccctttatac cggctgtccg tcatttttaa atataggttt tcattttctc   9420
```

```
ccaccagctt atatacctta gcaggagaca ttccttccgt atctttacg cagcggtatt   9480
tttcgatcag tttttcaat tccggtgata ttctcattt agccattat tatttccttc   9540
ctcttttcta cagtatttaa agataccca agaagctaat tataacaaga cgaactccaa   9600
ttcactgttc cttgcattct aaaaccttaa ataccagaaa acagcttttt caaagttgtt   9660
ttcaaagttg gcgtataaca tagtatcgac ggagccgatt ttgaaaccac aattatgggt   9720
gatgctgcca acttactgat ttagtgtatg atggtgtttt tgaggtgctc cagtggcttc   9780
tgtgtctatc agctgtccct cctgttcagc tactgacggg gtggtgcgta acggcaaaag   9840
caccgccgga catcagcgct atctctgctc tcactgccgt aaaacatggc aactgcagtt   9900
cacttacacc gcttctcaac ccggtacgca ccagaaaatc attgatatgg ccatgaatgg   9960
cgttggatgc cgggcaacag cccgcattat gggcgttggc ctcaacacga ttttacgtca  10020
cttaaaaaac tcaggccgca gtcggtaacc tcgcgcatac agccgggcag tgacgtcatc  10080
gtctgcgcgg aaatggacga acagtggggc tatgtcgggg ctaaatcgcg ccagcgctgg  10140
ctgttttacg cgtatgacag tctccggaag acggttgttg cgcacgtatt cggtgaacgc  10200
actatggcga cgctggggcg tcttatgagc ctgctgtcac cctttgacgt ggtgatatgg  10260
atgacggatg gctggccgct gtatgaatcc cgcctgaagg gaaagctgca cgtaatcagc  10320
aagcgatata cgcagcgaat tgagcggcat aacctgaatc tgaggcagca cctggcacgg  10380
ctgggacgga agtcgctgtc gttctcaaaa tcggtggagc tgcatgacaa agtcatcggg  10440
cattatctga acataaaaca ctatcaataa gttggagtca ttacccaatt atgatagaat  10500
ttacaagcta taaggttatt gtcctgggtt tcaagcatta gtccatgcaa gttttatgc   10560
tttgcccatt ctatagatat attgataagc gcgctgccta tgccttgccc cctgaaatcc  10620
ttacatacgg cgatatcttc tatataaaag atatattatc ttatcagtat tgtcaatata  10680
ttcaaggcaa tctgcctcct catcctcttc atcctcttcg tcttggtagc tttttaaata  10740
tggcgcttca tagagtaatt ctgtaaaggt ccaattctcg ttttcatacc tcggtataat  10800
cttacctatc acctcaaatg gttcgctggg tttatcgcac ccccgaacac gagcacggca  10860
cccgcgacca ctatgccaag aatgccaag gtaaaaattg ccggcccgc catgaagtcc    10920
gtgaatgccc cgacggccga agtgaagggc aggccgccac ccggccgcc gccctcactg   10980
cccggcacct ggtcgctgaa tgtcgatgcc agcacctgcg gcacgtcaat gcttccggc   11040
gtcgcgctcg ggctgatcgc ccatcccgtt actgccccga tcccggcaat ggcaaggact  11100
gccagcgctg ccattttggg ggtgaggccg ttcgcggccg aggggcgcag cccctggggg   11160
gatgggaggc ccgcgttagc gggccgggag ggttcgagaa gggccgccac ccccttcgg   11220
cgtgcgcggt cacgcgcaca gggcgcagcc ctggttaaaa acaaggttta taaatattgg  11280
tttaaaagca ggttaaaaga caggttagcg gtggccgaaa aacgggcgga aaccttgca   11340
aatgctggat tttctgcctg tggacagccc ctcaaatgtc aataggtgcg cccctcatct  11400
gtcagcactc tgcccctcaa gtgtcaagga tcgcgcccct catctgtcag tagtcgcgcc  11460
cctcaagtgt caataccgca gggcacttat ccccaggctt gtccacatca tctgtgggaa  11520
actcgcgtaa aatcaggcgt tttcgccgat ttgcgaggct ggccagctcc acgtcgccgg  11580
ccgaaatcga gcctgcccct catctgtcaa cgccgcgccg ggtgagtcgg cccctcaagt  11640
gtcaacgtcc gcccctcatc tgtcagtgag gccaagttt tccgcgaggt atccacaacg  11700
ccggcggccg cggtgtctcg cacacggctt cgacggcgtt tctggcgcgt ttgcagggcc  11760
atagacggcc gccagcccag cggcgagggc aaccagcccg g                     11801
```